United States Patent
Garcia-Martinez et al.

(10) Patent No.: US 10,800,841 B2
(45) Date of Patent: *Oct. 13, 2020

(54) METHODS OF TREATING AUTOIMMUNITY USING SPECIFIC ANTI-IL-6 ANTIBODIES

(71) Applicant: ALDERBIO HOLDINGS LLC, Las Vegas, NV (US)

(72) Inventors: Leon Garcia-Martinez, Woodinville, WA (US); Anne Elisabeth Carvalho Jensen, Snohomish, WA (US); Katie Anderson, Kirkland, WA (US); Benjamin H. Dutzar, Seattle, WA (US); Ethan W. Ojala, Snohomish, WA (US); John Latham, Seattle, WA (US); Brian R. Kovacevich, Snohomish, WA (US); Jeffrey T. L. Smith, Bellevue, WA (US)

(73) Assignee: VITAERIS, INC., Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/703,414

(22) Filed: Sep. 13, 2017

(65) Prior Publication Data

US 2018/0100013 A1    Apr. 12, 2018

Related U.S. Application Data

(60) Division of application No. 14/604,419, filed on Jan. 23, 2015, now Pat. No. 9,771,421, which is a continuation of application No. 12/601,295, filed as application No. PCT/US2008/064432 on May 21, 2008, now abandoned.

(60) Provisional application No. 60/924,550, filed on May 21, 2007.

(51) Int. Cl.
| | | |
|---|---|---|
| *C07K 16/30* | (2006.01) | |
| *A61K 39/395* | (2006.01) | |
| *C07K 16/24* | (2006.01) | |
| *A61K 45/06* | (2006.01) | |
| *A61K 39/00* | (2006.01) | |

(52) U.S. Cl.
CPC ........ *C07K 16/248* (2013.01); *A61K 39/3955* (2013.01); *A61K 45/06* (2013.01); *A61K 2039/505* (2013.01); *C07K 2317/20* (2013.01); *C07K 2317/24* (2013.01); *C07K 2317/34* (2013.01); *C07K 2317/41* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,468,607 A | 11/1995 | Revel et al. |
| 5,468,608 A | 11/1995 | Revel et al. |
| 5,468,609 A | 11/1995 | Revel et al. |
| 5,541,312 A | 7/1996 | Revel et al. |
| 5,545,623 A | 8/1996 | Matsumori |
| 5,554,513 A | 9/1996 | Revel et al. |
| 5,556,947 A | 9/1996 | Bock et al. |
| 5,559,012 A | 9/1996 | Brailly et al. |
| 5,618,700 A | 4/1997 | Novick et al. |
| 5,621,077 A | 4/1997 | Novick et al. |
| 5,627,052 A | 5/1997 | Schrader |
| 5,646,005 A | 7/1997 | Kudsk |
| 5,670,373 A | 9/1997 | Kishimoto |
| 5,707,624 A | 1/1998 | Nickoloff et al. |
| 5,795,965 A | 8/1998 | Tsuchiya et al. |
| 5,817,790 A | 10/1998 | Tsuchiya et al. |
| 5,854,398 A | 12/1998 | Chang et al. |
| 5,856,135 A | 1/1999 | Tsuchiya et al. |
| 5,859,205 A | 1/1999 | Adair et al. |
| 5,866,689 A | 2/1999 | Kishimoto et al. |
| 5,882,872 A | 3/1999 | Kudsk |
| 5,888,510 A | 3/1999 | Kishimoto et al. |
| 5,888,511 A | 3/1999 | Skurkovich et al. |
| 6,074,636 A | 6/2000 | Nichols |
| 6,083,501 A | 7/2000 | Miyata et al. |
| 6,086,874 A | 7/2000 | Yoshida et al. |
| 6,121,423 A | 9/2000 | Tsuchiya et al. |
| 6,231,536 B1 | 5/2001 | Lentz |
| 6,235,281 B1 | 5/2001 | Stenzel et al. |
| 6,261,560 B1 | 7/2001 | Tsujinaka et al. |
| 6,306,393 B1 | 10/2001 | Goldenberg |
| 6,342,587 B1 | 1/2002 | Barbas, III et al. |
| 6,395,498 B1 | 5/2002 | Tartaglia et al. |
| 6,399,054 B1 | 6/2002 | Casorati et al. |

(Continued)

FOREIGN PATENT DOCUMENTS

| | | |
|---|---|---|
| EP | 0 488 470 | 6/1992 |
| JP | 2003-066047 | 3/2003 |

(Continued)

OTHER PUBLICATIONS

Park, J.Y. and Pillinger, M.H., "Interleukin-6 in the Pathogenesis of Rheumatoid Arthritis", Bulletin of the NYU Hospital for Joint Diseases 2007; vol. 65 (Suppl. 1): S4-10.

(Continued)

*Primary Examiner* — Bridget E Bunner
*Assistant Examiner* — Fozia Hamud
(74) *Attorney, Agent, or Firm* — Baker, Donelson, Bearman, Caldwell & Berkowitz, PC; Robin L. Teskin

(57) ABSTRACT

Methods of treating individuals with autoimmune conditions characterized by elevated IL-6 levels comprising the administration of anti-IL-6 antibodies or antibody fragments are provided.

17 Claims, 18 Drawing Sheets

Specification includes a Sequence Listing.

(56) References Cited

U.S. PATENT DOCUMENTS

| | | |
|---|---|---|
| 6,407,218 B1 | 6/2002 | Tamarkin et al. |
| 6,419,944 B2 | 7/2002 | Tobinick |
| 6,528,051 B2 | 3/2003 | Tamarkin et al. |
| 6,551,592 B2 | 4/2003 | Lindhofer et al. |
| 6,709,660 B1 | 3/2004 | Scarlato et al. |
| 6,723,319 B1 | 4/2004 | Ito et al. |
| 6,897,206 B2 | 5/2005 | Sackeyfio et al. |
| 6,936,698 B2 | 8/2005 | Taylor |
| 6,939,547 B2 | 9/2005 | Aoki et al. |
| 6,984,383 B1 | 1/2006 | Co et al. |
| 6,989,244 B1 | 1/2006 | Tsuchiya et al. |
| 6,994,853 B1 | 2/2006 | Lindhofer et al. |
| 7,018,632 B2 | 3/2006 | Lindhofer et al. |
| 7,108,981 B2 | 9/2006 | Aoki et al. |
| 7,169,573 B2 | 1/2007 | Kurosawa et al. |
| 7,179,893 B2 | 2/2007 | Le et al. |
| 7,235,365 B2 | 6/2007 | Aoki et al. |
| 7,261,894 B2 | 8/2007 | Sims et al. |
| 7,282,567 B2 | 10/2007 | Goldenberg et al. |
| 7,285,269 B2 | 10/2007 | Babcook et al. |
| 7,288,406 B2 | 10/2007 | Bogin et al. |
| 7,291,721 B2 | 11/2007 | Giles-Komar et al. |
| 7,320,792 B2 | 1/2008 | Ito et al. |
| 7,345,217 B2 | 3/2008 | Zhang et al. |
| 7,374,756 B2 | 5/2008 | Aoki et al. |
| 7,392,140 B2 | 6/2008 | Serena et al. |
| 7,393,648 B2 | 7/2008 | Rother |
| 7,431,927 B2 | 10/2008 | Couto et al. |
| 7,462,697 B2 | 12/2008 | Couto et al. |
| 7,468,184 B2 | 12/2008 | Sato et al. |
| 7,479,543 B2 | 1/2009 | Tsuchiya et al. |
| 7,482,436 B2 | 1/2009 | Sigimura et al. |
| 7,504,106 B2 | 3/2009 | Skurkovich et al. |
| 7,504,256 B1 | 3/2009 | Ogawa et al. |
| 7,521,052 B2 | 4/2009 | Okuda et al. |
| 7,534,427 B2 | 5/2009 | Goldenberg et al. |
| 7,560,112 B2 | 7/2009 | Chen et al. |
| 7,582,298 B2 | 9/2009 | Stevens et al. |
| 7,611,857 B2 | 11/2009 | Medlock et al. |
| 7,612,182 B2 | 11/2009 | Giles-Komar et al. |
| 7,622,555 B2 | 11/2009 | Davids et al. |
| 7,634,360 B2 | 12/2009 | Davalos et al. |
| 7,655,417 B2 | 2/2010 | Chung et al. |
| 7,662,378 B2 | 2/2010 | Goldenberg et al. |
| 7,695,716 B2 | 4/2010 | Dachman et al. |
| 7,727,528 B2 | 6/2010 | Adcock |
| 7,790,463 B2 | 9/2010 | Mor et al. |
| 7,824,674 B2 | 11/2010 | Ito et al. |
| 7,833,755 B2 | 11/2010 | Chen et al. |
| 7,833,786 B2 | 11/2010 | Giles-Komar et al. |
| 7,863,419 B2 | 1/2011 | Taylor et al. |
| 7,906,117 B2 | 3/2011 | Smith et al. |
| 7,915,388 B2 | 3/2011 | Wu et al. |
| 7,919,095 B2 | 4/2011 | Smith et al. |
| 7,935,340 B2 | 5/2011 | Garcia-Martinez et al. |
| 8,017,121 B2 | 5/2011 | Kushimoto et al. |
| 7,955,597 B2 | 6/2011 | Giles-Komar et al. |
| 7,993,641 B2 | 8/2011 | Waldmann et al. |
| 8,062,864 B2 | 11/2011 | Garcia-Martinez et al. |
| 8,062,866 B2 | 11/2011 | Frey et al. |
| 8,067,003 B2 | 11/2011 | Chen et al. |
| 8,080,528 B2 | 12/2011 | Kenley et al. |
| 8,173,126 B2 | 5/2012 | Yoshizaki et al. |
| 8,178,101 B2 | 5/2012 | Garcia-Martinez et al. |
| 8,188,231 B2 | 5/2012 | Lazar et al. |
| 8,226,611 B2 | 7/2012 | Chen et al. |
| 8,252,286 B2 | 8/2012 | Smith |
| RE43,672 E | 9/2012 | Chen et al. |
| 8,268,582 B2 | 9/2012 | Cregg et al. |
| 8,277,804 B2 | 10/2012 | Smith |
| 8,323,649 B2 | 12/2012 | Garcia-Martinez et al. |
| 8,337,847 B2 | 12/2012 | Smith et al. |
| 8,404,235 B2 | 3/2013 | Smith |
| 8,420,089 B2 | 4/2013 | Smith |
| 8,535,671 B2 | 9/2013 | Smith |
| 8,623,362 B2 | 1/2014 | Chen et al. |
| 8,992,908 B2 | 3/2015 | Smith et al. |
| 8,992,920 B2* | 3/2015 | Smith .................. A61K 38/16 424/134.1 |
| 8,999,330 B2 | 4/2015 | Smith |
| 9,085,615 B2 | 7/2015 | Garcia-Martinez et al. |
| 9,187,560 B2 | 11/2015 | Smith et al. |
| 9,452,227 B2 | 9/2016 | Garcia-Martinez et al. |
| 9,468,676 B2 | 10/2016 | Smith |
| 9,546,213 B2 | 1/2017 | Smith et al. |
| 9,701,747 B2 | 7/2017 | Smith et al. |
| 9,717,793 B2* | 8/2017 | Smith .................. A61K 31/454 |
| 9,724,410 B2 | 8/2017 | Smith et al. |
| 9,725,509 B2 | 8/2017 | Garcia-Martinez et al. |
| 9,725,514 B2 | 8/2017 | Takahashi et al. |
| 9,758,579 B2 | 9/2017 | Garcia-Martinez et al. |
| 9,765,138 B2 | 9/2017 | Smith |
| 9,775,921 B2 | 10/2017 | Garcia-Martinez et al. |
| 9,821,057 B2 | 11/2017 | Smith et al. |
| 9,884,912 B2 | 2/2018 | Garcia-Martinez et al. |
| 9,926,370 B2 | 3/2018 | Smith |
| 9,957,321 B2 | 5/2018 | Smith et al. |
| 9,994,635 B2* | 6/2018 | Smith .................. C07K 16/248 |
| 10,227,404 B2 | 3/2019 | Smith |
| 2003/0180806 A1 | 9/2003 | Kamei et al. |
| 2003/0219839 A1 | 11/2003 | Bowdish et al. |
| 2003/0229030 A1 | 12/2003 | Theoharides |
| 2004/0001831 A1 | 1/2004 | Rottman et al. |
| 2004/0086979 A1 | 5/2004 | Zhang et al. |
| 2004/0115197 A1 | 6/2004 | Yoshizaki et al. |
| 2004/0185040 A1 | 9/2004 | Garcia-Martinez et al. |
| 2005/0033031 A1 | 2/2005 | Couto |
| 2005/0043517 A1 | 2/2005 | Giles-Komar et al. |
| 2005/0048578 A1 | 3/2005 | Zhang |
| 2005/0118652 A1 | 6/2005 | Lee et al. |
| 2006/0018904 A1 | 1/2006 | Chung et al. |
| 2006/0040363 A1 | 2/2006 | Kucherlapati et al. |
| 2006/0051348 A1 | 3/2006 | Gorlach |
| 2006/0078532 A1 | 4/2006 | Omoigui |
| 2006/0078533 A1 | 4/2006 | Omoigui |
| 2006/0121042 A1 | 6/2006 | Dall'Acqua et al. |
| 2006/0134113 A1 | 6/2006 | Mihara |
| 2006/0159675 A1 | 7/2006 | Jiao et al. |
| 2006/0165696 A1 | 7/2006 | Okano et al. |
| 2006/0171943 A1 | 8/2006 | Comeau et al. |
| 2006/0210563 A1 | 9/2006 | De Silanes et al. |
| 2006/0270045 A1 | 11/2006 | Cregg et al. |
| 2006/0275294 A1 | 12/2006 | Omoigui |
| 2006/0281130 A1 | 12/2006 | Bock et al. |
| 2006/0292147 A1 | 12/2006 | Yoshizaki et al. |
| 2007/0036785 A1 | 2/2007 | Kishimoto et al. |
| 2007/0036788 A1 | 2/2007 | Sheriff et al. |
| 2007/0048306 A1 | 3/2007 | Giles-Komar et al. |
| 2007/0098714 A1 | 5/2007 | Nishimoto et al. |
| 2007/0134242 A1 | 6/2007 | Nishimoto et al. |
| 2008/0033027 A1 | 2/2008 | Bascomb et al. |
| 2008/0081041 A1 | 4/2008 | Nemeth |
| 2008/0124325 A1 | 5/2008 | Ito et al. |
| 2008/0166348 A1 | 7/2008 | Kupper et al. |
| 2008/0260687 A1 | 10/2008 | Aoki et al. |
| 2009/0022719 A1 | 1/2009 | Mihara et al. |
| 2009/0035281 A1 | 2/2009 | Savino et al. |
| 2009/0104187 A1 | 4/2009 | Kovacevich et al. |
| 2009/0181029 A1 | 7/2009 | Okuda et al. |
| 2009/0238825 A1 | 9/2009 | Kovacevich et al. |
| 2009/0311718 A1 | 12/2009 | Fukushima et al. |
| 2010/0061986 A1 | 3/2010 | Takahashi et al. |
| 2010/0150829 A1 | 6/2010 | Garcia-Martinez et al. |
| 2010/0290993 A1 | 11/2010 | Garcia-Martinez et al. |
| 2011/0104146 A1 | 5/2011 | Faraday |
| 2011/0217303 A1 | 9/2011 | Smith et al. |
| 2011/0218229 A1 | 9/2011 | Giles-Komar et al. |
| 2011/0293622 A1 | 12/2011 | Garcia-Martinez et al. |
| 2012/0096569 A1 | 4/2012 | Giles-Komar et al. |
| 2012/0121594 A1 | 5/2012 | Smith |
| 2012/0128626 A1 | 5/2012 | Smith |
| 2012/0142900 A1 | 6/2012 | Garcia-Martinez et al. |
| 2012/0183531 A1 | 7/2012 | Lucas |
| 2012/0189629 A1 | 7/2012 | Smith |

(56) References Cited

U.S. PATENT DOCUMENTS

| | | |
|---|---|---|
| 2012/0288504 A1 | 11/2012 | Smith |
| 2012/0294852 A1 | 11/2012 | Smith |
| 2012/0301460 A1 | 11/2012 | Bao et al. |
| 2013/0017575 A1 | 1/2013 | Garcia-Martinez et al. |
| 2013/0028860 A1 | 1/2013 | Smith et al. |
| 2013/0034554 A1 | 2/2013 | Garcia-Martinez et al. |
| 2013/0058949 A1 | 3/2013 | Smith |
| 2013/0101598 A1 | 4/2013 | Smith |
| 2013/0183264 A1 | 7/2013 | Smith |
| 2013/0183293 A1 | 7/2013 | Smith et al. |
| 2013/0224201 A1 | 8/2013 | Garcia-Martinez et al. |
| 2013/0323238 A1 | 12/2013 | Smith |
| 2014/0079702 A1 | 3/2014 | Smith |
| 2014/0099311 A1 | 4/2014 | Chen et al. |

FOREIGN PATENT DOCUMENTS

| | | |
|---|---|---|
| JP | 2005-535341 | 11/2005 |
| JP | 2007-528691 | 10/2007 |
| JP | 2008-538931 | 11/2008 |
| TW | I445546 | 7/2014 |
| WO | 88/07089 | 9/1988 |
| WO | 91/02078 | 2/1991 |
| WO | 91/09967 | 7/1991 |
| WO | 2003/010541 | 2/2003 |
| WO | 2003/045318 | 6/2003 |
| WO | 2004/016740 | 2/2004 |
| WO | 2004/039826 | 5/2004 |
| WO | 2004/048552 | 6/2004 |
| WO | 2004/078938 | 9/2004 |
| WO | 2004/106377 | 12/2004 |
| WO | 2006/119115 | 11/2006 |
| WO | 2007/076927 | 7/2007 |
| WO | 2007/104529 | 9/2007 |
| WO | 2008/019061 | 2/2008 |
| WO | 2008/045140 | 4/2008 |
| WO | 2008/065378 | 5/2008 |
| WO | 2008/144757 | 11/2008 |
| WO | 2008/144763 | 11/2008 |
| WO | 2010/065072 | 6/2010 |
| WO | 2010/065077 | 6/2010 |
| WO | 2010-065078 | 6/2010 |
| WO | 2010/065079 | 6/2010 |
| WO | 2011/066369 | 6/2011 |
| WO | 2011/066371 | 6/2011 |
| WO | 2011/066374 | 6/2011 |
| WO | 2011/066378 | 6/2011 |
| WO | 2012/071554 | 5/2012 |
| WO | 2012/071561 | 5/2012 |
| WO | 2015-054293 | 4/2015 |

OTHER PUBLICATIONS

Alonzi, T. et al., "Interleukin 6 is required for the development of collagen-induced arthritis", J Exp Med. Feb. 16, 1998; 187(4): 461-468.

Altschuler, E.L. and R.E. Kast, "Using histamine (H1) antagonists, in particular atypical antipsychotics, to treat anemia of chronic disease via interleukin-6 suppression", Medical Hypotheses, 2005; 65: 65-67.

Chen, X. et al., "Blockade of interleukin-6 signaling augments regulatory T-cell reconstitution and attenuates the severity of graft-versus-host disease", Blood. 2009; 114: 891-900.

Diaz, J.A., "Inflammation and Acute Venous Thrombosis", US Oncology & Hematology, 2011, 68-71.

Dicato, M., "Anemia in Cancer: Some Pathophysiological Aspects", The Oncologist, 2003; 8(suppl 1): 19-21.

Fuji, H. et al., "Induction of Interleukin-6 by Proton Beam Irradiation Depends on Targeted Organ", J. Jpn. Soc. Ther. Radiol. Oncol. 2004; 16: 219-224. Abstract.

Hainsworth, J.D. et al., "Treatment of Metastatic Renal Cell Carcinoma With a Combination of Bevacizumab and Erlotinib", J. Clin. Oncol. 2005: 23: 7889-7896.

Hashizume, M. et al., "Tocilizumab, a humanized anti-interleukin-6 receptor antibody, improved anemia in monkey arthritis by suppressing IL-6-induced hepcidin production", Rheumatol. Int., 2010; 30: 917-923.

Kalweit et al., "Markers of Activated Hemostasis and Fibrinolysis in Patients with Pulmonary Malignancies: Comparison of Plasma Levels in Central Veinous and Pulmonary Veinous Blood", Thrombosis Research, 2000. 97: 105-111.

Lowe, G.D.O. et al., "Interleukin-6, Fibrin D-Dimer, and Coagulation Factors VII and XIIa in Prediction of Coronary Heart Disease", Arterioscler Thromb Vasc Biol., 2004; 24: 1529-1534.

Mirovitz A., et al., "Cytokines levels, severity of acute mucositis and the need of PEG tube installation during chemo-radiation for head and neck cancer—a prospective pilot study", Radiat Oncol. Feb. 25, 2010; 5(16): 1-7.

Omoigui, S., "The Interleukin-6 inflammation pathway from cholesterol to aging—Role of statins, bisphosphonates and plant polyphenols in aging and age-related diseases", Immunity & Ageing, Mar. 20, 2007; 4:1-22.

Oya, M. et al., "High Preoperative Plasma D-dimer Level is Associated with Advanced Tumor Stage and Short Survival After Curative Resection in Patients with Colorectal Cancer", Jpn. J. Clin. Oncol., 2001, 31(8): 388-394.

Richey, L.M. et al., "Defining Cancer Cachexia in Head and Neck Squamous Cell Carcinoma", Clin. Cancer Res., 2007; 13(22): 6561-6567.

Vandenabeele, P. et al., "Increased IL-6 Production and IL-6-Mediated Ig Secretion in Murine Host-vs-Graft Disease", J. Immunol. May 1, 1993, 150: 4179-4187.

Van Zaanen, H.C.T. et al., "Endogenous Interleukin 6 Production in Multiple Myeloma Patients Treated with Chronic Monoclonal Anti-IL6 Antibodies Indicates the Existence of a Positive Feed-back Loop", J. Clin. Invest., 1996, 98(6): 1441-1448.

Yellen, S.B. et al., "Measuring Fatigue and Other Anemia-Related Symptoms with the Functional Assessment of Cancer Therapy (FACT) Measurement System", Journal of Pain and Symptom Management, 1997. 13(2): 63-74.

Zaki, M.H. et al., "CNTO 328, A Monoclonal Antibody to IL-6, Inhibits Human Tumor-Induced Cachexia in Nude Mice", Int. J. Cancer, 2004, 111: 592-595.

Adam et al., "D-dimer antigen: current concepts and future prospects," Blood, 2009; 112:2878-2887.

Alder Biopharmaceuticals. Phase 2a Study of ALD518 for Treatment of Non Small Cell Lung Cancer (NSCLC) Symptoms. MPR, Jun. 7, 2010. Web. May 7, 2014. <http://www.empr.com/phase-2a-study-of-ald518-for-treatment-of-non-small-cell-lung-cancer-nsclc-symptoms/article/171887/>.

Armstrong, "Bristol-Myers Rheumatoid Arthritis Drug Works in Mid-Stage Trial," Bloomberg. Oct. 26, 2013. Web. May 8, 2014.

Arnaud et al., "Statins Reduce Interleukin-6-Induced C-Reactive Protein in Human Hepatocytes: New Evidence for Direct Antiinflammatory Effects of Statins," Arteriosclerosis, Thrombosis, and Vascular Biology, 2005; 25: 1231-1236.

Bataille et al., "Biologic effects of anti-interleukin-6 murine monoclonal antibody in advanced multiple myeloma," Blood, American Society of Hematology, 1995. 86(2):685-691.

Beck et al., "Alleviation of Systemic Manifestations of Castleman's Disease by Monoclonal Anti-Interleukin-6 Antibody," New Engl. J. Med., Mar. 1994; 330(9):602-605.

Beheiri et al., "Role of elevated .alpha.sub.2.sub.-macroglobulin revisited: results of a case-control study in children with symptomatic thromboembolism," J Thromb Haemost. 2007; 5:1179-84.

Bellone et al., "High serum levels of interleukin-6 in endometrial carcinoma are associated with uterine serous papillary histology, a highly aggressive and chemotherapy-resistant variant of endometrial cancer," Gyn. Oncol. 2005; 98:92-98.

Blay et al., "Role of Interleukin-6 in the Paraneoplastic Inflammatory Syndrome Associate with Renal-Cell Carcinoma," In. J. Cancer 1997; 72:424-430.

Bristol-Myers Squibb. Promising Phase IIb Data on Clazakizumab in Patients With Moderate-to-Severe Rheumatoid Arthritis to Be Presented at the 2013 Annual Meeting of the American College of Rheumatology. Oct. 28, 2013. Web.

(56) References Cited

OTHER PUBLICATIONS

Bristol-Myers Squibb. Partnering News, R&D News. Bristol-Myers Squibb and Alder Biopharmaceuticals Enter Global Agreement on Rheumatoid Arthritis Biologic. MPR, Nov. 10, 2010. Web. May 7, 2014. <http://news.bms.com/press-release/rd-news/bristol-myers-squibb-and-alder-biopharmaceuticals-enter-global-agreement-rheum>.
Buccheri et al., "Plasma Levels of D-Dimer in Lung Carcinoma," Cancer, 2003; 97:3044-52.
Burks et al. PNAS; 1997, vol. 94, pp. 412-417.
Carrier et al., Thromb Res, 2008; 123:177-83.
Carter et al., Current Protocols in Immunology (2004) John Wiley & Sons, Inc. pp. 9.4.1-9.4.23.
Casset et al., Biochemical and Biophysical Research Communications, 2003, vol. 307, pp. 198-205.
Cata et al., "The effects of thalidomide and minocycline on taxol-induced hyperalgesia in rats," Brain Res. Sep. 10, 2008; 1-18.
Chang et al., "Construction and expression of synthetic single-chain variable domain fragement antibody (SCFV-A33) in Pichia Pastoris," Abs. Gen. Meet. Am. Soc. Microbiol.; 103(21).
Clarke et al., "A phase I, pharmacokinetic (PK), and preliminary efficacy assessment of ALD518, a humanized anti-IL-6 antibody, in patients with advanced cancer", 2009, retrieved from the Internet Mar. 2, 2015; URL: https://meetinglibrary.asco.org/print/582471.
ClinicalTrials.gov: "Safety, Efficacy and Pharmacokinetics Study of ALD518 in Patients with Active Rheumatoid Arthritis", Sep. 10, 2010, Retrieved from the Internet Mar. 2, 2015; URL: https://clinicaltrials.gov/ct2/show/NCT00867516.
Colman; Research in Immunol., 1994, vol. 145, pp. 33-36.
Cregg et al., "Recent Advances in the Expression of Foreign Genes in Pichia pastoris," Biotechnology. Aug. 1993, vol. 11, pp. 905-910.
Damschroder et al., Molecular Immunology 41(10):985-1000 Aug. 2004.
Derhasching et al., "Effect of interleukin-6 blockade on tissue factor-induced coagulation in human endotoxemia," Critical Care Medicine, 2004; 32(5):1136-1140.
De Wildt, et al., "Isolation and Characterization of Single Anti-U1A-Specific B Cells from Autoimmune Patients," Annals of the NY Acad Sci, Apr. 5, 1997; 815:440-442.
Ding et al., Expert Opinion Investigation Drugs, Oct. 2009; 18(10):457-466.
Dohmen et al., "Production of recombinant Ig molecules from antigen-selected single B cells and restricted usage of Ig-gene segments by anti-D antibodies," J Immunol Meth, Mar. 1, 2005; 298(1-2):9-20.
Domingo-Domenech et al., Clin. Cancer Res. 2006; 12(18): 5578-5586.
Emille et al., "Administration of an Anti-Interleukin-6 Monoclonal Antibody to Patients with Acquired Imunodeficiency Syndrome and Lymphoma: Effect on Lymphoma Growth and on B Clinical Symptoms," Blood, 1994. 84(8):2472-2479.
"Fanconi anemia", www.nhlbi.nih.gov/health/health-topics/topics/fanconi/prevention.html; downloaded Nov. 20, 2013; 1 page.
Fayad et al., "Interleukin-6 and interleukin-10 levels in chronic lyphocytic leukemia; correlation with phenotypic characteristics and outcome," Blood, 2001; 97:256-263.
Filep and Kebir, Future Cardiol. 2008, 4:495-504.
Fonesca et al., "Interleukin-6 as a key player in systemic inflammation and joint destruction," Autoimmun. Rev., Jun. 2009; 8:533-542.
Fujimoto-Ouchi et al., "Capecitabine improves cancer cachexia and normalizes IL-6 and PTHrP levels in mouse cancer cachexia models," Cancer Chemotherapy and Pharmacology, 2006. 59(6):807-815.
Groopman and Itri, "Chemotherapy-Induced Anemia in Adults: Incidence and Treatment," Journal of the National Cancer Institute 1999. 91(19):1616-1634.
Haddad et al., "Chemotherapy-induced thrombosis," Thromb. Res. 2006;118(5):555-568. Epub Jan. 4, 2006.
Hamzaoui, K. et al., "Interleukin-6 in peripheral blood and inflammatory sites in Behcet's disease," Mediators of Inflammation 1992. 1(4):281-285.
"Hemolytic anemia", www.nhlbi.nih.gov/health/health-topics/topics/ha/prevention.html; downloaded Nov. 21, 2013; 1 page.
Heremans et al., "Protective effect of anti-interleukin (IL)-6 antibody against endotoxin, associated with paradoxically increased IL-6 levels," Immunology, 1992. 22(9):2395-2401.
Hinton, et al., "An engineered human IgG1 antibody antibody with longer serum half-life," The Journal of Immunology, the American Association of Immunologists, 2006. 176(1):346-356.
Hudson et al., Nature Medicine, Jan. 2003; 9(1): 129-134.
Immunobiology, The Immune System in Health and Disease, Third Edition, Janeway and Travers, Ed., 1997.
Ito et al., "HMG-CoA reductase inhibitors reduce interleukin-6 synthesis in human vascular smooth muscle cells," Cardiovascular Drugs Ther. Mar. 2003; 16(2):121-126.
Johnson et al., Circulation, 2004, 109:726-32.
Kedar et al., "Thalomide Reduces Serum C-Reactive Protein and Interleukin-6 and Induces Response to IL-2 in a Fraction of Metastatic Renal Cell Cancer Patients Who Failed IL-2-Based Therapy", Int. J. Cancer (2004); 110:260-265.
King et al., Radiology, 2008; 247:854-61.
Klein et al., "Murine anti-interleukin-6 monoclonal antibody therapy for a patient with plasma cell leukemia," Blood, 1991. 78(5):1198-1204.
Kobayashi et al. Protein Engineering; 1999; vol. 12, pp. 879-844.
Kodituwakku et al., "Isolation of antigen-specific B cells," Immunology and Cell Biology (2003); 81:163-170.
Kosuge et al., Circ J., 2007, 71:186-90.
Kruip et al., Arch Intern Med, 2002; 162:1631-5.
Lab Tests Online, D-Dimer: The Test, Oct. 20, 2008 [Retrieved from the internet Jun. 17, 2010; <URL:http://web.archive.org/web/20071020065024/http://www.laptestsonline.org/understanding/analytes/d.sub.-dimer/test.html>]; pp. 1-2.
Lab Tests Online, Hypercoagulable Disorders, Mar. 1, 2008 [Retrieved from the internet Jun. 17, 2010: URL: http://web.archive.org/web/20080301224129/http://www.labtestsonline.org/understanding/conditions/hypercoagulable.sub.--disorders-6.html>.
Lederman et al., 1991, Mol. Immunol., vol. 28, pp. 1171-1181.
Levi, M., et al., "Differential Effects of Anti-cytokine Treatment on Bronchoalveolar Hemostasis in Endotoxemic Chimpanzees", Am. J. Respir. Crit. Care Med., 1998; 158:92-98.
Levi, B J Haematol, 2004; 124:567-76.
Li et al., Proc. Natl. Acad. Sci. USA, 1980, vol. 77, pp. 3211-3214.
Maini et al., Arthritis & Rheumatism, Sep. 2006; 54(9):2817-2829.
Matsuyama et al., "Anti-interleukin-6 receptor antibody (Tocilizumab) treatment of multicentric Castleman's disease," Intl. Med. 2007; 46(11):771-774.
Meager et al., Hybridoma 6(3): 305-311, Jun. 1987.
Mease et al., "ALD518 (BMS945429), A High Affinity Monoclonal Antibody Directed Against Interleukin-6, Reduces Disease Activity and Achieves Remission in Patients with Rheumatoid Arthritis and Inadequate Response to Methotrexate," [abstract]. Arthritis Rheum 2010; 62 Suppl 10:2168.
Menapace and Khorana, Curr Opin Hematol, 2010; 17:450-6.
Montero-Julian et al., "Pharmacokinetic study of anti-interleukin-6 (IL-6) therapy with monoclonal antibodies; enhancement of IL-6 clearance by cocktails of anti-IL-6 antibodies," Blood 1995; 85(4): 917-924.
Nishimoto et al., "Improvement in Castleman's disease by humanized anti-interleukin-6 receptor antibody therapy"; Blood, Jan. 1, 2000; 95(1):56-61.
Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease," Blood, Nov. 15, 2008; 112(10):3959-3964.
O'Brien et al., Methods in Molecular Biology, vol. 207: Recombinant Antibodies for Cancer Therapy: Methods and Protocols, Humana Press, pp. 81-100 (2003).
Ogasawara et al., Atherosclerosis, 2004, 174:349-56.

(56) References Cited

OTHER PUBLICATIONS

Ogata et al., "Pathological Role of Interleukin-6 in Psoriatic Arthritis", Arthritis, 2012. vol. 2012, 6 Pages.
Ogata et al., "Psoriatic arthritis in two patients with an inadequate response to treatment with tocilizumab", Joint Bone Spine, 2011. 79(2012): 85-87.
Okuda et al., "Successful use of a humanized anti-interleukin-6 receptor antibody, tocilizumab, to treat amyloid A amyloidosis complicating juvenile idiopathic arthritis," Arthritis & Rheumatism, 54(9):2997-3000 (2006).
Padlan, Mol. Immunology 31(3): 169-217 Feb. 1994.
Palareti et al., N Engl J Med, 2006; 355:1780-9.
Paul, Fundamental Immunology, 3rd Edition, 1993, pp. 292-295.
"Pernicious anemica", www.nhlbi.nih.gov/health/health-topics/topics/prnanmia/prevention.html; downloaded Nov. 21, 2013; 2 pages.
Phillips, A., J Pharm Pharmacology, 2001, vol. 53, pp. 1169-1174.
Pirollo et al., Cancer Res., 2008; 68(5): 1247-1250.
Popkov, M. et al., "Rabbit Immune Repertories as Sources for Therapeutic Monoclonal Antibodies: The Impact of Kappa Allotype-correlated Variation in Cysteine Content on Antibody Libraries Selected by Phage Display," J. Mol. Biol., Jan. 10, 2003; 325(2):325-335.
Portolano et al., Journal of Immunology 150(3): 880-887 Feb. 1993.
Ridker et al., Rosuvastatin to Prevent Vascular Events in Men and Women with Elevated C-Reactive Protein.
Righini et al., Thromb Haemost, 2006; 95:715-9.
Rossi et al., Bone Marrow Transplantation, 2005; 36(9): 771-779.
Rudikoff et al. Proc Natl Acad Sci USA 1982 vol. 79 p. 1979-1983.
Salgado, R. et al., "Circulating interleukin-6 predicts survival in patients with metastatic breast cancer," Intl. J. Cancer, Feb. 20, 2003; 103(5):642-646.
Schutgens et al., J Lab Clin Med, 2004; 144:100-7.
"Sickle cell anemia," Harvard Medical School Faculty: Sickle cell anemia, Sep. 2009; downloaded from www.intelihealth.com/IH/ihtPrint/WSIHW000/9339/9453.html?hide=t&k=basePrint; 4 pages.
Simmons et al., "Expression of full-length immunoglobulins in *Escherichia coli*: rapid and efficient production of aglycosylated antibodies," J. Immunol. Meth., Elsevier Science Publishers B.V., Amsterdam NL; 263(1-2):133-147.
Simonsson, et al., "Single, Antigen-Specific B Cells Used to Generate Fab Fragments Using CD40-Mediated Amplification or Direct PCR Cloning," Biotechniques, May 1, 1995; 18(5):862, 864-869.
Song, C.J. et al., "C-reactive protein contributes to the hypercoagulable state in coronary artery disease", J. Thromb. Haemost. 2006; 4:98-106.
Song et al., Atherosclerosis, 2009, 202:596-604.
Steenbakkers et al., "Efficient Generation of Monoclonal Antibodies from Preselected Antigen-Specific B Cells," Molecular Biology Reports, 1994; 19:125-134.
Strassmann et al., "Evidence for the involvement of interleukin 6 in experimental cancer cachexia," Journal of Clinical Investigation, 1992. 89(5):1681-1684.
Strassmann et al., "Inhibition of Experimental Cancer Cachexia by Anti-Cytokine and Anti-Cytokine-Receptor Therapy," Cytokines and Molecular Therapy, 1995. 1(2):107-113.
Tamura, et al., "Involvement of human interleukin 6 in experimental cachexia induced by a human uterine cervical carcinoma xenograft," Clinical Cancer Research, 1995. 1(1):1353-1358.
Taylor et al., "Effect of anti-IL-6 and anti-10 monoclonal antibodies on the suppression of the normal T lymphocyte mitogenic response by steady state sickle cell disease sera," Immunol. Invest., 2001; 30(3): 209-219.
Thomson Reuters: "Antibody ALD-518 (heavy and light chain sequences)", Thomson Reuters, Jan. 15, 2008, Retrieved from the Internet Mar. 2, 2015; URL: https://integrity.thomson-pharma.com/integrity/xmlxsl/pk_prod_list.xml_prod_list_list_prod_prp_par_pro=&p_val_pro=&p_oper_pro=&p_par_tar=&p_val_tar=&p_oper_tar=&p_par_ref=&p_val_ref=&p_val_ref=&p_oper_ref=&p_p.
Trikha, Clinical Cancer Research, 2003; 9:4653-4665.

Vajdos et al., Journal of Molecular Biology 320(2): 415-428 Jul. 2002.
Van Belle et al., JAMA, 2006; 295:172-9.
Van der Poll et al., Journal of Experimental Medicine, 1994, 79:1253-1259.
Van Zaanen et al., "Chimaeric anti-interleukin 6 monoclonal antibodies in treatment of advaced multiple myeloma a phase I dose-escalating study," British J. Haem. 1998; 102:783-790.
Vidal et al., European Journal of Cancer, 2005, vol. 41, pp. 2812-2818.
Weitkamp et al., "Generation of recombinant human monoclonal antibodies to rotavirus from single antigen-specific B cells selected with fluorescent virus-like particles," Journal of Immunological Methods, Apr. 1, 2003; 275(1-2):223-237.
Wells, Biochemistry 29:8509-8517 (1990).
Wells et al., Ann Intern Med. 2001; 135:98-107.
Wells et al., Evaluation of D-dimer in the Diagnosis of Suspected Deep-Vein Thrombosis: The New England Journal of Medicine, Sep. 25, 2003; 1227-1235.
Wendling, D. et al., "Treatment of Severe Rheumatoid Arthritis by Anti-Interleukin 6 Monoclonal Antibody", The Journal of Rheumatology, 1993; 20(2): 259-262.
Wijdenes, et al., Molecular Immunology, Nov. 1991; 28(11): 1183-1192.
Wilde, J.T. et al., "Plasma D-dimer levels and their relationship to serum fibrinogen/fibrin degradation products in hypercoagulable states", Br. J. Haematol. 1989; 71(1):65-70. (Abstract).
Zaki et al., "2003 ASCO Annual Meeting—Developmental Therapeutics—Clinical Pharmacology and Immunotherapy," Proc. Am. Soc. Clin. Oncol. 2003. 22:697.
Zhuang et al., "Diagnosis of factors causing senile deep venous thrombosis and therapy advance thereof," Geriatrics & Health Care, vol. 11, No. 2., pp. 127-129, 2005.
English language translation of Zhuang et al. (NPL Cite No. 10), first and last paragraph, 2005.
Pabinger, I. and Cihan, A., "Biomarkers and Venous Thromboembolism", Arterioscler Thromb Vasc Biol. 2009; 29: 332-336.
Brorson K, et al. "Mutational analysis of avidity and tine specificity of anti-levan antibodies," J Immunol. Dec. 15, 1999;163(12):6694-701.
Brummell DA, et al. "Probing the combining site of an anti-carbohydrate antibody by saturation-mutagenesis: role of the heavy-chain CDR3 residues," Biochemistry. Feb. 2, 1993;32(4):1180-7.
Hennigan S, et al. "Interleukin-6 inhibitors in the treatment of rheumatoid arthritis," Ther Clin Risk Manag. Aug. 2008;4 (4):767-75.
Iwasa T, et al. "Multiple ulcers in the small and large intestines occurred during tocilizumab therapy for rheumatoid arthritis," Endoscopy. Jan. 2011;43(1):70-2.
Lalla RV, et al. "Anti-inflammatory agents in the management of alimentary mucositis," Support Care Cancer. Jun. 2006;14(6):558-65.
Naka T, et al. "The paradigm of IL-6: from basic science to medicine," Arthritis Res. 2002;4 Suppl 3:S233-42.
Samimi M, et al. "[Persistent aphthous mouth ulcers associated with tocilizumab: two cases]" Ann Dermatol Venereol. Feb. 2013;140(2):120-4.
Vitiello G, et al. "Tocilizumab-induced mucosal ulcers in a patient with relapsing polychondritis: An adverse drug reaction?" Semin Arthritis Rheum. Oct. 2016;46(2):e9-e10.
Casulo C, et al. "Incidence of hypogammaglobulinemia in patients receiving rituximab and the use of intravenous immunoglobulin for recurrent infections," Clin Lymphoma Myeloma Leuk. Apr. 2013;13(2):106-11.
Choi J, et al. "Tocilizumab (Anti-IL6-Receptor) Therapy for Donor-Specific Antibody (DSA+ ) Antibody Mediated Rejection (ABMR+ ) Resistant to IVIG + Rituxan Trearment. Abstract# 2249," Transplantation, Jul. 15, 2014; 98:128-9.
Clinical Trial NCT02108600, Jun. 2017, 7 pages.
Freise AC, et al. "In vivo imaging with antibodies and engineered fragments," Mol Immunol. Oct. 2015;67(2 Pt A):142-52.

(56) References Cited

OTHER PUBLICATIONS

Haddad E, et al. "Treatment of B-lymphoproliferative disorder with a monoclonal anti-interleukin-6 antibody in 12 patients: a multi-center phase 1-2 clinical trial," Blood. Mar. 15, 2001;97(6):1590-7.

Hychko, et al. "A Systematic Review and Meta-Analysis of Rituximab in Antibody-mediated Renal Allograft Rejection," Int J Organ Transplant Med. 2011;2(2):51-6.

Kasiske BL, et al. "KDIGO clinical practice guideline for the care of kidney transplant recipients: a summary," Kidney Int. Feb. 2010;77(4):299-311.

Liang Y, et al. "Graft produced interleukin-6 functions as a danger signal and promotes rejection after transplantation," Transplantation. Sep. 27, 2007;84(6):771-7.

Mechanisms of Carcinogenesis, Section 3, 2008, International Agency for Research on Cancer, 37 pages.

Mori T, et al. "Efficacy of mouth rinse in preventing oral mucositis in patients receiving high-dose cytarabine for allogeneic hematopoietic stem cell transplantation," Int J Hematol. Dec. 2008;88(5):583-587.

Waiser J, et al. "Interleukin-6 expression after renal transplantation," Nephrol Dial Transplant. Apr. 1997;12(4):753-9.

Wingard JR, et al. "Hematopoietic stem cell transplantation: an overview of infection risks and epidemiology," Infect Dis Clin North Am. Jun. 2010;24(2):257-72.

Xenaki KT, et al. "Antibody or Antibody Fragments: Implications for Molecular Imaging and Targeted Therapy of Solid Tumors," Front Immunol. Oct. 2017, 12;8:1287.

\* cited by examiner

FIG. 2

```
          FR1                              CDR1              FR2                CDR2        FR3
          1                          23 24    34 35                      49 50   56 57                              88
RbtVL     AYDMTQTPASVEVAVGGTVTINC     QASETIYSWLS  WYQQKPGQPPKLLIY     QASDLAS  GVPSRFSGSGAGTEYLTLISGVQCDDAATYYC
          |||-|  ||||   |||           ||-|||-|||  ||||||| |||||||     |||-|||  |||||||||||| |||| ||-|  |||||||
L12A      DIQMTQSPSTLSASVGDRVTITC     RASQSISSWLA  WYQQKPGKAPKLLIY     KASSLES  GVPSRFSGSGSGTEFTLTISSLQPDDFATYYC    (SEQ ID NO: 652)
V1        DIQMTQSPSTLSASVGDRVTITC     RASQSISSWLA  WYQQKPGKAPKLLIY     DASSLES  GVPSRFSGSGSGTEFTLTISSLQPDDFATYYC    (SEQ ID NO: 653)
Vx02      DIQMTQSPSSLSASVGDRVTITC     RASQSISSYLN  WYQQKPGKAPKLLIY     AASSLQS  GVPSRFSGSGSGTDFTLTISSLQPEDFATYYC    (SEQ ID NO: 654)

VLh       DIQMTQSPSTLSASVGDRVTITC     QASETIYSWLS  WYQQKPGKAPKLLIY     QASDLAS  GVPSRFSGSGSGTEFTLTISSLQPDDFATYYC

CDR3          FR4
          89       100 101     111
RbtVL     QQGYSGSNVDNV  FGGGTEVVKR        (SEQ ID NO: 651)
          |||||||||||   |||||-||-
                        FGGGTKVEIKR       (SEQ ID NO: 656)

VLh       QQGYSGSNVDNV  FGGGTKVEIKR       (SEQ ID NO: 655)

FR1                                           CDR1       FR2                 CDR2              FR3
          1                                       30 31 35    36                  49 50                        66 67                                    98
RbtVH     QEQLKESGGGRLVTPGTPLTLTCTASGFSLN     DHAMG  WVRQAPGKGLEYIG     FINS-GGSARYASWAEG  RFTISRTST--TVDLKMTSLTTEDTATYFCVR
          |-||-|||| |||-| |-|-||-|||||--|     |-|||  ||||||||||-|-     ||||-||||||||-|||  ||||||-|      |||-||  |||-  |||-|| |
3-64-04   QVQLVESGGGLVQPGGSLRLSCAASGFTFS      SYAMH  WVRQAPGKGLEYVS     AISSNGGSTYYADSVKG  RFTISRDNSKNTLYLQMNSLRAEDTAVYYCAR        (SEQ ID NO: 658)
3-66-04   EVQLVESGGGLVQPGGSLRLSCAASGFTVS      SNYMS  WVRQAPGKGLEWVS     VIYS-GGSTYYADSVKG  RFTISRDNSKNTLYLQMNSLRAEDTAVYYCAR        (SEQ ID NO: 659)
3-53-02   EVQLVETGGGLIQPGGSLRLSCAASGFTVS      SNYMS  WVRQAPGKGLEWVS     VIYS-GGSTYYADSVKG  RFTISRDNSKNTLYLQMNSLRAEDTAVYYCAR        (SEQ ID NO: 660)

VHh       QVQLVESGGGLVQPGGSLRLSCAASGFSLN      DHAMG  WVRQAPGKGLEYVG     FINS-GGSARYAS[A]EG  RFTISRDNSKNTLYLQMNSLRAEDTAVYYCAR

CDR3               FR4
          99          110 111    121
RbtVH     GGAVWSIHSFDP  WGPGTLVTVSS    (SEQ ID NO: 657)
          ||||||||||||  ||-|||||||
                        WGQGTLVTVSS    (SEQ ID NO: 662)

VHh       GGAVWSIHSFDP  WGQGTLVTVSS    (SEQ ID NO: 661)
```

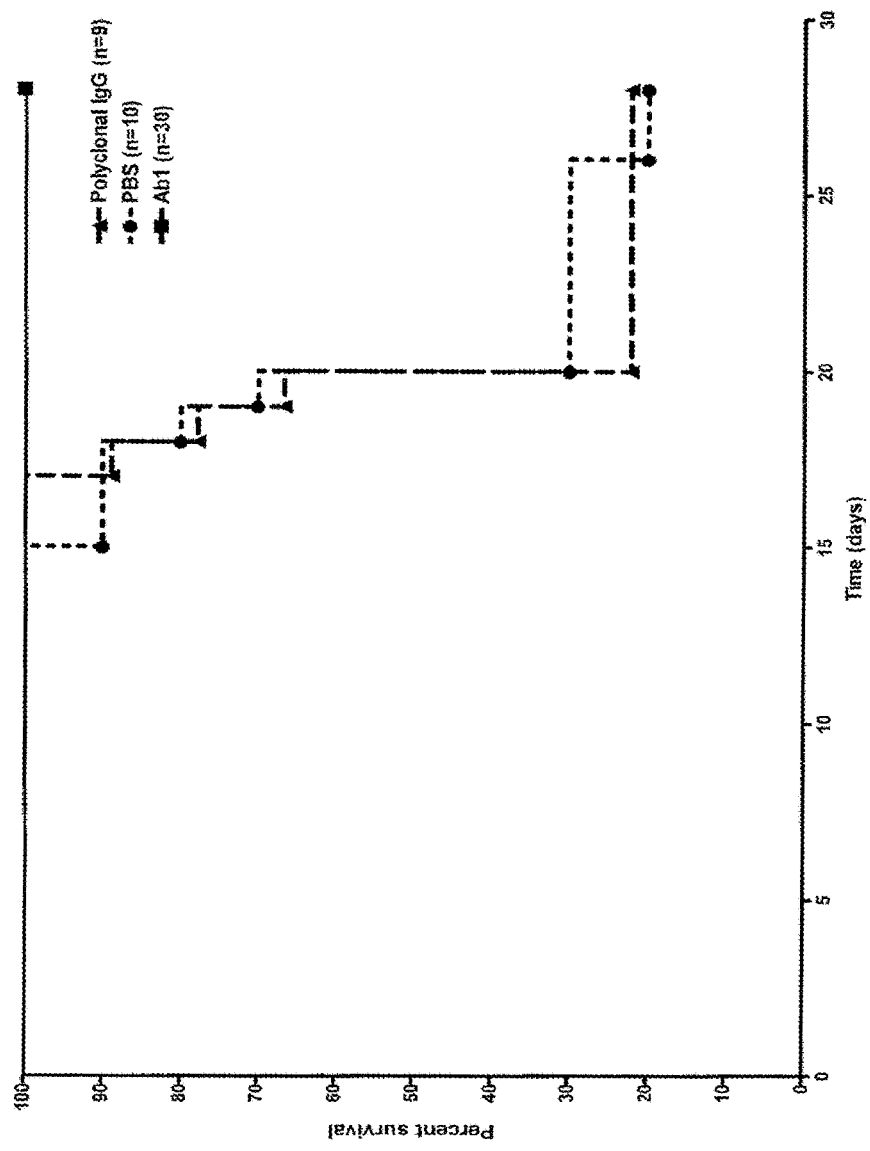

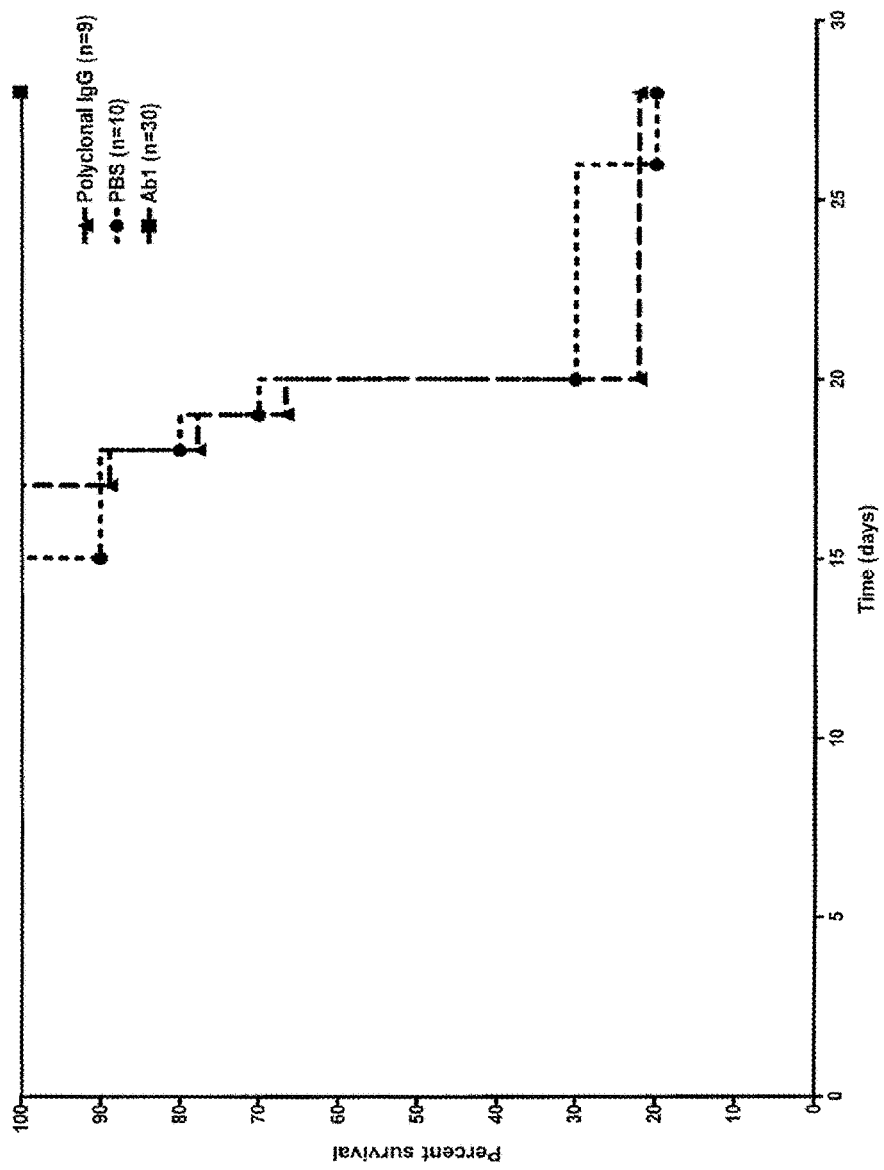

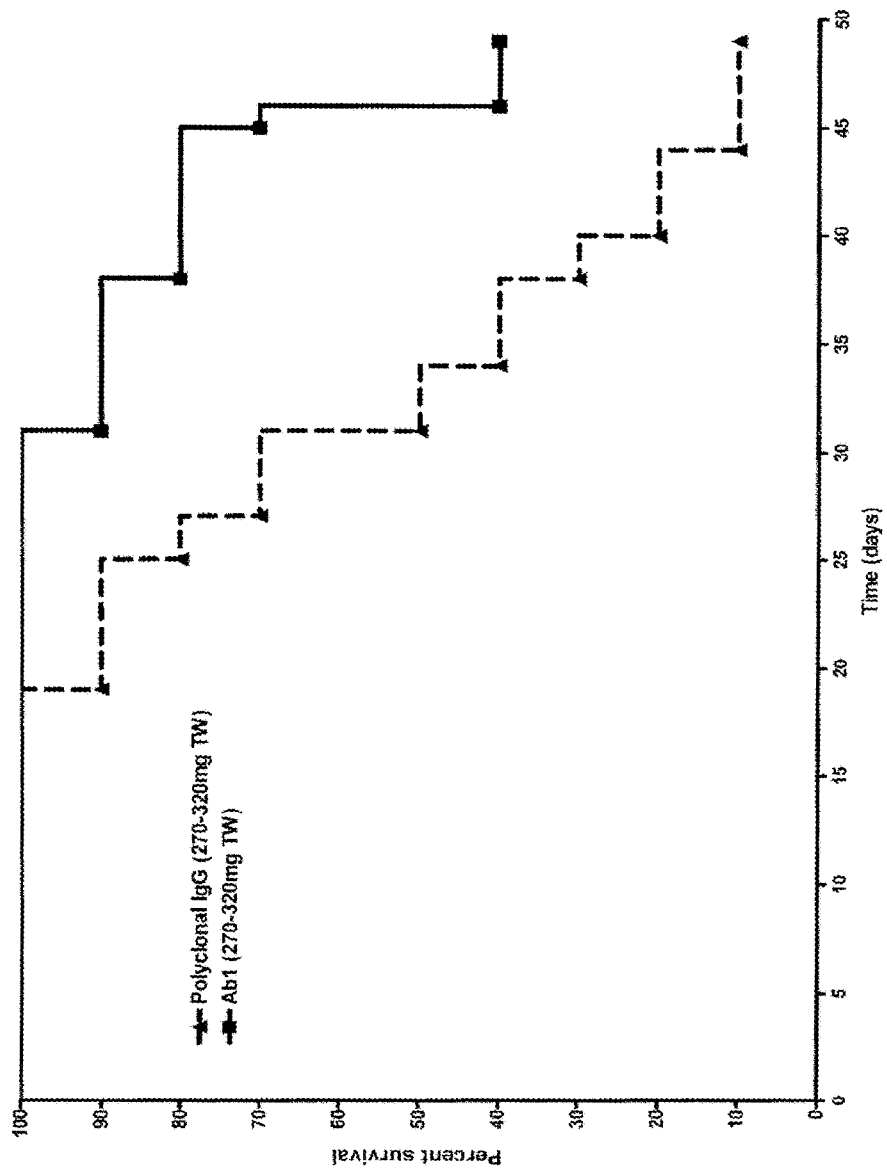

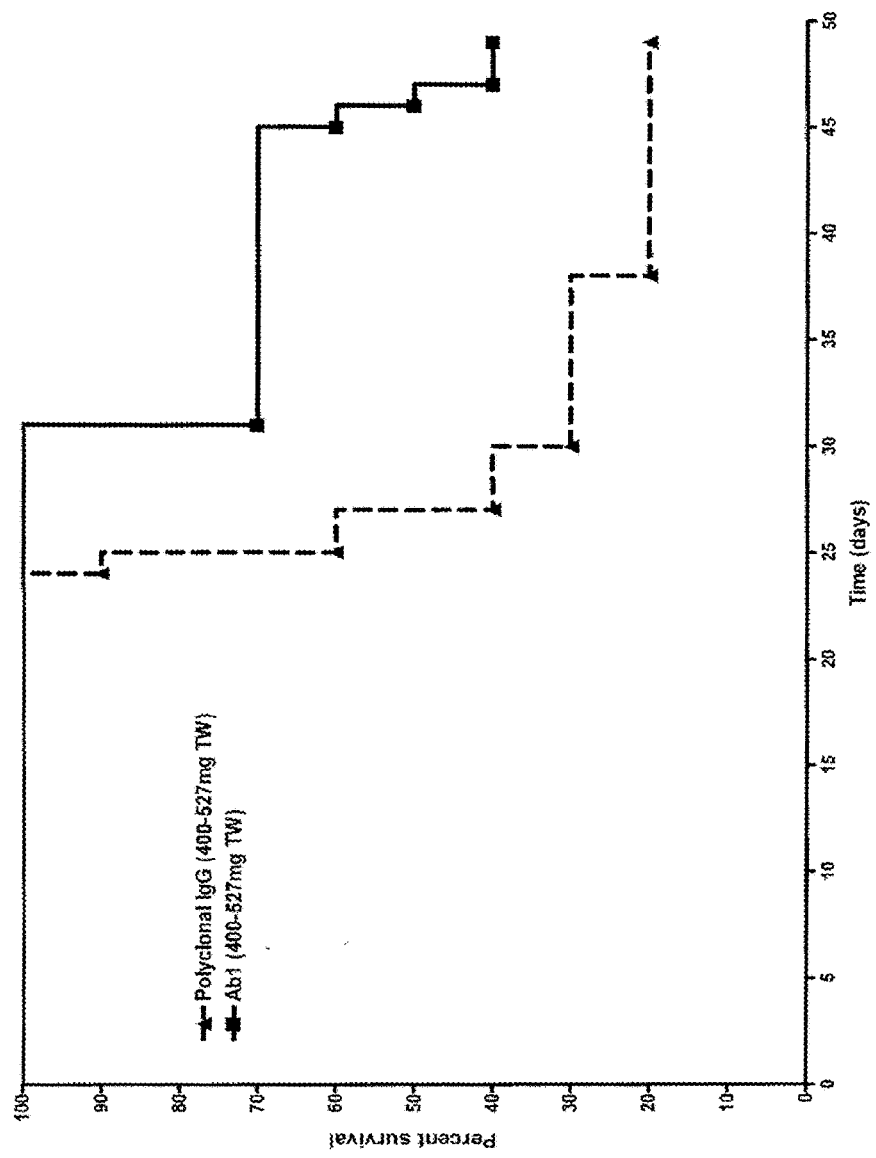

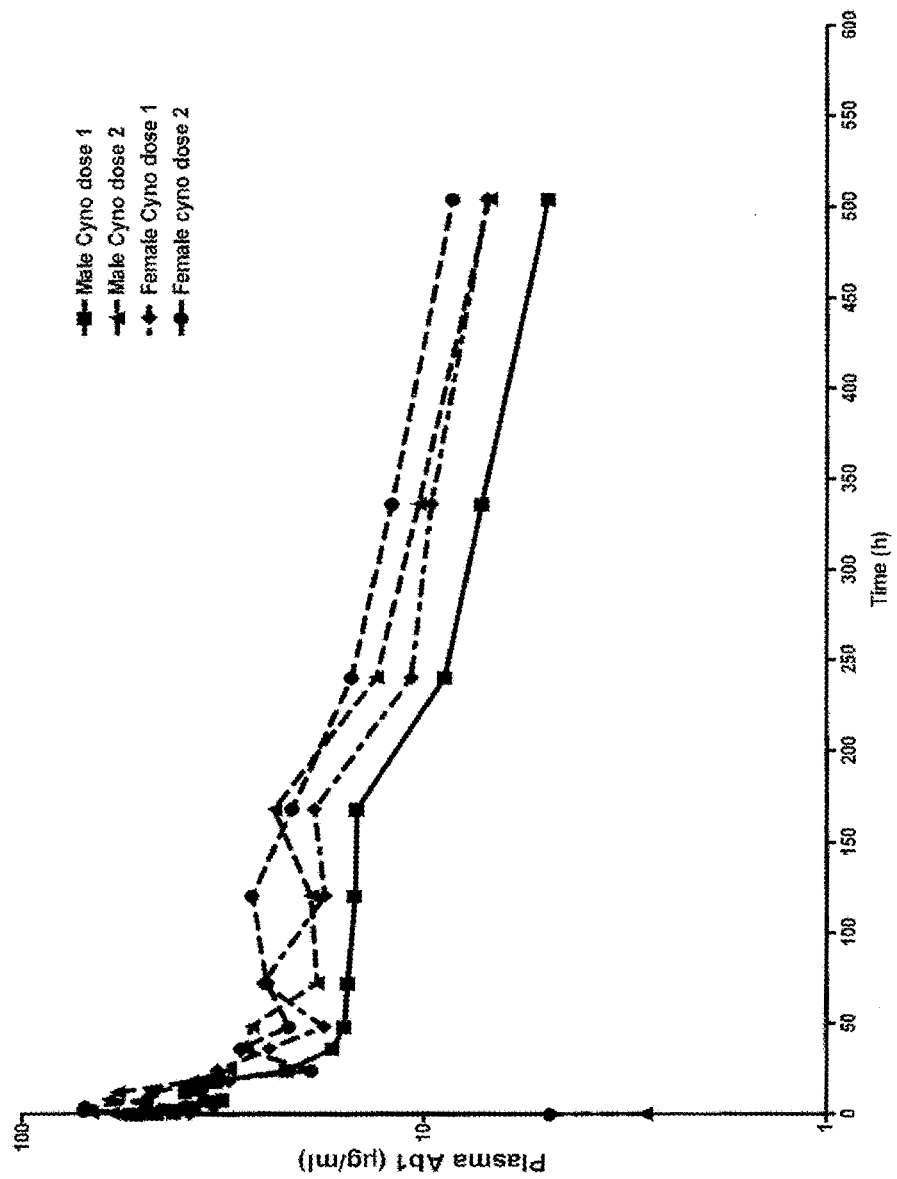

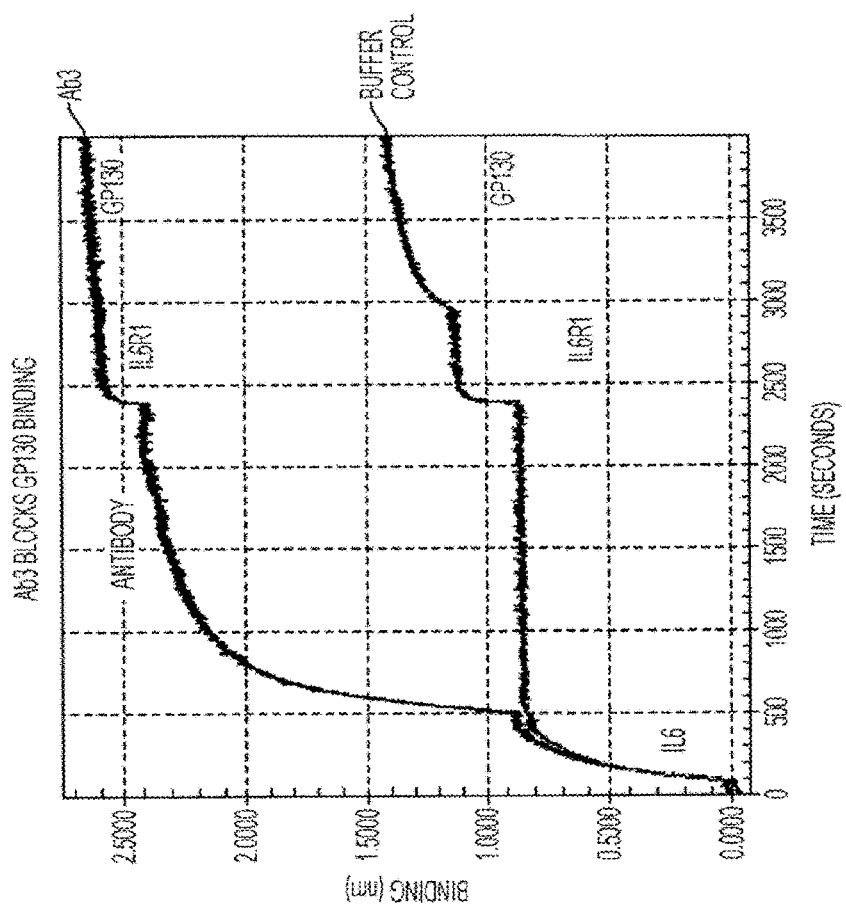

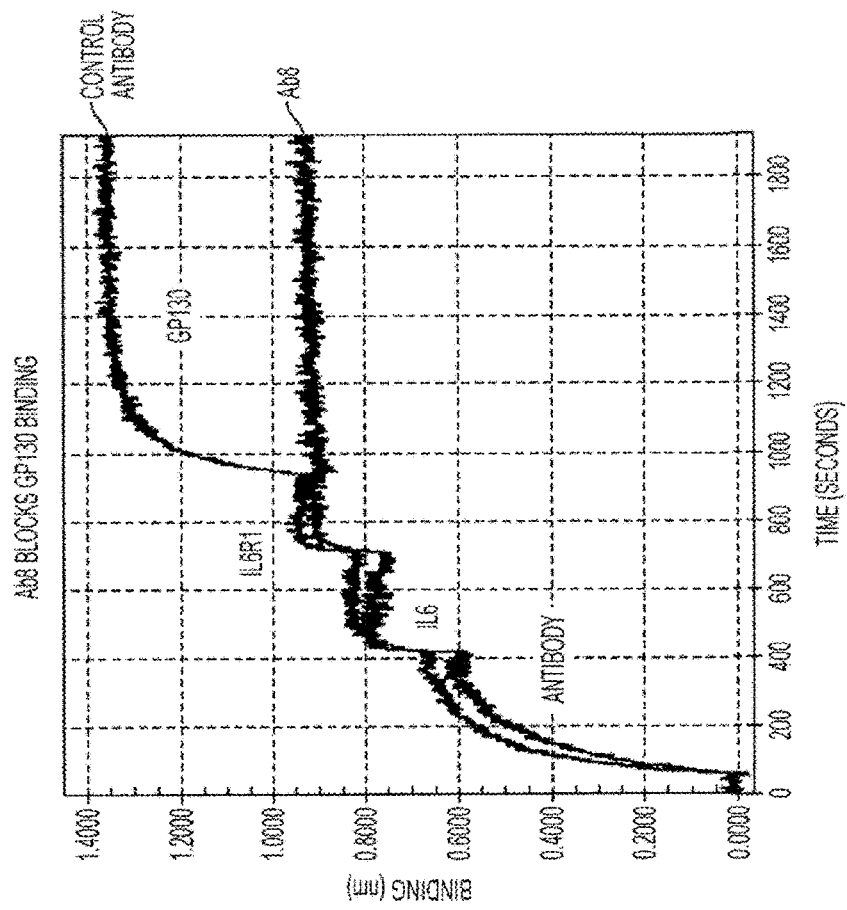

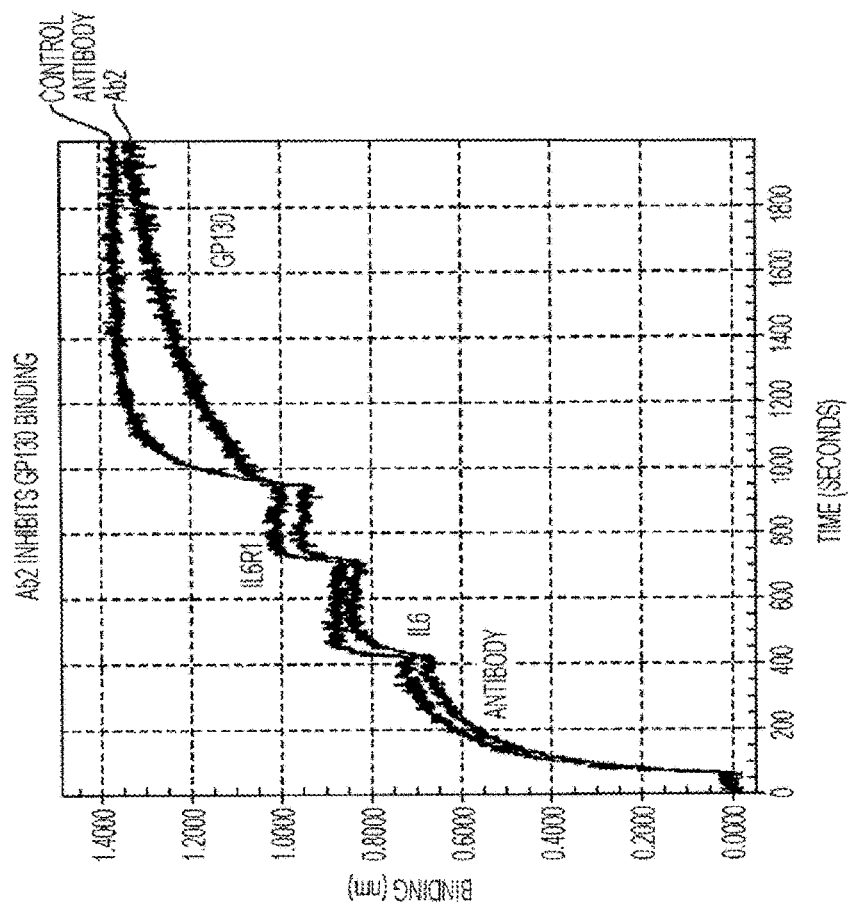

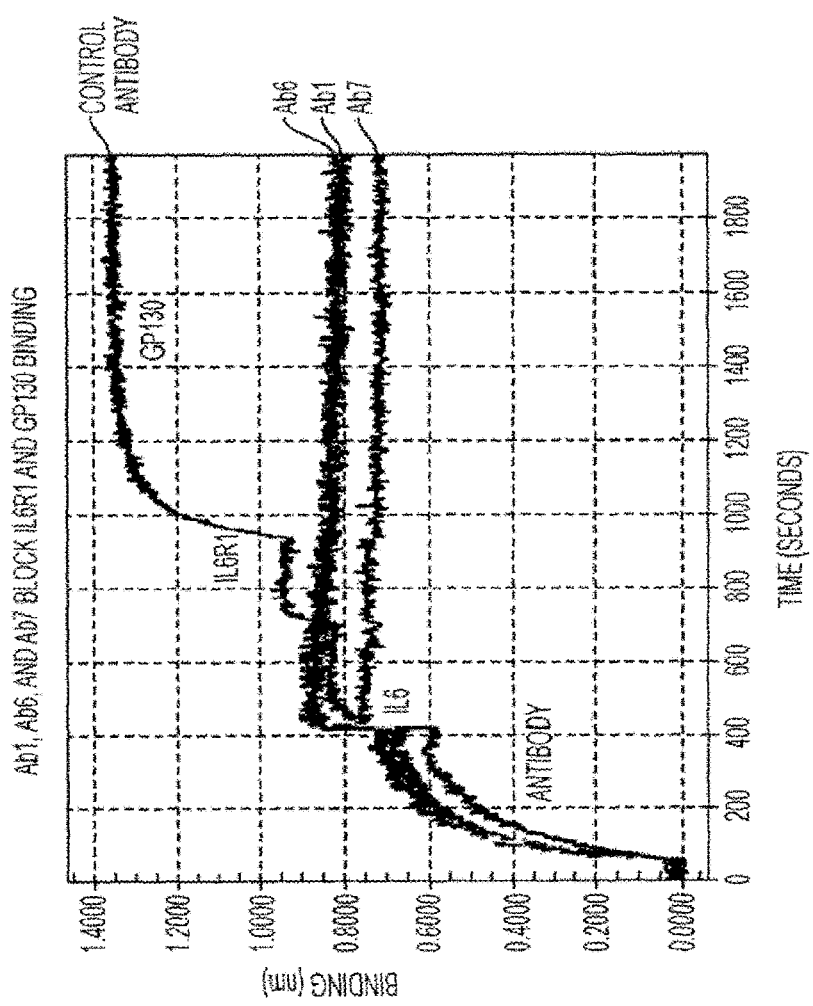

FIG. 11

| Antibody | Blocks IL6 binding to R1 | Blocks IL6 binding to GP130 | Reference |
|---|---|---|---|
| Ab1 | Yes | Yes | 021051 |
| Ab2 | No | Partial | 021050 |
| Ab3 | No | Yes | 021030 |
| Ab4 | No | Yes | 021050 |
| Ab6 | Yes | Yes | 021051 |
| Ab7 | Yes | Yes | 021051 |
| Ab8 | No | Yes | 021051 |

FIG. 12

| | | | | |
|---|---|---|---|---|
| 1 VPPGEDSKDVAAPHR (SEQ ID NO: 590) | 20 ENNLNLPKMAEKDGC (SEQ ID NO: 609) | 39 QMSTKVLIQFLQKKA (SEQ ID NO: 628) |
| 2 GEDSKDVAAPHRQPL (SEQ ID NO: 591) | 21 LNLPKMAEKDGCFQS (SEQ ID NO: 610) | 40 TKVLIQFLQKKAKNL (SEQ ID NO: 629) |
| 3 SKDVAAPHRQPLTSS (SEQ ID NO: 592) | 22 PKMAEKDGCFQSGFN (SEQ ID NO: 611) | 41 LIQFLQKKAKNLDAI (SEQ ID NO: 630) |
| 4 VAAPHRQPLTSSERI (SEQ ID NO: 593) | 23 AEKDGCFQSGFNEET (SEQ ID NO: 612) | 42 FLQKKAKNLDAITTP (SEQ ID NO: 631) |
| 5 PHRQPLTSSERIDKQ (SEQ ID NO: 594) | 24 DGCFQSGFNEETCLV (SEQ ID NO: 613) | 43 KKAKNLDAITTPDPT (SEQ ID NO: 632) |
| 6 QPLTSSERIDKQIRY (SEQ ID NO: 595) | 25 FQSGFNEETCLVKII (SEQ ID NO: 614) | 44 KNLDAITTPDPTTNA (SEQ ID NO: 633) |
| 7 TSSERIDKQIRYILD (SEQ ID NO: 596) | 26 GFNEETCLVKIITGL (SEQ ID NO: 615) | 45 DAITTPDPTTNASLL (SEQ ID NO: 634) |
| 8 ERIDKQIRYILDGIS (SEQ ID NO: 597) | 27 EETCLVKIITGLLEF (SEQ ID NO: 616) | 46 TTPDPTTNASLLTKL (SEQ ID NO: 635) |
| 9 DKQIRYILDGISALR (SEQ ID NO: 598) | 28 CLVKIITGLLEFEVY (SEQ ID NO: 617) | 47 DPTTNASLLTKLQAQ (SEQ ID NO: 636) |
| 10 IRYILDGISALRKET (SEQ ID NO: 599) | 29 KIITGLLEFEVYLEY (SEQ ID NO: 618) | 48 TNASLLTKLQAQNQW (SEQ ID NO: 637) |
| 11 ILDGISALRKETCNK (SEQ ID NO: 600) | 30 TGLLEFEVYLEYLQN (SEQ ID NO: 619) | 49 SLLTKLQAQNQWLQD (SEQ ID NO: 638) |
| 12 GISALRKETCNKSNM (SEQ ID NO: 601) | 31 LEFEVYLEYLQNRFE (SEQ ID NO: 620) | 50 TKLQAQNQWLQDMTT (SEQ ID NO: 639) |
| 13 ALRKETCNKSNMCES (SEQ ID NO: 602) | 32 EVYLEYLQNRFESSE (SEQ ID NO: 621) | 51 QAQNQWLQDMTTHLI (SEQ ID NO: 640) |
| 14 KETCNKSNMCESSKE (SEQ ID NO: 603) | 33 LEYLQNRFESSEEQA (SEQ ID NO: 622) | 52 NQWLQDMTTHLILRS (SEQ ID NO: 641) |
| 15 CNKSNMCESSKEALA (SEQ ID NO: 604) | 34 LQNRFESSEEQARAV (SEQ ID NO: 623) | 53 LQDMTTHLILRSFKE (SEQ ID NO: 642) |
| 16 SNMCESSKEALAENN (SEQ ID NO: 605) | 35 RFESSEEQARAVQMS (SEQ ID NO: 624) | 54 MTTHLILRSFKEFLQ (SEQ ID NO: 643) |
| 17 CESSKEALAENNLNL (SEQ ID NO: 606) | 36 SSEEQARAVQMSTKV (SEQ ID NO: 625) | 55 HLILRSFKEFLQSSL (SEQ ID NO: 644) |
| 18 SKEALAENNLNLPKM (SEQ ID NO: 607) | 37 EQARAVQMSTKVLIQ (SEQ ID NO: 626) | 56 LRSFKEFLQSSLRAL (SEQ ID NO: 645) |
| 19 ALAENNLNLPKMAEK (SEQ ID NO: 608) | 38 RAVQMSTKVLIQFLQ (SEQ ID NO: 627) | 57 FKEFLQSSLRALRQM (SEQ ID NO: 646) | es

SEQUENCE LISTING

```
<160> NUMBER OF SEQ ID NOS: 662

<210> SEQ ID NO 1
<211> LENGTH: 183
<212> TYPE: PRT
<213> ORGANISM: Homo sapiens

<400> SEQUENCE: 1

Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
                20                  25                  30

Asp Gly Ile Ser Ala Leu Arg Lys Glu Thr Cys Asn Lys Ser Asn Met
            35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95

Leu Glu Tyr Leu Gln Asn Arg Phe Glu Ser Ser Glu Glu Gln Ala Arg
                100                 105                 110

Ala Val Gln Met Ser Thr Lys Val Leu Ile Gln Phe Leu Gln Lys Lys
            115                 120                 125

Ala Lys Asn Leu Asp Ala Ile Thr Thr Pro Asp Pro Thr Thr Asn Ala
    130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
                180

<210> SEQ ID NO 2
<211> LENGTH: 163
<212> TYPE: PRT
<213> ORGANISM: Oryctolagus cuniculus

<400> SEQUENCE: 2

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
                20                  25                  30

Val Ser Ala Ala Val Gly Gly Thr Val Thr Ile Lys Cys Gln Ala Ser
            35                  40                  45
```

Gln Ser Ile Asn Asn Glu Leu Ser Trp Tyr Gln Gln Lys Pro Gly Gln
            50                  55                  60

Arg Pro Lys Leu Leu Ile Tyr Arg Ala Ser Thr Leu Ala Ser Gly Val
 65                  70                  75                  80

Ser Ser Arg Phe Lys Gly Ser Gly Ser Gly Thr Glu Phe Thr Leu Thr
                 85                  90                  95

Ile Ser Asp Leu Glu Cys Ala Asp Ala Ala Thr Tyr Tyr Cys Gln Gln
                100                 105                 110

Gly Tyr Ser Leu Arg Asn Ile Asp Asn Ala Phe Gly Gly Gly Thr Glu
                115                 120                 125

Val Val Val Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn

<210> SEQ ID NO 3
<211> LENGTH: 166
<212> TYPE: PRT
<213> ORGANISM: Oryctolagus cuniculus

<400> SEQUENCE: 3

Met Glu Thr Gly Leu Arg Trp Leu Leu Leu Val Ala Val Leu Lys Gly
 1                   5                  10                  15

Val Gln Cys Gln Ser Leu Glu Glu Ser Gly Gly Arg Leu Val Thr Pro
                20                  25                  30

Gly Thr Pro Leu Thr Leu Thr Cys Thr Ala Ser Gly Phe Ser Leu Ser
             35                  40                  45

Asn Tyr Tyr Val Thr Trp Val Arg Gln Ala Pro Gly Lys Gly Leu Glu
         50                  55                  60

Trp Ile Gly Ile Ile Tyr Gly Ser Asp Glu Thr Ala Tyr Ala Thr Trp
 65                  70                  75                  80

Ala Ile Gly Arg Phe Thr Ile Ser Lys Thr Ser Thr Thr Val Asp Leu
                 85                  90                  95

Lys Met Thr Ser Leu Thr Ala Ala Asp Thr Ala Thr Tyr Phe Cys Ala
                100                 105                 110

Arg Asp Asp Ser Ser Asp Trp Asp Ala Lys Phe Asn Leu Trp Gly Gln
                115                 120                 125

Gly Thr Leu Val Thr Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys
                165

<210> SEQ ID NO 4
<211> LENGTH: 11
<212> TYPE: PRT
<213> ORGANISM: Oryctolagus cuniculus

<400> SEQUENCE: 4

Gln Ala Ser Gln Ser Ile Asn Asn Glu Leu Ser
 1                   5                  10

<210> SEQ ID NO 5
<211> LENGTH: 7
<212> TYPE: PRT

<213> ORGANISM: Oryctolagus cuniculus

<400> SEQUENCE: 5

Arg Ala Ser Thr Leu Ala Ser
1               5

<210> SEQ ID NO 6
<211> LENGTH: 12
<212> TYPE: PRT
<213> ORGANISM: Oryctolagus cuniculus

<400> SEQUENCE: 6

Gln Gln Gly Tyr Ser Leu Arg Asn Ile Asp Asn Ala
1               5                   10

<210> SEQ ID NO 7
<211> LENGTH: 5
<212> TYPE: PRT
<213> ORGANISM: Oryctolagus cuniculus

<400> SEQUENCE: 7

Asn Tyr Tyr Val Thr
1               5

<210> SEQ ID NO 8
<211> LENGTH: 16
<212> TYPE: PRT
<213> ORGANISM: Oryctolagus cuniculus

<400> SEQUENCE: 8

Ile Ile Tyr Gly Ser Asp Glu Thr Ala Tyr Ala Thr Trp Ala Ile Gly
1               5                   10                  15

<210> SEQ ID NO 9
<211> LENGTH: 12
<212> TYPE: PRT
<213> ORGANISM: Oryctolagus cuniculus

<400> SEQUENCE: 9

Asp Asp Ser Ser Asp Trp Asp Ala Lys Phe Asn Leu
1               5                   10

<210> SEQ ID NO 10
<211> LENGTH: 491
<212> TYPE: DNA
<213> ORGANISM: Oryctolagus cuniculus

<400> SEQUENCE: 10

| | | | | | |
|---|---|---|---|---|---|
| atggacacga | gggcccccac | tcagctgctg | gggctcctgc | tgctctggct | cccaggtgcc | 60 |
| agatgtgcct | atgatatgac | ccagactcca | gcctcggtgt | ctgcagctgt | gggaggcaca | 120 |
| gtcaccatca | agtgccaggc | cagtcagagc | attaacaatg | aattatcctg | gtatcagcag | 180 |
| aaaccagggc | agcgtcccaa | gctcctgatc | tatagggcat | ccactctggc | atctggggtc | 240 |
| tcatcgcggt | tcaaaggcag | tggatctggg | acagagttca | ctctcaccat | cagcgacctg | 300 |
| gagtgtgccg | atgctgccac | ttactactgt | caacagggtt | atagtctgag | gaatattgat | 360 |
| aatgctttcg | gcggagggac | cgaggtggtg | gtcaaacgta | cggtagcggc | ccatctgtc | 420 |
| ttcatcttcc | cgccatctga | tgagcagttg | aaatctggaa | ctgcctctgt | tgtgtgcctg | 480 |
| ctgaataact | t | | | | | 491 |

<210> SEQ ID NO 11

```
<211> LENGTH: 499
<212> TYPE: DNA
<213> ORGANISM: Oryctolagus cuniculus

<400> SEQUENCE: 11
atggagactg ggctgcgctg gcttctcctg gtcgctgtgc tcaaaggtgt ccagtgtcag      60
tcgctggagg agtccggggg tcgcctggtc acgcctggga cacccctgac actcacctgc     120
acagcctctg gattctccct cagtaactac tacgtgacct gggtccgcca ggctccaggg     180
aaggggctgg aatggatcgg aatcatttat ggtagtgatg aaacggccta cgcgacctgg     240
gcgataggcc gattcaccat ctccaaaacc tcgaccacgg tggatctgaa aatgaccagt     300
ctgacagccg cggacacggc cacctatttc tgtgccagag atgatagtag tgactgggat     360
gcaaaattta acttgtgggg ccaaggcacc ctggtcaccg tctcgagcgc ctccaccaag     420
ggcccatcgg tcttccccct ggcaccctcc tccaagagca cctctggggg cacagcggcc     480
ctgggctgcc tggtcaagg                                                  499

<210> SEQ ID NO 12
<211> LENGTH: 33
<212> TYPE: DNA
<213> ORGANISM: Oryctolagus cuniculus

<400> SEQUENCE: 12
caggccagtc agagcattaa caatgaatta tcc                                   33

<210> SEQ ID NO 13
<211> LENGTH: 21
<212> TYPE: DNA
<213> ORGANISM: Oryctolagus cuniculus

<400> SEQUENCE: 13
agggcatcca ctctggcatc t                                                21

<210> SEQ ID NO 14
<211> LENGTH: 36
<212> TYPE: DNA
<213> ORGANISM: Oryctolagus cuniculus

<400> SEQUENCE: 14
caacagggtt atagtctgag gaatattgat aatgct                                36

<210> SEQ ID NO 15
<211> LENGTH: 15
<212> TYPE: DNA
<213> ORGANISM: Oryctolagus cuniculus

<400> SEQUENCE: 15
aactactacg tgacc                                                       15

<210> SEQ ID NO 16
<211> LENGTH: 48
<212> TYPE: DNA
<213> ORGANISM: Oryctolagus cuniculus

<400> SEQUENCE: 16
atcatttatg gtagtgatga aacggcctac gcgacctggg cgataggc                   48

<210> SEQ ID NO 17
<211> LENGTH: 36
<212> TYPE: DNA
<213> ORGANISM: Oryctolagus cuniculus
```

<400> SEQUENCE: 17
gatgatagta gtgactggga tgcaaaattt aacttg                36

<210> SEQ ID NO 18
<211> LENGTH: 109
<212> TYPE: PRT
<213> ORGANISM: Oryctolagus cuniculus

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Trp Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu
            100                 105

<210> SEQ ID NO 19
<211> LENGTH: 109
<212> TYPE: PRT
<213> ORGANISM: Oryctolagus cuniculus

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Ser Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu
            100                 105

<210> SEQ ID NO 20
<211> LENGTH: 99
<212> TYPE: PRT
<213> ORGANISM: Oryctolagus cuniculus

<400> SEQUENCE: 20

Ile Gln Met Thr Gln Ser Pro Ser Ser Leu Ser Ala Ser Val Gly Asp
1               5                   10                  15

Arg Val Thr Ile Thr Cys Gln Ala Ser Gln Ser Ile Asn Asn Glu Leu
            20                  25                  30

Ser Trp Tyr Gln Gln Lys Pro Gly Lys Ala Pro Lys Leu Leu Ile Tyr
        35                  40                  45

Arg Ala Ser Thr Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Asp
65                  70                  75                  80

Asp Phe Ala Thr Tyr Tyr Cys Gln Gln Gly Tyr Ser Leu Arg Asn Ile
                85                  90                  95

Asp Asn Ala

<210> SEQ ID NO 21
<211> LENGTH: 165
<212> TYPE: PRT
<213> ORGANISM: Oryctolagus cuniculus

<400> SEQUENCE: 21

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Asn Cys Gln Ala Ser
        35                  40                  45

Glu Thr Ile Tyr Ser Trp Leu Ser Trp Tyr Gln Gln Lys Pro Gly Gln
    50                  55                  60

Pro Pro Lys Leu Leu Ile Tyr Gln Ala Ser Asp Leu Ala Ser Gly Val
65                  70                  75                  80

Pro Ser Arg Phe Ser Gly Ser Gly Ala Gly Thr Glu Tyr Thr Leu Thr
                85                  90                  95

Ile Ser Gly Val Gln Cys Asp Asp Ala Ala Thr Tyr Tyr Cys Gln Gln
            100                 105                 110

Gly Tyr Ser Gly Ser Asn Val Asp Asn Val Phe Gly Gly Gly Thr Glu
        115                 120                 125

Val Val Val Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr
                165

<210> SEQ ID NO 22
<211> LENGTH: 167
<212> TYPE: PRT
<213> ORGANISM: Oryctolagus cuniculus

<400> SEQUENCE: 22

Met Glu Thr Gly Leu Arg Trp Leu Leu Leu Val Ala Val Leu Lys Gly
1               5                   10                  15

Val Gln Cys Gln Glu Gln Leu Lys Glu Ser Gly Gly Arg Leu Val Thr
            20                  25                  30

Pro Gly Thr Pro Leu Thr Leu Thr Cys Thr Ala Ser Gly Phe Ser Leu
        35                  40                  45

Asn Asp His Ala Met Gly Trp Val Arg Gln Ala Pro Gly Lys Gly Leu
    50                  55                  60

Glu Tyr Ile Gly Phe Ile Asn Ser Gly Gly Ser Ala Arg Tyr Ala Ser
65                  70                  75                  80

Trp Ala Glu Gly Arg Phe Thr Ile Ser Arg Thr Ser Thr Thr Val Asp
                85                  90                  95

```
Leu Lys Met Thr Ser Leu Thr Thr Glu Asp Thr Ala Thr Tyr Phe Cys
            100                 105                 110

Val Arg Gly Gly Ala Val Trp Ser Ile His Ser Phe Asp Pro Trp Gly
        115                 120                 125

Pro Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys
                165

<210> SEQ ID NO 23
<211> LENGTH: 11
<212> TYPE: PRT
<213> ORGANISM: Oryctolagus cuniculus

<400> SEQUENCE: 23

Gln Ala Ser Glu Thr Ile Tyr Ser Trp Leu Ser
1               5                   10

<210> SEQ ID NO 24
<211> LENGTH: 7
<212> TYPE: PRT
<213> ORGANISM: Oryctolagus cuniculus

<400> SEQUENCE: 24

Gln Ala Ser Asp Leu Ala Ser
1               5

<210> SEQ ID NO 25
<211> LENGTH: 12
<212> TYPE: PRT
<213> ORGANISM: Oryctolagus cuniculus

<400> SEQUENCE: 25

Gln Gln Gly Tyr Ser Gly Ser Asn Val Asp Asn Val
1               5                   10

<210> SEQ ID NO 26
<211> LENGTH: 5
<212> TYPE: PRT
<213> ORGANISM: Oryctolagus cuniculus

<400> SEQUENCE: 26

Asp His Ala Met Gly
1               5

<210> SEQ ID NO 27
<211> LENGTH: 16
<212> TYPE: PRT
<213> ORGANISM: Oryctolagus cuniculus

<400> SEQUENCE: 27

Phe Ile Asn Ser Gly Gly Ser Ala Arg Tyr Ala Ser Trp Ala Glu Gly
1               5                   10                  15

<210> SEQ ID NO 28
<211> LENGTH: 12
<212> TYPE: PRT
<213> ORGANISM: Oryctolagus cuniculus

<400> SEQUENCE: 28

Gly Gly Ala Val Trp Ser Ile His Ser Phe Asp Pro
```

<210> SEQ ID NO 29
<211> LENGTH: 511
<212> TYPE: DNA
<213> ORGANISM: Oryctolagus cuniculus

<400> SEQUENCE: 29

```
atggacacga gggcccccac tcagctgctg gggctcctgc tgctctggct cccaggtgcc      60
agatgtgcct atgatatgac ccagactcca gcctctgtgg aggtagctgt gggaggcaca     120
gtcaccatca attgccaggc cagtgagacc atttacagtt ggttatcctg gtatcagcag     180
aagccagggc agcctcccaa gctcctgatc taccaggcat ccgatctggc atctggggtc     240
ccatcgcgat tcagcggcag tgggctgggg acagagtaca ctctcaccat cagcggcgtg     300
cagtgtgacg atgctgccac ttactactgt caacagggtt atagtggtag taatgttgat     360
aatgttttcg gcggagggac cgaggtggtg gtcaaacgta cggtagcggc cccatctgtc     420
ttcatcttcc cgccatctga tgagcagttg aaatctggaa ctgcctctgt tgtgtgcctg     480
ctgaataact tctatcccag agaggccaaa g                                    511
```

<210> SEQ ID NO 30
<211> LENGTH: 501
<212> TYPE: DNA
<213> ORGANISM: Oryctolagus cuniculus

<400> SEQUENCE: 30

```
atggagactg ggctgcgctg gcttctcctg gtcgctgtgc tcaaaggtgt ccagtgtcag      60
gagcagctga aggagtccgg gggtcgcctg gtcacgcctg gacaccctct gacacttacc     120
tgcacagcct ctggattctc cctcaatgac catgcaatgg gctgggtccg ccaggctcca     180
gggaaggggc tggaatacat cggattcatt aatagtggtg gtagcgcacg ctacgcgagc     240
tgggcagaag gccgattcac catctccaga acctcgacca cggtggatct gaaaatgacc     300
agtctgacaa ccgaggacac ggccacctat ttctgtgtca gaggggggtgc tgtttggagt     360
attcatagtt ttgatccctg gggcccaggg accctggtca ccgtctcgag cgcctccacc     420
aagggcccat cggtcttccc cctggcaccc tcctccaaga gcacctctgg gggcacagcg     480
gccctgggct gcctggtcaa g                                               501
```

<210> SEQ ID NO 31
<211> LENGTH: 33
<212> TYPE: DNA
<213> ORGANISM: Oryctolagus cuniculus

<400> SEQUENCE: 31

```
caggccagtg agaccattta cagttggtta tcc                                   33
```

<210> SEQ ID NO 32
<211> LENGTH: 21
<212> TYPE: DNA
<213> ORGANISM: Oryctolagus cuniculus

<400> SEQUENCE: 32

```
caggcatccg atctggcatc t                                                21
```

<210> SEQ ID NO 33
<211> LENGTH: 36
<212> TYPE: DNA
<213> ORGANISM: Oryctolagus cuniculus

<400> SEQUENCE: 33
caacagggtt atagtggtag taatgttgat aatgtt                                    36

<210> SEQ ID NO 34
<211> LENGTH: 15
<212> TYPE: DNA
<213> ORGANISM: Oryctolagus cuniculus

<400> SEQUENCE: 34
gaccatgcaa tgggc                                                           15

<210> SEQ ID NO 35
<211> LENGTH: 48
<212> TYPE: DNA
<213> ORGANISM: Oryctolagus cuniculus

<400> SEQUENCE: 35
ttcattaata gtggtggtag cgcacgctac gcgagctggg cagaaggc                       48

<210> SEQ ID NO 36
<211> LENGTH: 36
<212> TYPE: DNA
<213> ORGANISM: Oryctolagus cuniculus

<400> SEQUENCE: 36
gggggtgctg tttggagtat tcatagtttt gatccc                                    36

<210> SEQ ID NO 37
<211> LENGTH: 164
<212> TYPE: PRT
<213> ORGANISM: Oryctolagus cuniculus

<400> SEQUENCE: 37

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
                20                  25                  30

Val Ser Ala Ala Val Gly Gly Thr Val Ser Ile Ser Cys Gln Ala Ser
            35                  40                  45

Gln Ser Val Tyr Asp Asn Asn Tyr Leu Ser Trp Phe Gln Gln Lys Pro
        50                  55                  60

Gly Gln Pro Pro Lys Leu Leu Ile Tyr Gly Ala Ser Thr Leu Ala Ser
65                  70                  75                  80

Gly Val Pro Ser Arg Phe Val Gly Ser Gly Ser Gly Thr Gln Phe Thr
                85                  90                  95

Leu Thr Ile Thr Asp Val Gln Cys Asp Asp Ala Ala Thr Tyr Tyr Cys
            100                 105                 110

Ala Gly Val Tyr Asp Asp Ser Asp Asn Ala Phe Gly Gly Gly Thr
        115                 120                 125

Glu Val Val Val Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn

<210> SEQ ID NO 38
<211> LENGTH: 166
<212> TYPE: PRT

<213> ORGANISM: Oryctolagus cuniculus

<400> SEQUENCE: 38

Met Glu Thr Gly Leu Arg Trp Leu Leu Leu Val Ala Val Leu Lys Gly
1               5                   10                  15
Val Gln Cys Gln Ser Leu Glu Glu Ser Gly Gly Arg Leu Val Thr Pro
            20                  25                  30
Gly Thr Pro Leu Thr Leu Thr Cys Thr Ala Ser Gly Phe Ser Leu Ser
        35                  40                  45
Val Tyr Tyr Met Asn Trp Val Arg Gln Ala Pro Gly Lys Gly Leu Glu
    50                  55                  60
Trp Ile Gly Phe Ile Thr Met Ser Asp Asn Ile Asn Tyr Ala Ser Trp
65                  70                  75                  80
Ala Lys Gly Arg Phe Thr Ile Ser Lys Thr Ser Thr Thr Val Asp Leu
                85                  90                  95
Lys Met Thr Ser Pro Thr Thr Glu Asp Thr Ala Thr Tyr Phe Cys Ala
            100                 105                 110
Arg Ser Arg Gly Trp Gly Thr Met Gly Arg Leu Asp Leu Trp Gly Pro
        115                 120                 125
Gly Thr Leu Val Thr Val Ser Ser Ala Ser Thr Lys Gly Pro Ser Val
    130                 135                 140
Phe Pro Leu Ala Pro Ser Ser Lys Ser Thr Ser Gly Gly Thr Ala Ala
145                 150                 155                 160
Leu Gly Cys Leu Val Lys
                165

<210> SEQ ID NO 39
<211> LENGTH: 13
<212> TYPE: PRT
<213> ORGANISM: Oryctolagus cuniculus

<400> SEQUENCE: 39

Gln Ala Ser Gln Ser Val Tyr Asp Asn Asn Tyr Leu Ser
1               5                   10

<210> SEQ ID NO 40
<211> LENGTH: 7
<212> TYPE: PRT
<213> ORGANISM: Oryctolagus cuniculus

<400> SEQUENCE: 40

Gly Ala Ser Thr Leu Ala Ser
1               5

<210> SEQ ID NO 41
<211> LENGTH: 11
<212> TYPE: PRT
<213> ORGANISM: Oryctolagus cuniculus

<400> SEQUENCE: 41

Ala Gly Val Tyr Asp Asp Asp Ser Asp Asn Ala
1               5                   10

<210> SEQ ID NO 42
<211> LENGTH: 5
<212> TYPE: PRT
<213> ORGANISM: Oryctolagus cuniculus

<400> SEQUENCE: 42

Val Tyr Tyr Met Asn

<210> SEQ ID NO 43
<211> LENGTH: 16
<212> TYPE: PRT
<213> ORGANISM: Oryctolagus cuniculus

<400> SEQUENCE: 43

Phe Ile Thr Met Ser Asp Asn Ile Asn Tyr Ala Ser Trp Ala Lys Gly
1               5                   10                  15

<210> SEQ ID NO 44
<211> LENGTH: 12
<212> TYPE: PRT
<213> ORGANISM: Oryctolagus cuniculus

<400> SEQUENCE: 44

Ser Arg Gly Trp Gly Thr Met Gly Arg Leu Asp Leu
1               5                   10

<210> SEQ ID NO 45
<211> LENGTH: 496
<212> TYPE: DNA
<213> ORGANISM: Oryctolagus cuniculus

<400> SEQUENCE: 45

```
atggacacga gggcccccac tcagctgctg gggctcctgc tgctctggct cccaggtgcc    60
acatttgccg ccgtgctgac ccagactcca tctcccgtgt ctgcagctgt gggaggcaca   120
gtcagcatca gttgccaggc cagtcagagt gtttatgaca caactactt atcctggttt   180
cagcagaaac cagggcagcc tcccaagctc ctgatctatg gtgcatccac tctggcatct   240
ggggtcccat cgcggttcgt gggcagtgga tctgggacac agttcactct caccatcaca   300
gacgtgcagt gtgacgatgc tgccacttac tattgtgcag gcgtttatga tgatgatagt   360
gataatgcct cggcggagg accgaggtg gtggtcaaac gtacggtagc ggccccatct   420
gtcttcatct ccccgccatc tgatgagcag ttgaaatctg gaactgcctc tgttgtgtgc   480
ctgctgaata acttct                                                   496
```

<210> SEQ ID NO 46
<211> LENGTH: 499
<212> TYPE: DNA
<213> ORGANISM: Oryctolagus cuniculus

<400> SEQUENCE: 46

```
atggagactg ggctgcgctg gcttctcctg gtggctgtgc tcaaaggtgt ccagtgtcag    60
tcgctggagg agtccggggg tcgcctggtc acccctggga cacccctgac actcacctgc   120
acagcctctg gattctccct cagtgtctac tacatgaact gggtccgcca ggctccaggg   180
aaggggctgg aatggatcgg attcattaca atgagtgata atataaatta cgcgagctgg   240
gcgaaaggcc gattcaccat ctccaaaacc tcgaccacgg tggatctgaa aatgaccagt   300
ccgacaaccg aggacacggc cacctatttc tgtgccagga gtcgtggctg ggtacaatg   360
ggtcggttgg atctctgggg ccaggcacc tcgtcaccg tctcgagcgc ctccaccaag   420
ggcccatcgg tcttccccct ggcaccctcc tccaagagca cctctggggg cacagcggcc   480
ctgggctgcc tggtcaagg                                                499
```

<210> SEQ ID NO 47
<211> LENGTH: 39

<210> SEQ ID NO 47
<211> LENGTH: 39
<212> TYPE: DNA
<213> ORGANISM: Oryctolagus cuniculus

<400> SEQUENCE: 47
caggccagtc agagtgttta tgacaacaac tacttatcc                              39

<210> SEQ ID NO 48
<211> LENGTH: 21
<212> TYPE: DNA
<213> ORGANISM: Oryctolagus cuniculus

<400> SEQUENCE: 48
ggtgcatcca ctctggcatc t                                                 21

<210> SEQ ID NO 49
<211> LENGTH: 33
<212> TYPE: DNA
<213> ORGANISM: Oryctolagus cuniculus

<400> SEQUENCE: 49
gcaggcgttt atgatgatga tagtgataat gcc                                    33

<210> SEQ ID NO 50
<211> LENGTH: 15
<212> TYPE: DNA
<213> ORGANISM: Oryctolagus cuniculus

<400> SEQUENCE: 50
gtctactaca tgaac                                                        15

<210> SEQ ID NO 51
<211> LENGTH: 48
<212> TYPE: DNA
<213> ORGANISM: Oryctolagus cuniculus

<400> SEQUENCE: 51
ttcattacaa tgagtgataa tataaattac gcgagctggg cgaaaggc                    48

<210> SEQ ID NO 52
<211> LENGTH: 36
<212> TYPE: DNA
<213> ORGANISM: Oryctolagus cuniculus

<400> SEQUENCE: 52
agtcgtggct ggggtacaat gggtcggttg gatctc                                 36

<210> SEQ ID NO 53
<211> LENGTH: 164
<212> TYPE: PRT
<213> ORGANISM: Oryctolagus cuniculus

<400> SEQUENCE: 53

Met Asp Thr Arg Ala Pro Thr Gln Leu Leu Gly Leu Leu Leu Trp
1               5                   10                  15

Leu Pro Gly Ala Ile Cys Asp Pro Val Leu Thr Gln Thr Pro Ser Pro
                20                  25                  30

Val Ser Ala Pro Val Gly Gly Thr Val Ser Ile Ser Cys Gln Ala Ser
            35                  40                  45

Gln Ser Val Tyr Glu Asn Asn Tyr Leu Ser Trp Phe Gln Gln Lys Pro
        50                  55                  60

Gly Gln Pro Pro Lys Leu Leu Ile Tyr Gly Ala Ser Thr Leu Asp Ser
65                  70                  75                  80

```
Gly Val Pro Ser Arg Phe Lys Gly Ser Gly Thr Gln Phe Thr
                85                  90                  95

Leu Thr Ile Thr Asp Val Gln Cys Asp Asp Ala Ala Thr Tyr Tyr Cys
            100                 105                 110

Ala Gly Val Tyr Asp Asp Ser Asp Ala Phe Gly Gly Gly Thr
        115                 120                 125

Glu Val Val Val Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn
```

<210> SEQ ID NO 54
<211> LENGTH: 167
<212> TYPE: PRT
<213> ORGANISM: Oryctolagus cuniculus

<400> SEQUENCE: 54

```
Met Glu Thr Gly Leu Arg Trp Leu Leu Leu Val Ala Val Leu Lys Gly
1               5                   10                  15

Val Gln Cys Gln Glu Gln Leu Lys Glu Ser Gly Gly Gly Leu Val Thr
            20                  25                  30

Pro Gly Gly Thr Leu Thr Leu Thr Cys Thr Ala Ser Gly Phe Ser Leu
        35                  40                  45

Asn Ala Tyr Tyr Met Asn Trp Val Arg Gln Ala Pro Gly Lys Gly Leu
    50                  55                  60

Glu Trp Ile Gly Phe Ile Thr Leu Asn Asn Asn Val Ala Tyr Ala Asn
65                  70                  75                  80

Trp Ala Lys Gly Arg Phe Thr Phe Ser Lys Thr Ser Thr Thr Val Asp
                85                  90                  95

Leu Lys Met Thr Ser Pro Thr Pro Glu Asp Thr Ala Thr Tyr Phe Cys
            100                 105                 110

Ala Arg Ser Arg Gly Trp Gly Ala Met Gly Arg Leu Asp Leu Trp Gly
        115                 120                 125

His Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys
                165
```

<210> SEQ ID NO 55
<211> LENGTH: 13
<212> TYPE: PRT
<213> ORGANISM: Oryctolagus cuniculus

<400> SEQUENCE: 55

```
Gln Ala Ser Gln Ser Val Tyr Glu Asn Asn Tyr Leu Ser
1               5                   10
```

<210> SEQ ID NO 56
<211> LENGTH: 7
<212> TYPE: PRT
<213> ORGANISM: Oryctolagus cuniculus

<400> SEQUENCE: 56

```
Gly Ala Ser Thr Leu Asp Ser
```

<210> SEQ ID NO 57
<211> LENGTH: 11
<212> TYPE: PRT
<213> ORGANISM: Oryctolagus cuniculus

<400> SEQUENCE: 57

Ala Gly Val Tyr Asp Asp Ser Asp Asp Ala
1               5                   10

<210> SEQ ID NO 58
<211> LENGTH: 5
<212> TYPE: PRT
<213> ORGANISM: Oryctolagus cuniculus

<400> SEQUENCE: 58

Ala Tyr Tyr Met Asn
1               5

<210> SEQ ID NO 59
<211> LENGTH: 16
<212> TYPE: PRT
<213> ORGANISM: Oryctolagus cuniculus

<400> SEQUENCE: 59

Phe Ile Thr Leu Asn Asn Asn Val Ala Tyr Ala Asn Trp Ala Lys Gly
1               5                   10                  15

<210> SEQ ID NO 60
<211> LENGTH: 12
<212> TYPE: PRT
<213> ORGANISM: Oryctolagus cuniculus

<400> SEQUENCE: 60

Ser Arg Gly Trp Gly Ala Met Gly Arg Leu Asp Leu
1               5                   10

<210> SEQ ID NO 61
<211> LENGTH: 494
<212> TYPE: DNA
<213> ORGANISM: Oryctolagus cuniculus

<400> SEQUENCE: 61
atggacacga gggcccccac tcagctgctg gggctcctgc tgctctggct cccaggtgcc      60
atatgtgacc ctgtgctgac ccagactcca tctcccgtat ctgcacctgt gggaggcaca     120
gtcagcatca gttgccaggc cagtcagagt gtttatgaga caactatttt atcctggttt     180
cagcagaaac cagggcagcc tcccaagctc ctgatctatg gtgcatccac tctggattct     240
ggggtcccat cgcggttcaa aggcagtgga tctgggacac agttcactct caccattaca     300
gacgtgcagt gtgacgatgc tgccacttac tattgtgcag cgtttatga tgatgatagt     360 gatgatgcct cggcggagg gaccgaggtg gtggtcaaac gtacggtagc ggccccatct     420
gtcttcatct tcccgccatc tgatgagcag ttgaaatctg gaactgcctc tgttgtgtgc     480
ctgctgaata actt                                                       494

<210> SEQ ID NO 62
<211> LENGTH: 502
<212> TYPE: DNA
<213> ORGANISM: Oryctolagus cuniculus

<400> SEQUENCE: 62

```
atggagactg ggctgcgctg gcttctcctg gtggctgtgc tcaaaggtgt ccagtgtcag      60
gagcagctga aggagtccgg aggaggcctg gtaacgcctg gaggaaccct gacactcacc     120
tgcacagcct ctggattctc cctcaatgcc tactacatga actgggtccg ccaggctcca     180 gggaagggc tggaatggat cggattcatt actctgaata taatgtagc ttacgcgaac       240 tgggcgaaag gccgattcac cttctccaaa acctcgacca cggtggatct gaaaatgacc     300
agtccgacac ccgaggacac ggccacctat ttctgtgcca ggagtcgtgg ctggggtgca     360
atgggtcggt tggatctctg ggccatggc accctggtca ccgtctcgag cgcctccacc      420
aagggcccat cggtcttccc cctggcaccc tcctccaaga gcacctctgg gggcacagcg     480
gccctgggct gcctggtcaa gg                                              502
```

<210> SEQ ID NO 63
<211> LENGTH: 39
<212> TYPE: DNA
<213> ORGANISM: Oryctolagus cuniculus

<400> SEQUENCE: 63

```
caggccagtc agagtgttta tgagaacaac tatttatcc                             39
```

<210> SEQ ID NO 64
<211> LENGTH: 21
<212> TYPE: DNA
<213> ORGANISM: Oryctolagus cuniculus

<400> SEQUENCE: 64

```
ggtgcatcca ctctggattc t                                                21
```

<210> SEQ ID NO 65
<211> LENGTH: 33
<212> TYPE: DNA
<213> ORGANISM: Oryctolagus cuniculus

<400> SEQUENCE: 65

```
gcaggcgttt atgatgatga tagtgatgat gcc                                   33
```

<210> SEQ ID NO 66
<211> LENGTH: 15
<212> TYPE: DNA
<213> ORGANISM: Oryctolagus cuniculus

<400> SEQUENCE: 66

```
gcctactaca tgaac                                                       15
```

<210> SEQ ID NO 67
<211> LENGTH: 48
<212> TYPE: DNA
<213> ORGANISM: Oryctolagus cuniculus

<400> SEQUENCE: 67

```
ttcattactc tgaataataa tgtagcttac gcgaactggg cgaaaggc                   48
```

<210> SEQ ID NO 68
<211> LENGTH: 36
<212> TYPE: DNA
<213> ORGANISM: Oryctolagus cuniculus

<400> SEQUENCE: 68

```
agtcgtggct ggggtgcaat gggtcggttg gatctc                                36
```

```
<210> SEQ ID NO 69
<211> LENGTH: 164
<212> TYPE: PRT
<213> ORGANISM: Oryctolagus cuniculus

<400> SEQUENCE: 69

Met Asp Thr Arg Ala Pro Thr Gln Leu Leu Gly Leu Leu Leu Trp
1               5                   10                  15

Leu Pro Gly Ala Thr Phe Ala Gln Val Leu Thr Gln Thr Pro Ser Pro
                20                  25                  30

Val Ser Ala Ala Val Gly Gly Thr Val Thr Ile Asn Cys Gln Ala Ser
                35                  40                  45

Gln Ser Val Asp Asp Asn Asn Trp Leu Gly Trp Tyr Gln Gln Lys Arg
    50                  55                  60

Gly Gln Pro Pro Lys Tyr Leu Ile Tyr Ser Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
                100                 105                 110

Ala Gly Gly Phe Ser Gly Asn Ile Phe Ala Phe Gly Gly Gly Thr Glu
                115                 120                 125

Val Val Val Lys Arg Thr Val Ala Ala Pro Ser Val Phe Ile Phe Pro
                130                 135                 140

Pro Ser Asp Glu Gln Leu Lys Ser Gly Thr Ala Ser Val Val Cys Leu
145                 150                 155                 160

Leu Asn Asn Phe

<210> SEQ ID NO 70
<211> LENGTH: 164
<212> TYPE: PRT
<213> ORGANISM: Oryctolagus cuniculus

<400> SEQUENCE: 70

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Thr Leu Thr Cys Thr Val Ser Gly Phe Ser Leu Ser
                35                  40                  45

Ser Tyr Ala Met Ser Trp Val Arg Gln Ala Pro Gly Lys Gly Leu Glu
    50                  55                  60

Trp Ile Gly Ile Ile Gly Gly Phe Gly Thr Thr Tyr Tyr Ala Thr Trp
65                  70                  75                  80

Ala Lys Gly Arg Phe Thr Ile Ser Lys Thr Ser Thr Thr Val Asp Leu
                85                  90                  95

Arg Ile Thr Ser Pro Thr Thr Glu Asp Thr Ala Thr Tyr Phe Cys Ala
                100                 105                 110

Arg Gly Gly Pro Gly Asn Gly Gly Asp Ile Trp Gly Gln Gly Thr Leu
                115                 120                 125

Val Thr Val Ser Ser Ala Ser Thr Lys Gly Pro Ser Val Phe Pro Leu
                130                 135                 140

Ala Pro Ser Ser Lys Ser Thr Ser Gly Gly Thr Ala Ala Leu Gly Cys
145                 150                 155                 160

Leu Val Lys Asp
```

<210> SEQ ID NO 71
<211> LENGTH: 13
<212> TYPE: PRT
<213> ORGANISM: Oryctolagus cuniculus

<400> SEQUENCE: 71

Gln Ala Ser Gln Ser Val Asp Asp Asn Asn Trp Leu Gly
1               5                   10

<210> SEQ ID NO 72
<211> LENGTH: 7
<212> TYPE: PRT
<213> ORGANISM: Oryctolagus cuniculus

<400> SEQUENCE: 72

Ser Ala Ser Thr Leu Ala Ser
1               5

<210> SEQ ID NO 73
<211> LENGTH: 10
<212> TYPE: PRT
<213> ORGANISM: Oryctolagus cuniculus

<400> SEQUENCE: 73

Ala Gly Gly Phe Ser Gly Asn Ile Phe Ala
1               5                   10

<210> SEQ ID NO 74
<211> LENGTH: 5
<212> TYPE: PRT
<213> ORGANISM: Oryctolagus cuniculus

<400> SEQUENCE: 74

Ser Tyr Ala Met Ser
1               5

<210> SEQ ID NO 75
<211> LENGTH: 16
<212> TYPE: PRT
<213> ORGANISM: Oryctolagus cuniculus

<400> SEQUENCE: 75

Ile Ile Gly Gly Phe Gly Thr Thr Tyr Tyr Ala Thr Trp Ala Lys Gly
1               5                   10                  15

<210> SEQ ID NO 76
<211> LENGTH: 9
<212> TYPE: PRT
<213> ORGANISM: Oryctolagus cuniculus

<400> SEQUENCE: 76

Gly Gly Pro Gly Asn Gly Gly Asp Ile
1               5

<210> SEQ ID NO 77
<211> LENGTH: 493
<212> TYPE: DNA
<213> ORGANISM: Oryctolagus cuniculus

<400> SEQUENCE: 77
atggacacga gggcccccac tcagctgctg gggctcctgc tgctctggct cccaggtgcc       60
acatttgccc aagtgctgac ccagactcca tcgcctgtgt ctgcagctgt gggaggcaca      120

```
gtcaccatca actgccaggc cagtcagagt gttgatgata caactggtt aggctggtat      180 cagcagaaac gagggcagcc tcccaagtac ctgatctatt ctgcatccac tctggcatct      240
ggggtcccat cgcggttcaa aggcagtgga tctgggacac agttcactct caccatcagc      300
gacctggagt gtgacgatgc tgccacttac tactgtgcag gcggttttag tggtaatatc      360
tttgctttcg gcggagggac cgaggtggtg gtcaaacgta cggtagcggc cccatctgtc      420
ttcatcttcc cgccatctga tgagcagttg aaatctggaa ctgcctctgt tgtgtgcctg      480
ctgaataact tct                                                         493

<210> SEQ ID NO 78
<211> LENGTH: 493
<212> TYPE: DNA
<213> ORGANISM: Oryctolagus cuniculus

<400> SEQUENCE: 78
atggagactg ggctgcgctg gcttctcctg gtcgctgtgc tcaaaggtgt ccagtgtcag       60
tcggtggagg agtccggggg tcgcctggtc acgcctggga cacccctgac actcacctgc      120
acagtctctg gcttctccct cagtagctat gcaatgagct gggtccgcca ggctccagga      180
aaggggctgg agtggatcgg aatcattggt ggttttggta ccacatacta cgcgacctgg      240
gcgaaaggcc gattcaccat ctccaaaacc tcgaccacgg tggatctgag aatcaccagt      300
ccgacaaccg aggacacggc cacctatttc tgtgccagag tggtcctgg taatggtggt      360 gacatctggg gccaagggac cctggtcacc gtctcgagcg cctccaccaa gggcccatcg      420
gtcttccccc tggcaccctc ctccaagagc acctctgggg gcacagcggc cctgggctgc      480
ctggtcaagg act                                                         493

<210> SEQ ID NO 79
<211> LENGTH: 39
<212> TYPE: DNA
<213> ORGANISM: Oryctolagus cuniculus

<400> SEQUENCE: 79
caggccagtc agagtgttga tgataacaac tggttaggc                              39

<210> SEQ ID NO 80
<211> LENGTH: 21
<212> TYPE: DNA
<213> ORGANISM: Oryctolagus cuniculus

<400> SEQUENCE: 80
tctgcatcca ctctggcatc t                                                 21

<210> SEQ ID NO 81
<211> LENGTH: 30
<212> TYPE: DNA
<213> ORGANISM: Oryctolagus cuniculus

<400> SEQUENCE: 81
gcaggcggtt ttagtggtaa tatctttgct                                        30

<210> SEQ ID NO 82
<211> LENGTH: 15
<212> TYPE: DNA
<213> ORGANISM: Oryctolagus cuniculus

<400> SEQUENCE: 82
agctatgcaa tgagc                                                        15
```

<210> SEQ ID NO 83
<211> LENGTH: 48
<212> TYPE: DNA
<213> ORGANISM: Oryctolagus cuniculus

<400> SEQUENCE: 83
atcattggtg gttttggtac cacatactac gcgacctggg cgaaaggc 48

<210> SEQ ID NO 84
<211> LENGTH: 27
<212> TYPE: DNA
<213> ORGANISM: Oryctolagus cuniculus

<400> SEQUENCE: 84
ggtggtcctg gtaatggtgg tgacatc 27

<210> SEQ ID NO 85
<211> LENGTH: 164
<212> TYPE: PRT
<213> ORGANISM: Oryctolagus cuniculus

<400> SEQUENCE: 85

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Val Pro Val Gly Gly Thr Val Thr Ile Lys Cys Gln Ser Ser
        35                  40                  45

Gln Ser Val Tyr Asn Asn Phe Leu Ser Trp Tyr Gln Gln Lys Pro Gly
    50                  55                  60

Gln Pro Pro Lys Leu Leu Ile Tyr Gln Ala Ser Lys Leu Ala Ser Gly
65                  70                  75                  80

Val Pro Asp Arg Phe Ser Gly Ser Gly Ser Gly Thr Gln Phe Thr Leu
                85                  90                  95

Thr Ile Ser Gly Val Gln Cys Asp Asp Ala Ala Thr Tyr Tyr Cys Leu
            100                 105                 110

Gly Gly Tyr Asp Asp Asp Ala Asp Asn Ala Phe Gly Gly Gly Thr Glu
        115                 120                 125

Val Val Val Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe

<210> SEQ ID NO 86
<211> LENGTH: 170
<212> TYPE: PRT
<213> ORGANISM: Oryctolagus cuniculus

<400> SEQUENCE: 86

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Asp Tyr Ala Met Ser Trp Val Arg Gln Ala Pro Gly Lys Gly Leu Glu

```
                    50                  55                  60
Trp Ile Gly Ile Ile Tyr Ala Gly Ser Gly Ser Thr Trp Tyr Ala Ser
 65                  70                  75                  80

Trp Ala Lys Gly Arg Phe Thr Ile Ser Lys Thr Ser Thr Thr Val Asp
                 85                  90                  95

Leu Lys Ile Thr Ser Pro Thr Glu Asp Thr Ala Thr Tyr Phe Cys
            100                 105                 110

Ala Arg Asp Gly Tyr Asp Asp Tyr Gly Asp Phe Asp Arg Leu Asp Leu
        115                 120                 125

Trp Gly Pro Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp
                165                 170
```

<210> SEQ ID NO 87
<211> LENGTH: 12
<212> TYPE: PRT
<213> ORGANISM: Oryctolagus cuniculus

<400> SEQUENCE: 87

```
Gln Ser Ser Gln Ser Val Tyr Asn Asn Phe Leu Ser
 1               5                  10
```

<210> SEQ ID NO 88
<211> LENGTH: 7
<212> TYPE: PRT
<213> ORGANISM: Oryctolagus cuniculus

<400> SEQUENCE: 88

```
Gln Ala Ser Lys Leu Ala Ser
 1               5
```

<210> SEQ ID NO 89
<211> LENGTH: 11
<212> TYPE: PRT
<213> ORGANISM: Oryctolagus cuniculus

<400> SEQUENCE: 89

```
Leu Gly Gly Tyr Asp Asp Ala Asp Asn Ala
 1               5                  10
```

<210> SEQ ID NO 90
<211> LENGTH: 5
<212> TYPE: PRT
<213> ORGANISM: Oryctolagus cuniculus

<400> SEQUENCE: 90

```
Asp Tyr Ala Met Ser
 1               5
```

<210> SEQ ID NO 91
<211> LENGTH: 17
<212> TYPE: PRT
<213> ORGANISM: Oryctolagus cuniculus

<400> SEQUENCE: 91

```
Ile Ile Tyr Ala Gly Ser Gly Ser Thr Trp Tyr Ala Ser Trp Ala Lys
 1               5                  10                  15

Gly
```

<210> SEQ ID NO 92
<211> LENGTH: 14
<212> TYPE: PRT
<213> ORGANISM: Oryctolagus cuniculus

<400> SEQUENCE: 92

Asp Gly Tyr Asp Asp Tyr Gly Asp Phe Asp Arg Leu Asp Leu
1               5                   10

<210> SEQ ID NO 93
<211> LENGTH: 492
<212> TYPE: DNA
<213> ORGANISM: Oryctolagus cuniculus

<400> SEQUENCE: 93
atggacacga gggcccccac tcagctgctg gggctcctgc tgctctggct cccaggtgcc    60
acatttgcag ccgtgctgac ccagacacca tcgcccgtgt ctgtacctgt gggaggcaca   120
gtcaccatca agtgccagtc cagtcagagt gtttataata atttcttatc gtggtatcag   180
cagaaaccag gcagcctcc caagctcctg atctaccagg catccaaact ggcatctggg    240
gtcccagata ggttcagcgg cagtggatct gggacacagt tcactctcac catcagcggc   300
gtgcagtgtg acgatgctgc cacttactac tgtctaggcg ttatgatga tgatgctgat    360 aatgctttcg gcggagggac cgaggtggtg gtcaaacgta cggtagcggc ccatctgtc    420 ttcatcttcc cgccatctga tgagcagttg aaatctggaa ctgcctctgt tgtgtgcctg   480
ctgaataact tc                                                       492

<210> SEQ ID NO 94
<211> LENGTH: 511
<212> TYPE: DNA
<213> ORGANISM: Oryctolagus cuniculus

<400> SEQUENCE: 94
atggagactg ggctgcgctg gcttctcctg gtcgctgtgc tcaaaggtgt ccagtgtcag    60
tcggtggagg agtccggggg tcgcctggtc acgcctggga caccctgac gctcacctgc    120 acagtctctg gaatcgacct cagtgactat gcaatgagct gggtccgcca ggctccaggg   180
aaggggctgg aatggatcgg aatcatttat gctggtagtg gtagcacatg gtacgcgagc   240
tgggcgaaag gccgattcac catctccaaa acctcgacca cggtggatct gaaaatcacc   300
agtccgacaa ccgaggacac ggccacctat ttctgtgcca gagatggata cgatgactat   360
ggtgatttcg atcgattgga tctctggggc ccaggcaccc tcgtcaccgt ctcgagcgcc   420
tccaccaagg gcccatcggt cttcccctg gcaccctcct ccaagagcac ctctgggggc    480
acagcggccc tgggctgcct ggtcaaggac t                                  511

<210> SEQ ID NO 95
<211> LENGTH: 36
<212> TYPE: DNA
<213> ORGANISM: Oryctolagus cuniculus

<400> SEQUENCE: 95
cagtccagtc agagtgttta taataatttc ttatcg                              36

<210> SEQ ID NO 96
<211> LENGTH: 21
<212> TYPE: DNA
<213> ORGANISM: Oryctolagus cuniculus

<400> SEQUENCE: 96
caggcatcca aactggcatc t                                              21

<210> SEQ ID NO 97
<211> LENGTH: 33
<212> TYPE: DNA
<213> ORGANISM: Oryctolagus cuniculus

<400> SEQUENCE: 97
ctaggcggtt atgatgatga tgctgataat gct                                 33

<210> SEQ ID NO 98
<211> LENGTH: 15
<212> TYPE: DNA
<213> ORGANISM: Oryctolagus cuniculus

<400> SEQUENCE: 98
gactatgcaa tgagc                                                     15

<210> SEQ ID NO 99
<211> LENGTH: 51
<212> TYPE: DNA
<213> ORGANISM: Oryctolagus cuniculus

<400> SEQUENCE: 99
atcatttatg ctggtagtgg tagcacatgg tacgcgagct gggcgaaagg c              51

<210> SEQ ID NO 100
<211> LENGTH: 42
<212> TYPE: DNA
<213> ORGANISM: Oryctolagus cuniculus

<400> SEQUENCE: 100
gatggatacg atgactatgg tgatttcgat cgattggatc tc                       42

<210> SEQ ID NO 101
<211> LENGTH: 164
<212> TYPE: PRT
<213> ORGANISM: Oryctolagus cuniculus

<400> SEQUENCE: 101

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Ser Ala Ala Val Gly Gly Thr Val Thr Ile Lys Cys Gln Ala Ser
        35                  40                  45

Gln Ser Ile Asn Asn Glu Leu Ser Trp Tyr Gln Lys Ser Gly Gln
    50                  55                  60

Arg Pro Lys Leu Leu Ile Tyr Arg Ala Ser Thr Leu Ala Ser Gly Val
65                  70                  75                  80

Ser Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Ser Leu Arg Asn Ile Asp Asn Ala Phe Gly Gly Gly Thr Glu
        115                 120                 125

Val Val Val Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe

<210> SEQ ID NO 102
<211> LENGTH: 166
<212> TYPE: PRT
<213> ORGANISM: Oryctolagus cuniculus

<400> SEQUENCE: 102

Met Glu Thr Gly Leu Arg Trp Leu Leu Leu Val Ala Val Leu Ser Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asn Tyr Tyr Met Thr Trp Val Arg Gln Ala Pro Gly Lys Gly Leu Glu
    50                  55                  60

Trp Ile Gly Met Ile Tyr Gly Ser Asp Glu Thr Ala Tyr Ala Asn Trp
65                  70                  75                  80

Ala Ile Gly Arg Phe Thr Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Asp Asp Ser Ser Asp Trp Asp Ala Lys Phe Asn Leu Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys
                165

<210> SEQ ID NO 103
<211> LENGTH: 11
<212> TYPE: PRT
<213> ORGANISM: Oryctolagus cuniculus

<400> SEQUENCE: 103

Gln Ala Ser Gln Ser Ile Asn Asn Glu Leu Ser
1               5                   10

<210> SEQ ID NO 104
<211> LENGTH: 7
<212> TYPE: PRT
<213> ORGANISM: Oryctolagus cuniculus

<400> SEQUENCE: 104

Arg Ala Ser Thr Leu Ala Ser
1               5

<210> SEQ ID NO 105
<211> LENGTH: 12
<212> TYPE: PRT
<213> ORGANISM: Oryctolagus cuniculus

<400> SEQUENCE: 105

Gln Gln Gly Tyr Ser Leu Arg Asn Ile Asp Asn Ala
1               5                   10

<210> SEQ ID NO 106
<211> LENGTH: 5
<212> TYPE: PRT
<213> ORGANISM: Oryctolagus cuniculus

<400> SEQUENCE: 106

Asn Tyr Tyr Met Thr
1               5

<210> SEQ ID NO 107
<211> LENGTH: 16
<212> TYPE: PRT
<213> ORGANISM: Oryctolagus cuniculus

<400> SEQUENCE: 107

Met Ile Tyr Gly Ser Asp Glu Thr Ala Tyr Ala Asn Trp Ala Ile Gly
1               5                   10                  15

<210> SEQ ID NO 108
<211> LENGTH: 12
<212> TYPE: PRT
<213> ORGANISM: Oryctolagus cuniculus

<400> SEQUENCE: 108

Asp Asp Ser Ser Asp Trp Asp Ala Lys Phe Asn Leu
1               5                   10

<210> SEQ ID NO 109
<211> LENGTH: 492
<212> TYPE: DNA
<213> ORGANISM: Oryctolagus cuniculus

<400> SEQUENCE: 109

| | |
|---|---|
| atggacacga gggcccccac tcagctgctg ggctcctgc tgctctggct cccaggtgcc | 60 |
| agatgtgcct atgatatgac ccagactcca gcctcggtgt ctgcagctgt gggaggcaca | 120 |
| gtcaccatca atgccaggc cagtcagagc attaacaatg aattatcctg gtatcagcag | 180 |
| aaatcagggc agcgtcccaa gctcctgatc tatagggcat ccactctggc atctggggtc | 240 |
| tcatcgcggt tcaaaggcag tggatctggg acagagttca ctctcaccat cagcgacctg | 300 |
| gagtgtgccg atgctgccac ttactactgt caacagggtt atagtctgag gaatattgat | 360 |
| aatgctttcg gcggagggac cgaggtggtg gtcaaacgta cggtagcggc cccatctgtc | 420 |
| ttcatcttcc cgccatctga tgagcagttg aaatctggaa ctgcctctgt tgtgtgcctg | 480 |
| ctgaataact tc | 492 |

<210> SEQ ID NO 110
<211> LENGTH: 499
<212> TYPE: DNA
<213> ORGANISM: Oryctolagus cuniculus

<400> SEQUENCE: 110

| | |
|---|---|
| atggagactg ggctgcgctg gcttctcctg gtcgctgtgc tctcaggtgt ccagtgtcag | 60 |
| tcgctggagg agtccggggg tcgcctggtc acgcctggga cacccctgac actcacctgc | 120 |
| acagcctctg gattctcccct cagtaactac tacatgacct gggtccgcca ggctccaggg | 180 |
| aaggggctgg aatggatcgg aatgatttat ggtagtgatg aaacagccta cgcgaactgg | 240 |
| gcgataggcc gattcaccat ctccaaaacc tcgaccacgg tggatctgaa aatgaccagt | 300 |
| ctgacagccg cggacacggc cacctatttc tgtgccagag atgatagtag tgactgggat | 360 |

```
gcaaaattta acttgtgggg ccaagggacc ctcgtcaccg tctcgagcgc ctccaccaag    420
ggcccatcgg tcttcccct ggcaccctcc tccaagagca cctctggggg cacagcggcc     480
ctgggctgcc tggtcaagg                                                 499
```

<210> SEQ ID NO 111
<211> LENGTH: 33
<212> TYPE: DNA
<213> ORGANISM: Oryctolagus cuniculus

<400> SEQUENCE: 111

```
caggccagtc agagcattaa caatgaatta tcc                                  33
```

<210> SEQ ID NO 112
<211> LENGTH: 21
<212> TYPE: DNA
<213> ORGANISM: Oryctolagus cuniculus

<400> SEQUENCE: 112

```
agggcatcca ctctggcatc t                                               21
```

<210> SEQ ID NO 113
<211> LENGTH: 36
<212> TYPE: DNA
<213> ORGANISM: Oryctolagus cuniculus

<400> SEQUENCE: 113

```
caacagggtt atagtctgag gaatattgat aatgct                               36
```

<210> SEQ ID NO 114
<211> LENGTH: 15
<212> TYPE: DNA
<213> ORGANISM: Oryctolagus cuniculus

<400> SEQUENCE: 114

```
aactactaca tgacc                                                      15
```

<210> SEQ ID NO 115
<211> LENGTH: 48
<212> TYPE: DNA
<213> ORGANISM: Oryctolagus cuniculus

<400> SEQUENCE: 115

```
atgatttatg gtagtgatga aacagcctac gcgaactggg cgataggc                  48
```

<210> SEQ ID NO 116
<211> LENGTH: 36
<212> TYPE: DNA
<213> ORGANISM: Oryctolagus cuniculus

<400> SEQUENCE: 116

```
gatgatagta gtgactggga tgcaaaattt aacttg                               36
```

<210> SEQ ID NO 117
<211> LENGTH: 109
<212> TYPE: PRT
<213> ORGANISM: Oryctolagus cuniculus

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr

```
              20                  25                  30

Tyr Met Thr Trp Val Arg Gln Ala Pro Gly Lys Gly Leu Glu Trp Val
                35                  40                  45

Gly Met Ile Tyr Gly Ser Asp Glu Thr Ala Tyr Ala Asn Trp Ala Ile
            50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu
                100                 105

<210> SEQ ID NO 118
<211> LENGTH: 109
<212> TYPE: PRT
<213> ORGANISM: Oryctolagus cuniculus

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
                20                  25                  30

Tyr Met Thr Trp Val Arg Gln Ala Pro Gly Lys Gly Leu Glu Trp Val
                35                  40                  45

Gly Met Ile Tyr Gly Ser Asp Glu Thr Ala Tyr Ala Asn Ser Ala Ile
            50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu
                100                 105

<210> SEQ ID NO 119
<211> LENGTH: 100
<212> TYPE: PRT
<213> ORGANISM: Oryctolagus cuniculus

<400> SEQUENCE: 119

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asn Asn Glu
                20                  25                  30

Leu Ser Trp Tyr Gln Gln Lys Pro Gly Lys Ala Pro Lys Leu Leu Ile
                35                  40                  45

Tyr Arg Ala Ser Thr Leu Ala Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Leu Arg Asn
                85                  90                  95

Ile Asp Asn Ala
            100

<210> SEQ ID NO 120
<211> LENGTH: 16
<212> TYPE: PRT
```

<213> ORGANISM: Oryctolagus cuniculus

<400> SEQUENCE: 120

Ile Ile Tyr Gly Ser Asp Glu Thr Ala Tyr Ala Thr Ser Ala Ile Gly
1               5                   10                  15

<210> SEQ ID NO 121
<211> LENGTH: 16
<212> TYPE: PRT
<213> ORGANISM: Oryctolagus cuniculus

<400> SEQUENCE: 121

Met Ile Tyr Gly Ser Asp Glu Thr Ala Tyr Ala Asn Ser Ala Ile Gly
1               5                   10                  15

<210> SEQ ID NO 122
<211> LENGTH: 123
<212> TYPE: PRT
<213> ORGANISM: Oryctolagus cuniculus

<400> SEQUENCE: 122

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
                20                  25                  30

Val Ser Ala Ala Val Gly Gly Thr Val Thr Ile Ser Cys Gln Ser Ser
            35                  40                  45

Gln Ser Val Gly Asn Asn Gln Asp Leu Ser Trp Phe Gln Gln Arg Pro
        50                  55                  60

Gly Gln Pro Pro Lys Leu Leu Ile Tyr Glu Ile Ser Lys Leu Glu Ser
65                  70                  75                  80

Gly Val Pro Ser Arg Phe Ser Gly Ser Gly Ser Gly Thr His Phe Thr
                85                  90                  95

Leu Thr Ile Ser Gly Val Gln Cys Asp Asp Ala Ala Thr Tyr Tyr Cys
            100                 105                 110

Leu Gly Gly Tyr Asp Asp Asp Ala Asp Asn Ala
        115                 120

<210> SEQ ID NO 123
<211> LENGTH: 128
<212> TYPE: PRT
<213> ORGANISM: Oryctolagus cuniculus

<400> SEQUENCE: 123

Met Glu Thr Gly Leu Arg Trp Leu Leu Leu Val Ala Val Leu Lys Gly
1               5                   10                  15

Val Gln Cys His Ser Val Glu Glu Ser Gly Gly Arg Leu Val Thr Pro
                20                  25                  30

Gly Thr Pro Leu Thr Leu Thr Cys Thr Val Ser Gly Phe Ser Leu Ser
            35                  40                  45

Ser Arg Thr Met Ser Trp Val Arg Gln Ala Pro Gly Lys Gly Leu Glu
        50                  55                  60

Trp Ile Gly Tyr Ile Trp Ser Gly Gly Ser Thr Tyr Tyr Ala Thr Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Leu Gly Asp Thr Gly Gly His Ala Tyr Ala Thr Arg Leu Asn Leu
            115                 120                 125

<210> SEQ ID NO 124
<211> LENGTH: 13
<212> TYPE: PRT
<213> ORGANISM: Oryctolagus cuniculus

<400> SEQUENCE: 124

Gln Ser Ser Gln Ser Val Gly Asn Asn Gln Asp Leu Ser
1               5                   10

<210> SEQ ID NO 125
<211> LENGTH: 7
<212> TYPE: PRT
<213> ORGANISM: Oryctolagus cuniculus

<400> SEQUENCE: 125

Glu Ile Ser Lys Leu Glu Ser
1               5

<210> SEQ ID NO 126
<211> LENGTH: 11
<212> TYPE: PRT
<213> ORGANISM: Oryctolagus cuniculus

<400> SEQUENCE: 126

Leu Gly Gly Tyr Asp Asp Asp Ala Asp Asn Ala
1               5                   10

<210> SEQ ID NO 127
<211> LENGTH: 5
<212> TYPE: PRT
<213> ORGANISM: Oryctolagus cuniculus

<400> SEQUENCE: 127

Ser Arg Thr Met Ser
1               5

<210> SEQ ID NO 128
<211> LENGTH: 16
<212> TYPE: PRT
<213> ORGANISM: Oryctolagus cuniculus

<400> SEQUENCE: 128

Tyr Ile Trp Ser Gly Gly Ser Thr Tyr Tyr Ala Thr Trp Ala Lys Gly
1               5                   10                  15

<210> SEQ ID NO 129
<211> LENGTH: 15
<212> TYPE: PRT
<213> ORGANISM: Oryctolagus cuniculus

<400> SEQUENCE: 129

Leu Gly Asp Thr Gly Gly His Ala Tyr Ala Thr Arg Leu Asn Leu
1               5                   10                  15

<210> SEQ ID NO 130
<211> LENGTH: 369
<212> TYPE: DNA
<213> ORGANISM: Oryctolagus cuniculus

<400> SEQUENCE: 130
atggacacga gggcccccac tcagctgctg gggctcctgc tgctctggct cccaggtgcc       60

-continued

```
acatttgcag ccgtgctgac ccagacacca tcacccgtgt ctgcagctgt gggaggcaca    120
gtcaccatca gttgccagtc cagtcagagt gttggtaata accaggactt atcctggttt    180
cagcagagac cagggcagcc tcccaagctc ctgatctacg aaatatccaa actggaatct    240
ggggtcccat cgcggttcag cggcagtgga tctgggacac acttcactct caccatcagc    300
ggcgtacagt gtgacgatgc tgccacttac tactgtctag gcggttatga tgatgatgct    360
gataatgct                                                            369
```

<210> SEQ ID NO 131
<211> LENGTH: 384
<212> TYPE: DNA
<213> ORGANISM: Oryctolagus cuniculus

<400> SEQUENCE: 131

```
atggagactg ggctgcgctg gcttctcctg gtcgctgtgc tcaaaggtgt ccagtgtcac     60
tcggtggagg agtccggggg tcgcctggtc acgcctggga caccctgac actcacctgc    120 acagtctctg gattctccct cagtagtcgt acaatgtcct gggtccgcca ggctccaggg    180
aaggggctgg agtggatcgg atacatttgg agtggtggta gcacatacta cgcgacctgg    240
gcgaaaggcc gattcaccat ctccaaaacc tcgaccacgg tggatctgaa aatcaccagt    300
ccgacaaccg aggacacggc cacctatttc tgtgccagat gggcgatac tggtggtcac    360 gcttatgcta ctcgcttaaa tctc                                            384
```

<210> SEQ ID NO 132
<211> LENGTH: 39
<212> TYPE: DNA
<213> ORGANISM: Oryctolagus cuniculus

<400> SEQUENCE: 132

```
cagtccagtc agagtgttgg taataaccag gacttatcc                            39
```

<210> SEQ ID NO 133
<211> LENGTH: 21
<212> TYPE: DNA
<213> ORGANISM: Oryctolagus cuniculus

<400> SEQUENCE: 133

```
gaaatatcca aactggaatc t                                               21
```

<210> SEQ ID NO 134
<211> LENGTH: 33
<212> TYPE: DNA
<213> ORGANISM: Oryctolagus cuniculus

<400> SEQUENCE: 134

```
ctaggcggtt atgatgatga tgctgataat gct                                  33
```

<210> SEQ ID NO 135
<211> LENGTH: 15
<212> TYPE: DNA
<213> ORGANISM: Oryctolagus cuniculus

<400> SEQUENCE: 135

```
agtcgtacaa tgtcc                                                      15
```

<210> SEQ ID NO 136
<211> LENGTH: 48
<212> TYPE: DNA
<213> ORGANISM: Oryctolagus cuniculus

<400> SEQUENCE: 136
tacatttgga gtggtggtag cacatactac gcgacctggg cgaaaggc         48

<210> SEQ ID NO 137
<211> LENGTH: 45
<212> TYPE: DNA
<213> ORGANISM: Oryctolagus cuniculus

<400> SEQUENCE: 137
ttgggcgata ctggtggtca cgcttatgct actcgcttaa atctc            45

<210> SEQ ID NO 138
<211> LENGTH: 123
<212> TYPE: PRT
<213> ORGANISM: Oryctolagus cuniculus

<400> SEQUENCE: 138

Met Asp Thr Arg Ala Pro Thr Gln Leu Leu Gly Leu Leu Leu Trp
1               5                   10                  15

Leu Pro Gly Ala Thr Phe Ala Ala Val Leu Thr Gln Thr Pro Ser Ser
            20                  25                  30

Val Ser Ala Ala Val Gly Gly Thr Val Ser Ile Ser Cys Gln Ser Ser
        35                  40                  45

Gln Ser Val Tyr Ser Asn Lys Tyr Leu Ala Trp Tyr Gln Gln Lys Pro
    50                  55                  60

Gly Gln Pro Pro Lys Leu Leu Ile Tyr Trp Thr Ser Lys Leu Ala Ser
65                  70                  75                  80

Gly Ala Pro Ser Arg Phe Ser Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Leu Gly Ala Tyr Asp Asp Asp Ala Asp Asn Ala
        115                 120

<210> SEQ ID NO 139
<211> LENGTH: 126
<212> TYPE: PRT
<213> ORGANISM: Oryctolagus cuniculus

<400> SEQUENCE: 139

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Lys Pro
            20                  25                  30

Asp Glu Thr Leu Thr Leu Thr Cys Thr Ala Ser Gly Phe Ser Leu Glu
        35                  40                  45

Gly Gly Tyr Met Thr Trp Val Arg Gln Ala Pro Gly Lys Gly Leu Glu
    50                  55                  60

Trp Ile Gly Ile Ser Tyr Asp Ser Gly Ser Thr Tyr Tyr Ala Ser Trp
65                  70                  75                  80

Ala Lys Gly Arg Phe Thr Ile Ser Lys Thr Ser Ser Thr Thr Val Asp
                85                  90                  95

Leu Lys Met Thr Ser Leu Thr Thr Glu Asp Thr Ala Thr Tyr Phe Cys
            100                 105                 110

Val Arg Ser Leu Lys Tyr Pro Thr Val Thr Ser Asp Leu
        115                 120                 125

<210> SEQ ID NO 140
<211> LENGTH: 13
<212> TYPE: PRT
<213> ORGANISM: Oryctolagus cuniculus

<400> SEQUENCE: 140

Gln Ser Ser Gln Ser Val Tyr Ser Asn Lys Tyr Leu Ala
1               5                   10

<210> SEQ ID NO 141
<211> LENGTH: 7
<212> TYPE: PRT
<213> ORGANISM: Oryctolagus cuniculus

<400> SEQUENCE: 141

Trp Thr Ser Lys Leu Ala Ser
1               5

<210> SEQ ID NO 142
<211> LENGTH: 11
<212> TYPE: PRT
<213> ORGANISM: Oryctolagus cuniculus

<400> SEQUENCE: 142

Leu Gly Ala Tyr Asp Asp Ala Asp Asn Ala
1               5                   10

<210> SEQ ID NO 143
<211> LENGTH: 5
<212> TYPE: PRT
<213> ORGANISM: Oryctolagus cuniculus

<400> SEQUENCE: 143

Gly Gly Tyr Met Thr
1               5

<210> SEQ ID NO 144
<211> LENGTH: 16
<212> TYPE: PRT
<213> ORGANISM: Oryctolagus cuniculus

<400> SEQUENCE: 144

Ile Ser Tyr Asp Ser Gly Ser Thr Tyr Tyr Ala Ser Trp Ala Lys Gly
1               5                   10                  15

<210> SEQ ID NO 145
<211> LENGTH: 12
<212> TYPE: PRT
<213> ORGANISM: Oryctolagus cuniculus

<400> SEQUENCE: 145

Ser Leu Lys Tyr Pro Thr Val Thr Ser Asp Asp Leu
1               5                   10

<210> SEQ ID NO 146
<211> LENGTH: 369
<212> TYPE: DNA
<213> ORGANISM: Oryctolagus cuniculus

<400> SEQUENCE: 146
atggacacga gggcccccac tcagctgctg gggctcctgc tgctctggct cccaggtgcc      60
acatttgcag ccgtgctgac ccagacacca tcgtccgtgt ctgcagctgt gggaggcaca     120
gtcagcatca gttgccagtc cagtcagagt gtttatagta ataagtacct agcctggtat     180

```
cagcagaaac cagggcagcc tcccaagctc ctgatctact ggacatccaa actggcatct      240
ggggccccat cacggttcag cggcagtgga tctgggacac aattcactct caccatcagc      300
ggcgtgcagt gtgacgatgc tgccacttac tactgtctag cgcttatga tgatgatgct      360 gataatgct                                                             369
```

```
<210> SEQ ID NO 147
<211> LENGTH: 378
<212> TYPE: DNA
<213> ORGANISM: Oryctolagus cuniculus

<400> SEQUENCE: 147
atggagactg ggctgcgctg gcttctcctg gtcgctgtgc tcaaaggtgt ccagtgtcag       60
tcggtggaag agtccggggg tcgcctggtc aagcctgacg aaaccctgac actcacctgc      120
acagcctctg gattctccct ggagggcggc tacatgacct gggtccgcca ggctccaggg      180
aaggggctgg aatggatcgg aatcagttat gatagtggta gcacatacta cgcgagctgg      240
gcgaaaggcc gattcaccat ctccaagacc tcgtcgacca cggtggatct gaaaatgacc      300
agtctgacaa ccgaggacac ggccacctat ttctgcgtca gatcactaaa atatcctact      360
gttacttctg atgacttg                                                   378
```

```
<210> SEQ ID NO 148
<211> LENGTH: 39
<212> TYPE: DNA
<213> ORGANISM: Oryctolagus cuniculus

<400> SEQUENCE: 148
cagtccagtc agagtgttta tagtaataag tacctagcc                             39
```

```
<210> SEQ ID NO 149
<211> LENGTH: 21
<212> TYPE: DNA
<213> ORGANISM: Oryctolagus cuniculus

<400> SEQUENCE: 149
tggacatcca aactggcatc t                                                21
```

```
<210> SEQ ID NO 150
<211> LENGTH: 33
<212> TYPE: DNA
<213> ORGANISM: Oryctolagus cuniculus

<400> SEQUENCE: 150
ctaggcgctt atgatgatga tgctgataat gct                                   33
```

```
<210> SEQ ID NO 151
<211> LENGTH: 15
<212> TYPE: DNA
<213> ORGANISM: Oryctolagus cuniculus

<400> SEQUENCE: 151
ggcggctaca tgacc                                                       15
```

```
<210> SEQ ID NO 152
<211> LENGTH: 48
<212> TYPE: DNA
<213> ORGANISM: Oryctolagus cuniculus

<400> SEQUENCE: 152
```
atcagttatg atagtggtag cacatactac gcgagctggg cgaaaggc         48

<210> SEQ ID NO 153
<211> LENGTH: 36
<212> TYPE: DNA
<213> ORGANISM: Oryctolagus cuniculus

<400> SEQUENCE: 153
tcactaaaat atcctactgt tacttctgat gacttg         36

<210> SEQ ID NO 154
<211> LENGTH: 123
<212> TYPE: PRT
<213> ORGANISM: Oryctolagus cuniculus

<400> SEQUENCE: 154

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
                20                  25                  30

Val Ser Ala Ala Val Gly Gly Thr Val Thr Ile Ser Cys Gln Ser Ser
            35                  40                  45

Gln Ser Val Tyr Asn Asn Asn Asp Leu Ala Trp Tyr Gln Gln Lys Pro
        50                  55                  60

Gly Gln Pro Pro Lys Leu Leu Ile Tyr Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Asp Asp Ala Ala Ala Tyr Tyr Cys
            100                 105                 110

Leu Gly Gly Tyr Asp Asp Asp Ala Asp Asn Ala
        115                 120

<210> SEQ ID NO 155
<211> LENGTH: 129
<212> TYPE: PRT
<213> ORGANISM: Oryctolagus cuniculus

<400> SEQUENCE: 155

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Thr Leu Thr Cys Thr Val Ser Gly Leu Ser Leu Ser
            35                  40                  45

Ser Asn Thr Ile Asn Trp Val Arg Gln Ala Pro Gly Lys Gly Leu Glu
        50                  55                  60

Trp Ile Gly Tyr Ile Trp Ser Gly Gly Ser Thr Tyr Tyr Ala Ser Trp
65                  70                  75                  80

Val Asn Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Gly Gly Tyr Ala Ser Gly Gly Tyr Pro Tyr Ala Thr Arg Leu Asp
        115                 120                 125

Leu

<210> SEQ ID NO 156
<211> LENGTH: 13
<212> TYPE: PRT
<213> ORGANISM: Oryctolagus cuniculus

<400> SEQUENCE: 156

Gln Ser Ser Gln Ser Val Tyr Asn Asn Asn Asp Leu Ala
1               5                   10

<210> SEQ ID NO 157
<211> LENGTH: 7
<212> TYPE: PRT
<213> ORGANISM: Oryctolagus cuniculus

<400> SEQUENCE: 157

Tyr Ala Ser Thr Leu Ala Ser
1               5

<210> SEQ ID NO 158
<211> LENGTH: 11
<212> TYPE: PRT
<213> ORGANISM: Oryctolagus cuniculus

<400> SEQUENCE: 158

Leu Gly Gly Tyr Asp Asp Asp Ala Asp Asn Ala
1               5                   10

<210> SEQ ID NO 159
<211> LENGTH: 5
<212> TYPE: PRT
<213> ORGANISM: Oryctolagus cuniculus

<400> SEQUENCE: 159

Ser Asn Thr Ile Asn
1               5

<210> SEQ ID NO 160
<211> LENGTH: 16
<212> TYPE: PRT
<213> ORGANISM: Oryctolagus cuniculus

<400> SEQUENCE: 160

Tyr Ile Trp Ser Gly Gly Ser Thr Tyr Tyr Ala Ser Trp Val Asn Gly
1               5                   10                  15

<210> SEQ ID NO 161
<211> LENGTH: 16
<212> TYPE: PRT
<213> ORGANISM: Oryctolagus cuniculus

<400> SEQUENCE: 161

Gly Gly Tyr Ala Ser Gly Gly Tyr Pro Tyr Ala Thr Arg Leu Asp Leu
1               5                   10                  15

<210> SEQ ID NO 162
<211> LENGTH: 369
<212> TYPE: DNA
<213> ORGANISM: Oryctolagus cuniculus

<400> SEQUENCE: 162
atggacacga gggcccccac tcagctgctg ggctcctgc tgctctggct cccaggtgcc      60
acatttgcag ccgtgctgac ccagacacca tcaccgtgt ctgcagctgt gggaggcaca     120
gtcaccatca gttgccagtc cagtcagagt gtttataata taacgactt agcctggtat     180

```
cagcagaaac cagggcagcc tcctaaactc ctgatctatt atgcatccac tctggcatct    240
ggggtcccat cgcggttcaa aggcagtgga tctgggacac agttcactct caccatcagc    300
ggcgtgcagt gtgacgatgc tgccgcttac tactgtctag gcggttatga tgatgatgct    360
gataatgct                                                            369

<210> SEQ ID NO 163
<211> LENGTH: 387
<212> TYPE: DNA
<213> ORGANISM: Oryctolagus cuniculus

<400> SEQUENCE: 163
atggagactg ggctgcgctg gcttctcctg gtcgctgtgc tcaaaggtgt ccagtgtcag     60
tcggtggagg agtccggggg tcgcctggtc acgcctggga cacccctgac actcacctgc    120
acagtatctg gattatccct cagtagcaat acaataaact gggtccgcca ggctccaggg    180
aaggggctgg agtggatcgg atacatttgg agtggtggta gtacatacta cgcgagctgg    240
gtgaatggtc gattcaccat ctccaaaacc tcgaccacgg tggatctgaa aatcaccagt    300
ccgacaaccg aggacacggc cacctatttc tgtgccagag ggggttacgc tagtggtggt    360
tatccttatg ccactcggtt ggatctc                                        387

<210> SEQ ID NO 164
<211> LENGTH: 39
<212> TYPE: DNA
<213> ORGANISM: Oryctolagus cuniculus

<400> SEQUENCE: 164
cagtccagtc agagtgttta taataataac gacttagcc                            39

<210> SEQ ID NO 165
<211> LENGTH: 21
<212> TYPE: DNA
<213> ORGANISM: Oryctolagus cuniculus

<400> SEQUENCE: 165
tatgcatcca ctctggcatc t                                               21

<210> SEQ ID NO 166
<211> LENGTH: 33
<212> TYPE: DNA
<213> ORGANISM: Oryctolagus cuniculus

<400> SEQUENCE: 166
ctaggcggtt atgatgatga tgctgataat gct                                  33

<210> SEQ ID NO 167
<211> LENGTH: 15
<212> TYPE: DNA
<213> ORGANISM: Oryctolagus cuniculus

<400> SEQUENCE: 167
agcaatacaa taaac                                                      15

<210> SEQ ID NO 168
<211> LENGTH: 48
<212> TYPE: DNA
<213> ORGANISM: Oryctolagus cuniculus

<400> SEQUENCE: 168
tacatttgga gtggtggtag tacatactac gcgagctggg tgaatggt                  48
```

<210> SEQ ID NO 169
<211> LENGTH: 48
<212> TYPE: DNA
<213> ORGANISM: Oryctolagus cuniculus

<400> SEQUENCE: 169
gggggttacg ctagtggtgg ttatccttat gccactcggt tggatctc           48

<210> SEQ ID NO 170
<211> LENGTH: 123
<212> TYPE: PRT
<213> ORGANISM: Oryctolagus cuniculus

<400> SEQUENCE: 170

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Ser
            20                  25                  30

Val Ser Ala Ala Val Gly Gly Thr Val Thr Ile Asn Cys Gln Ser Ser
        35                  40                  45

Gln Ser Val Tyr Asn Asn Asp Tyr Leu Ser Trp Tyr Gln Gln Arg Pro
    50                  55                  60

Gly Gln Arg Pro Lys Leu Leu Ile Tyr Gly Ala Ser Lys Leu Ala Ser
65                  70                  75                  80

Gly Val Pro Ser Arg Phe Lys Gly Ser Gly Ser Gly Lys Gln Phe Thr
                85                  90                  95

Leu Thr Ile Ser Gly Val Gln Cys Asp Asp Ala Ala Thr Tyr Tyr Cys
            100                 105                 110

Leu Gly Asp Tyr Asp Asp Asp Ala Asp Asn Thr
        115                 120

<210> SEQ ID NO 171
<211> LENGTH: 123
<212> TYPE: PRT
<213> ORGANISM: Oryctolagus cuniculus

<400> SEQUENCE: 171

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Thr Leu Ser
        35                  40                  45

Thr Asn Tyr Tyr Leu Ser Trp Val Arg Gln Ala Pro Gly Lys Gly Leu
    50                  55                  60

Glu Trp Ile Gly Ile Ile Tyr Pro Ser Gly Asn Thr Tyr Cys Ala Lys
65                  70                  75                  80

Trp Ala Lys Gly Arg Phe Thr Ile Ser Lys Thr Ser Ser Thr Thr Val
                85                  90                  95

Asp Leu Lys Met Thr Ser Pro Thr Thr Glu Asp Thr Ala Thr Tyr Phe
            100                 105                 110

Cys Ala Arg Asn Tyr Gly Gly Asp Glu Ser Leu
        115                 120

<210> SEQ ID NO 172
<211> LENGTH: 13
<212> TYPE: PRT

<213> ORGANISM: Oryctolagus cuniculus

<400> SEQUENCE: 172

Gln Ser Ser Gln Ser Val Tyr Asn Asn Asp Tyr Leu Ser
1               5                   10

<210> SEQ ID NO 173
<211> LENGTH: 7
<212> TYPE: PRT
<213> ORGANISM: Oryctolagus cuniculus

<400> SEQUENCE: 173

Gly Ala Ser Lys Leu Ala Ser
1               5

<210> SEQ ID NO 174
<211> LENGTH: 11
<212> TYPE: PRT
<213> ORGANISM: Oryctolagus cuniculus

<400> SEQUENCE: 174

Leu Gly Asp Tyr Asp Asp Asp Ala Asp Asn Thr
1               5                   10

<210> SEQ ID NO 175
<211> LENGTH: 6
<212> TYPE: PRT
<213> ORGANISM: Oryctolagus cuniculus

<400> SEQUENCE: 175

Thr Asn Tyr Tyr Leu Ser
1               5

<210> SEQ ID NO 176
<211> LENGTH: 16
<212> TYPE: PRT
<213> ORGANISM: Oryctolagus cuniculus

<400> SEQUENCE: 176

Ile Ile Tyr Pro Ser Gly Asn Thr Tyr Cys Ala Lys Trp Ala Lys Gly
1               5                   10                  15

<210> SEQ ID NO 177
<211> LENGTH: 8
<212> TYPE: PRT
<213> ORGANISM: Oryctolagus cuniculus

<400> SEQUENCE: 177

Asn Tyr Gly Gly Asp Glu Ser Leu
1               5

<210> SEQ ID NO 178
<211> LENGTH: 369
<212> TYPE: DNA
<213> ORGANISM: Oryctolagus cuniculus

<400> SEQUENCE: 178
atggacacga gggcccccac tcagctgctg gggctcctgc tgctctggct cccaggtgcc      60
acatttgcag ccgtgctgac ccagacacca tcctccgtgt ctgcagctgt gggaggcaca     120
gtcaccatca attgccagtc cagtcagagt gtttataata cgactactt atcctggtat     180 caacagaggc cagggcaacg tcccaagctc ctaatctatg gtgcttccaa actggcatct     240
ggggtcccgt cacggttcaa aggcagtgga tctgggaaac agtttactct caccatcagc     300

```
ggcgtgcagt gtgacgatgc tgccacttac tactgtctgg gcgattatga tgatgatgct    360
gataatact                                                             369

<210> SEQ ID NO 179
<211> LENGTH: 369
<212> TYPE: DNA
<213> ORGANISM: Oryctolagus cuniculus

<400> SEQUENCE: 179
atggagactg ggctgcgctg gcttctcctg gtcgctgtgc tcaaaggtgt ccagtgtcag     60
tcgctggagg agtccggggg tcgcctggtc acgcctggga cccccctgac actcacttgc    120
acagtctctg gattcaccct cagtaccaac tactacctga gctgggtccg ccaggctcca    180
gggaaggggc tagaatggat cggaatcatt tatcctagtg gtaacacata ttgcgcgaag    240
tgggcgaaag ccgattcac catctccaaa acctcgtcga ccacggtgga tctgaaaatg    300
accagtccga caaccgagga cacagccacg tatttctgtg ccagaaatta tggtggtgat    360
gaaagtttg                                                             369

<210> SEQ ID NO 180
<211> LENGTH: 39
<212> TYPE: DNA
<213> ORGANISM: Oryctolagus cuniculus

<400> SEQUENCE: 180
cagtccagtc agagtgttta taataacgac tacttatcc                            39

<210> SEQ ID NO 181
<211> LENGTH: 21
<212> TYPE: DNA
<213> ORGANISM: Oryctolagus cuniculus

<400> SEQUENCE: 181
ggtgcttcca aactggcatc t                                               21

<210> SEQ ID NO 182
<211> LENGTH: 33
<212> TYPE: DNA
<213> ORGANISM: Oryctolagus cuniculus

<400> SEQUENCE: 182
ctgggcgatt atgatgatga tgctgataat act                                  33

<210> SEQ ID NO 183
<211> LENGTH: 18
<212> TYPE: DNA
<213> ORGANISM: Oryctolagus cuniculus

<400> SEQUENCE: 183
accaactact acctgagc                                                   18

<210> SEQ ID NO 184
<211> LENGTH: 48
<212> TYPE: DNA
<213> ORGANISM: Oryctolagus cuniculus

<400> SEQUENCE: 184
atcatttatc ctagtggtaa cacatattgc gcgaagtggg cgaaaggc                  48

<210> SEQ ID NO 185
```

```
<211> LENGTH: 24
<212> TYPE: DNA
<213> ORGANISM: Oryctolagus cuniculus

<400> SEQUENCE: 185
aattatggtg gtgatgaaag tttg                                              24

<210> SEQ ID NO 186
<211> LENGTH: 119
<212> TYPE: PRT
<213> ORGANISM: Oryctolagus cuniculus

<400> SEQUENCE: 186
```

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Glu Ala Ala Val Gly Gly Thr Val Thr Ile Lys Cys Gln Ala Ser
        35                  40                  45

Glu Thr Ile Gly Asn Ala Leu Ala Trp Tyr Gln Gln Lys Ser Gly Gln
    50                  55                  60

Pro Pro Lys Leu Leu Ile Tyr Lys Ala Ser Lys Leu Ala Ser Gly Val
65                  70                  75                  80

Pro Ser Arg Phe Lys Gly Ser Gly Ser Gly Thr Glu Tyr Thr Leu Thr
                85                  90                  95

Ile Ser Asp Leu Glu Cys Ala Asp Ala Ala Thr Tyr Tyr Cys Gln Trp
            100                 105                 110

Cys Tyr Phe Gly Asp Ser Val
        115

```
<210> SEQ ID NO 187
<211> LENGTH: 128
<212> TYPE: PRT
<213> ORGANISM: Oryctolagus cuniculus

<400> SEQUENCE: 187
```

Met Glu Thr Gly Leu Arg Trp Leu Leu Leu Val Thr Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Thr Ala Ser Gly Phe Asp Phe
        35                  40                  45

Ser Ser Gly Tyr Tyr Met Cys Trp Val Arg Gln Ala Pro Gly Lys Gly
    50                  55                  60

Leu Glu Trp Ile Ala Cys Ile Phe Thr Ile Thr Asn Thr Tyr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Leu Cys Ala Arg Gly Ile Tyr Ser Asp Asn Asn Tyr Tyr Ala Leu
        115                 120                 125

```
<210> SEQ ID NO 188
<211> LENGTH: 11
<212> TYPE: PRT
<213> ORGANISM: Oryctolagus cuniculus

<400> SEQUENCE: 188
```

```
<210> SEQ ID NO 189
<211> LENGTH: 7
<212> TYPE: PRT
<213> ORGANISM: Oryctolagus cuniculus

<400> SEQUENCE: 189

Gln Ala Ser Glu Thr Ile Gly Asn Ala Leu Ala
1               5                   10

<210> SEQ ID NO 189
<211> LENGTH: 7
<212> TYPE: PRT
<213> ORGANISM: Oryctolagus cuniculus

<400> SEQUENCE: 189

Lys Ala Ser Lys Leu Ala Ser
1               5

<210> SEQ ID NO 190
<211> LENGTH: 9
<212> TYPE: PRT
<213> ORGANISM: Oryctolagus cuniculus

<400> SEQUENCE: 190

Gln Trp Cys Tyr Phe Gly Asp Ser Val
1               5

<210> SEQ ID NO 191
<211> LENGTH: 6
<212> TYPE: PRT
<213> ORGANISM: Oryctolagus cuniculus

<400> SEQUENCE: 191

Ser Gly Tyr Tyr Met Cys
1               5

<210> SEQ ID NO 192
<211> LENGTH: 17
<212> TYPE: PRT
<213> ORGANISM: Oryctolagus cuniculus

<400> SEQUENCE: 192

Cys Ile Phe Thr Ile Thr Thr Asn Thr Tyr Tyr Ala Ser Trp Ala Lys
1               5                   10                  15
Gly

<210> SEQ ID NO 193
<211> LENGTH: 11
<212> TYPE: PRT
<213> ORGANISM: Oryctolagus cuniculus

<400> SEQUENCE: 193

Gly Ile Tyr Ser Asp Asn Asn Tyr Tyr Ala Leu
1               5                   10

<210> SEQ ID NO 194
<211> LENGTH: 357
<212> TYPE: DNA
<213> ORGANISM: Oryctolagus cuniculus

<400> SEQUENCE: 194
atggacacga gggcccccac tcagctgctg gggctcctgc tgctctggct cccaggtgcc    60
agatgtgatg ttgtgatgac ccagactcca gcctccgtgg aggcagctgt gggaggcaca   120
gtcaccatca agtgccaggc cagtgagacc attggcaatg cattagcctg gtatcagcag   180
aaatcagggc agcctcccaa gctcctgatc tacaaggcat ccaaactggc atctggggtc   240
ccatcgcggt tcaaaggcag tggatctggg acagagtaca ctctcaccat cagcgacctg   300
```

```
gagtgtgccg atgctgccac ttactactgt caatggtgtt attttggtga tagtgtt        357
```

<210> SEQ ID NO 195
<211> LENGTH: 384
<212> TYPE: DNA
<213> ORGANISM: Oryctolagus cuniculus

<400> SEQUENCE: 195

```
atggagactg ggctgcgctg gcttctcctg gtcactgtgc tcaaaggtgt ccagtgtcag        60
gagcagctgg tggagtccgg gggaggcctg gtccagcctg agggatccct gacactcacc       120
tgcacagcct ctggattcga cttcagtagc ggctactaca tgtgctgggt ccgccaggct       180
ccagggaagg ggctggagtg gatcgcgtgt attttcacta ttactactaa cacttactac       240
gcgagctggg cgaaaggccg attcaccatc tccaagacct cgtcgaccac ggtgactctg       300
caaatgacca gtctgacagc cgcggacacg gccacctatc tctgtgcgag agggatttat       360
tctgataata attattatgc cttg                                              384
```

<210> SEQ ID NO 196
<211> LENGTH: 33
<212> TYPE: DNA
<213> ORGANISM: Oryctolagus cuniculus

<400> SEQUENCE: 196

```
caggccagtg agaccattgg caatgcatta gcc                                     33
```

<210> SEQ ID NO 197
<211> LENGTH: 21
<212> TYPE: DNA
<213> ORGANISM: Oryctolagus cuniculus

<400> SEQUENCE: 197

```
aaggcatcca aactggcatc t                                                  21
```

<210> SEQ ID NO 198
<211> LENGTH: 27
<212> TYPE: DNA
<213> ORGANISM: Oryctolagus cuniculus

<400> SEQUENCE: 198

```
caatggtgtt attttggtga tagtgtt                                            27
```

<210> SEQ ID NO 199
<211> LENGTH: 18
<212> TYPE: DNA
<213> ORGANISM: Oryctolagus cuniculus

<400> SEQUENCE: 199

```
agcggctact acatgtgc                                                      18
```

<210> SEQ ID NO 200
<211> LENGTH: 51
<212> TYPE: DNA
<213> ORGANISM: Oryctolagus cuniculus

<400> SEQUENCE: 200

```
tgtattttca ctattactac taacacttac tacgcgagct gggcgaaagg c                 51
```

<210> SEQ ID NO 201
<211> LENGTH: 33
<212> TYPE: DNA
<213> ORGANISM: Oryctolagus cuniculus

<400> SEQUENCE: 201
gggatttatt ctgataataa ttattatgcc ttg                33

<210> SEQ ID NO 202
<211> LENGTH: 119
<212> TYPE: PRT
<213> ORGANISM: Oryctolagus cuniculus

<400> SEQUENCE: 202

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Glu Ala Ala Val Gly Gly Thr Val Thr Ile Lys Cys Gln Ala Ser
        35                  40                  45

Glu Ser Ile Gly Asn Ala Leu Ala Trp Tyr Gln Gln Lys Pro Gly Gln
    50                  55                  60

Pro Pro Lys Leu Leu Ile Tyr Lys Ala Ser Thr Leu Ala Ser Gly Val
65                  70                  75                  80

Pro Ser Arg Phe Ser Gly Ser Gly Ser Gly Thr Glu Phe Thr Leu Thr
                85                  90                  95

Ile Ser Gly Val Gln Cys Ala Asp Ala Ala Tyr Tyr Cys Gln Trp
            100                 105                 110

Cys Tyr Phe Gly Asp Ser Val
        115

<210> SEQ ID NO 203
<211> LENGTH: 128
<212> TYPE: PRT
<213> ORGANISM: Oryctolagus cuniculus

<400> SEQUENCE: 203

Met Glu Thr Gly Leu Arg Trp Leu Leu Leu Val Ala Val Leu Lys Gly
1               5                   10                  15

Val Gln Cys Gln Gln Gln Leu Val Glu Ser Gly Gly Gly Leu Val Lys
            20                  25                  30

Pro Gly Ala Ser Leu Thr Leu Thr Cys Lys Ala Ser Gly Phe Ser Phe
        35                  40                  45

Ser Ser Gly Tyr Tyr Met Cys Trp Val Arg Gln Ala Pro Gly Lys Gly
    50                  55                  60

Leu Glu Ser Ile Ala Cys Ile Phe Thr Ile Thr Asp Asn Thr Tyr Tyr
65                  70                  75                  80

Ala Asn Trp Ala Lys Gly Arg Phe Thr Ile Ser Lys Pro Ser Ser Pro
                85                  90                  95

Thr Val Thr Leu Gln Met Thr Ser Leu Thr Ala Ala Asp Thr Ala Thr
            100                 105                 110

Tyr Phe Cys Ala Arg Gly Ile Tyr Ser Thr Asp Asn Tyr Tyr Ala Leu
        115                 120                 125

<210> SEQ ID NO 204
<211> LENGTH: 11
<212> TYPE: PRT
<213> ORGANISM: Oryctolagus cuniculus

<400> SEQUENCE: 204

Gln Ala Ser Glu Ser Ile Gly Asn Ala Leu Ala
1               5                   10

<210> SEQ ID NO 205
<211> LENGTH: 7
<212> TYPE: PRT
<213> ORGANISM: Oryctolagus cuniculus

<400> SEQUENCE: 205

Lys Ala Ser Thr Leu Ala Ser
1               5

<210> SEQ ID NO 206
<211> LENGTH: 9
<212> TYPE: PRT
<213> ORGANISM: Oryctolagus cuniculus

<400> SEQUENCE: 206

Gln Trp Cys Tyr Phe Gly Asp Ser Val
1               5

<210> SEQ ID NO 207
<211> LENGTH: 6
<212> TYPE: PRT
<213> ORGANISM: Oryctolagus cuniculus

<400> SEQUENCE: 207

Ser Gly Tyr Tyr Met Cys
1               5

<210> SEQ ID NO 208
<211> LENGTH: 17
<212> TYPE: PRT
<213> ORGANISM: Oryctolagus cuniculus

<400> SEQUENCE: 208

Cys Ile Phe Thr Ile Thr Asp Asn Thr Tyr Tyr Ala Asn Trp Ala Lys
1               5                   10                  15

Gly

<210> SEQ ID NO 209
<211> LENGTH: 11
<212> TYPE: PRT
<213> ORGANISM: Oryctolagus cuniculus

<400> SEQUENCE: 209

Gly Ile Tyr Ser Thr Asp Asn Tyr Tyr Ala Leu
1               5                   10

<210> SEQ ID NO 210
<211> LENGTH: 357
<212> TYPE: DNA
<213> ORGANISM: Oryctolagus cuniculus

<400> SEQUENCE: 210
atggacacga gggcccccac tcagctgctg gggctcctgc tgctctggct cccaggtgcc        60
agatgtgatg ttgtgatgac ccagactcca gcctccgtgg aggcagctgt gggaggcaca       120
gtcaccatca agtgccaggc cagtgagagc attggcaatg cattagcctg gtatcagcag       180
aaaccagggc agcctcccaa gctcctgatc tacaaggcat ccactctggc atctggggtc       240
ccatcgcggt tcagcggcag tggatctggg acagagttca ctctcaccat cagcggcgtg       300
cagtgtgccg atgctgccgc ttactactgt caatggtgtt attttggtga tagtgtt         357

<210> SEQ ID NO 211
<211> LENGTH: 384
<212> TYPE: DNA
<213> ORGANISM: Oryctolagus cuniculus

<400> SEQUENCE: 211

```
atggagactg ggctgcgctg gcttctcctg gtcgctgtgc tcaaaggtgt ccagtgtcag      60
cagcagctgg tggagtccgg gggaggcctg gtcaagccgg ggcatccct gacactcacc      120 tgcaaagcct ctggattctc cttcagtagc ggctactaca tgtgctgggt ccgccaggct     180
ccagggaagg ggctggagtc gatcgcatgc attttactta ttactgataa cacttactac    240
gcgaactggg cgaaaggccg attcaccatc tccaagccct cgtcgccac ggtgactctg     300 caaatgacca gtctgacagc cgcggacacg gccacctatt tctgtgcgag ggggatttat     360
tctactgata attattatgc cttg                                            384
```

<210> SEQ ID NO 212
<211> LENGTH: 33
<212> TYPE: DNA
<213> ORGANISM: Oryctolagus cuniculus

<400> SEQUENCE: 212

```
caggccagtg agagcattgg caatgcatta gcc                                   33
```

<210> SEQ ID NO 213
<211> LENGTH: 21
<212> TYPE: DNA
<213> ORGANISM: Oryctolagus cuniculus

<400> SEQUENCE: 213

```
aaggcatcca ctctggcatc t                                                21
```

<210> SEQ ID NO 214
<211> LENGTH: 27
<212> TYPE: DNA
<213> ORGANISM: Oryctolagus cuniculus

<400> SEQUENCE: 214

```
caatggtgtt attttggtga tagtgtt                                          27
```

<210> SEQ ID NO 215
<211> LENGTH: 18
<212> TYPE: DNA
<213> ORGANISM: Oryctolagus cuniculus

<400> SEQUENCE: 215

```
agcggctact acatgtgc                                                    18
```

<210> SEQ ID NO 216
<211> LENGTH: 51
<212> TYPE: DNA
<213> ORGANISM: Oryctolagus cuniculus

<400> SEQUENCE: 216

```
tgcatttta ctattactga taacacttac tacgcgaact gggcgaaagg c                51
```

<210> SEQ ID NO 217
<211> LENGTH: 33
<212> TYPE: DNA
<213> ORGANISM: Oryctolagus cuniculus

<400> SEQUENCE: 217
gggatttatt ctactgataa ttattatgcc ttg                              33

<210> SEQ ID NO 218
<211> LENGTH: 123
<212> TYPE: PRT
<213> ORGANISM: Oryctolagus cuniculus

<400> SEQUENCE: 218

```
Met Asp Thr Arg Ala Pro Thr Gln Leu Leu Gly Leu Leu Leu Leu Trp
1               5                   10                  15
Leu Pro Gly Ala Arg Cys Asp Val Val Met Thr Gln Thr Pro Ala Ser
            20                  25                  30
Val Glu Ala Ala Val Gly Gly Thr Val Thr Ile Lys Cys Gln Ala Ser
        35                  40                  45
Gln Ser Val Ser Ser Tyr Leu Asn Trp Tyr Gln Gln Lys Pro Gly Gln
    50                  55                  60
Pro Pro Lys Leu Leu Ile Tyr Arg Ala Ser Thr Leu Glu Ser Gly Val
65                  70                  75                  80
Pro Ser Arg Phe Lys Gly Ser Gly Ser Gly Thr Glu Phe Thr Leu Thr
                85                  90                  95
Ile Ser Asp Leu Glu Cys Ala Asp Ala Ala Thr Tyr Tyr Cys Gln Cys
            100                 105                 110
Thr Tyr Gly Thr Ser Ser Ser Tyr Gly Ala Ala
        115                 120
```

<210> SEQ ID NO 219
<211> LENGTH: 133
<212> TYPE: PRT
<213> ORGANISM: Oryctolagus cuniculus

<400> SEQUENCE: 219

```
Met Glu Thr Gly Leu Arg Trp Leu Leu Leu Val Ala Val Leu Lys Gly
1               5                   10                  15
Val Gln Cys Gln Ser Val Glu Glu Ser Gly Gly Arg Leu Val Thr Pro
            20                  25                  30
Gly Thr Pro Leu Thr Leu Thr Cys Thr Val Ser Gly Ile Ser Leu Ser
        35                  40                  45
Ser Asn Ala Ile Ser Trp Val Arg Gln Ala Pro Gly Lys Gly Leu Glu
    50                  55                  60
Trp Ile Gly Ile Ile Ser Tyr Ser Gly Thr Thr Tyr Tyr Ala Ser Trp
65                  70                  75                  80
Ala Lys Gly Arg Phe Thr Ile Ser Lys Thr Ser Ser Thr Thr Val Asp
                85                  90                  95
Leu Lys Ile Thr Ser Pro Thr Thr Glu Asp Thr Ala Thr Tyr Phe Cys
            100                 105                 110
Ala Arg Asp Asp Pro Thr Thr Val Met Val Met Leu Ile Pro Phe Gly
        115                 120                 125
Ala Gly Met Asp Leu
    130
```

<210> SEQ ID NO 220
<211> LENGTH: 11
<212> TYPE: PRT
<213> ORGANISM: Oryctolagus cuniculus

<400> SEQUENCE: 220

```
Gln Ala Ser Gln Ser Val Ser Ser Tyr Leu Asn
1               5                   10
```

<210> SEQ ID NO 221
<211> LENGTH: 7
<212> TYPE: PRT
<213> ORGANISM: Oryctolagus cuniculus

<400> SEQUENCE: 221

Arg Ala Ser Thr Leu Glu Ser
1               5

<210> SEQ ID NO 222
<211> LENGTH: 13
<212> TYPE: PRT
<213> ORGANISM: Oryctolagus cuniculus

<400> SEQUENCE: 222

Gln Cys Thr Tyr Gly Thr Ser Ser Ser Tyr Gly Ala Ala
1               5                   10

<210> SEQ ID NO 223
<211> LENGTH: 5
<212> TYPE: PRT
<213> ORGANISM: Oryctolagus cuniculus

<400> SEQUENCE: 223

Ser Asn Ala Ile Ser
1               5

<210> SEQ ID NO 224
<211> LENGTH: 16
<212> TYPE: PRT
<213> ORGANISM: Oryctolagus cuniculus

<400> SEQUENCE: 224

Ile Ile Ser Tyr Ser Gly Thr Thr Tyr Tyr Ala Ser Trp Ala Lys Gly
1               5                   10                  15

<210> SEQ ID NO 225
<211> LENGTH: 19
<212> TYPE: PRT
<213> ORGANISM: Oryctolagus cuniculus

<400> SEQUENCE: 225

Asp Asp Pro Thr Thr Val Met Val Met Leu Ile Pro Phe Gly Ala Gly
1               5                   10                  15

Met Asp Leu

<210> SEQ ID NO 226
<211> LENGTH: 369
<212> TYPE: DNA
<213> ORGANISM: Oryctolagus cuniculus

<400> SEQUENCE: 226
atggacacga gggcccccac tcagctgctg gggctcctgc tgctctggct cccaggtgcc      60
agatgtgatg ttgtgatgac ccagactcca gcctccgtgg aggcagctgt gggaggcaca     120
gtcaccatca gtgccaggc cagtcagagc gttagtagct acttaaactg gtatcagcag     180
aaaccagggc agcctcccaa gctcctgatc tacagggcat ccactctgga atctggggtc     240
ccatcgcggt tcaaaggcag tggatctggg acagagttca ctctcaccat cagcgacctg     300
gagtgtgccg atgctgccac ttactactgt caatgtactt atggtactag tagtagttat     360
ggtgctgct                                                            369

<210> SEQ ID NO 227
<211> LENGTH: 399
<212> TYPE: DNA
<213> ORGANISM: Oryctolagus cuniculus

<400> SEQUENCE: 227

```
atggagactg ggctgcgctg gcttctcctg gtcgctgtgc tcaaaggtgt ccagtgtcag      60
tcggtggagg agtccggggg tcgcctggtc acgcctggga caccctgac actcacctgc      120
accgtctctg gtatctccct cagtagcaat gcaataagct gggtccgcca ggctccaggg     180
aaggggctgg aatggatcgg aatcattagt tatagtggta ccacatacta cgcgagctgg     240
gcgaaaggcc gattcaccat ctccaaaacc tcgtcgacca cggtggatct gaaaatcact     300
agtccgacaa ccgaggacac ggccacctac ttctgtgcca gagatgaccc tacgacagtt     360
atggttatgt tgatacctttt tggagccggc atggacctc                          399
```

<210> SEQ ID NO 228
<211> LENGTH: 33
<212> TYPE: DNA
<213> ORGANISM: Oryctolagus cuniculus

<400> SEQUENCE: 228

```
caggccagtc agagcgttag tagctactta aac                                   33
```

<210> SEQ ID NO 229
<211> LENGTH: 21
<212> TYPE: DNA
<213> ORGANISM: Oryctolagus cuniculus

<400> SEQUENCE: 229

```
agggcatcca ctctggaatc t                                                21
```

<210> SEQ ID NO 230
<211> LENGTH: 39
<212> TYPE: DNA
<213> ORGANISM: Oryctolagus cuniculus

<400> SEQUENCE: 230

```
caatgtactt atggtactag tagtagttat ggtgctgct                             39
```

<210> SEQ ID NO 231
<211> LENGTH: 15
<212> TYPE: DNA
<213> ORGANISM: Oryctolagus cuniculus

<400> SEQUENCE: 231

```
agcaatgcaa taagc                                                       15
```

<210> SEQ ID NO 232
<211> LENGTH: 48
<212> TYPE: DNA
<213> ORGANISM: Oryctolagus cuniculus

<400> SEQUENCE: 232

```
atcattagtt atagtggtac cacatactac gcgagctggg cgaaaggc                   48
```

<210> SEQ ID NO 233
<211> LENGTH: 57
<212> TYPE: DNA
<213> ORGANISM: Oryctolagus cuniculus

<400> SEQUENCE: 233 gatgaccctacgacagttatggttatgttgataccttttgagccggcatggacctc 57

<210> SEQ ID NO 234
<211> LENGTH: 125
<212> TYPE: PRT
<213> ORGANISM: Oryctolagus cuniculus

<400> SEQUENCE: 234

```
Met Asp Thr Arg Ala Pro Thr Gln Leu Leu Gly Leu Leu Leu Leu Trp
1               5                   10                  15
Leu Pro Gly Ala Thr Phe Ala Gln Val Leu Thr Gln Thr Ala Ser Pro
            20                  25                  30
Val Ser Ala Ala Val Gly Gly Thr Val Thr Ile Asn Cys Gln Ala Ser
        35                  40                  45
Gln Ser Val Tyr Lys Asn Asn Tyr Leu Ser Trp Tyr Gln Gln Lys Pro
    50                  55                  60
Gly Gln Pro Pro Lys Gly Leu Ile Tyr Ser Ala Ser Thr Leu Asp Ser
65                  70                  75                  80
Gly Val Pro Leu Arg Phe Ser Gly Ser Gly Ser Gly Thr Gln Phe Thr
                85                  90                  95
Leu Thr Ile Ser Asp Val Gln Cys Asp Asp Ala Ala Thr Tyr Tyr Cys
            100                 105                 110
Leu Gly Ser Tyr Asp Cys Ser Ser Gly Asp Cys Tyr Ala
        115                 120                 125
```

<210> SEQ ID NO 235
<211> LENGTH: 119
<212> TYPE: PRT
<213> ORGANISM: Oryctolagus cuniculus

<400> SEQUENCE: 235

```
Met Glu Thr Gly Leu Arg Trp Leu Leu Leu Val Ala Val Leu Lys Gly
1               5                   10                  15
Val Gln Cys Gln Ser Leu Glu Glu Ser Gly Gly Asp Leu Val Lys Pro
            20                  25                  30
Glu Gly Ser Leu Thr Leu Thr Cys Thr Ala Ser Gly Phe Ser Phe Ser
        35                  40                  45
Ser Tyr Trp Met Cys Trp Val Arg Gln Ala Pro Gly Lys Gly Leu Glu
    50                  55                  60
Trp Ile Ala Cys Ile Val Thr Gly Asn Gly Asn Thr Tyr Tyr Ala Asn
65                  70                  75                  80
Trp Ala Lys Gly Arg Phe Thr Ile Ser Lys Thr Ser Ser Thr Thr Val
                85                  90                  95
Thr Leu Gln Met Thr Ser Leu Thr Ala Ala Asp Thr Ala Thr Tyr Phe
            100                 105                 110
Cys Ala Lys Ala Tyr Asp Leu
        115
```

<210> SEQ ID NO 236
<211> LENGTH: 13
<212> TYPE: PRT
<213> ORGANISM: Oryctolagus cuniculus

<400> SEQUENCE: 236

```
Gln Ala Ser Gln Ser Val Tyr Lys Asn Asn Tyr Leu Ser
1               5                   10
```

<210> SEQ ID NO 237
<211> LENGTH: 7
<212> TYPE: PRT
<213> ORGANISM: Oryctolagus cuniculus

<400> SEQUENCE: 237

Ser Ala Ser Thr Leu Asp Ser
1               5

<210> SEQ ID NO 238
<211> LENGTH: 13
<212> TYPE: PRT
<213> ORGANISM: Oryctolagus cuniculus

<400> SEQUENCE: 238

Leu Gly Ser Tyr Asp Cys Ser Ser Gly Asp Cys Tyr Ala
1               5                   10

<210> SEQ ID NO 239
<211> LENGTH: 5
<212> TYPE: PRT
<213> ORGANISM: Oryctolagus cuniculus

<400> SEQUENCE: 239

Ser Tyr Trp Met Cys
1               5

<210> SEQ ID NO 240
<211> LENGTH: 17
<212> TYPE: PRT
<213> ORGANISM: Oryctolagus cuniculus

<400> SEQUENCE: 240

Cys Ile Val Thr Gly Asn Gly Asn Thr Tyr Tyr Ala Asn Trp Ala Lys
1               5                   10                  15

Gly

<210> SEQ ID NO 241
<211> LENGTH: 4
<212> TYPE: PRT
<213> ORGANISM: Oryctolagus cuniculus

<400> SEQUENCE: 241

Ala Tyr Asp Leu
1

<210> SEQ ID NO 242
<211> LENGTH: 375
<212> TYPE: DNA
<213> ORGANISM: Oryctolagus cuniculus

<400> SEQUENCE: 242

```
atggacacga gggcccccac tcagctgctg gggctcctgc tgctctggct cccaggtgcc    60
acatttgccc aagtgctgac ccagactgca tcgcccgtgt ctgcagctgt gggaggcaca   120
gtcaccatca actgccaggc cagtcagagt gtttataaga caaactactt atcctggtat   180
cagcagaaac cagggcagcc tcccaaaggc ctgatctatt ctgcatcgac tctagattct   240
ggggtcccat gcggttcag cggcagtgga tctgggacac agttcactct caccatcagc   300
gacgtgcagt gtgacgatgc tgccacttac tactgtctag cagttatga ttgtagtagt   360
ggtgattgtt atgct                                                    375
```

<210> SEQ ID NO 243
<211> LENGTH: 357
<212> TYPE: DNA
<213> ORGANISM: Oryctolagus cuniculus

<400> SEQUENCE: 243

| | | | | | |
|---|---|---|---|---|---|
| atggagactg | ggctgcgctg | gcttctcctg | gtcgctgtgc | tcaaaggtgt | ccagtgtcag | 60 |
| tcgttggagg | agtccggggg | agacctggtc | aagcctgagg | gatccctgac | actcacctgc | 120 |
| acagcctctg | gattctcctt | cagtagctac | tggatgtgct | gggtccgcca | ggctccaggg | 180 |
| aaggggctgg | agtggatcgc | atgcattgtt | actggtaatg | gtaacactta | ctacgcgaac | 240 |
| tgggcgaaag | gccgattcac | catctccaaa | acctcgtcga | ccacggtgac | tctgcaaatg | 300 |
| accagtctga | cagccgcgga | cacggccacc | tattttgtg | cgaaagccta | tgacttg | 357 |

<210> SEQ ID NO 244
<211> LENGTH: 39
<212> TYPE: DNA
<213> ORGANISM: Oryctolagus cuniculus

<400> SEQUENCE: 244
caggccagtc agagtgttta taagaacaac tacttatcc                      39

<210> SEQ ID NO 245
<211> LENGTH: 21
<212> TYPE: DNA
<213> ORGANISM: Oryctolagus cuniculus

<400> SEQUENCE: 245
tctgcatcga ctctagattc t                                          21

<210> SEQ ID NO 246
<211> LENGTH: 39
<212> TYPE: DNA
<213> ORGANISM: Oryctolagus cuniculus

<400> SEQUENCE: 246
ctaggcagtt atgattgtag tagtggtgat tgttatgct                       39

<210> SEQ ID NO 247
<211> LENGTH: 15
<212> TYPE: DNA
<213> ORGANISM: Oryctolagus cuniculus

<400> SEQUENCE: 247
agctactgga tgtgc                                                 15

<210> SEQ ID NO 248
<211> LENGTH: 51
<212> TYPE: DNA
<213> ORGANISM: Oryctolagus cuniculus

<400> SEQUENCE: 248
tgcattgtta ctggtaatgg taacacttac tacgcgaact gggcgaaagg c         51

<210> SEQ ID NO 249
<211> LENGTH: 12
<212> TYPE: DNA
<213> ORGANISM: Oryctolagus cuniculus

<400> SEQUENCE: 249
gcctatgact tg                                                    12

<210> SEQ ID NO 250
<211> LENGTH: 123
<212> TYPE: PRT
<213> ORGANISM: Oryctolagus cuniculus

<400> SEQUENCE: 250

Met Asp Thr Arg Ala Pro Thr Gln Leu Leu Gly Leu Leu Leu Trp
1               5                   10                  15

Leu Pro Gly Ser Thr Phe Ala Ala Val Leu Thr Gln Thr Pro Ser Pro
            20                  25                  30

Val Ser Ala Ala Val Gly Gly Thr Val Ser Ile Ser Cys Gln Ala Ser
        35                  40                  45

Gln Ser Val Tyr Asp Asn Asn Tyr Leu Ser Trp Tyr Gln Gln Lys Pro
    50                  55                  60

Gly Gln Pro Pro Lys Leu Leu Ile Tyr Gly Ala Ser Thr Leu Ala Ser
65                  70                  75                  80

Gly Val Pro Ser Arg Phe Lys Gly Thr Gly Ser Gly Thr Gln Phe Thr
                85                  90                  95

Leu Thr Ile Thr Asp Val Gln Cys Asp Asp Ala Ala Thr Tyr Tyr Cys
            100                 105                 110

Ala Gly Val Phe Asn Asp Asp Ser Asp Asp Ala
        115                 120

<210> SEQ ID NO 251
<211> LENGTH: 125
<212> TYPE: PRT
<213> ORGANISM: Oryctolagus cuniculus

<400> SEQUENCE: 251

Met Glu Thr Gly Leu Arg Trp Leu Leu Leu Val Ala Val Pro Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Leu Ser Gly Phe Ser Leu Ser
        35                  40                  45

Ala Tyr Tyr Met Ser Trp Val Arg Gln Ala Pro Gly Lys Gly Leu Glu
    50                  55                  60

Trp Ile Gly Phe Ile Thr Leu Ser Asp His Ile Ser Tyr Ala Arg Trp
65                  70                  75                  80

Ala Lys Gly Arg Phe Thr Ile Ser Lys Thr Ser Thr Thr Val Asp Leu
                85                  90                  95

Lys Met Thr Ser Pro Thr Thr Glu Asp Thr Ala Thr Tyr Phe Cys Ala
            100                 105                 110

Arg Ser Arg Gly Trp Gly Ala Met Gly Arg Leu Asp Leu
        115                 120                 125

<210> SEQ ID NO 252
<211> LENGTH: 13
<212> TYPE: PRT
<213> ORGANISM: Oryctolagus cuniculus

<400> SEQUENCE: 252

Gln Ala Ser Gln Ser Val Tyr Asp Asn Asn Tyr Leu Ser
1               5                   10

<210> SEQ ID NO 253
<211> LENGTH: 7

<212> TYPE: PRT
<213> ORGANISM: Oryctolagus cuniculus

<400> SEQUENCE: 253

Gly Ala Ser Thr Leu Ala Ser
1               5

<210> SEQ ID NO 254
<211> LENGTH: 11
<212> TYPE: PRT
<213> ORGANISM: Oryctolagus cuniculus

<400> SEQUENCE: 254

Ala Gly Val Phe Asn Asp Asp Ser Asp Asp Ala
1               5                   10

<210> SEQ ID NO 255
<211> LENGTH: 5
<212> TYPE: PRT
<213> ORGANISM: Oryctolagus cuniculus

<400> SEQUENCE: 255

Ala Tyr Tyr Met Ser
1               5

<210> SEQ ID NO 256
<211> LENGTH: 16
<212> TYPE: PRT
<213> ORGANISM: Oryctolagus cuniculus

<400> SEQUENCE: 256

Phe Ile Thr Leu Ser Asp His Ile Ser Tyr Ala Arg Trp Ala Lys Gly
1               5                   10                  15

<210> SEQ ID NO 257
<211> LENGTH: 12
<212> TYPE: PRT
<213> ORGANISM: Oryctolagus cuniculus

<400> SEQUENCE: 257

Ser Arg Gly Trp Gly Ala Met Gly Arg Leu Asp Leu
1               5                   10

<210> SEQ ID NO 258
<211> LENGTH: 369
<212> TYPE: DNA
<213> ORGANISM: Oryctolagus cuniculus

<400> SEQUENCE: 258
atggacacga gggcccccac tcagctgctg gggctcctgc tgctctggct cccaggttcc        60
acatttgccg ccgtgctgac ccagactcca tctcccgtgt ctgcagctgt gggaggcaca      120
gtcagcatca gttgccaggc cagtcagagt gtttatgaca caactatttt atcctggtat      180
cagcagaaac caggacagcc tcccaagctc ctgatctatg gtgcatccac tctggcatct      240
ggggtcccat cgcggttcaa aggcacggga tctgggacac agttcactct caccatcaca      300
gacgtgcagt gtgacgatgc tgccacttac tattgtgcag gcgttttaa tgatgatagt       360 gatgatgcc                                                              369

<210> SEQ ID NO 259
<211> LENGTH: 375
<212> TYPE: DNA
<213> ORGANISM: Oryctolagus cuniculus

<400> SEQUENCE: 259

| | |
|---|---|
| atggagactg ggctgcgctg gcttctcctg gtcgctgtgc ccaaaggtgt ccagtgtcag | 60 |
| tcgctggagg agtccggggg tcgcctggtc acgcctggga caccctgac actcacctgc | 120 |
| acactctctg gattctccct cagtgcatac tatatgagct gggtccgcca ggctccaggg | 180 |
| aaggggctgg aatggatcgg attcattact ctgagtgatc atatatctta cgcgaggtgg | 240 |
| gcgaaaggcc gattcaccat ctccaaaacc tcgaccacgg tggatctgaa aatgaccagt | 300 |
| ccgacaaccg aggacacggc cacctatttc tgtgccagga gtcgtggctg gggtgcaatg | 360 |
| ggtcggttgg atctc | 375 |

<210> SEQ ID NO 260
<211> LENGTH: 39
<212> TYPE: DNA
<213> ORGANISM: Oryctolagus cuniculus

<400> SEQUENCE: 260

| | |
|---|---|
| caggccagtc agagtgttta tgacaacaac tatttatcc | 39 |

<210> SEQ ID NO 261
<211> LENGTH: 21
<212> TYPE: DNA
<213> ORGANISM: Oryctolagus cuniculus

<400> SEQUENCE: 261

| | |
|---|---|
| ggtgcatcca ctctggcatc t | 21 |

<210> SEQ ID NO 262
<211> LENGTH: 33
<212> TYPE: DNA
<213> ORGANISM: Oryctolagus cuniculus

<400> SEQUENCE: 262

| | |
|---|---|
| gcaggcgttt ttaatgatga tagtgatgat gcc | 33 |

<210> SEQ ID NO 263
<211> LENGTH: 15
<212> TYPE: DNA
<213> ORGANISM: Oryctolagus cuniculus

<400> SEQUENCE: 263

| | |
|---|---|
| gcatactata tgagc | 15 |

<210> SEQ ID NO 264
<211> LENGTH: 48
<212> TYPE: DNA
<213> ORGANISM: Oryctolagus cuniculus

<400> SEQUENCE: 264

| | |
|---|---|
| ttcattactc tgagtgatca tatatcttac gcgaggtggg cgaaaggc | 48 |

<210> SEQ ID NO 265
<211> LENGTH: 36
<212> TYPE: DNA
<213> ORGANISM: Oryctolagus cuniculus

<400> SEQUENCE: 265

| | |
|---|---|
| agtcgtggct ggggtgcaat gggtcggttg gatctc | 36 |

<210> SEQ ID NO 266

```
<211> LENGTH: 123
<212> TYPE: PRT
<213> ORGANISM: Oryctolagus cuniculus

<400> SEQUENCE: 266

Met Asp Thr Arg Ala Pro Thr Gln Leu Leu Gly Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Thr Ile Ser Cys Gln Ala Ser
            35                  40                  45

Gln Ser Val Tyr Asn Asn Lys Asn Leu Ala Trp Tyr Gln Gln Lys Ser
        50                  55                  60

Gly Gln Pro Pro Lys Leu Leu Ile Tyr Trp Ala Ser Thr Leu Ala Ser
65                  70                  75                  80

Gly Val Ser Ser Arg Phe Ser Gly Ser Gly Ser Gly Thr Gln Phe Thr
                85                  90                  95

Leu Thr Val Ser Gly Val Gln Cys Asp Asp Ala Ala Thr Tyr Tyr Cys
            100                 105                 110

Leu Gly Val Phe Asp Asp Asp Ala Asp Asn Ala
        115                 120

<210> SEQ ID NO 267
<211> LENGTH: 121
<212> TYPE: PRT
<213> ORGANISM: Oryctolagus cuniculus

<400> SEQUENCE: 267

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Ser
            35                  40                  45

Ser Tyr Ser Met Thr Trp Val Arg Gln Ala Pro Gly Lys Gly Leu Glu
        50                  55                  60

Tyr Ile Gly Val Ile Gly Thr Ser Gly Ser Thr Tyr Tyr Ala Thr Trp
65                  70                  75                  80

Ala Lys Gly Arg Phe Thr Ile Ser Arg Thr Ser Thr Thr Val Ala Leu
                85                  90                  95

Lys Ile Thr Ser Pro Thr Thr Glu Asp Thr Ala Thr Tyr Phe Cys Val
            100                 105                 110

Arg Ser Leu Ser Ser Ile Thr Phe Leu
        115                 120

<210> SEQ ID NO 268
<211> LENGTH: 13
<212> TYPE: PRT
<213> ORGANISM: Oryctolagus cuniculus

<400> SEQUENCE: 268

Gln Ala Ser Gln Ser Val Tyr Asn Asn Lys Asn Leu Ala
1               5                   10

<210> SEQ ID NO 269
<211> LENGTH: 7
<212> TYPE: PRT
<213> ORGANISM: Oryctolagus cuniculus
```

<400> SEQUENCE: 269

Trp Ala Ser Thr Leu Ala Ser
1               5

<210> SEQ ID NO 270
<211> LENGTH: 11
<212> TYPE: PRT
<213> ORGANISM: Oryctolagus cuniculus

<400> SEQUENCE: 270

Leu Gly Val Phe Asp Asp Asp Ala Asp Asn Ala
1               5                   10

<210> SEQ ID NO 271
<211> LENGTH: 5
<212> TYPE: PRT
<213> ORGANISM: Oryctolagus cuniculus

<400> SEQUENCE: 271

Ser Tyr Ser Met Thr
1               5

<210> SEQ ID NO 272
<211> LENGTH: 16
<212> TYPE: PRT
<213> ORGANISM: Oryctolagus cuniculus

<400> SEQUENCE: 272

Val Ile Gly Thr Ser Gly Ser Thr Tyr Tyr Ala Thr Trp Ala Lys Gly
1               5                   10                  15

<210> SEQ ID NO 273
<211> LENGTH: 8
<212> TYPE: PRT
<213> ORGANISM: Oryctolagus cuniculus

<400> SEQUENCE: 273

Ser Leu Ser Ser Ile Thr Phe Leu
1               5

<210> SEQ ID NO 274
<211> LENGTH: 369
<212> TYPE: DNA
<213> ORGANISM: Oryctolagus cuniculus

<400> SEQUENCE: 274

```
atggacacga gggcccccac tcagctgctg gggctcctgc tgctctggct cccaggtgcc    60
acattcgcag ccgtgctgac ccagacacca tcgcccgtgt ctgcggctgt gggaggcaca   120
gtcaccatca gttgccaggc cagtcagagt gtttataaca caaaaatttt agcctggtat   180
cagcagaaat cagggcagcc tcccaagctc ctgatctact gggcatccac tctggcatct   240
ggggtctcat cgcggttcag cggcagtgga tctgggacac agttcactct caccgtcagc   300
ggcgtgcagt gtgacgatgc tgccacttac tactgtctag gcgtttttga tgatgatgct   360
gataatgct                                                          369
```

<210> SEQ ID NO 275
<211> LENGTH: 363
<212> TYPE: DNA
<213> ORGANISM: Oryctolagus cuniculus

<400> SEQUENCE: 275

```
atggagactg ggctgcgctg gcttctcctg gtcgctgtgc tcaaaggtgt ccaatgtcag    60
tcggtggagg agtccggggg tcgcctggtc acgcctggga caccctgac actcacctgc    120 acagcctctg gattctccct cagtagctac tccatgacct gggtccgcca ggctccaggg    180
aaggggctgg aatatatcgg agtcattggt actagtggta gcacatacta cgcgacctgg    240
gcgaaaggcc gattcaccat ctccagaacc tcgaccacgg tggctctgaa aatcaccagt    300
ccgacaaccg aggacacggc cacctatttc tgtgtcagga gtctttcttc tattactttc    360
ttg                                                                 363

<210> SEQ ID NO 276
<211> LENGTH: 39
<212> TYPE: DNA
<213> ORGANISM: Oryctolagus cuniculus

<400> SEQUENCE: 276
caggccagtc agagtgttta taacaacaaa aatttagcc                           39

<210> SEQ ID NO 277
<211> LENGTH: 21
<212> TYPE: DNA
<213> ORGANISM: Oryctolagus cuniculus

<400> SEQUENCE: 277
tgggcatcca ctctggcatc t                                              21

<210> SEQ ID NO 278
<211> LENGTH: 33
<212> TYPE: DNA
<213> ORGANISM: Oryctolagus cuniculus

<400> SEQUENCE: 278
ctaggcgttt ttgatgatga tgctgataat gct                                 33

<210> SEQ ID NO 279
<211> LENGTH: 15
<212> TYPE: DNA
<213> ORGANISM: Oryctolagus cuniculus

<400> SEQUENCE: 279
agctactcca tgacc                                                     15

<210> SEQ ID NO 280
<211> LENGTH: 48
<212> TYPE: DNA
<213> ORGANISM: Oryctolagus cuniculus

<400> SEQUENCE: 280
gtcattggta ctagtggtag cacatactac gcgacctggg cgaaaggc                 48

<210> SEQ ID NO 281
<211> LENGTH: 24
<212> TYPE: DNA
<213> ORGANISM: Oryctolagus cuniculus

<400> SEQUENCE: 281
agtctttctt ctattacttt cttg                                           24

<210> SEQ ID NO 282
<211> LENGTH: 120
<212> TYPE: PRT
<213> ORGANISM: Oryctolagus cuniculus
```

```
<400> SEQUENCE: 282

Met Asp Thr Arg Ala Pro Thr Gln Leu Leu Gly Leu Leu Leu Leu Trp
1               5                   10                  15

Leu Pro Gly Ala Arg Cys Ala Phe Glu Leu Thr Gln Thr Pro Ala Ser
            20                  25                  30

Val Glu Ala Ala Val Gly Gly Thr Val Thr Ile Asn Cys Gln Ala Ser
        35                  40                  45

Gln Asn Ile Tyr Arg Tyr Leu Ala Trp Tyr Gln Gln Lys Pro Gly Gln
    50                  55                  60

Pro Pro Lys Phe Leu Ile Tyr Leu Ala Ser Thr Leu Ala Ser Gly Val
65                  70                  75                  80

Pro Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Ser
            100                 105                 110

Tyr Tyr Ser Ser Asn Ser Val Ala
            115                 120

<210> SEQ ID NO 283
<211> LENGTH: 128
<212> TYPE: PRT
<213> ORGANISM: Oryctolagus cuniculus

<400> SEQUENCE: 283

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Asp Leu Val Gln
            20                  25                  30

Pro Glu Gly Ser Leu Thr Leu Thr Cys Thr Ala Ser Gly Leu Asp Phe
        35                  40                  45

Ser Ser Gly Tyr Trp Ile Cys Trp Val Arg Gln Val Pro Gly Lys Gly
    50                  55                  60

Leu Glu Trp Ile Gly Cys Ile Tyr Thr Gly Ser Ser Gly Ser Thr Phe
65                  70                  75                  80

Tyr Ala Ser Trp Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Gly Tyr Ser Gly Phe Gly Tyr Phe Lys Leu
            115                 120                 125

<210> SEQ ID NO 284
<211> LENGTH: 11
<212> TYPE: PRT
<213> ORGANISM: Oryctolagus cuniculus

<400> SEQUENCE: 284

Gln Ala Ser Gln Asn Ile Tyr Arg Tyr Leu Ala
1               5                   10

<210> SEQ ID NO 285
<211> LENGTH: 7
<212> TYPE: PRT
<213> ORGANISM: Oryctolagus cuniculus

<400> SEQUENCE: 285

Leu Ala Ser Thr Leu Ala Ser
```

<210> SEQ ID NO 286
<211> LENGTH: 10
<212> TYPE: PRT
<213> ORGANISM: Oryctolagus cuniculus

<400> SEQUENCE: 286

Gln Ser Tyr Tyr Ser Ser Asn Ser Val Ala
1               5                   10

<210> SEQ ID NO 287
<211> LENGTH: 6
<212> TYPE: PRT
<213> ORGANISM: Oryctolagus cuniculus

<400> SEQUENCE: 287

Ser Gly Tyr Trp Ile Cys
1               5

<210> SEQ ID NO 288
<211> LENGTH: 18
<212> TYPE: PRT
<213> ORGANISM: Oryctolagus cuniculus

<400> SEQUENCE: 288

Cys Ile Tyr Thr Gly Ser Ser Gly Ser Thr Phe Tyr Ala Ser Trp Ala
1               5                   10                  15

Lys Gly

<210> SEQ ID NO 289
<211> LENGTH: 10
<212> TYPE: PRT
<213> ORGANISM: Oryctolagus cuniculus

<400> SEQUENCE: 289

Gly Tyr Ser Gly Phe Gly Tyr Phe Lys Leu
1               5                   10

<210> SEQ ID NO 290
<211> LENGTH: 360
<212> TYPE: DNA
<213> ORGANISM: Oryctolagus cuniculus

<400> SEQUENCE: 290
atggacacga gggcccccac tcagctgctg gggctcctgc tgctctggct cccaggtgcc     60
agatgtgcat tcgaattgac ccagactcca gcctccgtgg aggcagctgt gggaggcaca    120
gtcaccatca attgccaggc cagtcagaac atttatagat acttagcctg gtatcagcag    180
aaaccagggc agcctcccaa gttcctgatc tatctggcat ctactctggc atctggggtc    240
ccatcgcggt ttaaaggcag tggatctggg acagagttca ctctcaccat cagcgacctg    300
gagtgtgccg atgctgccac ttactactgt caaagttatt atagtagtaa tagtgtcgct    360

<210> SEQ ID NO 291
<211> LENGTH: 384
<212> TYPE: DNA
<213> ORGANISM: Oryctolagus cuniculus

<400> SEQUENCE: 291
atggagactg ggctgcgctg gcttctcctg gtcgctgtgc tcaaaggtgt ccagtgtcag     60
gagcagctgg tggagtccgg gggagacctg gtccagcctg aggatccct gacactcacc    120

```
tgcacagctt ctgagttaga cttcagtagc ggctactgga tatgctgggt ccgccaggtt    180
ccagggaagg ggctggagtg gatcggatgc atttatactg gtagtagtgg tagcactttt    240
tacgcgagtt gggcgaaagg ccgattcacc atctccaaaa cctcgtcgac cacggtgact    300
ctgcaaatga ccagtctgac agccgcggac acgccacct atttctgtgc gagaggttat     360
agtggctttg gttactttaa gttg                                            384
```

<210> SEQ ID NO 292
<211> LENGTH: 33
<212> TYPE: DNA
<213> ORGANISM: Oryctolagus cuniculus

<400> SEQUENCE: 292

```
caggccagtc agaacattta tagatactta gcc                                  33
```

<210> SEQ ID NO 293
<211> LENGTH: 21
<212> TYPE: DNA
<213> ORGANISM: Oryctolagus cuniculus

<400> SEQUENCE: 293

```
ctggcatcta ctctggcatc t                                               21
```

<210> SEQ ID NO 294
<211> LENGTH: 30
<212> TYPE: DNA
<213> ORGANISM: Oryctolagus cuniculus

<400> SEQUENCE: 294

```
caaagttatt atagtagtaa tagtgtcgct                                      30
```

<210> SEQ ID NO 295
<211> LENGTH: 18
<212> TYPE: DNA
<213> ORGANISM: Oryctolagus cuniculus

<400> SEQUENCE: 295

```
agcggctact ggatatgc                                                   18
```

<210> SEQ ID NO 296
<211> LENGTH: 54
<212> TYPE: DNA
<213> ORGANISM: Oryctolagus cuniculus

<400> SEQUENCE: 296

```
tgcatttata ctggtagtag tggtagcact ttttacgcga gttgggcgaa aggc           54
```

<210> SEQ ID NO 297
<211> LENGTH: 30
<212> TYPE: DNA
<213> ORGANISM: Oryctolagus cuniculus

<400> SEQUENCE: 297

```
ggttatagtg gctttggtta ctttaagttg                                      30
```

<210> SEQ ID NO 298
<211> LENGTH: 122
<212> TYPE: PRT
<213> ORGANISM: Oryctolagus cuniculus

<400> SEQUENCE: 298

```
Met Asp Thr Arg Ala Pro Thr Gln Leu Leu Gly Leu Leu Leu Leu Trp
1               5                   10                  15
Leu Pro Gly Ala Arg Cys Ala Tyr Asp Met Thr Gln Thr Pro Ala Ser
            20                  25                  30
Val Glu Val Ala Val Gly Gly Thr Val Thr Ile Lys Cys Gln Ala Ser
        35                  40                  45
Glu Asp Ile Tyr Arg Leu Leu Ala Trp Tyr Gln Gln Lys Pro Gly Gln
50                  55                  60
Pro Pro Lys Leu Leu Ile Tyr Asp Ser Ser Asp Leu Ala Ser Gly Val
65                  70                  75                  80
Pro Ser Arg Phe Lys Gly Ser Gly Ser Gly Thr Glu Phe Thr Leu Ala
                85                  90                  95
Ile Ser Gly Val Gln Cys Asp Asp Ala Ala Thr Tyr Tyr Cys Gln Gln
            100                 105                 110
Ala Trp Ser Tyr Ser Asp Ile Asp Asn Ala
            115                 120
```

<210> SEQ ID NO 299
<211> LENGTH: 123
<212> TYPE: PRT
<213> ORGANISM: Oryctolagus cuniculus

<400> SEQUENCE: 299

```
Met Glu Thr Gly Leu Arg Trp Leu Leu Leu Val Ala Val Leu Lys Gly
1               5                   10                  15
Val Gln Cys Gln Ser Val Glu Glu Ser Gly Gly Arg Leu Val Thr Pro
            20                  25                  30
Gly Thr Pro Leu Thr Leu Thr Cys Thr Ala Ser Gly Phe Ser Leu Ser
            35                  40                  45
Ser Tyr Tyr Met Ser Trp Val Arg Gln Ala Pro Gly Lys Gly Leu Glu
50                  55                  60
Trp Ile Gly Ile Ile Thr Thr Ser Gly Asn Thr Phe Tyr Ala Ser Trp
65                  70                  75                  80
Ala Lys Gly Arg Leu Thr Ile Ser Arg Thr Ser Thr Thr Val Asp Leu
                85                  90                  95
Lys Ile Thr Ser Pro Thr Thr Glu Asp Thr Ala Thr Tyr Phe Cys Ala
            100                 105                 110
Arg Thr Ser Asp Ile Phe Tyr Tyr Arg Asn Leu
            115                 120
```

<210> SEQ ID NO 300
<211> LENGTH: 11
<212> TYPE: PRT
<213> ORGANISM: Oryctolagus cuniculus

<400> SEQUENCE: 300

```
Gln Ala Ser Glu Asp Ile Tyr Arg Leu Leu Ala
1               5                   10
```

<210> SEQ ID NO 301
<211> LENGTH: 7
<212> TYPE: PRT
<213> ORGANISM: Oryctolagus cuniculus

<400> SEQUENCE: 301

```
Asp Ser Ser Asp Leu Ala Ser
1               5
```

<210> SEQ ID NO 302
<211> LENGTH: 12
<212> TYPE: PRT
<213> ORGANISM: Oryctolagus cuniculus

<400> SEQUENCE: 302

Gln Gln Ala Trp Ser Tyr Ser Asp Ile Asp Asn Ala
1               5                   10

<210> SEQ ID NO 303
<211> LENGTH: 5
<212> TYPE: PRT
<213> ORGANISM: Oryctolagus cuniculus

<400> SEQUENCE: 303

Ser Tyr Tyr Met Ser
1               5

<210> SEQ ID NO 304
<211> LENGTH: 16
<212> TYPE: PRT
<213> ORGANISM: Oryctolagus cuniculus

<400> SEQUENCE: 304

Ile Ile Thr Thr Ser Gly Asn Thr Phe Tyr Ala Ser Trp Ala Lys Gly
1               5                   10                  15

<210> SEQ ID NO 305
<211> LENGTH: 10
<212> TYPE: PRT
<213> ORGANISM: Oryctolagus cuniculus

<400> SEQUENCE: 305

Thr Ser Asp Ile Phe Tyr Tyr Arg Asn Leu
1               5                   10

<210> SEQ ID NO 306
<211> LENGTH: 366
<212> TYPE: DNA
<213> ORGANISM: Oryctolagus cuniculus

<400> SEQUENCE: 306

```
atggacacga gggcccccac tcagctgctg ggctcctgc tgctctggct cccaggtgcc    60
agatgtgcct atgatatgac ccagactcca gcctctgtgg aggtagctgt gggaggcaca   120
gtcaccatca gtgccaggc cagtgaggac atttataggt tattggcctg gtatcaacag   180
aaaccagggc agcctcccaa gctcctgatc tatgattcat ccgatctggc atctggggtc   240
ccatcgcggt tcaaaggcag tggatctggg acagagttca ctctcgccat cagcggtgtg   300
cagtgtgacg atgctgccac ttactactgt caacaggctt ggagttatag tgatattgat   360
aatgct                                                              366
```

<210> SEQ ID NO 307
<211> LENGTH: 369
<212> TYPE: DNA
<213> ORGANISM: Oryctolagus cuniculus

<400> SEQUENCE: 307

```
atggagactg ggctgcgctg cttctcctg gtcgctgtgc tcaaaggtgt ccagtgtcag    60
tcggtggagg agtccggggg tcgcctggtc acgccgggga cacccctgac actcacctgc   120
acagcctctg gattctccct cagtagctac tacatgagct gggtccgcca ggctccaggg   180
```

-continued

```
aagggggctgg aatggatcgg aatcattact actagtggta atacatttta cgcgagctgg    240
gcgaaaggcc ggctcaccat ctccagaacc tcgaccacgg tggatctgaa aatcaccagt    300
ccgacaaccg aggacacggc cacctatttc tgtgccagaa cttctgatat ttttattat     360 cgtaacttg                                                              369
```

<210> SEQ ID NO 308
<211> LENGTH: 33
<212> TYPE: DNA
<213> ORGANISM: Oryctolagus cuniculus

<400> SEQUENCE: 308

```
caggccagtg aggacattta taggttattg gcc                                   33
```

<210> SEQ ID NO 309
<211> LENGTH: 21
<212> TYPE: DNA
<213> ORGANISM: Oryctolagus cuniculus

<400> SEQUENCE: 309

```
gattcatccg atctggcatc t                                                21
```

<210> SEQ ID NO 310
<211> LENGTH: 36
<212> TYPE: DNA
<213> ORGANISM: Oryctolagus cuniculus

<400> SEQUENCE: 310

```
caacaggctt ggagttatag tgatattgat aatgct                                36
```

<210> SEQ ID NO 311
<211> LENGTH: 15
<212> TYPE: DNA
<213> ORGANISM: Oryctolagus cuniculus

<400> SEQUENCE: 311

```
agctactaca tgagc                                                       15
```

<210> SEQ ID NO 312
<211> LENGTH: 48
<212> TYPE: DNA
<213> ORGANISM: Oryctolagus cuniculus

<400> SEQUENCE: 312

```
atcattacta ctagtggtaa tacattttac gcgagctggg cgaaaggc                   48
```

<210> SEQ ID NO 313
<211> LENGTH: 30
<212> TYPE: DNA
<213> ORGANISM: Oryctolagus cuniculus

<400> SEQUENCE: 313

```
acttctgata ttttttatta tcgtaacttg                                       30
```

<210> SEQ ID NO 314
<211> LENGTH: 123
<212> TYPE: PRT
<213> ORGANISM: Oryctolagus cuniculus

<400> SEQUENCE: 314

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Ala Ser Pro
                20                  25                  30

Val Ser Ala Ala Val Gly Ala Thr Val Thr Ile Asn Cys Gln Ser Ser
            35                  40                  45

Gln Ser Val Tyr Asn Asp Met Asp Leu Ala Trp Phe Gln Gln Lys Pro
        50                  55                  60

Gly Gln Pro Pro Lys Leu Leu Ile Tyr Ser Ala Ser Thr Leu Ala Ser
65                  70                  75                  80

Gly Val Pro Ser Arg Phe Ser Gly Ser Gly Ser Gly Thr Glu Phe Thr
                85                  90                  95

Leu Thr Ile Ser Gly Val Gln Cys Asp Asp Ala Ala Thr Tyr Tyr Cys
            100                 105                 110

Leu Gly Ala Phe Asp Asp Asp Ala Asp Asn Thr
        115                 120

<210> SEQ ID NO 315
<211> LENGTH: 129
<212> TYPE: PRT
<213> ORGANISM: Oryctolagus cuniculus

<400> SEQUENCE: 315

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Thr Leu Thr Cys Thr Val Ser Gly Phe Ser Leu Thr
            35                  40                  45

Arg His Ala Ile Thr Trp Val Arg Gln Ala Pro Gly Lys Gly Leu Glu
        50                  55                  60

Trp Ile Gly Cys Ile Trp Ser Gly Gly Ser Thr Tyr Tyr Ala Thr Trp
65                  70                  75                  80

Ala Lys Gly Arg Phe Thr Ile Ser Lys Thr Ser Thr Thr Val Asp Leu
                85                  90                  95

Arg Ile Thr Ser Pro Thr Thr Glu Asp Thr Ala Thr Tyr Phe Cys Ala
            100                 105                 110

Arg Val Ile Gly Asp Thr Ala Gly Tyr Ala Tyr Phe Thr Gly Leu Asp
        115                 120                 125

Leu

<210> SEQ ID NO 316
<211> LENGTH: 13
<212> TYPE: PRT
<213> ORGANISM: Oryctolagus cuniculus

<400> SEQUENCE: 316

Gln Ser Ser Gln Ser Val Tyr Asn Asp Met Asp Leu Ala
1               5                   10

<210> SEQ ID NO 317
<211> LENGTH: 7
<212> TYPE: PRT
<213> ORGANISM: Oryctolagus cuniculus

<400> SEQUENCE: 317

Ser Ala Ser Thr Leu Ala Ser
1               5

<210> SEQ ID NO 318

```
<211> LENGTH: 11
<212> TYPE: PRT
<213> ORGANISM: Oryctolagus cuniculus

<400> SEQUENCE: 318

Leu Gly Ala Phe Asp Asp Asp Ala Asp Asn Thr
1               5                   10

<210> SEQ ID NO 319
<211> LENGTH: 5
<212> TYPE: PRT
<213> ORGANISM: Oryctolagus cuniculus

<400> SEQUENCE: 319

Arg His Ala Ile Thr
1               5

<210> SEQ ID NO 320
<211> LENGTH: 16
<212> TYPE: PRT
<213> ORGANISM: Oryctolagus cuniculus

<400> SEQUENCE: 320

Cys Ile Trp Ser Gly Gly Ser Thr Tyr Tyr Ala Thr Trp Ala Lys Gly
1               5                   10                  15

<210> SEQ ID NO 321
<211> LENGTH: 16
<212> TYPE: PRT
<213> ORGANISM: Oryctolagus cuniculus

<400> SEQUENCE: 321

Val Ile Gly Asp Thr Ala Gly Tyr Ala Tyr Phe Thr Gly Leu Asp Leu
1               5                   10                  15

<210> SEQ ID NO 322
<211> LENGTH: 369
<212> TYPE: DNA
<213> ORGANISM: Oryctolagus cuniculus

<400> SEQUENCE: 322
atggacacga gggcccccac tcagctgctg ggctcctgc  tgctctggct cccaggtgcc      60
acgtttgcag ccgtgctgac ccagactgca tcacccgtgt ctgccgctgt gggagccaca     120
gtcaccatca actgccagtc cagtcagagt gtttataatg acatggactt agcctggttt     180
cagcagaaac cagggcagcc tcccaagctc ctgatctatt ctgcatccac tctggcatct     240
ggggtcccat cgcggttcag cggcagtgga tctgggacag agttcactct caccatcagc     300
ggcgtgcagt gtgacgatgc tgccacttac tactgtctag cgcttttga tgatgatgct     360 gataatact                                                             369

<210> SEQ ID NO 323
<211> LENGTH: 387
<212> TYPE: DNA
<213> ORGANISM: Oryctolagus cuniculus

<400> SEQUENCE: 323
atggagactg ggctgcgctg gcttctcctg gtcgctgtgc tcaaaggtgt ccagtgtcag      60
tcggtggagg agtccggggg tcgcctggtc acgcctggga cacccctgac actcacctgc     120
acagtctctg gattctccct cactaggcat gcaataacct gggtccgcca ggctccaggg     180
aaggggctgg aatggatcgg atgcatttgg agtggtggta gcacatacta cgcgacctgg     240
```

-continued gcgaaaggcc gattcaccat ctccaaaacc tcgaccacgg tggatctcag aatcaccagt    300
ccgacaaccg aggacacggc cacctacttc tgtgccagag tcattggcga tactgctggt    360
tatgcttatt ttacggggct tgacttg    387

<210> SEQ ID NO 324
<211> LENGTH: 39
<212> TYPE: DNA
<213> ORGANISM: Oryctolagus cuniculus

<400> SEQUENCE: 324
cagtccagtc agagtgttta taatgacatg gacttagcc    39

<210> SEQ ID NO 325
<211> LENGTH: 21
<212> TYPE: DNA
<213> ORGANISM: Oryctolagus cuniculus

<400> SEQUENCE: 325
tctgcatcca ctctggcatc t    21

<210> SEQ ID NO 326
<211> LENGTH: 33
<212> TYPE: DNA
<213> ORGANISM: Oryctolagus cuniculus

<400> SEQUENCE: 326
ctaggcgctt ttgatgatga tgctgataat act    33

<210> SEQ ID NO 327
<211> LENGTH: 15
<212> TYPE: DNA
<213> ORGANISM: Oryctolagus cuniculus

<400> SEQUENCE: 327
aggcatgcaa taacc    15

<210> SEQ ID NO 328
<211> LENGTH: 48
<212> TYPE: DNA
<213> ORGANISM: Oryctolagus cuniculus

<400> SEQUENCE: 328
tgcatttgga gtggtggtag cacatactac gcgacctggg cgaaaggc    48

<210> SEQ ID NO 329
<211> LENGTH: 48
<212> TYPE: DNA
<213> ORGANISM: Oryctolagus cuniculus

<400> SEQUENCE: 329
gtcattggcg atactgctgg ttatgcttat tttacggggc ttgacttg    48

<210> SEQ ID NO 330
<211> LENGTH: 121
<212> TYPE: PRT
<213> ORGANISM: Oryctolagus cuniculus

<400> SEQUENCE: 330

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser

```
              20                  25                  30
Val Glu Val Ala Val Gly Gly Thr Val Thr Ile Lys Cys Gln Ala Ser
             35                  40                  45

Gln Ser Val Tyr Asn Trp Leu Ser Trp Tyr Gln Gln Lys Pro Gly Gln
         50                  55                  60

Pro Pro Lys Leu Leu Ile Tyr Thr Ala Ser Ser Leu Ala Ser Gly Val
 65                  70                  75                  80

Pro Ser Arg Phe Ser Gly Ser Gly Ser Gly Thr Glu Phe Thr Leu Thr
                 85                  90                  95

Ile Ser Gly Val Glu Cys Ala Asp Ala Ala Thr Tyr Tyr Cys Gln Gln
            100                 105                 110

Gly Tyr Thr Ser Asp Val Asp Asn Val
            115                 120

<210> SEQ ID NO 331
<211> LENGTH: 130
<212> TYPE: PRT
<213> ORGANISM: Oryctolagus cuniculus

<400> SEQUENCE: 331

Met Glu Thr Gly Leu Arg Trp Leu Leu Leu Val Ala Val Leu Lys Gly
  1               5                  10                  15

Val Gln Cys Gln Ser Leu Glu Glu Ala Gly Gly Arg Leu Val Thr Pro
             20                  25                  30

Gly Thr Pro Leu Thr Leu Thr Cys Thr Val Ser Gly Ile Asp Leu Ser
         35                  40                  45

Ser Tyr Ala Met Gly Trp Val Arg Gln Ala Pro Gly Lys Gly Leu Glu
     50                  55                  60

Tyr Ile Gly Ile Ile Ser Ser Ser Gly Ser Thr Tyr Tyr Ala Thr Trp
 65                  70                  75                  80

Ala Lys Gly Arg Phe Thr Ile Ser Gln Ala Ser Ser Thr Thr Val Asp
                 85                  90                  95

Leu Lys Ile Thr Ser Pro Thr Thr Glu Asp Ser Ala Thr Tyr Phe Cys
            100                 105                 110

Ala Arg Gly Gly Ala Gly Ser Gly Gly Val Trp Leu Leu Asp Gly Phe
            115                 120                 125

Asp Pro
    130

<210> SEQ ID NO 332
<211> LENGTH: 11
<212> TYPE: PRT
<213> ORGANISM: Oryctolagus cuniculus

<400> SEQUENCE: 332

Gln Ala Ser Gln Ser Val Tyr Asn Trp Leu Ser
  1               5                  10

<210> SEQ ID NO 333
<211> LENGTH: 7
<212> TYPE: PRT
<213> ORGANISM: Oryctolagus cuniculus

<400> SEQUENCE: 333

Thr Ala Ser Ser Leu Ala Ser
  1               5

<210> SEQ ID NO 334
```

```
<211> LENGTH: 11
<212> TYPE: PRT
<213> ORGANISM: Oryctolagus cuniculus

<400> SEQUENCE: 334

Gln Gln Gly Tyr Thr Ser Asp Val Asp Asn Val
1               5                   10

<210> SEQ ID NO 335
<211> LENGTH: 5
<212> TYPE: PRT
<213> ORGANISM: Oryctolagus cuniculus

<400> SEQUENCE: 335

Ser Tyr Ala Met Gly
1               5

<210> SEQ ID NO 336
<211> LENGTH: 16
<212> TYPE: PRT
<213> ORGANISM: Oryctolagus cuniculus

<400> SEQUENCE: 336

Ile Ile Ser Ser Ser Gly Ser Thr Tyr Tyr Ala Thr Trp Ala Lys Gly
1               5                   10                  15

<210> SEQ ID NO 337
<211> LENGTH: 16
<212> TYPE: PRT
<213> ORGANISM: Oryctolagus cuniculus

<400> SEQUENCE: 337

Gly Gly Ala Gly Ser Gly Gly Val Trp Leu Leu Asp Gly Phe Asp Pro
1               5                   10                  15

<210> SEQ ID NO 338
<211> LENGTH: 363
<212> TYPE: DNA
<213> ORGANISM: Oryctolagus cuniculus

<400> SEQUENCE: 338
atggacacga gggcccccac tcagctgctg ggctcctgc tgctctggct cccaggtgcc      60
agatgtgcct atgatatgac ccagactcca gcctctgtgg aggtagctgt gggaggcaca     120
gtcaccatca agtgccaggc cagtcagagt gtttataatt ggttatcctg gtatcagcag    180
aaaccagggc agcctcccaa gctcctgatc tatactgcat ccagtctggc atctggggtc    240
ccatcgcggt tcagtggcag tggatctggg acagagttca ctctcaccat cagcggcgtg    300
gagtgtgccg atgctgccac ttactactgt caacagggtt atactagtga tgttgataat    360
gtt                                                                  363

<210> SEQ ID NO 339
<211> LENGTH: 390
<212> TYPE: DNA
<213> ORGANISM: Oryctolagus cuniculus

<400> SEQUENCE: 339
atggagactg ggctgcgctg gcttctcctg gtcgctgtgc tcaaaggtgt ccagtgtcag      60
tcgctggagg aggccggggg tcgcctggtc acgcctggga cacccctgac actcacctgc    120
acagtctctg gaatcgacct cagtagctat gcaatgggct gggtccgcca ggctccaggg    180
aaggggctgg aatacatcgg aatcattagt agtagtggta gcacatacta cgcgacctgg    240
```

-continued gcgaaaggcc gattcaccat ctcacaagcc tcgtcgacca cggtggatct gaaaattacc    300
agtccgacaa ccgaggactc ggccacatat ttctgtgcca gagggggtgc tggtagtggt    360
ggtgtttggc tgcttgatgg ttttgatccc                                    390

<210> SEQ ID NO 340
<211> LENGTH: 33
<212> TYPE: DNA
<213> ORGANISM: Oryctolagus cuniculus

<400> SEQUENCE: 340
caggccagtc agagtgttta taattggtta tcc                                33

<210> SEQ ID NO 341
<211> LENGTH: 21
<212> TYPE: DNA
<213> ORGANISM: Oryctolagus cuniculus

<400> SEQUENCE: 341
actgcatcca gtctggcatc t                                             21

<210> SEQ ID NO 342
<211> LENGTH: 33
<212> TYPE: DNA
<213> ORGANISM: Oryctolagus cuniculus

<400> SEQUENCE: 342
caacagggtt atactagtga tgttgataat gtt                                33

<210> SEQ ID NO 343
<211> LENGTH: 15
<212> TYPE: DNA
<213> ORGANISM: Oryctolagus cuniculus

<400> SEQUENCE: 343
agctatgcaa tgggc                                                    15

<210> SEQ ID NO 344
<211> LENGTH: 48
<212> TYPE: DNA
<213> ORGANISM: Oryctolagus cuniculus

<400> SEQUENCE: 344
atcattagta gtagtggtag cacatactac gcgacctggg cgaaaggc                48

<210> SEQ ID NO 345
<211> LENGTH: 48
<212> TYPE: DNA
<213> ORGANISM: Oryctolagus cuniculus

<400> SEQUENCE: 345
gggggtgctg gtagtggtgg tgtttggctg cttgatggtt ttgatccc                48

<210> SEQ ID NO 346
<211> LENGTH: 123
<212> TYPE: PRT
<213> ORGANISM: Oryctolagus cuniculus

<400> SEQUENCE: 346

Met Asp Thr Arg Ala Pro Thr Gln Leu Leu Gly Leu Leu Leu Leu Trp
1               5                   10                  15

Leu Pro Gly Ala Lys Cys Ala Asp Val Val Met Thr Gln Thr Pro Ala

```
            20                  25                  30
Ser Val Ser Ala Ala Val Gly Gly Thr Val Thr Ile Asn Cys Gln Ala
        35                  40                  45

Ser Glu Asn Ile Tyr Asn Trp Leu Ala Trp Tyr Gln Gln Lys Pro Gly
 50                  55                  60

Gln Pro Pro Lys Leu Leu Ile Tyr Thr Val Gly Asp Leu Ala Ser Gly
 65                  70                  75                  80

Val Ser Ser Arg Phe Lys Gly Ser Gly Ser Gly Thr Glu Phe Thr Leu
            85                  90                  95

Thr Ile Ser Asp Leu Glu Cys Ala Asp Ala Ala Thr Tyr Tyr Cys Gln
            100                 105                 110

Gln Gly Tyr Ser Ser Ser Tyr Val Asp Asn Val
            115                 120
```

<210> SEQ ID NO 347
<211> LENGTH: 130
<212> TYPE: PRT
<213> ORGANISM: Oryctolagus cuniculus

<400> SEQUENCE: 347

```
Met Glu Thr Gly Leu Arg Trp Leu Leu Leu Val Ala Val Leu Lys Gly
 1               5                  10                  15

Val Gln Cys Gln Glu Gln Leu Lys Glu Ser Gly Gly Arg Leu Val Thr
            20                  25                  30

Pro Gly Thr Pro Leu Thr Leu Thr Cys Thr Val Ser Gly Phe Ser Leu
        35                  40                  45

Asn Asp Tyr Ala Val Gly Trp Phe Arg Gln Ala Pro Gly Lys Gly Leu
 50                  55                  60

Glu Trp Ile Gly Tyr Ile Arg Ser Ser Gly Thr Thr Ala Tyr Ala Thr
 65                  70                  75                  80

Trp Ala Lys Gly Arg Phe Thr Ile Ser Ala Thr Ser Thr Thr Val Asp
            85                  90                  95

Leu Lys Ile Thr Ser Pro Thr Thr Glu Asp Thr Ala Thr Tyr Phe Cys
            100                 105                 110

Ala Arg Gly Gly Ala Gly Ser Ser Gly Val Trp Ile Leu Asp Gly Phe
            115                 120                 125

Ala Pro
    130
```

<210> SEQ ID NO 348
<211> LENGTH: 11
<212> TYPE: PRT
<213> ORGANISM: Oryctolagus cuniculus

<400> SEQUENCE: 348

```
Gln Ala Ser Glu Asn Ile Tyr Asn Trp Leu Ala
 1               5                  10
```

<210> SEQ ID NO 349
<211> LENGTH: 7
<212> TYPE: PRT
<213> ORGANISM: Oryctolagus cuniculus

<400> SEQUENCE: 349

```
Thr Val Gly Asp Leu Ala Ser
 1               5
```

<210> SEQ ID NO 350

<210> SEQ ID NO 350
<211> LENGTH: 12
<212> TYPE: PRT
<213> ORGANISM: Oryctolagus cuniculus

<400> SEQUENCE: 350

Gln Gln Gly Tyr Ser Ser Ser Tyr Val Asp Asn Val
1               5                   10

<210> SEQ ID NO 351
<211> LENGTH: 5
<212> TYPE: PRT
<213> ORGANISM: Oryctolagus cuniculus

<400> SEQUENCE: 351

Asp Tyr Ala Val Gly
1               5

<210> SEQ ID NO 352
<211> LENGTH: 16
<212> TYPE: PRT
<213> ORGANISM: Oryctolagus cuniculus

<400> SEQUENCE: 352

Tyr Ile Arg Ser Ser Gly Thr Thr Ala Tyr Ala Thr Trp Ala Lys Gly
1               5                   10                  15

<210> SEQ ID NO 353
<211> LENGTH: 16
<212> TYPE: PRT
<213> ORGANISM: Oryctolagus cuniculus

<400> SEQUENCE: 353

Gly Gly Ala Gly Ser Ser Gly Val Trp Ile Leu Asp Gly Phe Ala Pro
1               5                   10                  15

<210> SEQ ID NO 354
<211> LENGTH: 369
<212> TYPE: DNA
<213> ORGANISM: Oryctolagus cuniculus

<400> SEQUENCE: 354

```
atggacacga gggcccccac tcagctgctg ggctcctgc tgctctggct cccaggtgcc      60
aaatgtgccg atgttgtgat gacccagact ccagcctccg tgtctgcagc tgtgggaggc    120
acagtcacca tcaattgcca ggccagtgag aacatttata attggttagc ctggtatcag    180
cagaaaccag gcagcctcc caagctcctg atctatactg taggcgatct ggcatctggg    240
gtctcatcgc ggttcaaagg cagtggatct gggacagagt tcactctcac catcagcgac    300
ctggagtgtg ccgatgctgc cacttactat tgtcaacagg gttatagtag tagttatgtt    360
gataatgtt                                                             369
```

<210> SEQ ID NO 355
<211> LENGTH: 390
<212> TYPE: DNA
<213> ORGANISM: Oryctolagus cuniculus

<400> SEQUENCE: 355

```
atggagactg ggctgcgctg gcttctcctg gtcgctgtgc tcaaaggtgt ccagtgtcag      60
gagcagctga aggagtccgg gggtcgcctg gtcacgcctg gacaccccct gacactcacc    120
tgcacagtct ctggattctc cctcaatgac tatgcagtgg gctggttccg ccaggctcca    180
gggaaggggc tggaatggat cggatacatt cgtagtagtg gtaccacagc ctacgcgacc    240
```
tgggcgaaag gccgattcac catctccgct acctcgacca cggtggatct gaaaatcacc    300
agtccgacaa ccgaggacac ggccacctat ttctgtgcca gagggggtgc tggtagtagt    360
ggtgtgtgga tccttgatgg ttttgctccc                                    390

<210> SEQ ID NO 356
<211> LENGTH: 33
<212> TYPE: DNA
<213> ORGANISM: Oryctolagus cuniculus

<400> SEQUENCE: 356
caggccagtg agaacattta taattggtta gcc                                 33

<210> SEQ ID NO 357
<211> LENGTH: 21
<212> TYPE: DNA
<213> ORGANISM: Oryctolagus cuniculus

<400> SEQUENCE: 357
actgtaggcg atctggcatc t                                              21

<210> SEQ ID NO 358
<211> LENGTH: 36
<212> TYPE: DNA
<213> ORGANISM: Oryctolagus cuniculus

<400> SEQUENCE: 358
caacagggtt atagtagtag ttatgttgat aatgtt                              36

<210> SEQ ID NO 359
<211> LENGTH: 15
<212> TYPE: DNA
<213> ORGANISM: Oryctolagus cuniculus

<400> SEQUENCE: 359
gactatgcag tgggc                                                     15

<210> SEQ ID NO 360
<211> LENGTH: 48
<212> TYPE: DNA
<213> ORGANISM: Oryctolagus cuniculus

<400> SEQUENCE: 360
tacattcgta gtagtggtac cacagcctac gcgacctggg cgaaaggc                 48

<210> SEQ ID NO 361
<211> LENGTH: 48
<212> TYPE: DNA
<213> ORGANISM: Oryctolagus cuniculus

<400> SEQUENCE: 361
gggggtgctg gtagtagtgg tgtgtggatc cttgatggtt ttgctccc                 48

<210> SEQ ID NO 362
<211> LENGTH: 121
<212> TYPE: PRT
<213> ORGANISM: Oryctolagus cuniculus

<400> SEQUENCE: 362

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser

-continued

```
                    20                  25                  30
Val Ser Ala Ala Val Gly Gly Thr Val Thr Ile Asn Cys Gln Ala Ser
                35                  40                  45

Gln Ser Val Tyr Gln Asn Asn Tyr Leu Ser Trp Phe Gln Gln Lys Pro
     50                  55                  60

Gly Gln Pro Pro Lys Leu Leu Ile Tyr Gly Ala Ala Thr Leu Ala Ser
 65                  70                  75                  80

Gly Val Pro Ser Arg Phe Lys Gly Ser Gly Ser Gly Thr Gln Phe Thr
                 85                  90                  95

Leu Thr Ile Ser Asp Leu Glu Cys Asp Asp Ala Ala Thr Tyr Tyr Cys
            100                 105                 110

Ala Gly Ala Tyr Arg Asp Val Asp Ser
            115                 120

<210> SEQ ID NO 363
<211> LENGTH: 130
<212> TYPE: PRT
<213> ORGANISM: Oryctolagus cuniculus

<400> SEQUENCE: 363

Met Glu Thr Gly Leu Arg Trp Leu Leu Leu Val Ala Val Leu Lys Gly
  1               5                  10                  15

Val Gln Cys Gln Ser Leu Glu Glu Ser Gly Gly Asp Leu Val Lys Pro
                 20                  25                  30

Gly Ala Ser Leu Thr Leu Thr Cys Thr Ala Ser Gly Phe Ser Phe Thr
             35                  40                  45

Ser Thr Tyr Tyr Ile Tyr Trp Val Arg Gln Ala Pro Gly Lys Gly Leu
     50                  55                  60

Glu Trp Ile Ala Cys Ile Asp Ala Gly Ser Ser Gly Ser Thr Tyr Tyr
 65                  70                  75                  80

Ala Thr Trp Val Asn Gly Arg Phe Thr Ile Ser Lys Thr Ser Ser Thr
                 85                  90                  95

Thr Val Thr Leu Gln Met Thr Ser Leu Thr Ala Ala Asp Thr Ala Thr
            100                 105                 110

Tyr Phe Cys Ala Lys Trp Asp Tyr Gly Gly Asn Val Trp Gly Gly Tyr
            115                 120                 125

Asp Leu
    130

<210> SEQ ID NO 364
<211> LENGTH: 13
<212> TYPE: PRT
<213> ORGANISM: Oryctolagus cuniculus

<400> SEQUENCE: 364

Gln Ala Ser Gln Ser Val Tyr Gln Asn Asn Tyr Leu Ser
  1               5                  10

<210> SEQ ID NO 365
<211> LENGTH: 7
<212> TYPE: PRT
<213> ORGANISM: Oryctolagus cuniculus

<400> SEQUENCE: 365

Gly Ala Ala Thr Leu Ala Ser
  1               5

<210> SEQ ID NO 366
```

```
<211> LENGTH: 9
<212> TYPE: PRT
<213> ORGANISM: Oryctolagus cuniculus

<400> SEQUENCE: 366

Ala Gly Ala Tyr Arg Asp Val Asp Ser
1               5

<210> SEQ ID NO 367
<211> LENGTH: 6
<212> TYPE: PRT
<213> ORGANISM: Oryctolagus cuniculus

<400> SEQUENCE: 367

Ser Thr Tyr Tyr Ile Tyr
1               5

<210> SEQ ID NO 368
<211> LENGTH: 18
<212> TYPE: PRT
<213> ORGANISM: Oryctolagus cuniculus

<400> SEQUENCE: 368

Cys Ile Asp Ala Gly Ser Ser Gly Ser Thr Tyr Tyr Ala Thr Trp Val
1               5                   10                  15

Asn Gly

<210> SEQ ID NO 369
<211> LENGTH: 13
<212> TYPE: PRT
<213> ORGANISM: Oryctolagus cuniculus

<400> SEQUENCE: 369

Trp Asp Tyr Gly Gly Asn Val Gly Trp Gly Tyr Asp Leu
1               5                   10

<210> SEQ ID NO 370
<211> LENGTH: 363
<212> TYPE: DNA
<213> ORGANISM: Oryctolagus cuniculus

<400> SEQUENCE: 370
atggacacga gggcccccac tcagctgctg ggctcctgc tgctctggct cccaggtgcc      60
acatttgctc aagtgctgac ccagactcca tcctccgtgt ctgcagctgt gggaggcaca     120
gtcaccatca attgccaggc cagtcagagt gtttatcaga caactactt atcctggttt      180
cagcagaaac cagggcagcc tcccaagctc ctgatctatg gtgcggccac tctggcatct     240
ggggtcccat cgcggttcaa aggcagtgga tctgggacac agttcactct caccatcagc     300
gacctggagt gtgacgatgc tgccacttac tactgtgcag gcgcttatag ggatgtggat     360
tct                                                                  363

<210> SEQ ID NO 371
<211> LENGTH: 390
<212> TYPE: DNA
<213> ORGANISM: Oryctolagus cuniculus

<400> SEQUENCE: 371
atggagactg ggctgcgctg gcttctcctg gtcgctgtgc tcaaaggtgt ccagtgtcag      60
tcgttggagg agtccggggg agacctggtc aagcctgggg catccctgac actcacctgc     120
acagcctctg gattctcctt tactagtacc tactacatct actgggtccg ccaggctcca     180
```

```
gggaaggggc tggagtggat cgcatgtatt gatgctggta gtagtggtag cacttactac    240
gcgacctggg tgaatggccg attcaccatc tccaaaacct cgtcgaccac ggtgactctg    300
caaatgacca gtctgacagc cgcggacacg gccacctatt tctgtgcgaa atgggattat    360
ggtggtaatg ttggttgggg ttatgacttg                                     390
```

<210> SEQ ID NO 372
<211> LENGTH: 39
<212> TYPE: DNA
<213> ORGANISM: Oryctolagus cuniculus

<400> SEQUENCE: 372

```
caggccagtc agagtgttta tcagaacaac tacttatcc                            39
```

<210> SEQ ID NO 373
<211> LENGTH: 21
<212> TYPE: DNA
<213> ORGANISM: Oryctolagus cuniculus

<400> SEQUENCE: 373

```
ggtgcggcca ctctggcatc t                                               21
```

<210> SEQ ID NO 374
<211> LENGTH: 27
<212> TYPE: DNA
<213> ORGANISM: Oryctolagus cuniculus

<400> SEQUENCE: 374

```
gcaggcgctt atagggatgt ggattct                                         27
```

<210> SEQ ID NO 375
<211> LENGTH: 18
<212> TYPE: DNA
<213> ORGANISM: Oryctolagus cuniculus

<400> SEQUENCE: 375

```
agtacctact acatctac                                                   18
```

<210> SEQ ID NO 376
<211> LENGTH: 54
<212> TYPE: DNA
<213> ORGANISM: Oryctolagus cuniculus

<400> SEQUENCE: 376

```
tgtattgatg ctggtagtag tggtagcact tactacgcga cctgggtgaa tggc           54
```

<210> SEQ ID NO 377
<211> LENGTH: 39
<212> TYPE: DNA
<213> ORGANISM: Oryctolagus cuniculus

<400> SEQUENCE: 377

```
tgggattatg gtggtaatgt tggttggggt tatgacttg                            39
```

<210> SEQ ID NO 378
<211> LENGTH: 120
<212> TYPE: PRT
<213> ORGANISM: Oryctolagus cuniculus

<400> SEQUENCE: 378

Met Asp Thr Arg Ala Pro Thr Gln Leu Leu Gly Leu Leu Leu Leu Trp
1               5                   10                  15

-continued

Leu Pro Gly Ala Arg Cys Ala Phe Glu Leu Thr Gln Thr Pro Ser Ser
              20                  25                  30

Val Glu Ala Ala Val Gly Gly Thr Val Thr Ile Lys Cys Gln Ala Ser
              35                  40                  45

Gln Ser Ile Ser Ser Tyr Leu Ala Trp Tyr Gln Lys Pro Gly Gln
 50                  55                  60

Pro Pro Lys Phe Leu Ile Tyr Arg Ala Ser Thr Leu Ala Ser Gly Val
65                  70                  75                  80

Pro Ser Arg Phe Lys Gly Ser Gly Ser Gly Thr Glu Phe Thr Leu Thr
              85                  90                  95

Ile Ser Asp Leu Glu Cys Ala Asp Ala Ala Thr Tyr Tyr Cys Gln Ser
              100                 105                 110

Tyr Tyr Asp Ser Val Ser Asn Pro
        115                 120

<210> SEQ ID NO 379
<211> LENGTH: 127
<212> TYPE: PRT
<213> ORGANISM: Oryctolagus cuniculus

<400> SEQUENCE: 379

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
              20                  25                  30

Glu Gly Ser Leu Thr Leu Thr Cys Lys Ala Ser Gly Leu Asp Leu Gly
              35                  40                  45

Thr Tyr Trp Phe Met Cys Trp Val Arg Gln Ala Pro Gly Lys Gly Leu
 50                  55                  60

Glu Trp Ile Ala Cys Ile Tyr Thr Gly Ser Ser Gly Ser Thr Phe Tyr
65                  70                  75                  80

Ala Ser Trp Val Asn Gly Arg Phe Thr Ile Ser Lys Thr Ser Ser Thr
              85                  90                  95

Thr Val Thr Leu Gln Met Thr Ser Leu Thr Ala Ala Asp Thr Ala Thr
              100                 105                 110

Tyr Phe Cys Ala Arg Gly Tyr Ser Gly Tyr Gly Tyr Phe Lys Leu
              115                 120                 125

<210> SEQ ID NO 380
<211> LENGTH: 11
<212> TYPE: PRT
<213> ORGANISM: Oryctolagus cuniculus

<400> SEQUENCE: 380

Gln Ala Ser Gln Ser Ile Ser Ser Tyr Leu Ala
1               5                   10

<210> SEQ ID NO 381
<211> LENGTH: 7
<212> TYPE: PRT
<213> ORGANISM: Oryctolagus cuniculus

<400> SEQUENCE: 381

Arg Ala Ser Thr Leu Ala Ser
1               5

<210> SEQ ID NO 382
<211> LENGTH: 10

<212> TYPE: PRT
<213> ORGANISM: Oryctolagus cuniculus

<400> SEQUENCE: 382

Gln Ser Tyr Tyr Asp Ser Val Ser Asn Pro
1               5                   10

<210> SEQ ID NO 383
<211> LENGTH: 6
<212> TYPE: PRT
<213> ORGANISM: Oryctolagus cuniculus

<400> SEQUENCE: 383

Thr Tyr Trp Phe Met Cys
1               5

<210> SEQ ID NO 384
<211> LENGTH: 18
<212> TYPE: PRT
<213> ORGANISM: Oryctolagus cuniculus

<400> SEQUENCE: 384

Cys Ile Tyr Thr Gly Ser Ser Gly Ser Thr Phe Tyr Ala Ser Trp Val
1               5                   10                  15

Asn Gly

<210> SEQ ID NO 385
<211> LENGTH: 10
<212> TYPE: PRT
<213> ORGANISM: Oryctolagus cuniculus

<400> SEQUENCE: 385

Gly Tyr Ser Gly Tyr Gly Tyr Phe Lys Leu
1               5                   10

<210> SEQ ID NO 386
<211> LENGTH: 360
<212> TYPE: DNA
<213> ORGANISM: Oryctolagus cuniculus

<400> SEQUENCE: 386
atggacacga gggcccccac tcagctgctg gggctcctgc tgctctggct cccaggtgcc    60
agatgtgcat tcgaattgac ccagactcca tcctccgtgg aggcagctgt gggaggcaca   120
gtcaccatca gtgccaggc cagtcagagc attagtagtt acttagcctg gtatcagcag   180
aaaccagggc agcctcccaa gttcctgatc tacagggcgt ccactctggc atctggggtc   240
ccatcgcgat tcaaaggcag tggatctggg acagagttca ctctcaccat cagcgacctg   300
gagtgtgccg atgctgccac ttactactgt caaagctatt atgatagtgt ttcaaatcct   360

<210> SEQ ID NO 387
<211> LENGTH: 381
<212> TYPE: DNA
<213> ORGANISM: Oryctolagus cuniculus

<400> SEQUENCE: 387
atggagactg ggctgcgctg gcttctcctg gtcgctgtgc tcaaaggtgt ccagtgtcag    60
tcgttggagg agtccggggg agacctggtc aagcctgagg atccctgac actcacctgc   120 aaagcctctg gactcgacct cggtacctac tggttcatgt gctgggtccg ccaggctcca   180
gggaaggggc tggagtggat cgcttgtatt tatactggta gtagtggttc cactttctac   240

```
gcgagctggg tgaatggccg attcaccatc tccaaaacct cgtcgaccac ggtgactctg    300
caaatgacca gtctgacagc cgcggacacg gccacttatt tttgtgcgag aggttatagt    360
ggttatggtt attttaagtt g                                              381
```

<210> SEQ ID NO 388
<211> LENGTH: 33
<212> TYPE: DNA
<213> ORGANISM: Oryctolagus cuniculus

<400> SEQUENCE: 388

```
caggccagtc agagcattag tagttactta gcc                                  33
```

<210> SEQ ID NO 389
<211> LENGTH: 21
<212> TYPE: DNA
<213> ORGANISM: Oryctolagus cuniculus

<400> SEQUENCE: 389

```
agggcgtcca ctctggcatc t                                               21
```

<210> SEQ ID NO 390
<211> LENGTH: 30
<212> TYPE: DNA
<213> ORGANISM: Oryctolagus cuniculus

<400> SEQUENCE: 390

```
caaagctatt atgatagtgt ttcaaatcct                                      30
```

<210> SEQ ID NO 391
<211> LENGTH: 18
<212> TYPE: DNA
<213> ORGANISM: Oryctolagus cuniculus

<400> SEQUENCE: 391

```
acctactggt tcatgtgc                                                   18
```

<210> SEQ ID NO 392
<211> LENGTH: 54
<212> TYPE: DNA
<213> ORGANISM: Oryctolagus cuniculus

<400> SEQUENCE: 392

```
tgtatttata ctggtagtag tggttccact ttctacgcga gctgggtgaa tggc           54
```

<210> SEQ ID NO 393
<211> LENGTH: 30
<212> TYPE: DNA
<213> ORGANISM: Oryctolagus cuniculus

<400> SEQUENCE: 393

```
ggttatagtg gttatggtta ttttaagttg                                      30
```

<210> SEQ ID NO 394
<211> LENGTH: 124
<212> TYPE: PRT
<213> ORGANISM: Oryctolagus cuniculus

<400> SEQUENCE: 394

```
Met Asp Thr Arg Ala Pro Thr Gln Leu Leu Gly Leu Leu Leu Leu Trp
1               5                   10                  15

Leu Pro Gly Val Thr Phe Ala Ile Glu Met Thr Gln Ser Pro Phe Ser
            20                  25                  30
```

```
Val Ser Ala Ala Val Gly Gly Thr Val Ser Ile Ser Cys Gln Ala Ser
            35                  40                  45

Gln Ser Val Tyr Lys Asn Asn Gln Leu Ser Trp Tyr Gln Gln Lys Ser
    50                  55                  60

Gly Gln Pro Pro Lys Leu Leu Ile Tyr Gly Ala Ser Ala Leu Ala Ser
65                  70                  75                  80

Gly Val Pro Ser Arg Phe Lys Gly Ser Gly Ser Gly Thr Glu Phe Thr
                85                  90                  95

Leu Thr Ile Ser Asp Val Gln Cys Asp Asp Ala Ala Thr Tyr Tyr Cys
            100                 105                 110

Ala Gly Ala Ile Thr Gly Ser Ile Asp Thr Asp Gly
            115                 120
```

```
<210> SEQ ID NO 395
<211> LENGTH: 130
<212> TYPE: PRT
<213> ORGANISM: Oryctolagus cuniculus

<400> SEQUENCE: 395

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Thr Ser Gly Phe Ser Phe Ser
        35                  40                  45

Ser Ser Tyr Phe Ile Cys Trp Val Arg Gln Ala Pro Gly Lys Gly Leu
    50                  55                  60

Glu Trp Ile Ala Cys Ile Tyr Gly Gly Asp Gly Ser Thr Tyr Tyr Ala
65                  70                  75                  80

Ser Trp Ala Lys Gly Arg Phe Thr Ile Ser Lys Thr Ser Ser Thr Thr
                85                  90                  95

Val Thr Leu Gln Met Thr Ser Leu Thr Ala Ala Asp Thr Ala Thr Tyr
            100                 105                 110

Phe Cys Ala Arg Glu Trp Ala Tyr Ser Gln Gly Tyr Phe Gly Ala Phe
        115                 120                 125

Asp Leu
    130
```

```
<210> SEQ ID NO 396
<211> LENGTH: 13
<212> TYPE: PRT
<213> ORGANISM: Oryctolagus cuniculus

<400> SEQUENCE: 396

Gln Ala Ser Gln Ser Val Tyr Lys Asn Asn Gln Leu Ser
1               5                   10
```

```
<210> SEQ ID NO 397
<211> LENGTH: 7
<212> TYPE: PRT
<213> ORGANISM: Oryctolagus cuniculus

<400> SEQUENCE: 397

Gly Ala Ser Ala Leu Ala Ser
1               5
```

```
<210> SEQ ID NO 398
<211> LENGTH: 12
```

```
<212> TYPE: PRT
<213> ORGANISM: Oryctolagus cuniculus

<400> SEQUENCE: 398

Ala Gly Ala Ile Thr Gly Ser Ile Asp Thr Asp Gly
1               5                   10

<210> SEQ ID NO 399
<211> LENGTH: 6
<212> TYPE: PRT
<213> ORGANISM: Oryctolagus cuniculus

<400> SEQUENCE: 399

Ser Ser Tyr Phe Ile Cys
1               5

<210> SEQ ID NO 400
<211> LENGTH: 17
<212> TYPE: PRT
<213> ORGANISM: Oryctolagus cuniculus

<400> SEQUENCE: 400

Cys Ile Tyr Gly Gly Asp Gly Ser Thr Tyr Tyr Ala Ser Trp Ala Lys
1               5                   10                  15

Gly

<210> SEQ ID NO 401
<211> LENGTH: 14
<212> TYPE: PRT
<213> ORGANISM: Oryctolagus cuniculus

<400> SEQUENCE: 401

Glu Trp Ala Tyr Ser Gln Gly Tyr Phe Gly Ala Phe Asp Leu
1               5                   10

<210> SEQ ID NO 402
<211> LENGTH: 372
<212> TYPE: DNA
<213> ORGANISM: Oryctolagus cuniculus

<400> SEQUENCE: 402
atggacacga gggcccccac tcagctgctg gggctcctgc tgctctggct cccaggtgtc      60
acatttgcca tcgaaatgac ccagagtcca ttctccgtgt ctgcagctgt gggaggcaca     120
gtcagcatca gttgccaggc cagtcagagt gtttataaga caaccaatt atcctggtat     180 cagcagaaat cagggcagcc tcccaagctc ctgatctatg gtgcatcggc tctggcatct     240
ggggtcccat cgcggttcaa aggcagtgga tctgggacag agttcactct caccatcagc     300
gacgtgcagt gtgacgatgc tgccacttac tactgtgcag gcgctattac tggtagtatt     360
gatacggatg gt                                                         372

<210> SEQ ID NO 403
<211> LENGTH: 390
<212> TYPE: DNA
<213> ORGANISM: Oryctolagus cuniculus

<400> SEQUENCE: 403
atggagactg ggctgcgctg gcttctcctg gtcgctgtgc tcaaaggtgt ccagtgtcag      60
tcgttggagg agtccggggg agacctggtc aagcctgggg catccctgac actcacctgc     120
acaacttctg gattctccct cagtagcagc tacttcattt gctgggtccg ccaggctcca     180
```

```
gggaaggggc tggagtggat cgcatgcatt tatggtggtg atggcagcac atactacgcg    240
agctgggcga aaggccgatt caccatctcc aaaacctcgt cgaccacggt gacgctgcaa    300
atgaccagtc tgacagccgc ggacacggcc acctatttct gtgcgagaga atgggcatat    360
agtcaaggtt attttggtgc ttttgatctc                                     390
```

<210> SEQ ID NO 404
<211> LENGTH: 39
<212> TYPE: DNA
<213> ORGANISM: Oryctolagus cuniculus

<400> SEQUENCE: 404

```
caggccagtc agagtgttta taagaacaac caattatcc                            39
```

<210> SEQ ID NO 405
<211> LENGTH: 21
<212> TYPE: DNA
<213> ORGANISM: Oryctolagus cuniculus

<400> SEQUENCE: 405

```
ggtgcatcgg ctctggcatc t                                              21
```

<210> SEQ ID NO 406
<211> LENGTH: 36
<212> TYPE: DNA
<213> ORGANISM: Oryctolagus cuniculus

<400> SEQUENCE: 406

```
gcaggcgcta ttactggtag tattgatacg gatggt                              36
```

<210> SEQ ID NO 407
<211> LENGTH: 18
<212> TYPE: DNA
<213> ORGANISM: Oryctolagus cuniculus

<400> SEQUENCE: 407

```
agcagctact tcatttgc                                                  18
```

<210> SEQ ID NO 408
<211> LENGTH: 51
<212> TYPE: DNA
<213> ORGANISM: Oryctolagus cuniculus

<400> SEQUENCE: 408

```
tgcatttatg gtggtgatgg cagcacatac tacgcgagct gggcgaaagg c              51
```

<210> SEQ ID NO 409
<211> LENGTH: 42
<212> TYPE: DNA
<213> ORGANISM: Oryctolagus cuniculus

<400> SEQUENCE: 409

```
gaatgggcat atagtcaagg ttattttggt gcttttgatc tc                        42
```

<210> SEQ ID NO 410
<211> LENGTH: 124
<212> TYPE: PRT
<213> ORGANISM: Oryctolagus cuniculus

<400> SEQUENCE: 410

```
Met Asp Thr Arg Ala Pro Thr Gln Leu Leu Gly Leu Leu Leu Leu Trp
1               5                   10                  15
```

-continued

```
Leu Pro Gly Ala Arg Cys Asp Val Val Met Thr Gln Thr Pro Ala Ser
             20                  25                  30

Val Glu Ala Ala Val Gly Gly Thr Val Thr Ile Lys Cys Gln Ala Ser
         35                  40                  45

Glu Asp Ile Ser Ser Tyr Leu Ala Trp Tyr Gln Gln Lys Pro Gly Gln
     50                  55                  60

Pro Pro Lys Leu Leu Ile Tyr Ala Ala Ser Asn Leu Glu Ser Gly Val
 65                  70                  75                  80

Ser Ser Arg Phe Lys Gly Ser Gly Ser Gly Thr Glu Tyr Thr Leu Thr
                 85                  90                  95

Ile Ser Asp Leu Glu Cys Ala Asp Ala Ala Thr Tyr Tyr Cys Gln Cys
            100                 105                 110

Thr Tyr Gly Thr Ile Ser Ile Ser Asp Gly Asn Ala
            115                 120

<210> SEQ ID NO 411
<211> LENGTH: 124
<212> TYPE: PRT
<213> ORGANISM: Oryctolagus cuniculus

<400> SEQUENCE: 411

Met Glu Thr Gly Leu Arg Trp Leu Leu Leu Val Ala Val Leu Lys Gly
  1               5                  10                  15

Val Gln Cys Gln Ser Val Glu Glu Ser Gly Gly Arg Leu Val Thr Pro
             20                  25                  30

Gly Thr Pro Leu Thr Leu Thr Cys Thr Val Ser Gly Phe Ser Leu Ser
         35                  40                  45

Ser Tyr Phe Met Thr Trp Val Arg Gln Ala Pro Gly Glu Gly Leu Glu
     50                  55                  60

Tyr Ile Gly Phe Ile Asn Pro Gly Gly Ser Ala Tyr Tyr Ala Ser Trp
 65                  70                  75                  80

Val Lys Gly Arg Phe Thr Ile Ser Lys Ser Ser Thr Thr Val Asp Leu
                 85                  90                  95

Lys Ile Thr Ser Pro Thr Thr Glu Asp Thr Ala Thr Tyr Phe Cys Ala
            100                 105                 110

Arg Val Leu Ile Val Ser Tyr Gly Ala Phe Thr Ile
            115                 120

<210> SEQ ID NO 412
<211> LENGTH: 11
<212> TYPE: PRT
<213> ORGANISM: Oryctolagus cuniculus

<400> SEQUENCE: 412

Gln Ala Ser Glu Asp Ile Ser Ser Tyr Leu Ala
  1               5                  10

<210> SEQ ID NO 413
<211> LENGTH: 7
<212> TYPE: PRT
<213> ORGANISM: Oryctolagus cuniculus

<400> SEQUENCE: 413

Ala Ala Ser Asn Leu Glu Ser
  1               5

<210> SEQ ID NO 414
<211> LENGTH: 14
<212> TYPE: PRT
```

<213> ORGANISM: Oryctolagus cuniculus

<400> SEQUENCE: 414

Gln Cys Thr Tyr Gly Thr Ile Ser Ile Ser Asp Gly Asn Ala
1               5                   10

<210> SEQ ID NO 415
<211> LENGTH: 5
<212> TYPE: PRT
<213> ORGANISM: Oryctolagus cuniculus

<400> SEQUENCE: 415

Ser Tyr Phe Met Thr
1               5

<210> SEQ ID NO 416
<211> LENGTH: 16
<212> TYPE: PRT
<213> ORGANISM: Oryctolagus cuniculus

<400> SEQUENCE: 416

Phe Ile Asn Pro Gly Gly Ser Ala Tyr Tyr Ala Ser Trp Val Lys Gly
1               5                   10                  15

<210> SEQ ID NO 417
<211> LENGTH: 11
<212> TYPE: PRT
<213> ORGANISM: Oryctolagus cuniculus

<400> SEQUENCE: 417

Val Leu Ile Val Ser Tyr Gly Ala Phe Thr Ile
1               5                   10

<210> SEQ ID NO 418
<211> LENGTH: 372
<212> TYPE: DNA
<213> ORGANISM: Oryctolagus cuniculus

<400> SEQUENCE: 418

```
atggacacga gggcccccac tcagctgctg gggctcctgc tgctctggct cccaggtgcc    60
agatgtgatg ttgtgatgac ccagactcca gcctccgtgg aggcagctgt gggaggcaca   120
gtcaccatca gtgccaggc cagtgaggat attagtagct acttagcctg gtatcagcag   180
aaaccagggc agcctcccaa gctcctgatc tatgctgcat ccaatctgga atctggggtc   240
tcatcgcgat tcaaaggcag tggatctggg acagagtaca ctctcaccat cagcgacctg   300
gagtgtgccg atgctgccac ctattactgt caatgtactt atggtactat ttctattagt   360
gatggtaatg ct                                                       372
```

<210> SEQ ID NO 419
<211> LENGTH: 372
<212> TYPE: DNA
<213> ORGANISM: Oryctolagus cuniculus

<400> SEQUENCE: 419

```
atggagactg gctgcgctg gcttctcctg gtcgctgtgc tcaaaggtgt ccaatgtcag    60
tcggtggagg agtccggggg tcgcctggtc acgcctggga cacccctgac actcacctgc   120
acagtctctg gattctccct cagtagctac ttcatgacct gggtccgcca ggctccaggg   180
gaggggctgg aatacatcgg attcattaat cctggtggta cgcttactta cgcgagctgg   240
gtgaaaggcc gattcaccat ctccaagtcc tcgaccacgg tagatctgaa aatcaccagt   300
```

-continued

```
ccgacaaccg aggacacggc cacctatttc tgtgccaggg ttctgattgt ttcttatgga    360
gcctttacca tc                                                       372

<210> SEQ ID NO 420
<211> LENGTH: 33
<212> TYPE: DNA
<213> ORGANISM: Oryctolagus cuniculus

<400> SEQUENCE: 420
caggccagtg aggatattag tagctactta gcc                                 33

<210> SEQ ID NO 421
<211> LENGTH: 21
<212> TYPE: DNA
<213> ORGANISM: Oryctolagus cuniculus

<400> SEQUENCE: 421
gctgcatcca atctggaatc t                                              21

<210> SEQ ID NO 422
<211> LENGTH: 42
<212> TYPE: DNA
<213> ORGANISM: Oryctolagus cuniculus

<400> SEQUENCE: 422
caatgtactt atggtactat ttctattagt gatggtaatg ct                       42

<210> SEQ ID NO 423
<211> LENGTH: 15
<212> TYPE: DNA
<213> ORGANISM: Oryctolagus cuniculus

<400> SEQUENCE: 423
agctacttca tgacc                                                     15

<210> SEQ ID NO 424
<211> LENGTH: 48
<212> TYPE: DNA
<213> ORGANISM: Oryctolagus cuniculus

<400> SEQUENCE: 424
ttcattaatc ctggtggtag cgcttactac gcgagctggg tgaaaggc                 48

<210> SEQ ID NO 425
<211> LENGTH: 33
<212> TYPE: DNA
<213> ORGANISM: Oryctolagus cuniculus

<400> SEQUENCE: 425
gttctgattg tttcttatgg agcctttacc atc                                 33

<210> SEQ ID NO 426
<211> LENGTH: 124
<212> TYPE: PRT
<213> ORGANISM: Oryctolagus cuniculus

<400> SEQUENCE: 426

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30
```

Val Ser Ala Val Gly Gly Thr Val Thr Ile Lys Cys Gln Ala Ser
         35                  40                  45

Glu Asp Ile Glu Ser Tyr Leu Ala Trp Tyr Gln Gln Lys Pro Gly Gln
 50                      55                  60

Pro Pro Lys Leu Leu Ile Tyr Gly Ala Ser Asn Leu Glu Ser Gly Val
 65                  70                  75                  80

Ser Ser Arg Phe Lys Gly Ser Gly Ser Gly Thr Glu Phe Thr Leu Thr
                 85                  90                  95

Ile Ser Asp Leu Glu Cys Ala Asp Ala Ala Thr Tyr Tyr Cys Gln Cys
                100                 105                 110

Thr Tyr Gly Ile Ile Ser Ile Ser Asp Gly Asn Ala
            115                 120

<210> SEQ ID NO 427
<211> LENGTH: 124
<212> TYPE: PRT
<213> ORGANISM: Oryctolagus cuniculus

<400> SEQUENCE: 427

Met Glu Thr Gly Leu Arg Trp Leu Leu Leu Val Ala Val Leu Lys Gly
 1               5                  10                  15

Val Gln Cys Gln Ser Val Glu Ser Gly Gly Arg Leu Val Thr Pro
             20                  25                  30

Gly Thr Pro Leu Thr Leu Thr Cys Thr Val Ser Gly Phe Ser Leu Ser
             35                  40                  45

Ser Tyr Phe Met Thr Trp Val Arg Gln Ala Pro Gly Glu Gly Leu Glu
 50                      55                  60

Tyr Ile Gly Phe Met Asn Thr Gly Asp Asn Ala Tyr Tyr Ala Ser Trp
 65                  70                  75                  80

Ala Lys Gly Arg Phe Thr Ile Ser Lys Thr Ser Thr Val Asp Leu
                 85                  90                  95

Lys Ile Thr Ser Pro Thr Thr Glu Asp Thr Ala Thr Tyr Phe Cys Ala
                100                 105                 110

Arg Val Leu Val Val Ala Tyr Gly Ala Phe Asn Ile
            115                 120

<210> SEQ ID NO 428
<211> LENGTH: 11
<212> TYPE: PRT
<213> ORGANISM: Oryctolagus cuniculus

<400> SEQUENCE: 428

Gln Ala Ser Glu Asp Ile Glu Ser Tyr Leu Ala
 1               5                  10

<210> SEQ ID NO 429
<211> LENGTH: 7
<212> TYPE: PRT
<213> ORGANISM: Oryctolagus cuniculus

<400> SEQUENCE: 429

Gly Ala Ser Asn Leu Glu Ser
 1               5

<210> SEQ ID NO 430
<211> LENGTH: 14
<212> TYPE: PRT
<213> ORGANISM: Oryctolagus cuniculus

<400> SEQUENCE: 430

```
Gln Cys Thr Tyr Gly Ile Ile Ser Ile Ser Asp Gly Asn Ala
1               5                   10

<210> SEQ ID NO 431
<211> LENGTH: 5
<212> TYPE: PRT
<213> ORGANISM: Oryctolagus cuniculus

<400> SEQUENCE: 431

Ser Tyr Phe Met Thr
1               5

<210> SEQ ID NO 432
<211> LENGTH: 16
<212> TYPE: PRT
<213> ORGANISM: Oryctolagus cuniculus

<400> SEQUENCE: 432

Phe Met Asn Thr Gly Asp Asn Ala Tyr Tyr Ala Ser Trp Ala Lys Gly
1               5                   10                  15

<210> SEQ ID NO 433
<211> LENGTH: 11
<212> TYPE: PRT
<213> ORGANISM: Oryctolagus cuniculus

<400> SEQUENCE: 433

Val Leu Val Val Ala Tyr Gly Ala Phe Asn Ile
1               5                   10

<210> SEQ ID NO 434
<211> LENGTH: 372
<212> TYPE: DNA
<213> ORGANISM: Oryctolagus cuniculus

<400> SEQUENCE: 434
atggacacga gggcccccac tcagctgctg gggctcctgc tgctctggct cccaggtgcc      60
agatgtgatg ttgtgatgac ccagactcca gcctccgtgt ctgcagctgt gggaggcaca     120
gtcaccatca agtgccaggc cagtgaggac attgaaagct atctagcctg gtatcagcag     180
aaaccagggc agcctcccaa gctcctgatc tatggtgcat ccaatctgga atctggggtc     240
tcatcgcggt tcaaaggcag tggatctggg acagagttca ctctcaccat cagcgacctg     300
gagtgtgccg atgctgccac ttactattgt caatgcactt atggtattat tagtattagt     360
gatggtaatg ct                                                         372

<210> SEQ ID NO 435
<211> LENGTH: 372
<212> TYPE: DNA
<213> ORGANISM: Oryctolagus cuniculus

<400> SEQUENCE: 435
atggagactg ggctgcgctg gcttctcctg gtcgctgtgc tcaaaggtgt ccagtgtcag      60
tcggtggagg agtccggggg tcgcctggtc acgcctggga cacccctgac actcacctgc     120
acagtgtctg gattctccct cagtagctac ttcatgacct gggtccgcca ggctccaggg     180
gaggggctgg aatacatcgg attcatgaat actggtgata acgcatacta cgcgagctgg     240
gcgaaaggcc gattcaccat ctccaaaacc tcgaccacgg tggatctgaa aatcaccagt     300
ccgacaaccg aggacacggc cacctatttc tgtgccaggg ttcttgttgt tgcttatgga     360
```

-continued gcctttaaca tc                                                           372

<210> SEQ ID NO 436
<211> LENGTH: 33
<212> TYPE: DNA
<213> ORGANISM: Oryctolagus cuniculus

<400> SEQUENCE: 436
caggccagtg aggacattga aagctatcta gcc                                     33

<210> SEQ ID NO 437
<211> LENGTH: 21
<212> TYPE: DNA
<213> ORGANISM: Oryctolagus cuniculus

<400> SEQUENCE: 437
ggtgcatcca atctggaatc t                                                  21

<210> SEQ ID NO 438
<211> LENGTH: 42
<212> TYPE: DNA
<213> ORGANISM: Oryctolagus cuniculus

<400> SEQUENCE: 438
caatgcactt atggtattat tagtattagt gatggtaatg ct                           42

<210> SEQ ID NO 439
<211> LENGTH: 15
<212> TYPE: DNA
<213> ORGANISM: Oryctolagus cuniculus

<400> SEQUENCE: 439
agctacttca tgacc                                                         15

<210> SEQ ID NO 440
<211> LENGTH: 48
<212> TYPE: DNA
<213> ORGANISM: Oryctolagus cuniculus

<400> SEQUENCE: 440
ttcatgaata ctggtgataa cgcatactac gcgagctggg cgaaaggc                     48

<210> SEQ ID NO 441
<211> LENGTH: 33
<212> TYPE: DNA
<213> ORGANISM: Oryctolagus cuniculus

<400> SEQUENCE: 441
gttcttgttg ttgcttatgg agcctttaac atc                                     33

<210> SEQ ID NO 442
<211> LENGTH: 124
<212> TYPE: PRT
<213> ORGANISM: Oryctolagus cuniculus

<400> SEQUENCE: 442

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
                20                  25                  30

Val Ser Glu Pro Val Gly Gly Thr Val Ser Ile Ser Cys Gln Ser Ser
            35                  40                  45

```
Lys Ser Val Met Asn Asn Tyr Leu Ala Trp Tyr Gln Gln Lys Pro
        50                  55                  60

Gly Gln Pro Pro Lys Leu Leu Ile Tyr Gly Ala Ser Asn Leu Ala Ser
 65                  70                  75                  80

Gly Val Pro Ser Arg Phe Ser Gly Ser Gly Ser Gly Thr Gln Phe Thr
                    85                  90                  95

Leu Thr Ile Ser Asp Val Gln Cys Asp Asp Ala Ala Thr Tyr Tyr Cys
                100                 105                 110

Gln Gly Gly Tyr Thr Gly Tyr Ser Asp His Gly Thr
            115                 120

<210> SEQ ID NO 443
<211> LENGTH: 127
<212> TYPE: PRT
<213> ORGANISM: Oryctolagus cuniculus

<400> SEQUENCE: 443

Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Lys Pro
                20                  25                  30

Asp Glu Thr Leu Thr Leu Thr Cys Thr Val Ser Gly Ile Asp Leu Ser
                35                  40                  45

Ser Tyr Pro Met Asn Trp Val Arg Gln Ala Pro Gly Lys Gly Leu Glu
 50                  55                  60

Trp Ile Gly Phe Ile Asn Thr Gly Gly Thr Ile Val Tyr Ala Ser Trp
 65                  70                  75                  80

Ala Lys Gly Arg Phe Thr Ile Ser Lys Thr Ser Thr Thr Val Asp Leu
                    85                  90                  95

Lys Met Thr Ser Pro Thr Thr Glu Asp Thr Ala Thr Tyr Phe Cys Ala
                100                 105                 110

Arg Gly Ser Tyr Val Ser Ser Gly Tyr Ala Tyr Tyr Phe Asn Val
            115                 120                 125

<210> SEQ ID NO 444
<211> LENGTH: 13
<212> TYPE: PRT
<213> ORGANISM: Oryctolagus cuniculus

<400> SEQUENCE: 444

Gln Ser Ser Lys Ser Val Met Asn Asn Tyr Leu Ala
 1               5                  10

<210> SEQ ID NO 445
<211> LENGTH: 7
<212> TYPE: PRT
<213> ORGANISM: Oryctolagus cuniculus

<400> SEQUENCE: 445

Gly Ala Ser Asn Leu Ala Ser
 1               5

<210> SEQ ID NO 446
<211> LENGTH: 12
<212> TYPE: PRT
<213> ORGANISM: Oryctolagus cuniculus

<400> SEQUENCE: 446

Gln Gly Gly Tyr Thr Gly Tyr Ser Asp His Gly Thr
 1               5                  10
```

-continued

<210> SEQ ID NO 447
<211> LENGTH: 5
<212> TYPE: PRT
<213> ORGANISM: Oryctolagus cuniculus

<400> SEQUENCE: 447

Ser Tyr Pro Met Asn
1               5

<210> SEQ ID NO 448
<211> LENGTH: 16
<212> TYPE: PRT
<213> ORGANISM: Oryctolagus cuniculus

<400> SEQUENCE: 448

Phe Ile Asn Thr Gly Gly Thr Ile Val Tyr Ala Ser Trp Ala Lys Gly
1               5                   10                  15

<210> SEQ ID NO 449
<211> LENGTH: 14
<212> TYPE: PRT
<213> ORGANISM: Oryctolagus cuniculus

<400> SEQUENCE: 449

Gly Ser Tyr Val Ser Ser Gly Tyr Ala Tyr Tyr Phe Asn Val
1               5                   10

<210> SEQ ID NO 450
<211> LENGTH: 372
<212> TYPE: DNA
<213> ORGANISM: Oryctolagus cuniculus

<400> SEQUENCE: 450
atggacacga gggcccccac tcagctgctg ggctcctgc tgctctggct cccaggtgcc    60
acatttgccg ccgtgctgac ccagactcca tctcccgtgt ctgaacctgt gggaggcaca   120
gtcagcatca gttgccagtc cagtaagagt gttatgaata caactactt agcctggtat    180 cagcagaaac cagggcagcc tcccaagctc ctgatctatg gtgcatccaa tctggcatct   240
ggggtcccat cacggttcag cggcagtgga tctgggacac agttcactct caccatcagc   300
gacgtgcagt gtgacgatgc tgccacttac tactgtcaag gcggttatac tggttatagt   360
gatcatggga ct                                                      372

<210> SEQ ID NO 451
<211> LENGTH: 381
<212> TYPE: DNA
<213> ORGANISM: Oryctolagus cuniculus

<400> SEQUENCE: 451
atggagactg ggctgcgctg gcttctcctg gtcgctgtgc tcaaaggtgt ccagtgtcag    60
tcggtggagg agtccggggg tcgcctggtc aagcctgacg aaaccctgac actcacctgc   120
acagtctctg gaatcgacct cagtagctat ccaatgaact gggtccgcca ggctccaggg   180
aaggggctgg aatggatcgg attcattaat actggtggta ccatagtcta cgcgagctgg   240
gcaaaaggcc gattcaccat ctccaaaacc tcgaccacgg tggatctgaa aatgaccagt   300
ccgacaaccg aggacacggc cacctatttc tgtgccagag gcagttatgt ttcatctggt   360
tatgcctact attttaatgt c                                            381

-continued

<210> SEQ ID NO 452
<211> LENGTH: 39
<212> TYPE: DNA
<213> ORGANISM: Oryctolagus cuniculus

<400> SEQUENCE: 452
cagtccagta agagtgttat gaataacaac tacttagcc                    39

<210> SEQ ID NO 453
<211> LENGTH: 21
<212> TYPE: DNA
<213> ORGANISM: Oryctolagus cuniculus

<400> SEQUENCE: 453
ggtgcatcca atctggcatc t                                        21

<210> SEQ ID NO 454
<211> LENGTH: 36
<212> TYPE: DNA
<213> ORGANISM: Oryctolagus cuniculus

<400> SEQUENCE: 454
caaggcggtt atactggtta tagtgatcat gggact                        36

<210> SEQ ID NO 455
<211> LENGTH: 15
<212> TYPE: DNA
<213> ORGANISM: Oryctolagus cuniculus

<400> SEQUENCE: 455
agctatccaa tgaac                                               15

<210> SEQ ID NO 456
<211> LENGTH: 48
<212> TYPE: DNA
<213> ORGANISM: Oryctolagus cuniculus

<400> SEQUENCE: 456
ttcattaata ctggtggtac catagtctac gcgagctggg caaaaggc           48

<210> SEQ ID NO 457
<211> LENGTH: 42
<212> TYPE: DNA
<213> ORGANISM: Oryctolagus cuniculus

<400> SEQUENCE: 457
ggcagttatg tttcatctgg ttatgcctac tattttaatg tc                 42

<210> SEQ ID NO 458
<211> LENGTH: 121
<212> TYPE: PRT
<213> ORGANISM: Oryctolagus cuniculus

<400> SEQUENCE: 458

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Ser Ile Ser Cys Gln Ser Ser
        35                  40                  45

Gln Ser Val Tyr Asn Asn Asn Trp Leu Ser Trp Phe Gln Gln Lys Pro
    50                  55                  60

Gly Gln Pro Pro Lys Leu Leu Ile Tyr Lys Ala Ser Thr Leu Ala Ser
65                  70                  75                  80

Gly Val Pro Ser Arg Phe Lys Gly Ser Gly Ser Gly Thr Gln Phe Thr
            85                  90                  95

Leu Thr Ile Ser Asp Val Gln Cys Asp Asp Val Ala Thr Tyr Tyr Cys
            100                 105                 110

Ala Gly Gly Tyr Leu Asp Ser Val Ile
            115                 120

<210> SEQ ID NO 459
<211> LENGTH: 126
<212> TYPE: PRT
<213> ORGANISM: Oryctolagus cuniculus

<400> SEQUENCE: 459

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
            35                  40                  45

Thr Tyr Ser Ile Asn Trp Val Arg Gln Ala Pro Gly Lys Gly Leu Glu
        50                  55                  60

Trp Ile Gly Ile Ile Ala Asn Ser Gly Thr Thr Phe Tyr Ala Asn Trp
65                  70                  75                  80

Ala Lys Gly Arg Phe Thr Val Ser Lys Thr Ser Thr Thr Val Asp Leu
            85                  90                  95

Lys Ile Thr Ser Pro Thr Thr Glu Asp Thr Ala Thr Tyr Phe Cys Ala
            100                 105                 110

Arg Glu Ser Gly Met Tyr Asn Glu Tyr Gly Lys Phe Asn Ile
            115                 120                 125

<210> SEQ ID NO 460
<211> LENGTH: 13
<212> TYPE: PRT
<213> ORGANISM: Oryctolagus cuniculus

<400> SEQUENCE: 460

Gln Ser Ser Gln Ser Val Tyr Asn Asn Asn Trp Leu Ser
1               5                   10

<210> SEQ ID NO 461
<211> LENGTH: 7
<212> TYPE: PRT
<213> ORGANISM: Oryctolagus cuniculus

<400> SEQUENCE: 461

Lys Ala Ser Thr Leu Ala Ser
1               5

<210> SEQ ID NO 462
<211> LENGTH: 9
<212> TYPE: PRT
<213> ORGANISM: Oryctolagus cuniculus

<400> SEQUENCE: 462

Ala Gly Gly Tyr Leu Asp Ser Val Ile
1               5

<210> SEQ ID NO 463

```
<211> LENGTH: 5
<212> TYPE: PRT
<213> ORGANISM: Oryctolagus cuniculus

<400> SEQUENCE: 463

Thr Tyr Ser Ile Asn
1               5

<210> SEQ ID NO 464
<211> LENGTH: 16
<212> TYPE: PRT
<213> ORGANISM: Oryctolagus cuniculus

<400> SEQUENCE: 464

Ile Ile Ala Asn Ser Gly Thr Thr Phe Tyr Ala Asn Trp Ala Lys Gly
1               5                   10                  15

<210> SEQ ID NO 465
<211> LENGTH: 13
<212> TYPE: PRT
<213> ORGANISM: Oryctolagus cuniculus

<400> SEQUENCE: 465

Glu Ser Gly Met Tyr Asn Glu Tyr Gly Lys Phe Asn Ile
1               5                   10

<210> SEQ ID NO 466
<211> LENGTH: 363
<212> TYPE: DNA
<213> ORGANISM: Oryctolagus cuniculus

<400> SEQUENCE: 466
atggacacga gggcccccac tcagctgctg gggctcctgc tgctctggct cccaggtgcc      60
acatttgccg ccgtgctgac ccagactcca tctcccgtgt ctgcagctgt gggaggcaca     120
gtcagcatca gttgccagtc cagtcagagt gtttataata caactggttt atcctggttt     180
cagcagaaac cagggcagcc tcccaagctc ctgatctaca aggcatccac tctggcatct     240
ggggtcccat cgcggttcaa aggcagtgga tctgggacac agttcactct caccatcagc     300
gacgtgcagt gtgacgatgt tgccacttac tactgtgcgg gcggttatct tgatagtgtt     360
att                                                                   363

<210> SEQ ID NO 467
<211> LENGTH: 378
<212> TYPE: DNA
<213> ORGANISM: Oryctolagus cuniculus

<400> SEQUENCE: 467
atggagactg ggctgcgctg gcttctcctg gtcgctgtgc tcaaaggtgt ccagtgtcag      60
tcggtggagg agtccggggg tcgcctggtc acgcctggga caccctgac actcacctgc     120 acagtctctg gattctccct cagtacctat tcaataaact gggtccgcca ggctccaggg     180
aagggcctgg aatggatcgg aatcattgct aatagtggta ccacattcta cgcgaactgg     240
gcgaaaggcc gattcaccgt ctccaaaacc tcgaccacgg tggatctgaa aatcaccagt     300
ccgacaaccg aggacacggc cacctatttc tgtgccagag agagtggaat gtacaatgaa     360
tatggtaaat ttaacatc                                                   378

<210> SEQ ID NO 468
<211> LENGTH: 39
<212> TYPE: DNA
```

```
<213> ORGANISM: Oryctolagus cuniculus

<400> SEQUENCE: 468
cagtccagtc agagtgttta taataacaac tggttatcc                    39

<210> SEQ ID NO 469
<211> LENGTH: 21
<212> TYPE: DNA
<213> ORGANISM: Oryctolagus cuniculus

<400> SEQUENCE: 469
aaggcatcca ctctggcatc t                                       21

<210> SEQ ID NO 470
<211> LENGTH: 27
<212> TYPE: DNA
<213> ORGANISM: Oryctolagus cuniculus

<400> SEQUENCE: 470
gcgggcggtt atcttgatag tgttatt                                 27

<210> SEQ ID NO 471
<211> LENGTH: 15
<212> TYPE: DNA
<213> ORGANISM: Oryctolagus cuniculus

<400> SEQUENCE: 471
acctattcaa taaac                                              15

<210> SEQ ID NO 472
<211> LENGTH: 48
<212> TYPE: DNA
<213> ORGANISM: Oryctolagus cuniculus

<400> SEQUENCE: 472
atcattgcta atagtggtac cacattctac gcgaactggg cgaaaggc          48

<210> SEQ ID NO 473
<211> LENGTH: 39
<212> TYPE: DNA
<213> ORGANISM: Oryctolagus cuniculus

<400> SEQUENCE: 473
gagagtggaa tgtacaatga atatggtaaa tttaacatc                    39

<210> SEQ ID NO 474
<211> LENGTH: 122
<212> TYPE: PRT
<213> ORGANISM: Oryctolagus cuniculus

<400> SEQUENCE: 474
```

Met Asp Thr Arg Ala Pro Thr Gln Leu Leu Gly Leu Leu Leu Leu Trp
1               5                   10                  15

Leu Pro Gly Ala Arg Cys Ala Ser Asp Met Thr Gln Thr Pro Ser Ser
            20                  25                  30

Val Ser Ala Ala Val Gly Gly Thr Val Thr Ile Asn Cys Gln Ala Ser
        35                  40                  45

Glu Asn Ile Tyr Ser Phe Leu Ala Trp Tyr Gln Gln Lys Pro Gly Gln
    50                  55                  60

Pro Pro Lys Leu Leu Ile Phe Lys Ala Ser Thr Leu Ala Ser Gly Val
65                  70                  75                  80

Ser Ser Arg Phe Lys Gly Ser Gly Ser Gly Thr Gln Phe Thr Leu Thr
            85                  90                  95

Ile Ser Asp Leu Glu Cys Asp Asp Ala Ala Thr Tyr Tyr Cys Gln Gln
            100                 105                 110

Gly Ala Thr Val Tyr Asp Ile Asp Asn Asn
            115                 120

<210> SEQ ID NO 475
<211> LENGTH: 128
<212> TYPE: PRT
<213> ORGANISM: Oryctolagus cuniculus

<400> SEQUENCE: 475

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ile Asp Leu Ser
            35                  40                  45

Ala Tyr Ala Met Ile Trp Val Arg Gln Ala Pro Gly Glu Gly Leu Glu
        50                  55                  60

Trp Ile Thr Ile Ile Tyr Pro Asn Gly Ile Thr Tyr Tyr Ala Asn Trp
65                  70                  75                  80

Ala Lys Gly Arg Phe Thr Val Ser Lys Thr Ser Thr Ala Met Asp Leu
                85                  90                  95

Lys Ile Thr Ser Pro Thr Thr Glu Asp Thr Ala Thr Tyr Phe Cys Ala
            100                 105                 110

Arg Asp Ala Glu Ser Ser Lys Asn Ala Tyr Trp Gly Tyr Phe Asn Val
            115                 120                 125

<210> SEQ ID NO 476
<211> LENGTH: 11
<212> TYPE: PRT
<213> ORGANISM: Oryctolagus cuniculus

<400> SEQUENCE: 476

Gln Ala Ser Glu Asn Ile Tyr Ser Phe Leu Ala
1               5                   10

<210> SEQ ID NO 477
<211> LENGTH: 7
<212> TYPE: PRT
<213> ORGANISM: Oryctolagus cuniculus

<400> SEQUENCE: 477

Lys Ala Ser Thr Leu Ala Ser
1               5

<210> SEQ ID NO 478
<211> LENGTH: 12
<212> TYPE: PRT
<213> ORGANISM: Oryctolagus cuniculus

<400> SEQUENCE: 478

Gln Gln Gly Ala Thr Val Tyr Asp Ile Asp Asn Asn
1               5                   10

<210> SEQ ID NO 479
<211> LENGTH: 5
<212> TYPE: PRT
<213> ORGANISM: Oryctolagus cuniculus

<400> SEQUENCE: 479

Ala Tyr Ala Met Ile
1               5

<210> SEQ ID NO 480
<211> LENGTH: 16
<212> TYPE: PRT
<213> ORGANISM: Oryctolagus cuniculus

<400> SEQUENCE: 480

Ile Ile Tyr Pro Asn Gly Ile Thr Tyr Tyr Ala Asn Trp Ala Lys Gly
1               5                   10                  15

<210> SEQ ID NO 481
<211> LENGTH: 15
<212> TYPE: PRT
<213> ORGANISM: Oryctolagus cuniculus

<400> SEQUENCE: 481

Asp Ala Glu Ser Ser Lys Asn Ala Tyr Trp Gly Tyr Phe Asn Val
1               5                   10                  15

<210> SEQ ID NO 482
<211> LENGTH: 366
<212> TYPE: DNA
<213> ORGANISM: Oryctolagus cuniculus

<400> SEQUENCE: 482
atggacacga gggcccccac tcagctgctg gggctcctgc tgctctggct cccaggtgcc      60
agatgtgcct ctgatatgac ccagactcca tcctccgtgt ctgcagctgt gggaggcaca     120
gtcaccatca attgccaggc cagtgagaac atttatagct ttttggcctg gtatcagcag     180
aaaccagggc agcctcccaa gctcctgatc ttcaaggctt ccactctggc atctggggtc     240
tcatcgcggt tcaaaggcag tggatctggg acacagttca ctctcaccat cagcgacctg     300
gagtgtgacg atgctgccac ttactactgt caacagggtg ctactgtgta tgatattgat     360
aataat                                                                366

<210> SEQ ID NO 483
<211> LENGTH: 384
<212> TYPE: DNA
<213> ORGANISM: Oryctolagus cuniculus

<400> SEQUENCE: 483
atggagactg ggctgcgctg gcttctcctg gtcgctgtgc tcaaaggtgt ccagtgtcag      60
tcgctggagg agtccggggg tcgcctggtc acgcctggga cacccctgac actcacctgc     120
acagtttctg gaatcgacct cagtgcctat gcaatgatct gggtccgcca ggctccaggg     180
gaggggctgg aatggatcac aatcatttat cctaatggta tcacatacta cgcgaactgg     240
gcgaaaggcc gattcaccgt ctccaaaacc tcgaccgcga tggatctgaa aatcaccagt     300
ccgacaaccg aggacacggc cacctatttc tgtgccagag atgcagaaag tagtaagaat     360
gcttattggg gctactttaa cgtc                                            384

<210> SEQ ID NO 484
<211> LENGTH: 33
<212> TYPE: DNA
<213> ORGANISM: Oryctolagus cuniculus

<400> SEQUENCE: 484

-continued caggccagtg agaacattta tagcttttg gcc                                   33

<210> SEQ ID NO 485
<211> LENGTH: 21
<212> TYPE: DNA
<213> ORGANISM: Oryctolagus cuniculus

<400> SEQUENCE: 485
aaggcttcca ctctggcatc t                                               21

<210> SEQ ID NO 486
<211> LENGTH: 36
<212> TYPE: DNA
<213> ORGANISM: Oryctolagus cuniculus

<400> SEQUENCE: 486
caacagggtg ctactgtgta tgatattgat aataat                               36

<210> SEQ ID NO 487
<211> LENGTH: 15
<212> TYPE: DNA
<213> ORGANISM: Oryctolagus cuniculus

<400> SEQUENCE: 487
gcctatgcaa tgatc                                                      15

<210> SEQ ID NO 488
<211> LENGTH: 48
<212> TYPE: DNA
<213> ORGANISM: Oryctolagus cuniculus

<400> SEQUENCE: 488
atcatttatc ctaatggtat cacatactac gcgaactggg cgaaaggc                  48

<210> SEQ ID NO 489
<211> LENGTH: 45
<212> TYPE: DNA
<213> ORGANISM: Oryctolagus cuniculus

<400> SEQUENCE: 489
gatgcagaaa gtagtaagaa tgcttattgg ggctacttta acgtc                     45

<210> SEQ ID NO 490
<211> LENGTH: 122
<212> TYPE: PRT
<213> ORGANISM: Oryctolagus cuniculus

<400> SEQUENCE: 490

Met Asp Thr Arg Ala Pro Thr Gln Leu Leu Gly Leu Leu Leu Leu Trp
 1               5                  10                  15

Leu Pro Gly Ala Arg Cys Ala Ser Asp Met Thr Gln Thr Pro Ser Ser
                20                  25                  30

Val Ser Ala Ala Val Gly Gly Thr Val Thr Ile Asn Cys Gln Ala Ser
            35                  40                  45

Glu Asn Ile Tyr Ser Phe Leu Ala Trp Tyr Gln Gln Lys Pro Gly Gln
        50                  55                  60

Pro Pro Lys Leu Leu Ile Phe Arg Ala Ser Thr Leu Ala Ser Gly Val
65                  70                  75                  80

Ser Ser Arg Phe Lys Gly Ser Gly Ser Gly Thr Gln Phe Thr Leu Thr
                85                  90                  95

```
Ile Ser Asp Leu Glu Cys Asp Asp Ala Ala Thr Tyr Tyr Cys Gln Gln
            100                 105                 110

Gly Ala Thr Val Tyr Asp Ile Asp Asn Asn
        115                 120

<210> SEQ ID NO 491
<211> LENGTH: 128
<212> TYPE: PRT
<213> ORGANISM: Oryctolagus cuniculus

<400> SEQUENCE: 491

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ala Tyr Ala Met Ile Trp Val Arg Gln Ala Pro Gly Glu Gly Leu Glu
    50                  55                  60

Trp Ile Thr Ile Ile Tyr Pro Asn Gly Ile Thr Tyr Tyr Ala Asn Trp
65                  70                  75                  80

Ala Lys Gly Arg Phe Thr Val Ser Lys Thr Ser Thr Ala Met Asp Leu
                85                  90                  95

Lys Ile Thr Ser Pro Thr Thr Glu Asp Thr Ala Thr Tyr Phe Cys Ala
            100                 105                 110

Arg Asp Ala Glu Ser Ser Lys Asn Ala Tyr Trp Gly Tyr Phe Asn Val
        115                 120                 125

<210> SEQ ID NO 492
<211> LENGTH: 11
<212> TYPE: PRT
<213> ORGANISM: Oryctolagus cuniculus

<400> SEQUENCE: 492

Gln Ala Ser Glu Asn Ile Tyr Ser Phe Leu Ala
1               5                   10

<210> SEQ ID NO 493
<211> LENGTH: 7
<212> TYPE: PRT
<213> ORGANISM: Oryctolagus cuniculus

<400> SEQUENCE: 493

Arg Ala Ser Thr Leu Ala Ser
1               5

<210> SEQ ID NO 494
<211> LENGTH: 12
<212> TYPE: PRT
<213> ORGANISM: Oryctolagus cuniculus

<400> SEQUENCE: 494

Gln Gln Gly Ala Thr Val Tyr Asp Ile Asp Asn Asn
1               5                   10

<210> SEQ ID NO 495
<211> LENGTH: 5
<212> TYPE: PRT
<213> ORGANISM: Oryctolagus cuniculus

<400> SEQUENCE: 495
```

```
Ala Tyr Ala Met Ile
1               5

<210> SEQ ID NO 496
<211> LENGTH: 16
<212> TYPE: PRT
<213> ORGANISM: Oryctolagus cuniculus

<400> SEQUENCE: 496

Ile Ile Tyr Pro Asn Gly Ile Thr Tyr Tyr Ala Asn Trp Ala Lys Gly
1               5                   10                  15

<210> SEQ ID NO 497
<211> LENGTH: 15
<212> TYPE: PRT
<213> ORGANISM: Oryctolagus cuniculus

<400> SEQUENCE: 497

Asp Ala Glu Ser Ser Lys Asn Ala Tyr Trp Gly Tyr Phe Asn Val
1               5                   10                  15

<210> SEQ ID NO 498
<211> LENGTH: 366
<212> TYPE: DNA
<213> ORGANISM: Oryctolagus cuniculus

<400> SEQUENCE: 498
atggacacga gggcccccac tcagctgctg gggctcctgc tgctctggct cccaggtgcc      60
agatgtgcct ctgatatgac ccagactcca tcctccgtgt ctgcagctgt gggaggcaca     120
gtcaccatca attgccaggc cagtgagaac atttatagct ttttggcctg gtatcagcag     180
aaaccagggc agcctcccaa gctcctgatc ttcagggctt ccactctggc atctggggtc     240
tcatcgcggt tcaaaggcag tggatctggg acacagttca ctctcaccat cagcgacctg     300
gagtgtgacg atgctgccac ttactactgt caacagggtg ctactgtgta tgatattgat     360
aataat                                                                366

<210> SEQ ID NO 499
<211> LENGTH: 384
<212> TYPE: DNA
<213> ORGANISM: Oryctolagus cuniculus

<400> SEQUENCE: 499
atggagactg ggctgcgctg gcttctcctg gtcgctgtgc tcaaaggtgt ccagtgtcag      60
tcgctggagg agtccggggg tcgcctggtc acgcctggga cacccctgac actcacctgc     120
acagtttctg gaatcgacct cagtgcctat gcaatgatct gggtccgcca ggctccaggg     180
gaggggctgg aatggatcac aatcatttat cctaatggta tcacatacta cgcgaactgg     240
gcgaaaggcc gattcaccgt ctccaaaacc tcgaccgcga tggatctgaa aatcaccagt     300
ccgacaaccg aggacacggc cacctatttc tgtgccagag atgcagaaag tagtaagaat     360
gcttattggg gctactttaa cgtc                                            384

<210> SEQ ID NO 500
<211> LENGTH: 33
<212> TYPE: DNA
<213> ORGANISM: Oryctolagus cuniculus

<400> SEQUENCE: 500
caggccagtg agaacattta tagctttttg gcc                                   33
```

<210> SEQ ID NO 501
<211> LENGTH: 21
<212> TYPE: DNA
<213> ORGANISM: Oryctolagus cuniculus

<400> SEQUENCE: 501
agggcttcca ctctggcatc t                                              21

<210> SEQ ID NO 502
<211> LENGTH: 36
<212> TYPE: DNA
<213> ORGANISM: Oryctolagus cuniculus

<400> SEQUENCE: 502
caacagggtg ctactgtgta tgatattgat aataat                              36

<210> SEQ ID NO 503
<211> LENGTH: 15
<212> TYPE: DNA
<213> ORGANISM: Oryctolagus cuniculus

<400> SEQUENCE: 503
gcctatgcaa tgatc                                                     15

<210> SEQ ID NO 504
<211> LENGTH: 48
<212> TYPE: DNA
<213> ORGANISM: Oryctolagus cuniculus

<400> SEQUENCE: 504
atcatttatc ctaatggtat cacatactac gcgaactggg cgaaaggc                 48

<210> SEQ ID NO 505
<211> LENGTH: 45
<212> TYPE: DNA
<213> ORGANISM: Oryctolagus cuniculus

<400> SEQUENCE: 505
gatgcagaaa gtagtaagaa tgcttattgg ggctacttta acgtc                    45

<210> SEQ ID NO 506
<211> LENGTH: 124
<212> TYPE: PRT
<213> ORGANISM: Oryctolagus cuniculus

<400> SEQUENCE: 506

Met Asp Thr Arg Ala Pro Thr Gln Leu Leu Gly Leu Leu Leu Leu Trp
1               5                   10                  15

Leu Pro Gly Ala Thr Phe Ala Ile Glu Met Thr Gln Thr Pro Ser Pro
            20                  25                  30

Val Ser Ala Ala Val Gly Gly Thr Val Thr Ile Asn Cys Gln Ala Ser
        35                  40                  45

Glu Ser Val Phe Asn Asn Met Leu Ser Trp Tyr Gln Gln Lys Pro Gly
    50                  55                  60

His Ser Pro Lys Leu Leu Ile Tyr Asp Ala Ser Asp Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Gly Val Glu Cys Asp Asp Ala Ala Thr Tyr Tyr Cys Ala
            100                 105                 110

Gly Tyr Lys Ser Asp Ser Asn Asp Gly Asp Asn Val
        115                 120

<210> SEQ ID NO 507
<211> LENGTH: 123
<212> TYPE: PRT
<213> ORGANISM: Oryctolagus cuniculus

<400> SEQUENCE: 507

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Asn
        35                  40                  45

Arg Asn Ser Ile Thr Trp Val Arg Gln Ala Pro Gly Glu Gly Leu Glu
    50                  55                  60

Trp Ile Gly Ile Ile Thr Gly Ser Gly Arg Thr Tyr Tyr Ala Asn Trp
65                  70                  75                  80

Ala Lys Gly Arg Phe Thr Ile Ser Lys Thr Ser Thr Thr Val Asp Leu
                85                  90                  95

Lys Met Thr Ser Pro Thr Thr Glu Asp Thr Ala Thr Tyr Phe Cys Ala
            100                 105                 110

Arg Gly His Pro Gly Leu Gly Ser Gly Asn Ile
        115                 120

<210> SEQ ID NO 508
<211> LENGTH: 12
<212> TYPE: PRT
<213> ORGANISM: Oryctolagus cuniculus

<400> SEQUENCE: 508

Gln Ala Ser Glu Ser Val Phe Asn Asn Met Leu Ser
1               5                   10

<210> SEQ ID NO 509
<211> LENGTH: 7
<212> TYPE: PRT
<213> ORGANISM: Oryctolagus cuniculus

<400> SEQUENCE: 509

Asp Ala Ser Asp Leu Ala Ser
1               5

<210> SEQ ID NO 510
<211> LENGTH: 13
<212> TYPE: PRT
<213> ORGANISM: Oryctolagus cuniculus

<400> SEQUENCE: 510

Ala Gly Tyr Lys Ser Asp Ser Asn Asp Gly Asp Asn Val
1               5                   10

<210> SEQ ID NO 511
<211> LENGTH: 5
<212> TYPE: PRT
<213> ORGANISM: Oryctolagus cuniculus

<400> SEQUENCE: 511

Arg Asn Ser Ile Thr
1               5

<210> SEQ ID NO 512
<211> LENGTH: 16
<212> TYPE: PRT
<213> ORGANISM: Oryctolagus cuniculus

<400> SEQUENCE: 512

Ile Ile Thr Gly Ser Gly Arg Thr Tyr Tyr Ala Asn Trp Ala Lys Gly
1               5                   10                  15

<210> SEQ ID NO 513
<211> LENGTH: 10
<212> TYPE: PRT
<213> ORGANISM: Oryctolagus cuniculus

<400> SEQUENCE: 513

Gly His Pro Gly Leu Gly Ser Gly Asn Ile
1               5                   10

<210> SEQ ID NO 514
<211> LENGTH: 372
<212> TYPE: DNA
<213> ORGANISM: Oryctolagus cuniculus

<400> SEQUENCE: 514
atggacacga gggcccccac tcagctgctg gggctcctgc tgctctggct cccaggtgcc      60
acatttgcca ttgaaatgac ccagactcca tcccccgtgt ctgccgctgt gggaggcaca     120
gtcaccatca attgccaggc cagtgagagt gttttaata atatgttatc ctggtatcag     180
cagaaaccag gcactctcc taagctcctg atctatgatg catccgatct ggcatctggg     240
gtcccatcgc ggttcaaagg cagtggatct gggacacagt tcactctcac catcagtggc     300
gtggagtgtg acgatgctgc cacttactat tgtgcagggt ataaaagtga tagtaatgat     360
ggcgataatg tt                                                         372

<210> SEQ ID NO 515
<211> LENGTH: 369
<212> TYPE: DNA
<213> ORGANISM: Oryctolagus cuniculus

<400> SEQUENCE: 515
atggagactg gctgcgctg gcttctcctg gtcgctgtgc tcaaaggtgt ccagtgtcag      60
tcgctggagg agtccggggg tcgcctggtc acgcctggga cacccctgac actcacctgc     120
acagtctctg gattctccct caacaggaat tcaataacct gggtccgcca ggctccaggg     180
gaggggctgg aatggatcgg aatcattact ggtagtggta aacgtacta cgcgaactgg     240 gcaaaaggcc gattcaccat ctccaaaacc tcgaccacgg tggatctgaa aatgaccagt     300
ccgacaaccg aggacacggc cacctatttc tgtgccagag ccatcctgg tcttggtagt     360 ggtaacatc                                                             369

<210> SEQ ID NO 516
<211> LENGTH: 36
<212> TYPE: DNA
<213> ORGANISM: Oryctolagus cuniculus

<400> SEQUENCE: 516
caggccagtg agagtgtttt taataatatg ttatcc                                36

<210> SEQ ID NO 517
<211> LENGTH: 21

```
<212> TYPE: DNA
<213> ORGANISM: Oryctolagus cuniculus

<400> SEQUENCE: 517
gatgcatccg atctggcatc t                                               21

<210> SEQ ID NO 518
<211> LENGTH: 39
<212> TYPE: DNA
<213> ORGANISM: Oryctolagus cuniculus

<400> SEQUENCE: 518
gcagggtata aaagtgatag taatgatggc gataatgtt                            39

<210> SEQ ID NO 519
<211> LENGTH: 15
<212> TYPE: DNA
<213> ORGANISM: Oryctolagus cuniculus

<400> SEQUENCE: 519
aggaattcaa taacc                                                      15

<210> SEQ ID NO 520
<211> LENGTH: 48
<212> TYPE: DNA
<213> ORGANISM: Oryctolagus cuniculus

<400> SEQUENCE: 520
atcattactg gtagtggtag aacgtactac gcgaactggg caaaaggc                  48

<210> SEQ ID NO 521
<211> LENGTH: 30
<212> TYPE: DNA
<213> ORGANISM: Oryctolagus cuniculus

<400> SEQUENCE: 521
ggccatcctg gtcttggtag tggtaacatc                                      30

<210> SEQ ID NO 522
<211> LENGTH: 121
<212> TYPE: PRT
<213> ORGANISM: Oryctolagus cuniculus

<400> SEQUENCE: 522

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Ser
                20                  25                  30

Val Ser Ala Ala Val Gly Gly Thr Val Thr Ile Asn Cys Gln Ser Ser
            35                  40                  45

Gln Ser Val Tyr Asn Asn Tyr Leu Ser Trp Tyr Gln Gln Lys Pro Gly
        50                  55                  60

Gln Pro Pro Lys Leu Leu Ile Tyr Thr Ala Ser Ser Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Glu Val Gln Cys Asp Asp Ala Ala Thr Tyr Tyr Cys Gln
            100                 105                 110

Gly Tyr Tyr Ser Gly Pro Ile Ile Thr
        115                 120
```

<210> SEQ ID NO 523
<211> LENGTH: 122
<212> TYPE: PRT
<213> ORGANISM: Oryctolagus cuniculus

<400> SEQUENCE: 523

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Asn
        35                  40                  45

Asn Tyr Tyr Ile Gln Trp Val Arg Gln Ala Pro Gly Glu Gly Leu Glu
    50                  55                  60

Trp Ile Gly Ile Ile Tyr Ala Gly Gly Ser Ala Tyr Tyr Ala Thr Trp
65                  70                  75                  80

Ala Asn Gly Arg Phe Thr Ile Ala Lys Thr Ser Ser Thr Thr Val Asp
                85                  90                  95

Leu Lys Met Thr Ser Leu Thr Thr Glu Asp Thr Ala Thr Tyr Phe Cys
            100                 105                 110

Ala Arg Gly Thr Phe Asp Gly Tyr Glu Leu
            115                 120

<210> SEQ ID NO 524
<211> LENGTH: 12
<212> TYPE: PRT
<213> ORGANISM: Oryctolagus cuniculus

<400> SEQUENCE: 524

Gln Ser Ser Gln Ser Val Tyr Asn Asn Tyr Leu Ser
1               5                   10

<210> SEQ ID NO 525
<211> LENGTH: 7
<212> TYPE: PRT
<213> ORGANISM: Oryctolagus cuniculus

<400> SEQUENCE: 525

Thr Ala Ser Ser Leu Ala Ser
1               5

<210> SEQ ID NO 526
<211> LENGTH: 10
<212> TYPE: PRT
<213> ORGANISM: Oryctolagus cuniculus

<400> SEQUENCE: 526

Gln Gly Tyr Tyr Ser Gly Pro Ile Ile Thr
1               5                   10

<210> SEQ ID NO 527
<211> LENGTH: 5
<212> TYPE: PRT
<213> ORGANISM: Oryctolagus cuniculus

<400> SEQUENCE: 527

Asn Tyr Tyr Ile Gln
1               5

<210> SEQ ID NO 528
<211> LENGTH: 16

<212> TYPE: PRT
<213> ORGANISM: Oryctolagus cuniculus

<400> SEQUENCE: 528

Ile Ile Tyr Ala Gly Gly Ser Ala Tyr Tyr Ala Thr Trp Ala Asn Gly
1               5                   10                  15

<210> SEQ ID NO 529
<211> LENGTH: 8
<212> TYPE: PRT
<213> ORGANISM: Oryctolagus cuniculus

<400> SEQUENCE: 529

Gly Thr Phe Asp Gly Tyr Glu Leu
1               5

<210> SEQ ID NO 530
<211> LENGTH: 363
<212> TYPE: DNA
<213> ORGANISM: Oryctolagus cuniculus

<400> SEQUENCE: 530
atggacacga gggcccccac tcagctgctg gggctcctgc tgctctggct cccaggtgcc      60
acatttgcgc aagtgctgac ccagactgca tcgtccgtgt ctgcagctgt gggaggcaca     120
gtcaccatca attgccagtc cagtcagagt gtttataata actacttatc ctggtatcag    180
cagaaaccag gcagcctcc caagctcctg atctatactg catccagcct ggcatctggg     240
gtcccatcgc ggttcaaagg cagtggatct gggacacagt tcactctcac catcagcgaa    300
gtgcagtgtg acgatgctgc cacttactac tgtcaaggct attatagtgg tcctataatt    360
act                                                                  363

<210> SEQ ID NO 531
<211> LENGTH: 366
<212> TYPE: DNA
<213> ORGANISM: Oryctolagus cuniculus

<400> SEQUENCE: 531
atggagactg ggctgcgctg gcttctcctg gtcgctgtgc tcaaaggtgt ccagtgtcag      60
tcgctggagg agtccggggg tcgcctggtc acgcctggga caccctgac actcacctgc     120
acagcctctg gattctccct caataactac tacataaat gggtccgcca ggctccaggg     180
gaggggctgg aatggatcgg gatcatttat gctggtggta gcgcatacta cgcgacctgg    240
gcaaacggcc gattcaccat cgccaaaacc tcgtcgacca cggtggatct gaagatgacc    300
agtctgacaa ccgaggacac ggccacctat ttctgtgcca gagggacatt tgatggttat    360
gagttg                                                               366

<210> SEQ ID NO 532
<211> LENGTH: 36
<212> TYPE: DNA
<213> ORGANISM: Oryctolagus cuniculus

<400> SEQUENCE: 532
cagtccagtc agagtgttta taataactac ttatcc                               36

<210> SEQ ID NO 533
<211> LENGTH: 21
<212> TYPE: DNA
<213> ORGANISM: Oryctolagus cuniculus

```
<400> SEQUENCE: 533
actgcatcca gcctggcatc t                                             21

<210> SEQ ID NO 534
<211> LENGTH: 30
<212> TYPE: DNA
<213> ORGANISM: Oryctolagus cuniculus

<400> SEQUENCE: 534
caaggctatt atagtggtcc tataattact                                    30

<210> SEQ ID NO 535
<211> LENGTH: 15
<212> TYPE: DNA
<213> ORGANISM: Oryctolagus cuniculus

<400> SEQUENCE: 535
aactactaca tacaa                                                    15

<210> SEQ ID NO 536
<211> LENGTH: 48
<212> TYPE: DNA
<213> ORGANISM: Oryctolagus cuniculus

<400> SEQUENCE: 536
atcatttatg ctggtggtag cgcatactac gcgacctggg caaacggc                48

<210> SEQ ID NO 537
<211> LENGTH: 24
<212> TYPE: DNA
<213> ORGANISM: Oryctolagus cuniculus

<400> SEQUENCE: 537
gggacatttg atggttatga gttg                                          24

<210> SEQ ID NO 538
<211> LENGTH: 122
<212> TYPE: PRT
<213> ORGANISM: Oryctolagus cuniculus

<400> SEQUENCE: 538

Met Asp Thr Arg Ala Pro Thr Gln Leu Leu Gly Leu Leu Leu Leu Trp
 1               5                  10                  15

Leu Pro Gly Ala Thr Phe Ala Gln Val Leu Thr Gln Thr Pro Ser Pro
             20                  25                  30

Val Ser Val Pro Val Gly Asp Thr Val Thr Ile Ser Cys Gln Ser Ser
         35                  40                  45

Glu Ser Val Tyr Ser Asn Asn Leu Leu Ser Trp Tyr Gln Gln Lys Pro
     50                  55                  60

Gly Gln Pro Pro Lys Leu Leu Ile Tyr Arg Ala Ser Asn Leu Ala Ser
 65                  70                  75                  80

Gly Val Pro Ser Arg Phe Lys Gly Ser Gly Ser Gly Thr Gln Phe Thr
                 85                  90                  95

Leu Thr Ile Ser Gly Ala Gln Cys Asp Asp Ala Ala Thr Tyr Tyr Cys
            100                 105                 110

Gln Gly Tyr Tyr Ser Gly Val Ile Asn Ser
            115                 120

<210> SEQ ID NO 539
<211> LENGTH: 124
```

<212> TYPE: PRT
<213> ORGANISM: Oryctolagus cuniculus

<400> SEQUENCE: 539

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Phe Met Ser Trp Val Arg Gln Ala Pro Gly Glu Gly Leu Glu
    50                  55                  60

Tyr Ile Gly Phe Ile Asn Pro Gly Gly Ser Ala Tyr Ala Ser Trp
65                  70                  75                  80

Ala Ser Gly Arg Leu Thr Ile Ser Lys Thr Ser Thr Val Asp Leu
                85                  90                  95

Lys Ile Thr Ser Pro Thr Thr Glu Asp Thr Ala Thr Tyr Phe Cys Ala
                100                 105                 110

Arg Ile Leu Ile Val Ser Tyr Gly Ala Phe Thr Ile
            115                 120
```

<210> SEQ ID NO 540
<211> LENGTH: 13
<212> TYPE: PRT
<213> ORGANISM: Oryctolagus cuniculus

<400> SEQUENCE: 540

```
Gln Ser Ser Glu Ser Val Tyr Ser Asn Asn Leu Leu Ser
1               5                   10
```

<210> SEQ ID NO 541
<211> LENGTH: 7
<212> TYPE: PRT
<213> ORGANISM: Oryctolagus cuniculus

<400> SEQUENCE: 541

```
Arg Ala Ser Asn Leu Ala Ser
1               5
```

<210> SEQ ID NO 542
<211> LENGTH: 10
<212> TYPE: PRT
<213> ORGANISM: Oryctolagus cuniculus

<400> SEQUENCE: 542

```
Gln Gly Tyr Tyr Ser Gly Val Ile Asn Ser
1               5                   10
```

<210> SEQ ID NO 543
<211> LENGTH: 5
<212> TYPE: PRT
<213> ORGANISM: Oryctolagus cuniculus

<400> SEQUENCE: 543

```
Ser Tyr Phe Met Ser
1               5
```

<210> SEQ ID NO 544
<211> LENGTH: 16
<212> TYPE: PRT
<213> ORGANISM: Oryctolagus cuniculus -continued

<400> SEQUENCE: 544

Phe Ile Asn Pro Gly Gly Ser Ala Tyr Tyr Ala Ser Trp Ala Ser Gly
1               5                   10                  15

<210> SEQ ID NO 545
<211> LENGTH: 11
<212> TYPE: PRT
<213> ORGANISM: Oryctolagus cuniculus

<400> SEQUENCE: 545

Ile Leu Ile Val Ser Tyr Gly Ala Phe Thr Ile
1               5                   10

<210> SEQ ID NO 546
<211> LENGTH: 366
<212> TYPE: DNA
<213> ORGANISM: Oryctolagus cuniculus

<400> SEQUENCE: 546

```
atggacacga gggcccccac tcagctgctg gggctcctgc tgctctggct cccaggtgcc    60
acatttgccc aagtgctgac ccagactcca tcccctgtgt ctgtccctgt gggagacaca   120
gtcaccatca gttgccagtc cagtgagagc gtttatagta taaacctctt atcctggtat   180
cagcagaaac cagggcagcc tcccaagctc ctgatctaca gggcatccaa tctggcatct   240
ggtgtcccat cgcggttcaa aggcagtgga tctgggacac agttcactct caccatcagc   300
ggcgcacagt gtgacgatgc tgccacttac tactgtcaag ctattatagg tggtgtcatt   360
aatagt                                                             366
```

<210> SEQ ID NO 547
<211> LENGTH: 372
<212> TYPE: DNA
<213> ORGANISM: Oryctolagus cuniculus

<400> SEQUENCE: 547

```
atggagactg ggctgcgctg gcttctcctg gtcgctgtgc tcaaaggtgt ccagtgtcag    60
tcggtggagg agtccggggg tcgcctggtc acgcctggga caccctgac actcacctgc    120
acagtgtctg gattctcccct cagtagctac ttcatgagct gggtccgcca ggctccaggg   180
agggggctgg aatacatcgg attcattaat cctggtggta cgcatacta cgcgagctgg   240
gcgagtggcc gactcaccat ctccaaaacc tcgaccacgg tagatctgaa aatcaccgt   300
ccgacaaccg aggacacggc cacctatttc tgtgccagga ttcttattgt ttcttatgga   360
gcctttacca tc                                                      372
```

<210> SEQ ID NO 548
<211> LENGTH: 39
<212> TYPE: DNA
<213> ORGANISM: Oryctolagus cuniculus

<400> SEQUENCE: 548

```
cagtccagtg agagcgttta tagtaataac ctcttatcc                         39
```

<210> SEQ ID NO 549
<211> LENGTH: 21
<212> TYPE: DNA
<213> ORGANISM: Oryctolagus cuniculus

<400> SEQUENCE: 549

```
agggcatcca atctggcatc t                                            21
```

<210> SEQ ID NO 550
<211> LENGTH: 30
<212> TYPE: DNA
<213> ORGANISM: Oryctolagus cuniculus

<400> SEQUENCE: 550
caaggctatt atagtggtgt cattaatagt                              30

<210> SEQ ID NO 551
<211> LENGTH: 15
<212> TYPE: DNA
<213> ORGANISM: Oryctolagus cuniculus

<400> SEQUENCE: 551
agctacttca tgagc                                              15

<210> SEQ ID NO 552
<211> LENGTH: 48
<212> TYPE: DNA
<213> ORGANISM: Oryctolagus cuniculus

<400> SEQUENCE: 552
ttcattaatc ctggtggtag cgcatactac gcgagctggg cgagtggc          48

<210> SEQ ID NO 553
<211> LENGTH: 33
<212> TYPE: DNA
<213> ORGANISM: Oryctolagus cuniculus

<400> SEQUENCE: 553
attcttattg tttcttatgg agcctttacc atc                          33

<210> SEQ ID NO 554
<211> LENGTH: 122
<212> TYPE: PRT
<213> ORGANISM: Oryctolagus cuniculus

<400> SEQUENCE: 554

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Thr
        35                  40                  45

Glu Ser Ile Gly Asn Glu Leu Ser Trp Tyr Gln Gln Lys Pro Gly Gln
    50                  55                  60

Ala Pro Lys Leu Leu Ile Tyr Ser Ala Ser Thr Leu Ala Ser Gly Val
65                  70                  75                  80

Pro Ser Arg Phe Lys Gly Ser Gly Ser Gly Thr Gln Phe Thr Leu Thr
                85                  90                  95

Ile Thr Gly Val Glu Cys Asp Asp Ala Ala Thr Tyr Tyr Cys Gln Gln
            100                 105                 110

Gly Tyr Ser Ser Ala Asn Ile Asp Asn Ala
        115                 120

<210> SEQ ID NO 555
<211> LENGTH: 128
<212> TYPE: PRT
<213> ORGANISM: Oryctolagus cuniculus -continued

<400> SEQUENCE: 555

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Lys Tyr Tyr Met Ser Trp Val Arg Gln Ala Pro Glu Lys Gly Leu Lys
    50                  55                  60

Tyr Ile Gly Tyr Ile Asp Ser Thr Val Asn Thr Tyr Tyr Ala Thr
65                  70                  75                  80

Trp Ala Arg Gly Arg Phe Thr Ile Ser Lys Thr Ser Thr Thr Val Asp
                85                  90                  95

Leu Lys Ile Thr Ser Pro Thr Ser Glu Asp Thr Ala Thr Tyr Phe Cys
            100                 105                 110

Ala Arg Gly Ser Thr Tyr Phe Thr Asp Gly Gly His Arg Leu Asp Leu
        115                 120                 125

<210> SEQ ID NO 556
<211> LENGTH: 11
<212> TYPE: PRT
<213> ORGANISM: Oryctolagus cuniculus

<400> SEQUENCE: 556

Gln Ala Thr Glu Ser Ile Gly Asn Glu Leu Ser
1               5                   10

<210> SEQ ID NO 557
<211> LENGTH: 7
<212> TYPE: PRT
<213> ORGANISM: Oryctolagus cuniculus

<400> SEQUENCE: 557

Ser Ala Ser Thr Leu Ala Ser
1               5

<210> SEQ ID NO 558
<211> LENGTH: 12
<212> TYPE: PRT
<213> ORGANISM: Oryctolagus cuniculus

<400> SEQUENCE: 558

Gln Gln Gly Tyr Ser Ser Ala Asn Ile Asp Asn Ala
1               5                   10

<210> SEQ ID NO 559
<211> LENGTH: 5
<212> TYPE: PRT
<213> ORGANISM: Oryctolagus cuniculus

<400> SEQUENCE: 559

Lys Tyr Tyr Met Ser
1               5

<210> SEQ ID NO 560
<211> LENGTH: 17
<212> TYPE: PRT
<213> ORGANISM: Oryctolagus cuniculus

<400> SEQUENCE: 560

Tyr Ile Asp Ser Thr Thr Val Asn Thr Tyr Tyr Ala Thr Trp Ala Arg

Gly

<210> SEQ ID NO 561
<211> LENGTH: 14
<212> TYPE: PRT
<213> ORGANISM: Oryctolagus cuniculus

<400> SEQUENCE: 561

Gly Ser Thr Tyr Phe Thr Asp Gly Gly His Arg Leu Asp Leu
1               5                   10

<210> SEQ ID NO 562
<211> LENGTH: 366
<212> TYPE: DNA
<213> ORGANISM: Oryctolagus cuniculus

<400> SEQUENCE: 562

```
atggacacga gggcccccac tcagctgctg gggctcctgc tgctctggct cccaggtgcc      60
agatgtgcct atgatatgac ccagactcca gcctctgtgg aggtagctgt gggaggcaca     120
gtcaccatca gtgccaggc cactgagagc attggcaatg agttatcctg gtatcagcag     180
aaaccagggc aggctcccaa gctcctgatc tattctgcat ccactctggc atctggggtc     240
ccatcgcggt tcaaaggcag tggatctggg acacagttca ctctcaccat caccggcgtg     300
gagtgtgatg atgctgccac ttactactgt caacagggtt atagtagtgc taatattgat     360
aatgct                                                                 366
```

<210> SEQ ID NO 563
<211> LENGTH: 384
<212> TYPE: DNA
<213> ORGANISM: Oryctolagus cuniculus

<400> SEQUENCE: 563

```
atggagactg ggctgcgctg gcttctcctg gtcgctgtgc tcaaaggtgt ccagtgtcag      60
tcgctggagg agtccggggg tcgcctggtc acgcctggga cacccctgac actcacctgc     120
accgtctctg gattctccct cagtaagtac tacatgagct gggtccgcca ggctccagag     180
aaggggctga atacatcgg atacattgat agtactactg ttaatacata ctacgcgacc     240
tgggcgagag gccgattcac catctccaaa acctcgacca cggtggatct gaagatcacc     300
agtccgacaa gtgaggacac ggccacctat ttctgtgcca gagaagtac ttattttact     360
gatggaggcc atcggttgga tctc                                             384
```

<210> SEQ ID NO 564
<211> LENGTH: 33
<212> TYPE: DNA
<213> ORGANISM: Oryctolagus cuniculus

<400> SEQUENCE: 564

```
caggccactg agagcattgg caatgagtta tcc                                   33
```

<210> SEQ ID NO 565
<211> LENGTH: 21
<212> TYPE: DNA
<213> ORGANISM: Oryctolagus cuniculus

<400> SEQUENCE: 565

```
tctgcatcca ctctggcatc t                                                21
```

<210> SEQ ID NO 566
<211> LENGTH: 36
<212> TYPE: DNA
<213> ORGANISM: Oryctolagus cuniculus

<400> SEQUENCE: 566
caacagggtt atagtagtgc taatattgat aatgct        36

<210> SEQ ID NO 567
<211> LENGTH: 15
<212> TYPE: DNA
<213> ORGANISM: Oryctolagus cuniculus

<400> SEQUENCE: 567
aagtactaca tgagc        15

<210> SEQ ID NO 568
<211> LENGTH: 51
<212> TYPE: DNA
<213> ORGANISM: Oryctolagus cuniculus

<400> SEQUENCE: 568
tacattgata gtactactgt aatacatac tacgcgacct gggcgagagg c        51

<210> SEQ ID NO 569
<211> LENGTH: 42
<212> TYPE: DNA
<213> ORGANISM: Oryctolagus cuniculus

<400> SEQUENCE: 569
ggaagtactt attttactga tggaggccat cggttggatc tc        42

<210> SEQ ID NO 570
<211> LENGTH: 122
<212> TYPE: PRT
<213> ORGANISM: Oryctolagus cuniculus

<400> SEQUENCE: 570

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Thr
        35                  40                  45

Glu Ser Ile Gly Asn Glu Leu Ser Trp Tyr Gln Gln Lys Pro Gly Gln
    50                  55                  60

Ala Pro Lys Leu Leu Ile Tyr Ser Ala Ser Thr Leu Ala Ser Gly Val
65                  70                  75                  80

Pro Ser Arg Phe Lys Gly Ser Gly Ser Gly Thr Gln Phe Thr Leu Thr
                85                  90                  95

Ile Thr Gly Val Glu Cys Asp Asp Ala Ala Thr Tyr Tyr Cys Gln Gln
            100                 105                 110

Gly Tyr Ser Ser Ala Asn Ile Asp Asn Ala
        115                 120

<210> SEQ ID NO 571
<211> LENGTH: 124
<212> TYPE: PRT
<213> ORGANISM: Oryctolagus cuniculus

<400> SEQUENCE: 571

```
Met Glu Thr Gly Leu Arg Trp Leu Leu Leu Val Ala Val Leu Lys Gly
1               5                   10                  15

Val Gln Cys Gln Ser Leu Glu Ser Gly Gly Arg Leu Val Thr Pro
            20                  25                  30

Gly Thr Pro Leu Thr Leu Thr Cys Thr Val Ser Gly Phe Ser Leu Ser
            35                  40                  45

Thr Tyr Asn Met Gly Trp Val Arg Gln Ala Pro Gly Lys Gly Leu Glu
        50                  55                  60

Trp Ile Gly Ser Ile Thr Ile Asp Gly Arg Thr Tyr Tyr Ala Ser Trp
65                  70                  75                  80

Ala Lys Gly Arg Phe Thr Val Ser Lys Ser Thr Thr Val Asp Leu
                85                  90                  95

Lys Met Thr Ser Leu Thr Thr Gly Asp Thr Ala Thr Tyr Phe Cys Ala
            100                 105                 110

Arg Ile Leu Ile Val Ser Tyr Gly Ala Phe Thr Ile
            115                 120

<210> SEQ ID NO 572
<211> LENGTH: 11
<212> TYPE: PRT
<213> ORGANISM: Oryctolagus cuniculus

<400> SEQUENCE: 572

Gln Ala Thr Glu Ser Ile Gly Asn Glu Leu Ser
1               5                   10

<210> SEQ ID NO 573
<211> LENGTH: 7
<212> TYPE: PRT
<213> ORGANISM: Oryctolagus cuniculus

<400> SEQUENCE: 573

Ser Ala Ser Thr Leu Ala Ser
1               5

<210> SEQ ID NO 574
<211> LENGTH: 12
<212> TYPE: PRT
<213> ORGANISM: Oryctolagus cuniculus

<400> SEQUENCE: 574

Gln Gln Gly Tyr Ser Ser Ala Asn Ile Asp Asn Ala
1               5                   10

<210> SEQ ID NO 575
<211> LENGTH: 5
<212> TYPE: PRT
<213> ORGANISM: Oryctolagus cuniculus

<400> SEQUENCE: 575

Thr Tyr Asn Met Gly
1               5

<210> SEQ ID NO 576
<211> LENGTH: 16
<212> TYPE: PRT
<213> ORGANISM: Oryctolagus cuniculus

<400> SEQUENCE: 576

Ser Ile Thr Ile Asp Gly Arg Thr Tyr Tyr Ala Ser Trp Ala Lys Gly
1               5                   10                  15
```

<210> SEQ ID NO 577
<211> LENGTH: 11
<212> TYPE: PRT
<213> ORGANISM: Oryctolagus cuniculus

<400> SEQUENCE: 577

Ile Leu Ile Val Ser Tyr Gly Ala Phe Thr Ile
1               5                   10

<210> SEQ ID NO 578
<211> LENGTH: 366
<212> TYPE: DNA
<213> ORGANISM: Oryctolagus cuniculus

<400> SEQUENCE: 578

```
atggacacga gggcccccac tcagctgctg gggctcctgc tgctctggct cccaggtgcc      60
agatgtgcct atgatatgac ccagactcca gcctctgtgg aggtagctgt gggaggcaca     120
gtcaccatca agtgccaggc cactgagagc attggcaatg agttatcctg gtatcagcag     180
aaaccagggc aggctcccaa gctcctgatc tattctgcat ccactctggc atctggggtc     240
ccatcgcggt tcaaaggcag tggatctggg acacagttca ctctcaccat caccggcgtg     300
gagtgtgatg atgctgccac ttactactgt caacagggtt atagtagtgc taatattgat     360
aatgct                                                                366
```

<210> SEQ ID NO 579
<211> LENGTH: 372
<212> TYPE: DNA
<213> ORGANISM: Oryctolagus cuniculus

<400> SEQUENCE: 579

```
atggagactg ggctgcgctg gcttctcctg gtcgctgtgc tcaaaggtgt ccagtgtcag      60
tcgctggagg agtccggggg tcgcctggta acgcctggga caccctgac actcacctgc      120
acagtctctg gattctcccct cagtacctac aacatgggct gggtccgcca ggctccaggg    180
aaggggctgg aatggatcgg aagtattact attgatggtc gcacatacta cgcgagctgg    240
gcgaaaggcc gattcaccgt ctccaaaagc tcgaccacgg tggatctgaa aatgaccagt    300
ctgacaaccg gggacacggc cacctatttc tgtgccagga ttcttattgt ttcttatggg    360
gcctttacca tc                                                        372
```

<210> SEQ ID NO 580
<211> LENGTH: 33
<212> TYPE: DNA
<213> ORGANISM: Oryctolagus cuniculus

<400> SEQUENCE: 580

```
caggccactg agagcattgg caatgagtta tcc                                   33
```

<210> SEQ ID NO 581
<211> LENGTH: 21
<212> TYPE: DNA
<213> ORGANISM: Oryctolagus cuniculus

<400> SEQUENCE: 581

```
tctgcatcca ctctggcatc t                                                21
```

<210> SEQ ID NO 582
<211> LENGTH: 36

<212> TYPE: DNA
<213> ORGANISM: Oryctolagus cuniculus

<400> SEQUENCE: 582
caacagggtt atagtagtgc taatattgat aatgct                                    36

<210> SEQ ID NO 583
<211> LENGTH: 15
<212> TYPE: DNA
<213> ORGANISM: Oryctolagus cuniculus

<400> SEQUENCE: 583
acctacaaca tgggc                                                           15

<210> SEQ ID NO 584
<211> LENGTH: 48
<212> TYPE: DNA
<213> ORGANISM: Oryctolagus cuniculus

<400> SEQUENCE: 584
agtattacta ttgatggtcg cacatactac gcgagctggg cgaaaggc                       48

<210> SEQ ID NO 585
<211> LENGTH: 33
<212> TYPE: DNA
<213> ORGANISM: Oryctolagus cuniculus

<400> SEQUENCE: 585
attcttattg tttcttatgg ggcctttacc atc                                       33

<210> SEQ ID NO 586
<211> LENGTH: 105
<212> TYPE: PRT
<213> ORGANISM: Artificial Sequence
<220> FEATURE:
<223> OTHER INFORMATION: Kappa constant domain of Ab1

<400> SEQUENCE: 586

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 587
<211> LENGTH: 315
<212> TYPE: DNA
<213> ORGANISM: Artificial Sequence
<220> FEATURE:
<223> OTHER INFORMATION: Kappa constant domain of Ab1

<400> SEQUENCE: 587
gtggctgcac catctgtctt catcttcccg ccatctgatg agcagttgaa atctggaact          60

```
gcctctgttg tgtgcctgct gaataacttc tatcccagag aggccaaagt acagtggaag    120
gtggataacg ccctccaatc gggtaactcc caggagagtg tcacagagca ggacagcaag    180
gacagcacct acagcctcag cagcaccctg acgctgagca agcagactac gagaaacac     240 aaagtctacg cctgcgaagt cacccatcag ggcctgagct cgcccgtcac aaagagcttc    300
aacaggggag agtgt                                                     315
```

```
<210> SEQ ID NO 588
<211> LENGTH: 330
<212> TYPE: PRT
<213> ORGANISM: Artificial Sequence
<220> FEATURE:
<223> OTHER INFORMATION: Gamma-1 constant domain of Ab1

<400> SEQUENCE: 588
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

```
                305                 310                 315                 320
Gln Lys Ser Leu Ser Leu Ser Pro Gly Lys
                    325                 330

<210> SEQ ID NO 589
<211> LENGTH: 990
<212> TYPE: DNA
<213> ORGANISM: Artificial Sequence
<220> FEATURE:
<223> OTHER INFORMATION: Gamma-1 constant domain of Ab1

<400> SEQUENCE: 589
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag cgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctggggggga     360 ccgtcagtct tcctcttccc cccaaaaccc aaggacaccc tcatgatctc ccggaccct      420 gaggtcacat gcgtggtggt ggacgtgagc cacgaagacc ctgaggtcaa gttcaactgg     480
tacgtggacg gcgtggaggt gcataatgcc aagacaaagc cgcggagga gcagtacgcc     540 agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990

<210> SEQ ID NO 590
<211> LENGTH: 15
<212> TYPE: PRT
<213> ORGANISM: Homo sapiens

<400> SEQUENCE: 590

Val Pro Pro Gly Glu Asp Ser Lys Asp Val Ala Ala Pro His Arg
1               5                   10                  15

<210> SEQ ID NO 591
<211> LENGTH: 15
<212> TYPE: PRT
<213> ORGANISM: Homo sapiens

<400> SEQUENCE: 591

Gly Glu Asp Ser Lys Asp Val Ala Ala Pro His Arg Gln Pro Leu
1               5                   10                  15

<210> SEQ ID NO 592
<211> LENGTH: 15
<212> TYPE: PRT
<213> ORGANISM: Homo sapiens

<400> SEQUENCE: 592
```

```
Ser Lys Asp Val Ala Ala Pro His Arg Gln Pro Leu Thr Ser Ser
1               5                   10                  15
```

<210> SEQ ID NO 593
<211> LENGTH: 15
<212> TYPE: PRT
<213> ORGANISM: Homo sapiens

<400> SEQUENCE: 593

```
Val Ala Ala Pro His Arg Gln Pro Leu Thr Ser Ser Glu Arg Ile
1               5                   10                  15
```

<210> SEQ ID NO 594
<211> LENGTH: 15
<212> TYPE: PRT
<213> ORGANISM: Homo sapiens

<400> SEQUENCE: 594

```
Pro His Arg Gln Pro Leu Thr Ser Ser Glu Arg Ile Asp Lys Gln
1               5                   10                  15
```

<210> SEQ ID NO 595
<211> LENGTH: 15
<212> TYPE: PRT
<213> ORGANISM: Homo sapiens

<400> SEQUENCE: 595

```
Gln Pro Leu Thr Ser Ser Glu Arg Ile Asp Lys Gln Ile Arg Tyr
1               5                   10                  15
```

<210> SEQ ID NO 596
<211> LENGTH: 15
<212> TYPE: PRT
<213> ORGANISM: Homo sapiens

<400> SEQUENCE: 596

```
Thr Ser Ser Glu Arg Ile Asp Lys Gln Ile Arg Tyr Ile Leu Asp
1               5                   10                  15
```

<210> SEQ ID NO 597
<211> LENGTH: 15
<212> TYPE: PRT
<213> ORGANISM: Homo sapiens

<400> SEQUENCE: 597

```
Glu Arg Ile Asp Lys Gln Ile Arg Tyr Ile Leu Asp Gly Ile Ser
1               5                   10                  15
```

<210> SEQ ID NO 598
<211> LENGTH: 15
<212> TYPE: PRT
<213> ORGANISM: Homo sapiens

<400> SEQUENCE: 598

```
Asp Lys Gln Ile Arg Tyr Ile Leu Asp Gly Ile Ser Ala Leu Arg
1               5                   10                  15
```

<210> SEQ ID NO 599
<211> LENGTH: 15
<212> TYPE: PRT
<213> ORGANISM: Homo sapiens

<400> SEQUENCE: 599

```
Ile Arg Tyr Ile Leu Asp Gly Ile Ser Ala Leu Arg Lys Glu Thr
1               5                   10                  15
```

<210> SEQ ID NO 600
<211> LENGTH: 15
<212> TYPE: PRT
<213> ORGANISM: Homo sapiens

<400> SEQUENCE: 600

Ile Leu Asp Gly Ile Ser Ala Leu Arg Lys Glu Thr Cys Asn Lys
1               5                   10                  15

<210> SEQ ID NO 601
<211> LENGTH: 15
<212> TYPE: PRT
<213> ORGANISM: Homo sapiens

<400> SEQUENCE: 601

Gly Ile Ser Ala Leu Arg Lys Glu Thr Cys Asn Lys Ser Asn Met
1               5                   10                  15

<210> SEQ ID NO 602
<211> LENGTH: 15
<212> TYPE: PRT
<213> ORGANISM: Homo sapiens

<400> SEQUENCE: 602

Ala Leu Arg Lys Glu Thr Cys Asn Lys Ser Asn Met Cys Glu Ser
1               5                   10                  15

<210> SEQ ID NO 603
<211> LENGTH: 15
<212> TYPE: PRT
<213> ORGANISM: Homo sapiens

<400> SEQUENCE: 603

Lys Glu Thr Cys Asn Lys Ser Asn Met Cys Glu Ser Ser Lys Glu
1               5                   10                  15

<210> SEQ ID NO 604
<211> LENGTH: 15
<212> TYPE: PRT
<213> ORGANISM: Homo sapiens

<400> SEQUENCE: 604

Cys Asn Lys Ser Asn Met Cys Glu Ser Ser Lys Glu Ala Leu Ala
1               5                   10                  15

<210> SEQ ID NO 605
<211> LENGTH: 15
<212> TYPE: PRT
<213> ORGANISM: Homo sapiens

<400> SEQUENCE: 605

Ser Asn Met Cys Glu Ser Ser Lys Glu Ala Leu Ala Glu Asn Asn
1               5                   10                  15

<210> SEQ ID NO 606
<211> LENGTH: 15
<212> TYPE: PRT
<213> ORGANISM: Homo sapiens

<400> SEQUENCE: 606

Cys Glu Ser Ser Lys Glu Ala Leu Ala Glu Asn Asn Leu Asn Leu
1               5                   10                  15

```
<210> SEQ ID NO 607
<211> LENGTH: 15
<212> TYPE: PRT
<213> ORGANISM: Homo sapiens

<400> SEQUENCE: 607

Ser Lys Glu Ala Leu Ala Glu Asn Asn Leu Asn Leu Pro Lys Met
1               5                   10                  15

<210> SEQ ID NO 608
<211> LENGTH: 15
<212> TYPE: PRT
<213> ORGANISM: Homo sapiens

<400> SEQUENCE: 608

Ala Leu Ala Glu Asn Asn Leu Asn Leu Pro Lys Met Ala Glu Lys
1               5                   10                  15

<210> SEQ ID NO 609
<211> LENGTH: 15
<212> TYPE: PRT
<213> ORGANISM: Homo sapiens

<400> SEQUENCE: 609

Glu Asn Asn Leu Asn Leu Pro Lys Met Ala Glu Lys Asp Gly Cys
1               5                   10                  15

<210> SEQ ID NO 610
<211> LENGTH: 15
<212> TYPE: PRT
<213> ORGANISM: Homo sapiens

<400> SEQUENCE: 610

Leu Asn Leu Pro Lys Met Ala Glu Lys Asp Gly Cys Phe Gln Ser
1               5                   10                  15

<210> SEQ ID NO 611
<211> LENGTH: 15
<212> TYPE: PRT
<213> ORGANISM: Homo sapiens

<400> SEQUENCE: 611

Pro Lys Met Ala Glu Lys Asp Gly Cys Phe Gln Ser Gly Phe Asn
1               5                   10                  15

<210> SEQ ID NO 612
<211> LENGTH: 15
<212> TYPE: PRT
<213> ORGANISM: Homo sapiens

<400> SEQUENCE: 612

Ala Glu Lys Asp Gly Cys Phe Gln Ser Gly Phe Asn Glu Glu Thr
1               5                   10                  15

<210> SEQ ID NO 613
<211> LENGTH: 15
<212> TYPE: PRT
<213> ORGANISM: Homo sapiens

<400> SEQUENCE: 613

Asp Gly Cys Phe Gln Ser Gly Phe Asn Glu Glu Thr Cys Leu Val
1               5                   10                  15

<210> SEQ ID NO 614
<211> LENGTH: 15
```

```
<212> TYPE: PRT
<213> ORGANISM: Homo sapiens

<400> SEQUENCE: 614

Phe Gln Ser Gly Phe Asn Glu Glu Thr Cys Leu Val Lys Ile Ile
1               5                   10                  15

<210> SEQ ID NO 615
<211> LENGTH: 15
<212> TYPE: PRT
<213> ORGANISM: Homo sapiens

<400> SEQUENCE: 615

Gly Phe Asn Glu Glu Thr Cys Leu Val Lys Ile Ile Thr Gly Leu
1               5                   10                  15

<210> SEQ ID NO 616
<211> LENGTH: 15
<212> TYPE: PRT
<213> ORGANISM: Homo sapiens

<400> SEQUENCE: 616

Glu Glu Thr Cys Leu Val Lys Ile Ile Thr Gly Leu Leu Glu Phe
1               5                   10                  15

<210> SEQ ID NO 617
<211> LENGTH: 15
<212> TYPE: PRT
<213> ORGANISM: Homo sapiens

<400> SEQUENCE: 617

Cys Leu Val Lys Ile Ile Thr Gly Leu Leu Glu Phe Glu Val Tyr
1               5                   10                  15

<210> SEQ ID NO 618
<211> LENGTH: 15
<212> TYPE: PRT
<213> ORGANISM: Homo sapiens

<400> SEQUENCE: 618

Lys Ile Ile Thr Gly Leu Leu Glu Phe Glu Val Tyr Leu Glu Tyr
1               5                   10                  15

<210> SEQ ID NO 619
<211> LENGTH: 15
<212> TYPE: PRT
<213> ORGANISM: Homo sapiens

<400> SEQUENCE: 619

Thr Gly Leu Leu Glu Phe Glu Val Tyr Leu Glu Tyr Leu Gln Asn
1               5                   10                  15

<210> SEQ ID NO 620
<211> LENGTH: 15
<212> TYPE: PRT
<213> ORGANISM: Homo sapiens

<400> SEQUENCE: 620

Leu Glu Phe Glu Val Tyr Leu Glu Tyr Leu Gln Asn Arg Phe Glu
1               5                   10                  15

<210> SEQ ID NO 621
<211> LENGTH: 15
<212> TYPE: PRT
```

```
<400> SEQUENCE: 621

Glu Val Tyr Leu Glu Tyr Leu Gln Asn Arg Phe Glu Ser Ser Glu
1               5                   10                  15

<210> SEQ ID NO 622
<211> LENGTH: 15
<212> TYPE: PRT
<213> ORGANISM: Homo sapiens

<400> SEQUENCE: 622

Leu Glu Tyr Leu Gln Asn Arg Phe Glu Ser Ser Glu Glu Gln Ala
1               5                   10                  15

<210> SEQ ID NO 623
<211> LENGTH: 15
<212> TYPE: PRT
<213> ORGANISM: Homo sapiens

<400> SEQUENCE: 623

Leu Gln Asn Arg Phe Glu Ser Ser Glu Glu Gln Ala Arg Ala Val
1               5                   10                  15

<210> SEQ ID NO 624
<211> LENGTH: 15
<212> TYPE: PRT
<213> ORGANISM: Homo sapiens

<400> SEQUENCE: 624

Arg Phe Glu Ser Ser Glu Glu Gln Ala Arg Ala Val Gln Met Ser
1               5                   10                  15

<210> SEQ ID NO 625
<211> LENGTH: 15
<212> TYPE: PRT
<213> ORGANISM: Homo sapiens

<400> SEQUENCE: 625

Ser Ser Glu Glu Gln Ala Arg Ala Val Gln Met Ser Thr Lys Val
1               5                   10                  15

<210> SEQ ID NO 626
<211> LENGTH: 15
<212> TYPE: PRT
<213> ORGANISM: Homo sapiens

<400> SEQUENCE: 626

Glu Gln Ala Arg Ala Val Gln Met Ser Thr Lys Val Leu Ile Gln
1               5                   10                  15

<210> SEQ ID NO 627
<211> LENGTH: 15
<212> TYPE: PRT
<213> ORGANISM: Homo sapiens

<400> SEQUENCE: 627

Arg Ala Val Gln Met Ser Thr Lys Val Leu Ile Gln Phe Leu Gln
1               5                   10                  15

<210> SEQ ID NO 628
<211> LENGTH: 15
<212> TYPE: PRT
<213> ORGANISM: Homo sapiens

<400> SEQUENCE: 628
```

Gln Met Ser Thr Lys Val Leu Ile Gln Phe Leu Gln Lys Lys Ala
1               5                   10                  15

<210> SEQ ID NO 629
<211> LENGTH: 15
<212> TYPE: PRT
<213> ORGANISM: Homo sapiens

<400> SEQUENCE: 629

Thr Lys Val Leu Ile Gln Phe Leu Gln Lys Lys Ala Lys Asn Leu
1               5                   10                  15

<210> SEQ ID NO 630
<211> LENGTH: 15
<212> TYPE: PRT
<213> ORGANISM: Homo sapiens

<400> SEQUENCE: 630

Leu Ile Gln Phe Leu Gln Lys Lys Ala Lys Asn Leu Asp Ala Ile
1               5                   10                  15

<210> SEQ ID NO 631
<211> LENGTH: 15
<212> TYPE: PRT
<213> ORGANISM: Homo sapiens

<400> SEQUENCE: 631

Phe Leu Gln Lys Lys Ala Lys Asn Leu Asp Ala Ile Thr Thr Pro
1               5                   10                  15

<210> SEQ ID NO 632
<211> LENGTH: 15
<212> TYPE: PRT
<213> ORGANISM: Homo sapiens

<400> SEQUENCE: 632

Lys Lys Ala Lys Asn Leu Asp Ala Ile Thr Thr Pro Asp Pro Thr
1               5                   10                  15

<210> SEQ ID NO 633
<211> LENGTH: 15
<212> TYPE: PRT
<213> ORGANISM: Homo sapiens

<400> SEQUENCE: 633

Lys Asn Leu Asp Ala Ile Thr Thr Pro Asp Pro Thr Thr Asn Ala
1               5                   10                  15

<210> SEQ ID NO 634
<211> LENGTH: 15
<212> TYPE: PRT
<213> ORGANISM: Homo sapiens

<400> SEQUENCE: 634

Asp Ala Ile Thr Thr Pro Asp Pro Thr Thr Asn Ala Ser Leu Leu
1               5                   10                  15

<210> SEQ ID NO 635
<211> LENGTH: 15
<212> TYPE: PRT
<213> ORGANISM: Homo sapiens

<400> SEQUENCE: 635

Thr Thr Pro Asp Pro Thr Thr Asn Ala Ser Leu Leu Thr Lys Leu 1               5                   10                  15

<210> SEQ ID NO 636
<211> LENGTH: 15
<212> TYPE: PRT
<213> ORGANISM: Homo sapiens

<400> SEQUENCE: 636

Asp Pro Thr Thr Asn Ala Ser Leu Leu Thr Lys Leu Gln Ala Gln
1               5                   10                  15

<210> SEQ ID NO 637
<211> LENGTH: 15
<212> TYPE: PRT
<213> ORGANISM: Homo sapiens

<400> SEQUENCE: 637

Thr Asn Ala Ser Leu Leu Thr Lys Leu Gln Ala Gln Asn Gln Trp
1               5                   10                  15

<210> SEQ ID NO 638
<211> LENGTH: 15
<212> TYPE: PRT
<213> ORGANISM: Homo sapiens

<400> SEQUENCE: 638

Ser Leu Leu Thr Lys Leu Gln Ala Gln Asn Gln Trp Leu Gln Asp
1               5                   10                  15

<210> SEQ ID NO 639
<211> LENGTH: 15
<212> TYPE: PRT
<213> ORGANISM: Homo sapiens

<400> SEQUENCE: 639

Thr Lys Leu Gln Ala Gln Asn Gln Trp Leu Gln Asp Met Thr Thr
1               5                   10                  15

<210> SEQ ID NO 640
<211> LENGTH: 15
<212> TYPE: PRT
<213> ORGANISM: Homo sapiens

<400> SEQUENCE: 640

Gln Ala Gln Asn Gln Trp Leu Gln Asp Met Thr Thr His Leu Ile
1               5                   10                  15

<210> SEQ ID NO 641
<211> LENGTH: 15
<212> TYPE: PRT
<213> ORGANISM: Homo sapiens

<400> SEQUENCE: 641

Asn Gln Trp Leu Gln Asp Met Thr Thr His Leu Ile Leu Arg Ser
1               5                   10                  15

<210> SEQ ID NO 642
<211> LENGTH: 15
<212> TYPE: PRT
<213> ORGANISM: Homo sapiens

<400> SEQUENCE: 642

Leu Gln Asp Met Thr Thr His Leu Ile Leu Arg Ser Phe Lys Glu
1               5                   10                  15

<210> SEQ ID NO 643
<211> LENGTH: 15
<212> TYPE: PRT
<213> ORGANISM: Homo sapiens

<400> SEQUENCE: 643

Met Thr Thr His Leu Ile Leu Arg Ser Phe Lys Glu Phe Leu Gln
1               5                   10                  15

<210> SEQ ID NO 644
<211> LENGTH: 15
<212> TYPE: PRT
<213> ORGANISM: Homo sapiens

<400> SEQUENCE: 644

His Leu Ile Leu Arg Ser Phe Lys Glu Phe Leu Gln Ser Ser Leu
1               5                   10                  15

<210> SEQ ID NO 645
<211> LENGTH: 15
<212> TYPE: PRT
<213> ORGANISM: Homo sapiens

<400> SEQUENCE: 645

Leu Arg Ser Phe Lys Glu Phe Leu Gln Ser Ser Leu Arg Ala Leu
1               5                   10                  15

<210> SEQ ID NO 646
<211> LENGTH: 15
<212> TYPE: PRT
<213> ORGANISM: Homo sapiens

<400> SEQUENCE: 646

Phe Lys Glu Phe Leu Gln Ser Ser Leu Arg Ala Leu Arg Gln Met
1               5                   10                  15

<210> SEQ ID NO 647
<211> LENGTH: 32
<212> TYPE: DNA
<213> ORGANISM: Artificial Sequence
<220> FEATURE:
<223> OTHER INFORMATION: Light Chain Forward Primer

<400> SEQUENCE: 647
agcgcttatt ccgctatcca gatgacccag tc                              32

<210> SEQ ID NO 648
<211> LENGTH: 22
<212> TYPE: DNA
<213> ORGANISM: Artificial Sequence
<220> FEATURE:
<223> OTHER INFORMATION: Light Chain Reverse Primer

<400> SEQUENCE: 648
cgtacgtttg atttccacct tg                                         22

<210> SEQ ID NO 649
<211> LENGTH: 32
<212> TYPE: DNA
<213> ORGANISM: Artificial Sequence
<220> FEATURE:
<223> OTHER INFORMATION: Heavy Chain Forward Primer

<400> SEQUENCE: 649
agcgcttatt ccgaggtgca gctggtggag tc                              32

<210> SEQ ID NO 650
<211> LENGTH: 20
<212> TYPE: DNA
<213> ORGANISM: Artificial Sequence
<220> FEATURE:
<223> OTHER INFORMATION: Heavy Chain Reverse Primer

<400> SEQUENCE: 650
ctcgagacgg tgacgagggt                                        20

<210> SEQ ID NO 651
<211> LENGTH: 111
<212> TYPE: PRT
<213> ORGANISM: Oryctolagus cuniculus

<400> SEQUENCE: 651

Ala Tyr Asp Met Thr Gln Thr Pro Ala Ser Val Glu Val Ala Val Gly
1               5                   10                  15

Gly Thr Val Thr Ile Asn Cys Gln Ala Ser Glu Thr Ile Tyr Ser Trp
            20                  25                  30

Leu Ser Trp Tyr Gln Gln Lys Pro Gly Gln Pro Pro Lys Leu Leu Ile
        35                  40                  45

Tyr Gln Ala Ser Asp Leu Ala Ser Gly Val Pro Ser Arg Phe Ser Gly
    50                  55                  60

Ser Gly Ala Gly Thr Glu Tyr Thr Leu Thr Ile Ser Gly Val Gln Cys
65                  70                  75                  80

Asp Asp Ala Ala Thr Tyr Tyr Cys Gln Gln Gly Tyr Ser Gly Ser Asn
                85                  90                  95

Val Asp Asn Val Phe Gly Gly Gly Thr Glu Val Val Val Lys Arg
            100                 105                 110

<210> SEQ ID NO 652
<211> LENGTH: 88
<212> TYPE: PRT
<213> ORGANISM: Homo sapiens

<400> SEQUENCE: 652

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys
                85

<210> SEQ ID NO 653
<211> LENGTH: 88
<212> TYPE: PRT
<213> ORGANISM: Homo sapiens

<400> SEQUENCE: 653

Asp Ile Gln Met Thr Gln Ser Pro Ser Thr Leu Ser Ala Ser Val Gly
1               5                   10                  15

-continued

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys
                85

<210> SEQ ID NO 654
<211> LENGTH: 88
<212> TYPE: PRT
<213> ORGANISM: Homo sapiens

<400> SEQUENCE: 654

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 655
<211> LENGTH: 111
<212> TYPE: PRT
<213> ORGANISM: Artificial Sequence
<220> FEATURE:
<223> OTHER INFORMATION: Humanized antibody

<400> SEQUENCE: 655

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Thr Ile Tyr Ser Trp
            20                  25                  30

Leu Ser Trp Tyr Gln Gln Lys Pro Gly Lys Ala Pro Lys Leu Leu Ile
        35                  40                  45

Tyr Gln Ala Ser Asp Leu Ala Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Gly Ser Asn
                85                  90                  95

Val Asp Asn Val Phe Gly Gly Gly Thr Lys Val Glu Ile Lys Arg
                100                 105                 110

<210> SEQ ID NO 656
<211> LENGTH: 11
<212> TYPE: PRT
<213> ORGANISM: Homo sapiens

<400> SEQUENCE: 656

```
Phe Gly Gly Gly Thr Lys Val Glu Ile Lys Arg
1               5                   10

<210> SEQ ID NO 657
<211> LENGTH: 118
<212> TYPE: PRT
<213> ORGANISM: Oryctolagus cuniculus

<400> SEQUENCE: 657

Gln Glu Gln Leu Lys Glu Ser Gly Gly Arg Leu Val Thr Pro Gly Thr
1               5                   10                  15

Pro Leu Thr Leu Thr Cys Thr Ala Ser Gly Phe Ser Leu Asn Asp His
            20                  25                  30

Ala Met Gly Trp Val Arg Gln Ala Pro Gly Lys Gly Leu Glu Tyr Ile
        35                  40                  45

Gly Phe Ile Asn Ser Gly Gly Ser Ala Arg Tyr Ala Ser Trp Ala Glu
    50                  55                  60

Gly Arg Phe Thr Ile Ser Arg Thr Ser Thr Thr Val Asp Leu Lys Met
65                  70                  75                  80

Thr Ser Leu Thr Thr Glu Asp Thr Ala Thr Tyr Phe Cys Val Arg Gly
                85                  90                  95

Gly Ala Val Trp Ser Ile His Ser Phe Asp Pro Trp Gly Pro Gly Thr
            100                 105                 110

Leu Val Thr Val Ser Ser
            115

<210> SEQ ID NO 658
<211> LENGTH: 98
<212> TYPE: PRT
<213> ORGANISM: Homo sapiens

<400> SEQUENCE: 658

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 659
<211> LENGTH: 97
<212> TYPE: PRT
<213> ORGANISM: Homo sapiens

<400> SEQUENCE: 659

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
```

```
                35                  40                  45
Ser Val Ile Tyr Ser Gly Gly Ser Thr Tyr Tyr Ala Asp Ser Val Lys
        50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                85                  90                  95
Arg

<210> SEQ ID NO 660
<211> LENGTH: 97
<212> TYPE: PRT
<213> ORGANISM: Homo sapiens

<400> SEQUENCE: 660

Glu Val Gln Leu Val Glu Thr Gly Gly Gly Leu Ile Gln Pro Gly Gly
 1               5                  10                  15
Ser Leu Arg Leu Ser Cys Ala Ala Ser Gly Phe Thr Val Ser Ser Asn
                20                  25                  30
Tyr Met Ser Trp Val Arg Gln Ala Pro Gly Lys Gly Leu Glu Trp Val
                35                  40                  45
Ser Val Ile Tyr Ser Gly Gly Ser Thr Tyr Tyr Ala Asp Ser Val Lys
        50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                85                  90                  95
Arg

<210> SEQ ID NO 661
<211> LENGTH: 120
<212> TYPE: PRT
<213> ORGANISM: Artificial Sequence
<220> FEATURE:
<223> OTHER INFORMATION: Humanized antibody

<400> SEQUENCE: 661

Gln Val Gln Leu Val Glu Ser Gly Gly Gly Leu Val Gln Pro Gly Gly
 1               5                  10                  15
Ser Leu Arg Leu Ser Cys Ser Ala Ser Gly Phe Ser Leu Asn Asp His
                20                  25                  30
Ala Met Gly Trp Val Arg Gln Ala Pro Gly Lys Gly Leu Glu Tyr Val
                35                  40                  45
Gly Phe Ile Asn Ser Gly Gly Ser Ala Arg Tyr Ala Ser Ser Ala Glu
        50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                85                  90                  95
Arg Gly Gly Ala Val Trp Ser Ile His Ser Phe Asp Pro Trp Gly Gln
                100                 105                 110
Gly Thr Leu Val Thr Val Ser Ser
        115                 120

<210> SEQ ID NO 662
<211> LENGTH: 11
<212> TYPE: PRT
```

```
<213> ORGANISM: Homo sapiens

<400> SEQUENCE: 662

Trp Gly Gln Gly Thr Leu Val Thr Val Ser Ser
1               5                   10
```

METHODS OF TREATING AUTOIMMUNITY USING SPECIFIC ANTI-IL-6 ANTIBODIES

RELATED APPLICATION DISCLOSURE

This application is a divisional of U.S. application Ser. No. 14/604,419, filed Jan. 23, 2015, now U.S. Pat. No. 9,771,421, which is a continuation of U.S. Application Ser. No. which is a 12/601,295 filed May 25, 2010, which is a U.S, 371 National Stage application of International Application No, PCT/U.S.2008/064432 filed on May 21, 2008, which claims priority to U.S. provisional application No. 60/924,550, filed on May 21, 2007, the disclosure of all of which are herein incorporated by reference in their entirety.

SEQUENCE LISTING DISCLOSURE

This application includes as part of its disclosure a biological sequence listing contained in a file named "5625o1005.txt" having a size of 242,479 bytes that was created Apr. 9, 2019, which is hereby incorporated by reference in its entirety.

BACKGROUND OF THE INVENTION

Field of the Invention

This invention pertains to antibodies and fragments thereof having binding specificity to IL-6. The invention also pertains to methods of screening for diseases and disorders associated with IL-6, and methods of preventing or treating diseases or disorders associated with IL-6 by administering said antibodies or fragments thereof.

Description of Related Art

Interleukin-6 (hereinafter "IL-6") (also known as interferon-$\beta_2$; B-cell differentiation factor; B-cell stimulatory factor-2; hepatocyte stimulatory factor; hybridoma growth factor; and plasmacytoma growth factor) is a multifunctional cytokine involved in numerous biological processes such as the regulation of the acute inflammatory response, the modulation of specific immune responses including B- and T-cell differentiation, bone metabolism, thrombopoiesis, epidermal proliferation, menses, neuronal cell differentiation, neuroprotection, aging, cancer, and the inflammatory reaction occurring in Alzheimer's disease. See A. Papassotiropoulos, et al, Neurobiology of Aging, 22:863-871 (2001).

IL-6 is a member of a family of cytokines that promote cellular responses through a receptor complex consisting of at least one subunit of the signal-transducing glycoprotein gp130 and the IL-6 receptor ("IL-6R")(also known as gp80). The IL-6R may also be present in a soluble form ("sIL-6R"). IL-6 binds to IL-6R, which then dimerizes the signal-transducing receptor gp130. See Jones, S A, J. Immunology, 175:3463-3468 (2005).

In humans, the gene encoding for IL-6 is organized in five exons and four introns, and maps to the short arm of chromosome 7 at 7p21. Translation of IL-6 RNA and post-translational processing result in the formation of a 21 to 28 kDa protein with 184 amino acids in its mature form. See A. Papassotiropoulos, et al, Neurobiology of Aging, 22:863-871 (2001).

As set forth in greater detail below, IL-6 is believed to play a role in the development of a multitude of diseases and disorders, including but not limited to fatigue, cachexia, autoimmune diseases, diseases of the skeletal system, cancer, heart disease, obesity, diabetes, asthma, alzheimer's disease and multiple sclerosis. Due to the perceived involvement of IL-6 in a wide range of diseases and disorders, there remains a need in the art for compositions and methods useful for preventing or treating diseases associated with IL-6, as well as methods of screening to identify patients having diseases or disorders associated with IL-6. Particularly preferred anti-IL-6 compositions are those having minimal or minimizing adverse reactions when administered to the patient. Compositions or methods that reduce or inhibit diseases or disorders associated with IL-6 are beneficial to the patient in need thereof.

BRIEF SUMMARY OF THE INVENTION

The present invention is directed to specific antibodies and fragments thereof having binding specificity for IL-6, in particular antibodies having specific epitopic specificity and/or functional properties. One embodiment of the invention encompasses specific humanized antibodies and fragments thereof capable of binding to IL-6 and/or the IL-6/IL-6R complex. These antibodies may bind soluble IL-6 or cell surface expressed IL-6. Also, these antibodies may inhibit the formation or the biological effects of of one or more of IL-6, IL-6/IL-6R complexes, IL-6/IL-6R/gp130 complexes and/or multimers of IL-6/IL-6R/gp130.

Another embodiment of this invention relates to the antibodies described herein, comprising the sequences of the $V_H$, $V_L$ and CDR polypeptides described herein, and the polynucleotides encoding them. In more specific embodiments of the invention these antibodies will block gp130 activation and/or possess binding affinities (Kds) less than 50 picomolar and/or $K_{off}$ values less than or equal to $10^{-4}$ $S^{-1}$.

In another embodiment of the invention these antibodies and humanized versions will be derived from rabbit immune cells (B lymphocytes) and may be selected based on their homology (sequence identity) to human germ line sequences. These antibodies may require minimal or no sequence modifications, thereby facilitating retention of functional properties after humanization.

In another embodiment of the invention the subject antibodies may be selected based on their activity in functional assays such as IL-6 driven T1165 proliferation assays, IL-6 simulated HepG2 haptoglobin production assays, and the like. A further embodiment of the invention is directed to fragments from anti-IL-6 antibodies encompassing $V_H$, $V_L$ and CDR polypeptides, e.g., derived from rabbit immune cells and the polynucleotides encoding the same, as well as the use of these antibody fragments and the polynucleotides encoding them in the creation of novel antibodies and polypeptide compositions capable of recognizing IL-6 and/or IL-6/IL-6R complexes or IL-6/IL-6R/gp130 complexes and/or multimers thereof.

The invention also contemplates conjugates of anti-IL-6 antibodies and binding fragments thereof conjugated to one or more functional or detectable moieties. The invention also contemplates methods of making said humanized anti-IL-6 or anti-IL-6/IL-6R complex antibodies and binding fragments thereof. In one embodiment, binding fragments include, but are not limited to, Fab, Fab', F(ab')$_2$, Fv and scFv fragments.

Embodiments of the invention pertain to the use of anti-IL-6 antibodies for the diagnosis, assessment and treatment of diseases and disorders associated with IL-6 or aberrant expression thereof. The invention also contemplates the use of fragments of anti-IL-6 antibodies for the diagnosis, assessment and treatment of diseases and disorders associated with IL-6 or aberrant expression thereof.

Preferred usages of the subject antibodies are the treatment and prevention of cancer associated fatigue, and/or cachexia and rheumatoid arthritis.

Other embodiments of the invention relate to the production of anti-IL-6 antibodies in recombinant host cells, preferably diploid yeast such as diploid *Pichia* and other yeast strains.

BRIEF DESCRIPTION OF THE SEVERAL VIEWS OF THE DRAWINGS

FIG. 2 shows alignments of variable light and variable heavy sequences between a rabbit antibody variable light and variable heavy sequences and homologous human sequences and the final humanized sequences. Framework regions are identified FR1-FR4. Complementarity determining regions are identified as CDR1-CDR3. Amino acid residues are numbered as shown. The initial rabbit sequences are called RbtVL and RbtVH for the variable light and variable heavy sequences respectively. Three of the most similar human germline antibody sequences, spanning from Framework 1 through to the end of Framework 3, are aligned below the rabbit sequences. The human sequence that is considered the most similar to the rabbit sequence is shown first. In this example those most similar sequences are L12A for the light chain and 3-64-04 for the heavy chain. Human CDR3 sequences are not shown. The closest human Framework 4 sequence is aligned below the rabbit Framework 4 sequence. The vertical dashes indicate a residue where the rabbit residue is identical with one or more of the human residues at the same position. The bold residues indicate that the human residue at that position is identical to the rabbit residue at the same position. The final humanized sequences are called VLh and VHh for the variable light and variable heavy sequences respectively. The underlined residues indicate that the residue is the same as the rabbit residue at that position but different than the human residues at that position in the three aligned human sequences.

FIG. 5 provides survival data for the antibody Ab1 progression groups versus control groups.

FIG. 6 provides additional survival data for the antibody Ab1 regression groups versus control groups.

FIG. 7 provides survival data for polyclonal human IgG at 10 mg/kg i.v. every three days (270-320 mg tumor size) versus antibody Ab1 at 10 mg/kg i.v. every three days (270-320 mg tumor size).

FIG. 8 provides survival data for polyclonal human IgG at 10 mg/kg i.v. every three days (400-527 mg tumor size) versus antibody Ab1 at 10 mg/kg i.v. every three days (400-527 mg tumor size).

FIG. 9 provides a pharamcokinetic profile of antibody Ab1. Plasma levels of antibody Ab1 were quantitated through antigen capture ELISA. This protein displays a half life of between 12 and 17 days consistent with other full length humanized antibodies.

FIGS. 10A-D provide binding data for antibodies Ab4, Ab3, Ab8 and Ab2, respectively. FIG. 10E provides binding data for antibodies Ab1, Ab6 and Ab7.

FIG. 11 summarizes the binding data of FIGS. 10A-E in tabular form.

FIG. 12 presents the sequences of the 15 amino acid peptides used in the peptide mapping experiment of Example 14.

DETAILED DESCRIPTION OF PREFERRED EMBODIMENTS

Definitions

Figure 1:
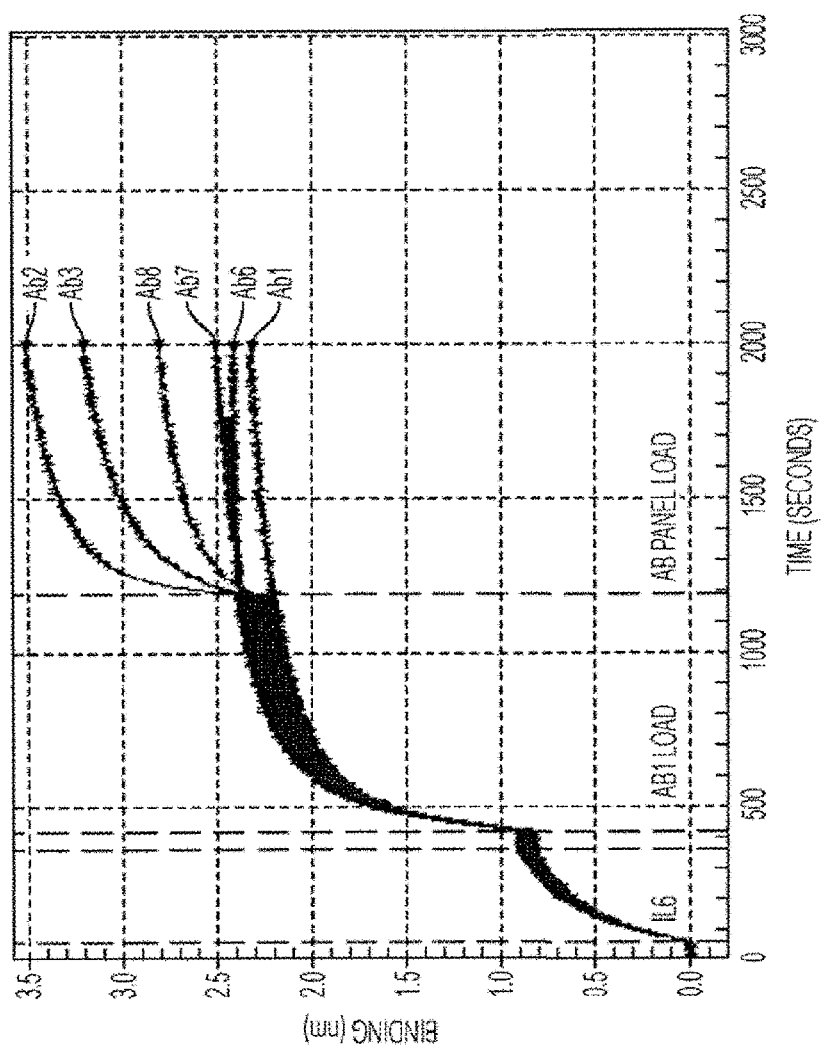
FIG. 1 shows that a variety of unique epitopes were recognized by the collection of anti-IL-6 antibodies prepared by the antibody selection protocol. Epitope variability was confirmed by antibody-IL-6 binding competition studies (ForteBio Octet).

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Interleukin-6 (IL-6): As used herein, interleukin-6 (IL-6) encompasses not only the following 212 amino acid sequence available as GenBank Protein Accession No. NP_000591:

```
                                          (SEQ ID NO: 1)
MNSFSTSAFGPVAFSLGLLLVLPAAFPAPVPPGEDSKDVAAPHRQPLTSS

ERIDKQIRYILDGISALRKETCNKSNMCESSKEALAENNLNLPKMAEKDG

CFQSGFNEETCLVKIITGLLEFEVYLEYLQNRFESSEEQARAVQMSTKVL

IQFLQKKAKNLDAITTPDPTTNASLLTKLQAQNQWLQDMTTHLILRSFKE

FLQSSLRALRQM,
``` but also any pre-pro, pro- and mature forms of this IL-6 amino acid sequence, as well as mutants and variants including allelic variants of this sequence.

Mating competent yeast species: In the present invention this is intended to broadly encompass any diploid or tetraploid yeast which can be grown in culture. Such species of yeast may exist in a haploid, diploid, or tetraploid form. The cells of a given ploidy may, under appropriate conditions, proliferate for indefinite number of generations in that form. Diploid cells can also sporulate to form haploid cells. Sequential mating can result in tetraploid strains through further mating or fusion of diploid strains. In the present invention the diploid or polyploidal yeast cells are preferably produced by mating or spheroplast fusion.

In one embodiment of the invention, the mating competent yeast is a member of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis;* and *Zygosaccharomyces.* Other types of yeast potentially useful in the invention include *Yarrowia, Rhodosporidium, Candida, Hansenula, Filobasium, Filobasidellla, Sporidiobolus, Bullera, Leucosporidium* and *Filobasidella.*

In a preferred embodiment of the invention, the mating competent yeast is a member of the genus *Pichia.* In a further preferred embodiment of the invention, the mating competent yeast of the genus *Pichia* is one of the following species: *Pichia pastoris, Pichia methanolica,* and *Hansenula polymorpha (Pichia angusta).* In a particularly preferred embodiment of the invention, the mating competent yeast of the genus *Pichia* is the species *Pichia pastoris.*

Haploid Yeast Cell: A cell having a single copy of each gene of its normal genomic (chromosomal) complement.

Polyploid Yeast Cell: A cell having more than one copy of its normal genomic (chromosomal) complement.

Diploid Yeast Cell: A cell having two copies (alleles) of essentially every gene of its normal genomic complement, typically formed by the process of fusion (mating) of two haploid cells.

Tetraploid Yeast Cell: A cell having four copies (alleles) of essentially every gene of its normal genomic complement, typically formed by the process of fusion (mating) of two haploid cells. Tetraploids may carry two, three, four, or more different expression cassettes. Such tetraploids might be obtained in *S. cerevisiae* by selective mating homozygotic heterothallic a/a and alpha/alpha diploids and in *Pichia* by sequential mating of haploids to obtain auxotrophic diploids. For example, a [met his] haploid can be mated with [ade his] haploid to obtain diploid [his]; and a [met arg] haploid can be mated with [ade arg] haploid to obtain diploid [arg]; then the diploid [his] x diploid [arg] to obtain a tetraploid prototroph. It will be understood by those of skill in the art that reference to the benefits and uses of diploid cells may also apply to tetraploid cells.

Yeast Mating: The process by which two haploid yeast cells naturally fuse to form one diploid yeast cell.

Meiosis: The process by which a diploid yeast cell undergoes reductive division to form four haploid spore products. Each spore may then germinate and form a haploid vegetatively growing cell line.

Selectable Marker: A selectable marker is a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two ts mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; G418; LYS3; MET1; MET3a; ADE1; ADE3; URA3; and the like.

Expression Vector: These DNA vectors contain elements that facilitate manipulation for the expression of a foreign protein within the target host cell. Conveniently, manipulation of sequences and production of DNA for transformation is first performed in a bacterial host, e.g. *E. coli,* and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T. (2000). Methods in yeast genetics: a Cold Spring Harbor Laboratory course manual Plainview, N.Y.: Cold Spring Harbor Laboratory Press.

Expression vectors for use in the methods of the invention will further include yeast specific sequences, including a selectable auxotrophic or drug marker for identifying transformed yeast strains. A drug marker may further be used to amplify copy number of the vector in a yeast host cell.

The polypeptide coding sequence of interest is operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included, e.g. a signal sequence, and the like. A yeast origin of replication is optional, as expression vectors are often integrated into the yeast genome.

In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad California). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The yeast promoter fragment may also serve as the site for homologous recombination and integration of the expression vector into the same site in the yeast genome; alternatively a selectable marker is used as the site for homologous recombination. *Pichia* transformation is described in Cregg et al. (1985) *Mol. Cell. Biol.* 5:3376-3385.

Examples of suitable promoters from *Pichia* include the AOX1 and promoter (Cregg et al. (1989) *Mol. Cell. Biol.* 9:1316-1323); ICL1 promoter (Menendez et al. (2003) *Yeast* 20(13): 1097-108); glyceraldehyde-3-phosphate dehydrogenase promoter (GAP) (Waterham et al. (1997) *Gene* 186(1): 37-44); and FLD1 promoter (Shen et al. (1998) *Gene* 216(1):93-102). The GAP promoter is a strong constitutive promoter and the AOX and FLD1 promoters are inducible.

Other yeast promoters include ADH1, alcohol dehydrogenase II, GAL4, PHO3, PHO5, Pyk, and chimeric promoters derived therefrom. Additionally, non-yeast promoters may be used in the invention such as mammalian, insect, plant, reptile, amphibian, viral, and avian promoters. Most typically the promoter will comprise a mammalian promoter (potentially endogenous to the expressed genes) or will comprise a yeast or viral promoter that provides for efficient transcription in yeast systems.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and, processed through one of the standard pathways available within the host cell. The *S. cerevisiae* alpha factor pre-pro signal has proven effective in the secretion of a variety of recombinant proteins from *P. pastoris*. Other yeast signal sequences include the alpha mating factor signal sequence, the invertase signal sequence, and signal sequences derived from other secreted yeast polypeptides. Additionally, these signal peptide sequences may be engineered to provide for enhanced secretion in diploid yeast expression systems. Other secretion signals of interest also include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 pre-protoxin sequence, PHA-E, FACE, human MCP-1, human serum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) Ann.Rev.Biochem. 58:913-949; and are known to those of skill in the art. Such methods utilize intermolecular DNA recombination that is mediated by a mixture of lambda and *E.coli*-encoded recombination proteins. Recombination occurs between specific attachment (att) sites on the interacting DNA molecules. For a description of att sites see Weisberg and Landy (1983) Site-Specific Recombination in Phage Lambda, in Lambda II, Weisberg, ed.(Cold Spring Harbor, N.Y.:Cold Spring Harbor Press), pp. 211-250. The DNA segments flanking the recombination sites are switched, such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein); cyclophilin; and the like. In one embodiment of the invention, each of the haploid parental strains expresses a distinct folding enzyme, e.g. one strain may express BIP, and the other strain may express PDI or combinations thereof.

The terms "desired protein" or "target protein" are used interchangeably and refer generally to a humanized antibody or a binding portion thereof described herein. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, single chain antibodies such as scFvs, camelbodies, nanobodies, IgNAR (single-chain antibodies derived from sharks), small-modular immunopharmaceuticals (SMIPs), and antibody fragments such as Fabs, Fab', F(ab')$_2$ and the like. See Streltsov V A, et al., Structure of a shark IgNAR antibody variable domain and modeling of an early-developmental isotype, Protein Sci. 2005 November; 14(11):2901-9. Epub 2005 Sep. 30; Greenberg A S, et al., A new antigen receptor gene family that undergoes rearrangement and extensive somatic diversification in sharks, Nature. 1995 Mar. 9; 374(6518):168-73; Nuttall S D, et al., Isolation of the new antigen receptor from wobbegong sharks, and use as a scaffold for the display of protein loop libraries, Mol Immunol. 2001 August; 38(4):313-26; Hamers-Casterman C, et al., Naturally occurring antibodies devoid of light chains, Nature. 1993 Jun. 3; 363(6428):446-8; Gill D S, et al., Biopharmaceutical drug discovery using novel protein scaffolds, Curr Opin Biotechnol. 2006 December; 17(6):653-8. Epub 2006 Oct. 19.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions ($V_L$ and $V_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, substrates, bioluminescent materials, radioactive materials, chemiluminescent moieties and the like, or specific binding moieties, such as streptavidin, avidin, or biotin, and the like may be utilized in the methods and compositions of the present invention. Examples of additional effector molecules are provided infra.

The term "polyploid yeast that stably expresses or expresses a desired secreted heterologous polypeptide for prolonged time" refers to a yeast culture that secretes said polypeptide for at least several days to a week, more preferably at least a month, still more preferably at least 1-6 months, and even more preferably for more than a year at threshold expression levels, typically at least 10-25 mg/liter and preferably substantially greater.

The term "polyploidal yeast culture that secretes desired amounts of recombinant polypeptide" refers to cultures that stably or for prolonged periods secrete at least 10-25 mg/liter of heterologous polypeptide, more preferably at least 50-500 mg/liter, and most preferably 500-1000 mg/liter or more.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism or host cell. Typical vectors include recombinant viruses (for polynucleotides) and liposomes (for polypeptides). A "DNA vector" is a replicon, such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription of mRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypepide encoded by said polynucleotide sequence.

"Amplification" of polynucleotide sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8(4):291-294). Polymerase chain reaction or PCR is a prototype of nucleic acid amplification, and use of PCR herein should be considered exemplary of other suitable amplification techniques.

The general structure of antibodies in vertebrates now is well understood (Edelman, G. M., Ann. N.Y. Acad. Sci., 190: 5 (1971)). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_C$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to $\gamma$, $\mu$, $\alpha$, $\delta$, and $\varepsilon$ (gamma, mu, alpha, delta, or epsilon) heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)); while the variable region determines the antigen with which it will react. Light chains are classified as either $\kappa$ (kappa) or $\lambda$ (lambda). Each heavy chain class can be paired with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain (V$_H$) followed by a number of constant domains. Each light chain has a variable domain (V$_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, J Mol. Biol. 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the anibody-antigen interaction (Kashmiri, S., Methods, 36:25-34 (2005)).

The expressions "framework region" or "FR" refer to one or more of the framework regions within the variable regions of the light and heavy chains of an antibody (See Kabat, E. A. et al., Sequences of Proteins of Immunological Interest, National Institutes of Health, Bethesda, Md., (1987)). These expressions include those amino acid sequence regions interposed between the CDRs within the variable regions of the light and heavy chains of an antibody.
Anti-IL-6 Antibodies and Binding Fragments Thereof The invention includes antibodies having binding specificity to IL-6 and possessing a variable light chain sequence comprising the sequence set forth below:

```
                                           (SEQ ID NO: 2)
MDTRAPTQLLGLLLLWLPGARCAYDMTQTPASVSAAVGGTVTIKCQASQS

INNELSWYQQKPGQRPKLLIYRASTLASGVSSRFKGSGSGTEFTLTISDL

ECADAATYYCQQGYSLRNIDNAFGGGTEVVVKRTVAAPSVFIFPPSDEQL

KSGTASVVCLLNN.
```

The invention also includes antibodies having binding specificity to IL-6 and possessing a variable heavy chain sequence comprising the sequence set forth below:

```
                                           (SEQ ID NO: 3)
METGLRWLLLVAVLKGVQCQSLEESGGRLVTPGTPLTLTCTASGFSLSNY

YVTWVRQAPGKGLEWIGIIYGSDETAYATWAIGRFTISKTSTTVDLKMTS

LTAADTATYFCARDDSSDWDAKFNLWGQGTLVTVSSASTKGPSVFPLAPS

SKSTSGGTAALGCLVK.
```

The invention further contemplates antibodies comprising one or more of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2, and/or one or more of the polypeptide sequences of SEQ ID NO: 7; SEQ ID NO: 8; and SEQ ID NO: 9 which correspond to the complementarity determining regions (CDRs, or hypervariable regions) of the variable heavy chain sequence of SEQ ID NO: 3, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2, and/or one or more of the polypeptide sequences of SEQ ID NO: 7; SEQ ID NO: 8; and SEQ ID NO: 9 which correspond to the complementarity-determining regions (CDRs, or hypervariable regions) of the variable heavy chain sequence of SEQ ID NO: 3, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 2. In another embodiment of the invention, antibody fragments of the invention comprise, or alternatively consist of, the polypeptide sequence of SEQ ID NO: 3.

In a further embodiment of the invention, fragments of the antibody having binding specificity to IL-6 comprise, or alternatively consist of, one or more of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2.

In a further embodiment of the invention, fragments of the antibody having binding specificity to IL-6 comprise, or alternatively consist of, one or more of the polypeptide sequences of SEQ ID NO: 7; SEQ ID NO: 8; and SEQ ID NO: 9 which correspond to the complementarity-determining regions (CDRs, or hypervariable regions) of the variable heavy chain sequence of SEQ ID NO: 3.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 2; the variable heavy chain region of SEQ ID NO: 3; the complementarity-determining regions (SEQ ID NO: 4; SEQ ID NO: 5; and SEQ ID NO: 6) of the variable light chain region of SEQ ID NO: 2; and the complementarity-determining regions (SEQ ID NO: 7; SEQ ID NO: 8; and SEQ ID NO: 9) of the variable heavy chain region of SEQ ID NO: 3.

The invention also contemplates variants wherein either of the heavy chain polypeptide sequences of SEQ ID NO: 18 or SEQ ID NO: 19 is substituted for the heavy chain polypeptide sequence of SEQ ID NO: 3; the light chain polypeptide sequence of SEQ ID NO: 20 is substituted for the light chain polypeptide sequence of SEQ ID NO: 2; and the heavy chain CDR sequence of SEQ ID NO: 120 is substituted for the heavy chain CDR sequence of SEQ ID NO: 8.

In a preferred embodiment of the invention, the anti-IL-6 antibody is Ab1, comprising SEQ ID NO: 2 and SEQ ID NO: 3, or the alternative SEQ ID NOs set forth above, and having at least one of the biological activities set forth herein.

In another embodiment, the invention includes antibodies having binding specificity to IL-6 and possessing a variable light chain sequence comprising the sequence set forth below:

```
                                              (SEQ ID NO: 21)
MDTRAPTQLLGLLLLWLPGARCAYDMTQTPASVEVAVGGTVTINCQASET

IYSWLSWYQQKPGQPPKLLIYQASDLASGVPSRFSGSGAGTEYTLTISGV

QCDDAATYYCQQGYSGSNVDNVFGGGTEVVVKRTVAAPSVFIFPPSDEQL

KSGTASVVCLLNNFY
```

The invention also includes antibodies having binding specificity to IL-6 and possessing a variable heavy chain sequence comprising the sequence set forth below:

```
                                              (SEQ ID NO: 22)
METGLRWLLLVAVLKGVQCQEQLKESGGRLVTPGTPLTLTCTASGFSLND

HAMGWVRQAPGKGLEYIGFINSGGSARYASWAEGRFTISRTSTTVDLKMT

SLTTEDTATYFCVRGGAVWSIHSFDPWGPGTLVTVSSASTKGPSVFPLAP

SSKSTSGGTAALGCLVK.
```

The invention further contemplates antibodies comprising one or more of the polypeptide sequences of SEQ ID NO: 23; SEQ ID NO: 24; and SEQ ID NO: 25 which correspond to the complementarity-determining regions (CDRs, or hypervariable regions) of the variable light chain sequence of SEQ ID NO: 21, and/or one or more of the polypeptide sequences of SEQ ID NO: 26; SEQ ID NO: 27; and SEQ ID NO: 28 which correspond to the complementarity-determining regions (CDRs, or hypervariable regions) of the variable heavy chain sequence of SEQ ID NO: 22, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 23; SEQ ID NO: 24; and SEQ ID NO: 25 which correspond to the complementarity-determining regions (CDRs, or hypervariable regions) of the variable light chain sequence of SEQ ID NO: 21, and/or one or more of the polypeptide sequences of SEQ ID NO: 26; SEQ ID NO: 27; and SEQ ID NO: 28 which correspond to the complementarity-determining regions (CDRs, or hypervariable regions) of the variable heavy chain sequence of SEQ ID NO: 22, or combinations of these polypeptide sequences. In another embodiment of the invention, the antibodies of the invention include combinations of the CDRs and the variable heavy and light chain sequences set forth above.

The invention also contemplates fragments of the antibody having binding specificity to. IL-6. In one embodiment of the invention, antibody fragments of the invention comprise, or alternatively consist of, the polypeptide sequence of SEQ ID NO: 21. In another embodiment of the invention, antibody fragments of the invention comprise, or alternatively consist of, the polypeptide sequence of SEQ ID NO: 22.

In a further embodiment of the invention, fragments of the antibody having binding specificity to IL-6 comprise, or alternatively consist of, one or more of the polypeptide sequences of SEQ ID NO: 23; SEQ ID NO: 24; and SEQ ID NO: 25 which correspond to the complementarity-determining regions (CDRs, or hypervariable regions) of the variable light chain sequence of SEQ ID NO: 21.

In a further embodiment of the invention, fragments of the antibody having binding specificity to IL-6 comprise, or alternatively consist of, one or more of the polypeptide sequences of SEQ ID NO: 26; SEQ ID NO: 27; and SEQ ID NO: 28 which correspond to the complementarity-determining regions (CDRs, or hypervariable regions) of the variable heavy chain sequence of SEQ ID NO: 22.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 21; the variable heavy chain region of SEQ ID NO: 22; the complementarity-determining regions (SEQ ID NO: 23; SEQ ID NO: 24; and SEQ ID NO: 25) of the variable light chain region of SEQ ID NO: 21; and the complementarity-determining regions (SEQ ID NO: 26; SEQ ID NO: 27; and SEQ ID NO: 28) of the variable heavy chain region of SEQ ID NO: 22.

In a preferred embodiment of the invention, the anti-IL-6 antibody is Ab2, comprising SEQ ID NO: 21 and SEQ ID NO: 22, and having at least one of the biological activities set forth herein.

In another embodiment, the invention includes antibodies having binding specificity to IL-6 and possessing a variable light chain sequence comprising the sequence set forth below:

```
                                              (SEQ ID NO: 37)
MDTRAPTQLLGLLLLWLPGATFAAVLTQTPSPVSAAVGGTVSISCQASQS

VYDNNYLSWFQQKPGQPPKLLIYGASTLASGVPSRFVGSGSGTQFTLTIT

DVQCDDAATYYCAGVYDDDSDNAFGGGTEVVVKRTVAAPSVFIFPPSDEQ

LKSGTASVVCLLNN
```

The invention also includes antibodies having binding specificity to IL-6 and possessing a variable heavy chain sequence comprising the sequence set forth below:

```
                                              (SEQ ID NO: 38)
METGLRWLLLVAVLKGVQCQSLEESGGRLVTPGTPLTLTCTASGFSLSVY

YMNWVRQAPGKGLEWIGFITMSDNINYASWAKGRFTISKTSTTVDLKMTS

PTTEDTATYFCARSRGWGTMGRLDLWGPGTLVTVSSASTKGPSVFPLAPS

SKSTSGGTAALGCLVK.
```

The invention further contemplates antibodies comprising one or more of the polypeptide sequences of SEQ ID NO: 39; SEQ ID NO: 40; and SEQ ID NO: 41 which correspond to the complementarity-determining regions (CDRs, or hypervariable regions) of the variable light chain sequence of SEQ ID NO: 37, and/or one or more of the polypeptide sequences of SEQ ID NO: 42; SEQ ID NO: 43; and SEQ ID NO: 44 which correspond to the complementarity-determining regions (CDRs, or hypervariable regions) of the variable heavy chain sequence of SEQ ID NO: 38, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 39; SEQ ID NO: 40; and SEQ ID NO: 41 which correspond to the complementarity-determining regions (CDRs, or hypervariable regions) of the variable light chain sequence of SEQ ID NO: 37, and/or one or more of the polypeptide sequences of SEQ ID NO: 42; SEQ ID NO: 43; and SEQ ID NO: 44 which correspond to the complementarity-determining regions (CDRs, or hypervariable regions) of the variable heavy chain sequence of SEQ ID NO: 38, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 37. In another embodiment of the invention, antibody fragments of the invention comprise, or alternatively consist of, the polypeptide sequence of SEQ ID NO: 38.

In a further embodiment of the invention, fragments of the antibody having binding specificity to IL-6 comprise, or alternatively consist of, one or more of the polypeptide sequences of SEQ ID NO: 39; SEQ ID NO: 40; and SEQ ID NO: 41 which correspond to the complementarity-determining regions (CDRs, or hypervariable regions) of the variable light chain sequence of SEQ ID NO: 37.

In a further embodiment of the invention, fragments of the antibody having binding specificity to IL-6 comprise, or alternatively consist of, one or more of the polypeptide sequences of SEQ ID NO: 42; SEQ ID NO: 43; and SEQ ID NO: 44 which correspond to the complementarity-determining regions (CDRs, or hypervariable regions) of the variable heavy chain sequence of SEQ ID NO: 38.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 37; the variable heavy chain region of SEQ ID NO: 38; the complementarity-determining regions (SEQ ID NO: 39; SEQ ID NO: 40; and SEQ ID NO: 41) of the variable light chain region of SEQ ID NO: 37; and the complementarity-determining regions (SEQ ID NO: 42; SEQ ID NO: 43; and SEQ ID NO: 44) of the variable heavy chain region of SEQ ID NO: 38.

In a preferred embodiment of the invention, the anti-IL-6 antibody is Ab3, comprising SEQ ID NO: 37 and SEQ ID NO: 38, and having at least one of the biological activities set forth herein.

In another embodiment, the invention includes antibodies having binding specificity to IL-6 and possessing a variable light chain sequence comprising the sequence set forth below:

(SEQ ID NO: 53)
MDTRAPTQLLGLLLLWLPGAICDPVLTQTPSPVSAPVGGTVSISCQASQS

VYENNYLSWFQQKPGQPPKLLIYGASTLDSGVPSRFKGSGSGTQFTLTIT

-continued
DVQCDDAATYYCAGVYDDDSDDAFGGGTEVVVKRTVAAPSVFIFPPSDEQ

LKSGTASVVCLLNN

The invention also includes antibodies having binding specificity to IL-6 and possessing a variable heavy chain sequence comprising the sequence set forth below:

(SEQ ID NO: 54)
METGLRWLLLVAVLKGVQCQEQLKESGGGLVTPGGTLTLTCTASGFSLNA

YYMNWVRQAPGKGLEWIGFITLNNNVAYANWAKGRFTFSKTSTTVDLKMT

SPTPEDTATYFCARSRGWGAMGRLDLWGHGTLVTVSSASTKGPSVFPLAP

SSKSTSGGTAALGCLVK.

The invention further contemplates antibodies comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 53, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 54, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 53, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 54, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 53. In another embodiment of the invention, antibody fragments of the invention comprise, or alternatively consist of, the polypeptide sequence of SEQ ID NO: 54.

In a further embodiment of the invention, fragments of the antibody having binding specificity to IL-6 comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 53.

In a further embodiment of the invention, fragments of the antibody having binding specificity to IL-6 comprise, or alternatively consist of, one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 54.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 53; the variable heavy chain region of SEQ ID NO: 54; the complementarity-determining regions (SEQ ID NO: 55; SEQ ID NO: 56; and SEQ ID NO: 57) of the variable light chain region of SEQ ID NO: 53; and the complementarity-determining regions (SEQ ID NO: 58; SEQ ID NO: 59; and SEQ ID NO: 60) of the variable heavy chain region of SEQ ID NO: 54.

In a preferred embodiment of the invention, the anti-IL-6 antibody is Ab4, comprising SEQ ID NO: 53 and SEQ ID NO: 54, and having at least- one of the biological activities set forth herein.

In another embodiment, the invention includes antibodies having binding specificity to IL-6 and possessing a variable light chain sequence comprising the sequence set forth below:

```
                                        (SEQ ID NO: 69)
MDTRAPTQLLGLLLLWLPGATFAQVLTQTPSPVSAAVGGTVTINCQASQS

VDDNNWLGWYQQKRGQPPKYLIYSASTLASGVPSRFKGSGSGTQFTLTIS

DLECDDAATYYCAGGFSGNIFAFGGGTEVVVKRTVAAPSVFIFPPSDEQL

KSGTASVVCLLNNF
```

The invention also includes antibodies having binding specificity to IL-6 and possessing a variable heavy chain sequence comprising the sequence set forth below:

```
                                        (SEQ ID NO: 70)
METGLRWLLLVAVLKGVQCQSVEESGGRLVTPGTPLTLTCTVSGFSLSSY

AMSWVRQAPGKGLEWIGIIGGFGTTYYATWAKGRFTISKTSTTVDLRITS

PTTEDTATYFCARGGPGNGGDIWGQGTLVTVSSASTKGPSVFPLAPSSKS

TSGGTAALGCLVKD.
```

The invention further contemplates antibodies comprising one or more of the polypeptide sequences of SEQ ID NO: 71; SEQ ID NO: 72; and SEQ ID NO: 73 which correspond to the complementarity-determining regions (CDRs, or hypervariable regions) of the variable light chain sequence of SEQ ID NO: 69, and/or one or more of the polypeptide sequences of SEQ ID NO: 74; SEQ ID NO: 75; and SEQ ID NO: 76 which correspond to the complementarity-determining regions (CDRs, or hypervariable regions) of the variable heavy chain sequence of SEQ ID NO: 70, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 71; SEQ ID NO: 72; and SEQ ID NO: 73 which correspond to the complementarity-determining regions (CDRs, or hypervariable regions) of the variable light chain sequence of SEQ ID NO: 69, and/or one or more of the polypeptide sequences of SEQ ID NO: 74; SEQ ID NO: 75; and SEQ ID NO: 76 which correspond to the complementarity-determining regions (CDRs, or hypervariable regions) of the variable heavy chain sequence of SEQ ID NO: 70, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 69. In another embodiment of the invention, antibody fragments of the invention comprise, or alternatively consist of, the polypeptide sequence of SEQ ID NO: 70.

In a further embodiment of the invention, fragments of the antibody having binding specificity to IL-6 comprise, or alternatively consist of, one or more of the polypeptide sequences of SEQ ID NO: 71; SEQ ID NO: 72; and SEQ ID NO: 73 which correspond to the complementarity-determining regions (CDRs, or hypervariable regions) of the variable light chain sequence of SEQ ID NO: 69.

In a further embodiment of the invention, fragments of the antibody having binding specificity to IL-6 comprise, or alternatively consist of, one or more of the polypeptide sequences of SEQ ID NO: 74; SEQ ID NO: 75; and SEQ ID NO: 76 which correspond to the complementarity-determining regions (CDRs, or hypervariable regions) of the variable heavy chain sequence of SEQ ID NO: 70.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 69; the variable heavy chain region of SEQ ID NO: 70; the complementarity-determining regions (SEQ ID NO: 71; SEQ 1D NO: 72; and SEQ ID NO: 73) of the variable light chain region of SEQ ID NO: 69; and the complementarity-determining regions (SEQ ID NO: 74; SEQ ID NO: 75; and SEQ ID NO: 76) of the variable heavy chain region of-SEQ ID NO: 70.

In a preferred embodiment of the invention, the anti-IL-6 antibody is Ab5, comprising SEQ ID NO: 69 and SEQ ID NO: 70, and having at least one of the biological activities set forth herein.

In another embodiment, the invention includes antibodies having binding specificity to IL-6 and possessing a variable light chain sequence comprising the sequence set forth below:

```
                                        (SEQ ID NO: 85)
MDTRAPTQLLGLLLLWLPGATFAAVLTQTPSPVSVPVGGTVTIKCQSSQS

VYNNFLSWYQQKPGQPPKLLIYQASKLASGVPDRFSGSGSGTQFTLTISG

VQCDDAATYYCLGGYDDDADNAFGGGTEVVVKRTVAAPSVFIFPPSDEQL

KSGTASVVCLLNNF
```

The invention also includes antibodies having binding specificity to IL-6 and possessing a variable heavy chain sequence comprising the sequence set forth below:

```
                                                    (SEQ ID NO: 86)
METGLRWLLLVAVLKGVQCQSVEESGGRLVTPGTPLTLTCTVSGIDLSDY

AMSWVRQAPGKGLEWIGIIYAGSGSTWYASWAKGRFTISKTSTTVDLKIT

SPTTEDTATYFCARDGYDDYGDFDRLDLWGPGTLVTVSSASTKGPSVFPL

APSSKSTSGGTAALGCLVKD.
```

The invention further contemplates antibodies comprising one or more of the polypeptide sequences of SEQ ID NO: 87; SEQ ID NO: 88; and SEQ ID NO: 89 which correspond to the complementarity-determining regions (CDRs, or hypervariable regions) of the variable light chain sequence of SEQ ID NO: 85, and/or one or more of the polypeptide sequences of SEQ ID NO: 90; SEQ ID NO: 91; and SEQ ID NO: 92 which correspond to the complementarity-determining regions (CDRs, or hypervariable regions) of the variable heavy chain sequence of SEQ ID NO: 86, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 87; SEQ ID NO: 88; and SEQ ID NO: 89 which correspond to the complementarity-determining regions (CDRs, or hypervariable regions) of the variable light chain sequence of SEQ ID NO: 85, and/or one or more of the polypeptide sequences of SEQ ID NO: 90; SEQ ID NO: 91; and SEQ ID NO: 92 which correspond to the complementarity-determining regions (CDRs, or hypervariable regions) of the variable heavy chain sequence of SEQ ID NO: 86, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 85. In another embodiment of the invention, antibody fragments of the invention comprise, or alternatively consist of, the polypeptide sequence of SEQ ID NO: 86.

In a further embodiment of the invention, fragments of the antibody having binding specificity to IL--6 comprise, or alternatively consist of, one or more of the polypeptide sequences of SEQ ID NO: 87; SEQ ID NO: 88; and SEQ ID NO: 89 which correspond to the complementarity-determining regions (CDRs, or hypervariable regions) of the variable light chain sequence of SEQ ID NO: 85.

In a further embodiment of the invention, fragments of the antibody having binding specificity to IL-6 comprise, or alternatively consist of, one or more of the polypeptide sequences of SEQ ID NO: 90; SEQ ID NO: 91; and SEQ ID NO: 92 which correspond to the complementarity-determining regions (CDRs, or hypervariable regions) of the variableheavy chain sequence of SEQ ID NO: 86.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 85; the variable heavy chain region of SEQ ID NO: 86; the complementarity-determining regions (SEQ ID NO: 87; SEQ ID NO: 88; and SEQ ID NO: 89) of the variable light chain region of SEQ ID NO: 85; and the .complementarity-determining regions (SEQ ID NO: 90; SEQ ID NO: 91; and SEQ ID NO: 92) of the variable heavy chain region of SEQ ID NO: 86.

In a preferred embodiment of the invention, the anti-IL-6 antibody is Ab6, comprising SEQ ID NO: 85 and SEQ ID NO: 86, and having at least one of the biological activities set forth herein.

In another embodiment, the invention includes antibodies having binding specificity to IL-6 and possessing a variable light chain sequence comprising the sequence set forth below:

```
                                                    (SEQ ID NO: 101)
MDTRAPTQLLGLLLLWLPGARCAYDMTQTPASVSAAVGGTVTIKCQASQS

INNELSWYQQKSGQRPKLLIYRASTLASGVSSRFKGSGSGTEFTLTISDL

ECADAATYYCQQGYSLRNIDNAFGGGTEVVVKRTVAAPSVFIFPPSDEQL

KSGTASVVCLLNNF
```

The invention also includes antibodies having binding specificity to IL-6 and possessing a variable heavy chain sequence comprising the sequence set forth below:

```
                                                    (SEQ ID NO: 102)
METGLRWLLLVAVLSGVQCQSLEESGGRLVTPGTPLTLTCTASGFSLSNY

YMTWVRQAPGKGLEWIGMIYGSDETAYANWAIGRFTISKTSTTVDLKMTS

LTAADTATYFCARDDSSDWDAKFNLWGQGTLVTVSSASTKGPSVFPLAPS

SKSTSGGTAALGCLVK.
```

The invention further contemplates antibodies comprising one or more of the polypeptide sequences of SEQ ID NO: 103; SEQ ID NO: 104; and SEQ ID NO: 105 which correspond to the complementarity-determining regions (CDRs, or hypervariable regions) of the variable light chain sequence of SEQ ID NO: 101, and/or one or more of the polypeptide sequences of SEQ ID NO: 106; SEQ ID NO: 107; and SEQ ID NO: 108 which correspond to the complementarity-determining regions (CDRs, or hypervariable regions) of the variable heavy chain sequence of SEQ ID NO: 102, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 103; SEQ ID NO: 104; and SEQ ID NO: 105 which correspond to the complementarity-determining regions (CDRs, or hypervariable regions) of the variable light chain sequence of SEQ ID NO: 101, and/or one or more of the polypeptide sequences of SEQ ID NO: 106; SEQ ID NO: 107; and SEQ ID NO: 108 which correspond to the complementarity-determining regions (CDRs, or hypervariable regions) of the variable heavy chain sequence of SEQ ID NO: 102, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 101. In another embodiment of the invention, antibody fragments of the invention comprise, or alternatively consist of, the polypeptide sequence of SEQ ID NO: 102.

In a further embodiment of the invention, fragments of the antibody having binding specificity to IL-6 comprise, or alternatively consist of, one or more of the polypeptide sequences of SEQ ID NO: 103; SEQ ID NO: 104; and SEQ ID NO: 105 which correspond to the complementarity-determining regions (CDRs, or hypervariable regions) of the variable light chain sequence of SEQ ID NO: 101.

In a further embodiment of the invention, fragments of the antibody having binding specificity to IL-6 comprise, or alternatively consist of, one or more of the polypeptide sequences of SEQ ID NO: 106; SEQ ID NO: 107; and SEQ ID NO: 108 which correspond to the complementarity-determining regions (CDRs, or hypervariable regions) of the variable heavy chain sequence of SEQ ID NO: 102.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 101; the variable heavy chain region of SEQ ID NO: 102; the complementarity-determining regions (SEQ ID NO: 103; SEQ ID NO: 104; and SEQ ID NO: 105) of the variable light chain region of SEQ ID NO: 101; and the complementarity-determining regions (SEQ ID NO: 106; SEQ ID NO: 107; and SEQ ID NO: 108) of the variable heavy chain region of SEQ ID NO: 102.

The invention also contemplates variants wherein either of the heavy chain polypeptide sequences of SEQ ID NO: 117 or SEQ ID NO: 118 is substituted for the heavy chain polypeptide sequence of SEQ ID NO: 102; the light chain polypeptide sequence of SEQ ID NO: 119 is substituted for the light chain polypeptide sequence of SEQ ID NO: 101; and the heavy chain CDR sequence of SEQ ID NO: 121 is substituted for the heavy chain CDR sequence of SEQ ID NO: 107.

In a preferred embodiment of the invention, the anti-IL-6 antibody is Ab7, comprising SEQ ID NO: 101 and SEQ ID NO: 102, or the alternative SEQ ID NOs set forth above, and having at least one of the biological activities set forth herein.

In another embodiment, the invention includes antibodies having binding specificity to IL-6 and possessing a variable light chain sequence comprising the sequence set forth below:

(SEQ ID NO: 122)
MDTRAPTQLLGLLLLWLPGATFAAVLTQTPSPVSAAVGGTVTISCQSSQS

VGNNQDLSWFQQRPGQPPKLLIYEISKLESGVPSRFSGSGSGTHFTLTIS

GVQCDDAATYYCLGGYDDDADNA

The invention also includes antibodies having binding specificity to IL-6 and possessing a variable heavy chain sequence comprising the sequence set forth below:

(SEQ ID NO: 123)
METGLRWLLLVAVLKGVQCHSVEESGGRLVTPGTPLTLTCTVSGFSLSSR

TMSWVRQAPGKGLEWIGYIWSGGSTYYATWAKGRFTISKTSTTVDLKITS

PTTEDTATYFCARLGDTGGHAYATRLNL.

The invention further contemplates antibodies comprising one or more of the polypeptide sequences of SEQ ID NO: 124; SEQ ID NO: 125; and SEQ ID NO: 126 which correspond to the complementarity-determining regions (CDRs, or hypervariable regions) of the variable light chain sequence of SEQ ID NO: 122, and/or one or more of the polypeptide sequences of SEQ ID NO: 127; SEQ ID NO: 128; and SEQ ID NO: 129 which correspond to the complementarity-determining regions (CDRs, or hypervariable regions) of the variable heavy chain sequence of SEQ ID NO: 123, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 124; SEQ ID NO: 125; and SEQ ID NO: 126 which correspond to the complementarity-determining regions (CDRs, or hypervariable regions) of the variable light chain sequence of SEQ ID NO: 122, and/or one or more of the polypeptide sequences of SEQ ID NO: 127; SEQ ID NO: 128; and SEQ ID NO: 129 which correspond to the complementarity-determining regions (CDRs, or hypervariable regions) of the variable heavy chain sequence of SEQ ID NO: 123, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 122. In another embodiment of the invention, antibody fragments of the invention comprise, or alternatively consist of, the polypeptide sequence of SEQ ID NO: 123.

In a further embodiment of the invention, fragments of the antibody having binding specificity to IL-6 comprise, or alternatively consist of, one or more of the polypeptide sequences of SEQ ID NO: 124; SEQ ID NO: 125; and SEQ ID NO: 126 which correspond to the complementarity-determining regions (CDRs, or hypervariable regions) of the variable light chain sequence of SEQ ID NO: 122.

In a further embodiment of the invention, fragments of the antibody having binding specificity to IL-6 comprise, or alternatively consist of, one or more of the polypeptide sequences of SEQ ID NO: 127; SEQ ID NO: 128; and SEQ ID NO: 129 which correspond to the complementarity-determining regions (CDRs, or hypervariable regions) of the variable heavy chain sequence of SEQ ID NO: 123.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 122; the variable heavy chain region of SEQ ID NO: 123; the complementarity-determining regions (SEQ ID NO: 124; SEQ ID NO: 125; and SEQ ID NO: 126) of the variable light chain region of SEQ ID NO: 122; and the complementarity-determining regions (SEQ ID NO: 127; SEQ ID NO: 128; and SEQ ID NO: 129) of the variable heavy chain region of SEQ ID NO: 123.

In a preferred embodiment of the invention, the anti-IL-6 antibody is Ab8, comprising SEQ ID NO: 122 and SEQ ID NO: 123, and having at least one of the biological activities set forth herein.

In another embodiment, the invention includes antibodies having binding specificity to IL-6 and possessing a variable light chain sequence comprising the sequence set forth below:

(SEQ ID NO: 138)
MDTRAPTQLLGLLLLWLPGATFAAVLTQTPSSVSAAVGGTVSISCQSSQS

VYSNKYLAWYQQKPGQPPKLLIYWTSKLASGAPSRFSGSGSGTQFTLTIS

GVQCDDAATYYCLGAYDDDADNA

The invention also includes antibodies having binding specificity to IL-6 and possessing a variable heavy chain sequence comprising the sequence set forth below:

(SEQ ID NO: 139)
METGLRWLLLVAVLKGVQCQSVEESGGRLVKPDETLTLTCTASGFSLEGG

YMTWVRQAPGKGLEWIGISYDSGSTYYASWAKGRFTISKTSSTTVDLKMT

SLTTEDTATYFCVRSLKYPTVTSDDL.

The invention further contemplates antibodies comprising one or more of the polypeptide sequences of SEQ ID NO: 140; SEQ ID NO: 141; and SEQ ID NO: 142 which correspond to the complementarity-determining regions (CDRs, or hypervariable regions) of the variable light chain sequence of SEQ ID NO: 138, and/or one or more of the polypeptide sequences of SEQ ID NO: 143; SEQ ID NO: 144; and SEQ ID NO: 145 which correspond to the complementarity-determining regions (CDRs, or hypervariable regions) of the variable heavy chain sequence of SEQ ID NO: 139, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 140; SEQ ID NO: 141; and SEQ ID NO: 142 which correspond to the complementarity-determining regions (CDRs, or hypervariable regions) of the variable light chain sequence of SEQ ID NO: 138, and/or one or more of the polypeptide sequences of SEQ ID NO: 143; SEQ ID NO: 144; and SEQ ID NO: 145 which correspond to the complementarity-determining regions (CDRs, or hypervariable regions) of the variable heavy chain sequence of SEQ ID NO: 139, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 138. In another embodiment of the invention, antibody fragments of the invention comprise, or alternatively consist of, the polypeptide sequence of SEQ ID NO: 139.

In a further embodiment of the invention, fragments of the antibody having binding specificity to IL-6 comprise, or alternatively consist of, one or more of the polypeptide sequences of SEQ ID NO: 140; SEQ ID NO: 141; and SEQ ID NO: 142 which correspond to the complementarity-determining regions (CDRs, or hypervariable regions) of the variable light chain sequence of SEQ ID NO: 138.

In a further embodiment of the invention, fragments of the antibody having binding specificity to IL-6 comprise, or alternatively consist of, one or more of the polypeptide sequences of SEQ ID NO: 143; SEQ ID NO: 144; and SEQ ID NO: 145 which correspond to the complementarity-determining regions (CDRs, or hypervariable regions) of the variable heavy chain sequence of SEQ ID NO: 139.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 138; the variable heavy chain region of SEQ ID NO: 139; the complementarity-determining regions (SEQ ID NO: 140; SEQ ID NO: 141; and SEQ ID NO: 142) of the variable light chain region of SEQ ID NO: 138; and the complementarity-determining regions (SEQ ID NO: 143; SEQ ID NO: 144; and SEQ ID NO: 145) of the variable heavy chain region of SEQ ID NO: 139.

In a preferred embodiment of the invention, the anti-IL-6 antibody is Ab9, comprising SEQ ID NO: 138 and SEQ ID NO: 139, and having at least one of the biological activities set forth herein.

In another embodiment, the invention includes antibodies having binding specificity to IL-6 and possessing a variable light chain sequence comprising the sequence set forth below:

(SEQ ID NO: 154)
MDTRAPTQLLGLLLLWLPGATFAAVLTQTPSPVSAAVGGTVTISCQSSQS

VYNNNDLAWYQQKPGQPPKLLIYYASTLASGVPSRFKGSGSGTQFTLTIS

GVQCDDAAAYYCLGGYDDDADNA

The invention also includes antibodies having binding specificity to IL-6 and possessing a variable heavy chain sequence comprising the sequence set forth below:

(SEQ ID NO: 155)
METGLRWLLLVAVLKGVQCQSVEESGGRLVTPGTPLTLTCTVSGLSLSSN

TINWVRQAPGKGLEWIGYIWSGGSTYYASWVNGRFTISKTSTTVDLKITS

PTTEDTATYFCARGGYASGGYPYATRLDL.

The invention further contemplates antibodies comprising one or more of the polypeptide sequences of SEQ ID NO: 156; SEQ ID NO: 157; and SEQ ID NO: 158 which correspond to the complementarity-determining regions (CDRs, or hypervariable regions) of the variable light chain sequence of SEQ ID NO: 154, and/or one or more of the polypeptide sequences of SEQ ID NO: 159; SEQ ID NO: 160; and SEQ ID NO: 161 which correspond to the complementarity-determining regions (CDRs, or hypervariable regions) of the variable heavy chain sequence of SEQ ID NO: 155, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 156; SEQ ID NO: 157; and SEQ ID NO: 158 which correspond to the complementarity-determining regions (CDRs, or hypervariable regions) of the variable light chain sequence of SEQ ID NO: 154, and/or one or more of the polypeptide sequences of SEQ ID NO: 159; SEQ ID NO: 160; and SEQ ID NO: 161 which correspond to the complementarity-determining regions (CDRs, or hypervariable regions) of the variable heavy chain sequence of SEQ ID NO: 155, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 154. In another embodiment of the invention, antibody fragments of the invention comprise, or alternatively consist of, the polypeptide sequence of SEQ ID NO: 155.

In a further embodiment of the invention, fragments of the antibody having binding specificity to IL-6 comprise, or alternatively consist of, one or more of the polypeptide sequences of SEQ ID NO: 156; SEQ ID NO: 157; and SEQ ID NO: 158 which correspond to the complementarity-determining regions (CDRs, or hypervariable regions) of the variable light chain sequence of SEQ ID NO: 154.

In a further embodiment of the invention, fragments of the antibody having binding specificity to IL-6 comprise, or alternatively consist of, one or more of the polypeptide sequences of SEQ ID NO: 159; SEQ 1D NO: 160; and SEQ ID NO: 161 which correspond to the complementarity-determining regions (CDRs, or hypervariable regions) of the variable heavy chain sequence of SEQ ID NO: 155.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 154; the variable heavy chain region of SEQ ID NO: 155; the complementarity-determining regions (SEQ ID NO: 156; SEQ ID NO: 157; and SEQ ID NO: 158) of the variable light chain region of SEQ ID NO: 154; and the complementarity-determining regions (SEQ ID NO: 159; SEQ ID NO: 160; and SEQ ID NO: 161) of the variable heavy chain region of SEQ ID NO: 155.

In a preferred embodiment of the invention, the anti-IL-6 antibody is Ab10, comprising SEQ ID NO: 154 and SEQ ID NO: 155, and having at least one of the biological activities set forth herein.

In another embodiment, the invention includes antibodies having binding specificity to IL-6 and possessing a variable light chain sequence comprising the sequence set forth below:

(SEQ ID NO: 170)
MDTRAPTQLLGLLLLWLPGATFAAVLTQTPSSVSAAVGGTVTINCQSSQS

VYNNDYLSWYQQRPGQRPKLLIYGASKLASGVPSRFKGSGSGKQFTLTIS

GVQCDDAATYYCLGDYDDDADNT

The invention also includes antibodies having binding specificity to IL-6 and possessing a variable heavy chain sequence comprising the sequence set forth below:

(SEQ ID NO: 171)
METGLRWLLLVAVLKGVQCQSLEESGGRLVTPGTPLTLTCTVSGFTLSTN

YYLSWVRQAPGKGLEWIGIIYPSGNTYCAKWAKGRFTISKTSSTTVDLKM

TSPTTEDTATYFCARNYGGDESL.

The invention further contemplates antibodies comprising one or more of the polypeptide sequences of SEQ ID NO: 172; SEQ ID NO: 173; and SEQ ID NO: 174 which correspond to the complementarity-determining regions (CDRs, or hypervariable regions) of the variable light chain sequence of SEQ ID NO: 170, and/or one or more of the polypeptide sequences of SEQ ID NO: 175; SEQ ID NO: 176; and SEQ ID NO: 177 which correspond to the complementarity-determining regions (CDRs, or hypervariable regions) of the variable heavy chain sequence of SEQ ID NO: 171, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 172; SEQ ID NO: 173; and SEQ ID NO: 174 which correspond to the complementarity-determining regions (CDRs, or hypervariable regions) of the variable light chain sequence of SEQ ID NO: 170, and/or one or more of the polypeptide sequences of SEQ ID NO: 175; SEQ ID NO: 176; and SEQ ID NO: 177 which correspond to the complementarity-determining regions (CDRs, or hypervariable regions) of the variable heavy chain sequence of SEQ ID NO: 171, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 170. In another embodiment of the invention, antibody fragments of the invention comprise, or alternatively consist of, the polypeptide sequence of SEQ ID NO: 171.

In a further embodiment of the invention, fragments of the antibody having binding specificity to IL-6 comprise, or alternatively consist of, one or more of the polypeptide sequences of SEQ ID NO: 172; SEQ ID NO: 173; and SEQ ID NO: 174 which correspond to the complementarity-determining regions (CDRs, or hypervariable regions) of the variable light chain sequence of SEQ ID NO: 170.

In a further embodiment of the invention, fragments of the antibody having binding specificity to IL-6 comprise, or alternatively consist of, one or more of the polypeptide sequences of SEQ ID NO: 175; SEQ ID NO: 176; and SEQ ID NO: 177 which correspond to the complementarity-determining regions (CDRs, or hypervariable regions) of the variable heavy chain sequence of SEQ ID NO: 171.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 170; the variable heavy chain region of SEQ ID NO: 171; the complementarity-determining regions (SEQ ID NO: 172; SEQ ID NO: 173; and SEQ ID NO: 174) of the variable light chain region of SEQ ID NO: 170; and the complementarity-determining regions (SEQ ID NO: 175; SEQ ID NO: 176; and SEQ ID NO: 177) of the variable heavy chain region of SEQ ID NO: 171.

In a preferred embodiment of the invention, the anti-IL-6 antibody is Ab11, comprising SEQ ID NO: 170 and SEQ ID NO: 171, and having at least one of the biological activities set forth herein.

In another embodiment, the invention includes antibodies having binding specificity to IL-6 and possessing a variable light chain sequence comprising the sequence set forth below:

(SEQ ID NO: 186)
MDTRAPTQLLGLLLLWLPGARCDVVMTQTPASVEAAVGGTVTIKCQASET

IGNALAWYQQKSGQPPKLLIYKASKLASGVPSRFKGSGSGTEYTLTISDL

ECADAATYYCQWCYFGDSV

The invention also includes antibodies having binding specificity to IL-6 and possessing a variable heavy chain sequence comprising the sequence set forth below:

(SEQ ID NO: 187)
METGLRWLLLVTVLKGVQCQEQLVESGGGLVQPEGSLTLTCTASGFDFSS

GYYMCWVRQAPGKGLEWIACIFTITTNTYYASWAKGRFTISKTSSTTVTL

QMTSLTAADTATYLCARGIYSDNNYYAL.

The invention further contemplates antibodies comprising one or more of the polypeptide sequences of SEQ ID NO: 188; SEQ ID NO: 189; and SEQ ID NO: 190 which correspond to the complementarity-determining regions (CDRs, or hypervariable regions) of the variable light chain sequence of SEQ ID NO: 186, and/or one or more of the polypeptide sequences of SEQ ID NO: 191; SEQ ID NO: 192; and SEQ ID NO: 193 which correspond-to the complementarity-determining regions (CDRs, or hypervariable regions) of the variable heavy chain sequence of SEQ ID NO: 187, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 188; SEQ ID NO: 189; and SEQ ID NO: 190 which correspond to the complementarity-determining regions (CDRs, or hypervariable regions) of the variable light chain sequence of SEQ ID NO: 186, and/or one or more of the polypeptide sequences of SEQ ID NO: 191; SEQ ID NO: 192; and SEQ ID NO: 193 which correspond to the complementarity-determining regions (CDRs, or hypervariable regions) of the variable heavy chain sequence of SEQ ID NO: 187, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 186. In another embodiment of the invention, antibody fragments of the invention comprise, or alternatively consist of, the polypeptide sequence of SEQ ID NO: 187.

In a further embodiment of the invention, fragments of the antibody having binding specificity to IL-6 comprise, or alternatively consist of, one or more of the polypeptide sequences of SEQ ID NO: 188; SEQ ID NO: 189; and SEQ ID NO: 190 which correspond to the complementarity-determining regions (CDRs, or hypervariable regions) of the variable light chain sequence of SEQ ID NO: 186.

In a further embodiment of the invention, fragments of the antibody having binding specificity to IL-6 comprise, or alternatively consist of, one or more of the polypeptide sequences of SEQ ID NO: 191; SEQ ID NO: 192; and SEQ ID NO: 193 which correspond to the complementarity-determining regions (CDRs, or hypervariable regions) of the variable heavy chain sequence of SEQ ID NO: 187.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 186; the variable heavy chain region of SEQ ID NO: 187; the complementarity-determining regions (SEQ ID NO: 188; SEQ ID NO: 189; and SEQ ID NO: 190) of the variable light chain region of SEQ ID NO: 186; and the complementarity-determining regions (SEQ ID NO: 191; SEQ ID NO: 192; and SEQ ID NO: 193) of the variable heavy chain region of SEQ ID NO: 187.

In a preferred embodiment of the invention, the anti-IL-6 antibody is Ab12, comprising SEQ ID NO: 186 and SEQ ID NO: 187, and having at least one of the biological activities set forth herein.

In another embodiment, the invention includes antibodies having binding specificity to IL-6 and possessing a variable light chain sequence comprising the sequence set forth below:

(SEQ ID NO: 202)
MDTRAPTQLLGLLLLWLPGARCDVVMTQTPASVEAAVGGTVTIKCQASES

IGNALAWYQQKPGQPPKLLIYKASTLASGVPSRFSGSGSGTEFTLTISGV

QCADAAAYYCQWCYFGDSV

The invention also includes antibodies having binding specificity to IL-6 and possessing a variable heavy chain sequence comprising the sequence set forth below:

(SEQ ID NO: 203)
METGLRWLLLVAVLKGVQCQQQLVESGGGLVKPGASLTLTCKASGFSFSS

GYYMCWVRQAPGKGLESIACIFTITDNTYYANWAKGRFTISKPSSPTVTL

QMTSLTAADTATYFCARGIYSTDNYYAL.

The invention further contemplates antibodies comprising one or more of the polypeptide sequences of SEQ ID NO: 204; SEQ ID NO: 205; and SEQ ID NO: 206 which correspond to the complementarity-determining regions (CDRs, or hypervariable regions) of the variable light chain sequence of SEQ ID NO: 202, and/or one or more of the polypeptide sequences of SEQ ID NO: 207; SEQ ID NO: 208; and SEQ ID NO: 209 which correspond to the complementarity-determining regions (CDRs, or hypervariable regions) of the variable heavy chain sequence of SEQ ID NO: 203, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 204; SEQ ID NO: 205; and SEQ ID NO: 206 which correspond to the complementarity-determining regions (CDRs, or hypervariable regions) of the variable light chain sequence of SEQ ID NO: 202, and/or one or more of the polypeptide sequences of SEQ ID NO: 207; SEQ ID NO: 208; and SEQ ID NO: 209 which correspond to the complementarity-determining regions (CDRs, or hypervariable regions) of the variable heavy chain sequence of SEQ ID NO: 203, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 202. In another embodiment of the invention, antibody fragments of the invention comprise, or alternatively consist of, the polypeptide sequence of SEQ ID NO: 203.

In a further embodiment of the invention, fragments of the antibody having binding specificity to. IL-6 comprise, or alternatively consist of, one or more of the polypeptide sequences of SEQ ID NO: 204; SEQ ID NO: 205; and SEQ ID NO: 206 which correspond to the complementarity-determining regions (CDRs, or hypervariable regions) of the variable light chain sequence of SEQ ID NO: 202.

In a further embodiment of the invention, fragments of the antibody having binding specificity to IL-6 comprise, or alternatively consist of, one or more of the polypeptide sequences of SEQ ID NO: 207; SEQ ID NO: 208; and SEQ ID NO: 209 which correspond to the complementarity-determining regions (CDRs, or hypervariable regions) of the variable heavy chain sequence of SEQ ID NO: 203.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 202; the variable heavy chain region of SEQ ID NO: 203; the complementarity-determining regions (SEQ ID NO: 204; SEQ ID NO: 205; and SEQ ID NO: 206) of the variable light chain region of SEQ ID NO: 202; and the complementarity-determining regions (SEQ ID NO: 207; SEQ ID NO: 208; and SEQ ID NO: 209) of the variable heavy chain region of SEQ ID NO: 203.

In a preferred embodiment of the invention, the anti-IL-6 antibody is Ab13, comprising SEQ ID NO: 202 and SEQ ID NO: 203, and having at least one of the biological activities set forth herein.

In another embodiment, the invention includes antibodies having binding specificity to IL-6 and possessing a variable light chain sequence comprising the sequence set forth below:

```
                                           (SEQ ID NO: 218)
MDTRAPTQLLGLLLLWLPGARCDVVMTQTPASVEAAVGGTVTIKCQASQS

VSSYLNWYQQKPGQPPKLLIYRASTLESGVPSRFKGSGSGTEFTLTISDL

ECADAATYYCQCTYGTSSSYGAA
```

The invention also includes antibodies having binding specificity to IL-6 and possessing a variable heavy chain sequence comprising the sequence set forth below:

```
                                           (SEQ ID NO: 219)
METGLRWLLLVAVLKGVQCQSVEESGGRLVTPGTPLTLTCTVSGISLSSN

AISWVRQAPGKGLEWIGIISYSGTTYYASWAKGRFTISKTSSTTVDLKIT

SPTTEDTATYFCARDDPTTVMVMLIPFGAGMDL.
```

The invention further contemplates antibodies comprising one or more of the polypeptide sequences of SEQ ID NO: 220; SEQ ID NO: 221; and SEQ ID NO: 222 which correspond to the complementarity-determining regions (CDRs, or hypervariable regions) of the variable light chain sequence of SEQ ID NO: 218, and/or one or more of the polypeptide sequences of SEQ ID NO: 223; SEQ ID NO: 224; and SEQ ID NO: 225 which correspond to the complementarity-determining regions (CDRs, or hypervariable regions) of the variable heavy chain sequence of SEQ ID NO: 219, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 220; SEQ ID NO: 221; and SEQ ID NO: 222 which correspond to the complementarity-determining regions (CDRs, or hypervariable regions) of the variable light chain sequence of SEQ ID NO: 218, and/or one or more of the polypeptide sequences of SEQ ID NO: 223; SEQ ID NO: 224; and SEQ ID NO: 225 which correspond to the complementarity-determining regions (CDRs, or hypervariable regions) of the variable heavy chain sequence of SEQ ID NO: 219, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 218. In another embodiment of the invention, antibody fragments of the invention comprise, or alternatively consist of, the polypeptide sequence of SEQ ID NO: 219.

In a further embodiment of the invention, fragments of the antibody having binding specificity to IL-6 comprise, or alternatively consist of, one or more of the polypeptide sequences of SEQ ID NO: 220; SEQ ID NO: 221; and SEQ ID NO: 222 which correspond to the complementarity-determining regions (CDRs, or hypervariable regions) of the variable light chain sequence of SEQ ID NO: 218.

In a further embodiment of the invention, fragments of the antibody having binding specificity to IL-6 comprise, or alternatively consist of, one or more of the polypeptide sequences of SEQ ID NO: 223; SEQ ID NO: 224; and SEQ ID NO: 225 which correspond to the complementarity-determining regions (CDRs, or hypervariable regions) of the variable heavy chain sequence of SEQ ID NO: 219.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 218; the variable heavy chain region of SEQ ID NO: 219; the complementarity-determining regions (SEQ ID NO: 220; SEQ ID NO: 221; and SEQ ID NO: 222) of the variable light chain region of SEQ ID NO: 218; and the complementarity-determining regions (SEQ ID NO: 223; SEQ ID NO: 224; and SEQ ID NO: 225) of the variable heavy chain region of SEQ ID NO: 219.

In a preferred embodiment of the invention, the anti-IL-6 antibody is Ab14, comprising SEQ ID NO: 218 and SEQ ID NO: 219, and having at least one of the biological activities set forth herein.

In another embodiment, the invention includes antibodies having binding specificity to IL-6 and possessing a variable light chain sequence comprising the sequence set forth below:

(SEQ ID NO: 234)
MDTRAPTQLLGLLLLWLPGATFAQVLTQTASPVSAAVGGTVTINCQASQS

VYKNNYLSWYQQKPGQPPKGLIYSASTLDSGVPLRFSGSGSGTQFTLTIS

DVQCDDAATYYCLGSYDCSSGDCYA

The invention also includes antibodies having binding specificity to IL-6 and possessing a variable heavy chain sequence comprising the sequence set forth below:

(SEQ ID NO: 235)
METGLRWLLLVAVLKGVQCQSLEESGGDLVKPEGSLTLTCTASGFSFSSY

WMCWVRQAPGKGLEWIACIVTGNGNTYYANWAKGRFTISKTSSTTVTLQM

TSLTAADTATYFCAKAYDL.

The invention further contemplates antibodies comprising one or more of the polypeptide sequences of SEQ ID NO: 236; SEQ ID NO: 237; and SEQ ID NO: 238 which correspond to the complementarity-determining regions (CDRs, or hypervariable regions) of the variable light chain sequence of SEQ ID NO: 234, and/or one or more of the polypeptide sequences of SEQ ID NO: 239; SEQ ID NO: 240; and SEQ ID NO: 241 which correspond to the complementarity-determining regions (CDRs, or hypervariable regions) of the variable heavy chain sequence of SEQ ID NO: 235, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 236; SEQ ID NO: 237; and SEQ ID NO: 238 which correspond to the complementarity-determining regions (CDRs, or hypervariable regions) of the variable light chain sequence of SEQ ID NO: 234, and/or one or more of the polypeptide sequences of SEQ ID NO: 239; SEQ ID NO: 240; and SEQ ID NO: 241 which correspond to the complementarity-determining regions (CDRs, or hypervariable regions) of the variable heavy chain sequence of SEQ ID NO: 235, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 234. In another embodiment of the invention, antibody fragments of the invention comprise, or alternatively consist of, the polypeptide sequence of SEQ ID NO: 235.

In a further embodiment of the invention, fragments of the antibody having binding specificity to IL-6 comprise, or alternatively consist of, one or more of the polypeptide sequences of SEQ ID NO: 236; SEQ ID NO: 237; and SEQ ID NO: 238 which correspond to the complementarity-determining regions (CDRs, or hypervariable regions) of the variable light chain sequence of SEQ ID NO: 234.

In a further embodiment of the invention, fragments of the antibody having binding specificity to IL-6 comprise, or alternatively consist of, one or more of the polypeptide sequences of SEQ ID NO: 239; SEQ ID NO: 240; and SEQ ID NO: 241 which correspond to the complementarity-determining regions (CDRs, or hypervariable regions) of the variable heavy chain sequence of SEQ ID NO: 235.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 234; the variable heavy chain region of SEQ ID NO: 235; the complementarity-determining regions (SEQ ID NO: 236; SEQ ID NO: 237; and SEQ ID NO: 238) of the variable light chain region of SEQ ID NO: 234; and the complementarity-determining regions (SEQ ID NO: 239; SEQ ID NO: 240; and SEQ ID NO: 241) of the variable heavy chain region of SEQ ID NO: 235.

In a preferred embodiment of the invention, the anti-IL-6 antibody is Ab15, comprising SEQ ID NO: 234 and SEQ ID NO: 235, and having at least one of the biological activities set forth herein.

In another embodiment, the invention includes antibodies having binding specificity to IL-6 and possessing a variable light chain sequence comprising the sequence set forth below:

(SEQ ID NO: 250)
MDTRAPTQLLGLLLLWLPGSTFAAVLTQTPSPVSAAVGGTVSISCQASQS

VYDNNYLSWYQQKPGQPPKLLIYGASTLASGVPSRFKGTGSGTQFTLTIT

DVQCDDAATYYCAGVFNDDSDDA

The invention also includes antibodies having binding specificity to IL-6 and possessing a variable heavy chain sequence comprising the sequence set forth below:

(SEQ ID NO: 251)
METGLRWLLLVAVPKGVQCQSLEESGGRLVTPGTPLTLTCTLSGFSLSAY

YMSWVRQAPGKGLEWIGFITLSDHISYARWAKGRFTISKTSTTVDLKMTS

PTTEDTATYFCARSRGWGAMGRLDL.

The invention further contemplates antibodies comprising one or more of the polypeptide sequences of SEQ ID NO: 252; SEQ ID NO: 253; and SEQ ID NO: 254 which correspond to the complementarity-determining regions (CDRs, or hypervariable regions) of the variable light chain sequence of SEQ ID NO: 250, and/or one or more of the polypeptide sequences of SEQ ID NO: 255; SEQ ID NO: 256; and SEQ ID NO: 257 which correspond to the complementarity-determining regions (CDRs, or hypervariable regions) of the variable heavy chain sequence of SEQ ID NO: 251, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 252; SEQ ID NO: 253; and SEQ ID NO: 254 which correspond to the complementarity-determining regions (CDRs, or hypervariable regions) of the variable light chain sequence of SEQ ID NO: 250, and/or one or more of the polypeptide sequences of SEQ ID NO: 255; SEQ ID NO: 256; and SEQ ID NO: 257 which correspond to the complementarity-determining regions (CDRs, or hypervariable regions) of the variable heavy chain sequence of SEQ ID NO: 251, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 250. In another embodiment of the invention, antibody fragments of the invention comprise, or alternatively consist of, the polypeptide sequence of SEQ ID NO: 251.

In a further embodiment of the invention, fragments of the antibody having binding specificity to IL-6 comprise, or alternatively consist of, one or more of the polypeptide sequences of SEQ ID NO: 252; SEQ ID NO: 253; and SEQ ID NO: 254 which correspond to the complementarity-determining regions (CDRs, or hypervariable regions) of the variable light chain sequence of SEQ ID NO: 250.

In a further embodiment of the invention, fragments of the antibody having binding specificity to IL-6 comprise, or alternatively consist of, one or more of the polypeptide sequences of SEQ ID NO: 255; SEQ ID NO: 256; and SEQ ID NO: 257 which correspond to the complementarity-determining regions (CDRs, or hypervariable regions) of the variable heavy chain sequence of SEQ ID NO: 251.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 250; the variable heavy chain region of SEQ ID NO: 251; the complementarity-determining regions (SEQ ID NO: 252; SEQ ID NO: 253; and SEQ ID NO: 254) of the variable light chain region of SEQ ID NO: 250; and the complementarity-determining regions (SEQ ID NO: 255; SEQ ID NO: 256; and SEQ ID NO: 257) of the variable heavy chain region of SEQ ID NO: 251.

In a preferred embodiment of the invention, the anti-IL-6 antibody is Ab16, comprising SEQ ID NO: 250 and SEQ ID NO: 251, and having at least one of the biological activities set forth herein.

In another embodiment, the invention includes antibodies having binding specificity to IL-6 and possessing a variable light chain sequence comprising the sequence set forth below:

(SEQ ID NO: 266)
MDTRAPTQLLGLLLLWLPGATFAAVLTQTPSPVSAAVGGTVTISCQASQS

VYNNKNLAWYQQKSGQPPKLLIYWASTLASGVSSRFSGSGSGTQFTLTVS

GVQCDDAATYYCLGVFDDDADNA

The invention also includes antibodies having binding specificity to IL-6 and possessing a variable heavy chain sequence comprising the sequence set forth below:

(SEQ ID NO: 267)
METGLRWLLLVAVLKGVQCQSVEESGGRLVTPGTPLTLTCTASGFSLSSY

SMTWVRQAPGKGLEYIGVIGTSGSTYYATWAKGRFTISRTSTTVALKITS

PTTEDTATYFCVRSLSSITFL.

The invention further contemplates antibodies comprising one or more of the polypeptide sequences of SEQ ID NO: 268; SEQ ID NO: 269; and SEQ ID NO: 270 which correspond to the complementarity-determining regions (CDRs, or hypervariable regions) of the variable light chain sequence of SEQ ID NO: 266, and/or one or more of the polypeptide sequences of SEQ ID NO: 271; SEQ ID NO: 272; and SEQ ID NO: 273 which correspond to the complementarity-determining regions (CDRs, or hypervariable regions) of the variable heavy chain sequence of SEQ ID NO: 267, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 268; SEQ ID NO: 269; and SEQ ID NO: 270 which correspond to the complementarity-determining regions (CDRs, or hypervariable regions) of the variable light chain sequence of SEQ ID NO: 266, and/or one or more of the polypeptide sequences of SEQ ID NO: 271; SEQ ID NO: 272; and SEQ ID NO: 273 which correspond to the complementarity-determining regions (CDRs, or hypervariable regions) of the variable heavy chain sequence of SEQ ID NO: 267, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 266. In another embodiment of the invention, antibody fragments of the invention comprise, or alternatively consist of, the polypeptide sequence of SEQ ID NO: 267.

In a further embodiment of the invention, fragments of the antibody having binding specificity to IL-6 comprise, or alternatively consist of, one or more of the polypeptide sequences of SEQ ID NO: 268; SEQ ID NO: 269; and SEQ ID NO: 270 which correspond to the complementarity-determining regions (CDRs, or hypervariable regions) of the variable light chain sequence of SEQ ID NO: 266.

In a further embodiment of the invention, fragments of the antibody having binding specificity to IL-6 comprise, or alternatively consist of, one or more of the polypeptide sequences of SEQ ID NO: 271; SEQ ID NO: 272; and SEQ ID NO: 273 which correspond to the complementarity-determining regions (CDRs, or hypervariable regions) of the variable heavy chain sequence of SEQ ID NO: 267.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 266; the variable heavy chain region of SEQ ID NO: 267; the complementarity-determining regions (SEQ ID NO: 268; SEQ ID NO: 269; and SEQ ID NO: 270) of the variable light chain region of SEQ ID NO: 266; and the complementarity-determining regions (SEQ ID NO: 271; SEQ ID NO: 272; and SEQ ID NO: 273) of the variable heavy chain region of SEQ ID NO: 267.

In a preferred embodiment of the invention, the anti-IL-6 antibody is Ab17, comprising SEQ ID NO: 266 and SEQ ID NO: 267, and having at least one of the biological activities set forth herein.

In another embodiment, the invention includes antibodies having binding specificity to IL-6 and possessing a variable light chain sequence comprising the sequence set forth below:

(SEQ ID NO: 282)
MDTRAPTQLLGLLLLWLPGARCAFELTQTPASVEAAVGGTVTINCQASQN

IYRYLAWYQQKPGQPPKFLIYLASTLASGVPSRFKGSGSGTEFTLTISDL

ECADAATYYCQSYYSSNSVA

The invention also includes antibodies having binding specificity to IL-6 and possessing a variable heavy chain sequence comprising the sequence set forth below:

(SEQ ID NO: 283)
METGLRWLLLVAVLKGVQCQEQLVESGGDLVQPEGSLTLTCTASELDFSS

GYWICWVRQVPGKGLEWIGCIYTGSSGSTFYASWAKGRFTISKTSSTTVT

LQMTSLTAADTATYFCARGYSGFGYFKL.

The invention further contemplates antibodies comprising one or more of the polypeptide sequences of SEQ ID NO: 284; SEQ ID NO: 285; and SEQ ID NO: 286 which correspond to the complementarity-determining regions (CDRs, or hypervariable regions) of the variable light chain sequence of SEQ ID NO: 282, and/or one or more of the polypeptide sequences of SEQ ID NO: 287; SEQ ID NO: 288; and SEQ ID NO: 289 which correspond to the complementarity-determining regions (CDRs, or hypervariable regions) of the variable heavy chain sequence of SEQ ID NO: 283, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 284; SEQ ID NO: 285; and SEQ ID NO: 286 which correspond to the complementarity-determining regions (CDRs, or hypervariable regions) of the variable light chain sequence of SEQ ID NO: 282, and/or one or more of the polypeptide sequences of SEQ ID NO: 287; SEQ ID NO: 288; and SEQ ID NO: 289 which correspond to the complementarity-determining regions (CDRs, or hypervariable regions) of the variable heavy chain sequence of SEQ ID NO: 283, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 282. In another embodiment of the invention, antibody fragments of the invention comprise, or alternatively consist of, the polypeptide sequence of SEQ ID NO: 283.

In a further embodiment of the invention, fragments of the antibody having binding specificity to IL-6 comprise, or alternatively consist of, one or more of the polypeptide sequences of SEQ ID NO: 284; SEQ ID NO: 285; and SEQ ID NO: 286 which correspond to the complementarity-determining regions (CDRs, or hypervariable regions) of the variable light chain sequence of SEQ ID NO: 282.

In a further embodiment of the invention, fragments of the antibody having binding specificity to IL-6 comprise, or alternatively consist of, one or more of the polypeptide sequences of SEQ ID NO: 287; SEQ ID NO: 288; and SEQ ID NO: 289 which correspond to the complementarity-determining regions (CDRs, or hypervariable regions) of the variable heavy chain sequence of SEQ ID NO: 283.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 282; the variable heavy chain region of SEQ ID NO: 283; the complementarity-determining regions (SEQ ID NO: 284; SEQ ID NO: 285; and SEQ ID NO: 286) of the variable light chain region of SEQ ID NO: 282; and the complementarity-determining regions (SEQ ID NO: 287; SEQ ID NO: 288; and SEQ ID NO: 289) of the variable heavy chain region of SEQ ID NO: 283.

In a preferred embodiment of the invention, the anti-IL-6 antibody is Ab18, comprising SEQ ID NO: 282 and SEQ ID NO: 283, and having at least one of the biological activities set forth herein.

In another embodiment, the invention includes antibodies having binding specificity to IL-6 and possessing a variable light chain sequence comprising the sequence set forth below:

(SEQ ID NO: 298)
MDTRAPTQLLGLLLLWLPGARCAYDMTQTPASVEVAVGGTVTIKCQASED

IYRLLAWYQQKPGQPPKLLIYDSSDLASGVPSRFKGSGSGTEFTLAISGV

QCDDAATYYCQQAWSYSDIDNA

The invention also includes antibodies having binding specificity to IL-6 and possessing a variable heavy chain sequence comprising the sequence set forth below:

(SEQ ID NO: 299)
METGLRWLLLVAVLKGVQCQSVEESGGRLVTPGTPLTLTCTASGFSLSSY

YMSWVRQAPGKGLEWIGIITTSGNTFYASWAKGRLTISRTSTTVDLKITS

PTTEDTATYFCARTSDIFYYRNL.

The invention further contemplates antibodies comprising one or more of the polypeptide sequences of SEQ ID NO: 300; SEQ ID NO: 301; and SEQ ID NO: 302 which correspond to the complementarity-determining regions (CDRs, or hypervariable regions) of the variable light chain sequence of SEQ ID NO: 298, and/or one or more of the polypeptide sequences of SEQ ID NO: 303; SEQ ID NO: 304; and SEQ ID NO: 305 which correspond to the complementarity-determining regions (CDRs, or hypervariable regions) of the variable heavy chain sequence of SEQ ID NO: 299, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 300; SEQ ID NO: 301; and SEQ ID NO: 302 which correspond to the complementarity-determining regions (CDRs, or hypervariable regions) of the variable light chain sequence of SEQ ID NO: 298, and/or one or more of the polypeptide sequences of SEQ ID NO: 303; SEQ ID NO: 304; and SEQ ID NO: 305 which correspond to the complementarity-determining regions (CDRs, or hypervariable regions) of the variable heavy chain sequence of SEQ ID NO: 299, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 298. In another embodiment of the invention, antibody fragments of the invention comprise, or alternatively consist of, the polypeptide sequence of SEQ ID NO: 299.

In a further embodiment of the invention, fragments of the antibody having binding specificity to IL-6 comprise, or alternatively consist of, one or more of the polypeptide sequences of SEQ ID NO: 300; SEQ ID NO: 301; and SEQ ID NO: 302 which correspond to the complementarity-determining regions (CDRs, or hypervariable regions) of the variable light chain sequence of SEQ ID NO: 298.

In a further embodiment of the invention, fragments of the antibody having binding specificity to IL-6 comprise, or alternatively consist of, one or more of the polypeptide sequences of SEQ ID NO: 303; SEQ ID NO: 304; and SEQ ID NO: 305 which correspond to the complementarity-determining regions (CDRs, or hypervariable regions) of the variable heavy chain sequence of SEQ ID NO: 299.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 298; the variable heavy chain region of SEQ ID NO: 299; the complementarity-determining regions (SEQ ID NO: 300; SEQ ID NO: 301; and SEQ ID NO: 302) of the variable light chain region of SEQ ID NO: 298; and the complementarity-determining regions (SEQ ID NO: 303; SEQ ID NO: 304; and SEQ ID NO: 305) of the variable heavy chain region of SEQ ID NO: 299.

In a preferred embodiment of the invention, the anti-IL-6 antibody is Ab19, comprising SEQ ID NO: 298 and SEQ ID NO: 299, and having at least one of the biological activities set forth herein.

In another embodiment, the invention includes antibodies having binding specificity to IL-6 and possessing a variable light chain sequence comprising the sequence set forth below:

(SEQ ID NO: 314)
MDTRAPTQLLGLLLLWLPGATFAAVLTQTASPVSAAVGATVTINCQSSQS

VYNDMDLAWFQQKPGQPPKLLIYSASTLASGVPSRFSGSGSGTEFTLTIS

GVQCDDAATYYCLGAFDDDADNT

The invention also includes antibodies having binding specificity to IL-6 and possessing a variable heavy chain sequence comprising the sequence set forth below:

(SEQ ID NO: 315)
METGLRWLLLVAVLKGVQCQSVEESGGRLVTPGTPLTLTCTVSGFSLTRH

AITWVRQAPGKGLEWIGCIWSGGSTYYATWAKGRFTISKTSTTVDLRITS

PTTEDTATYFCARVIGDTAGYAYFTGLDL.

The invention further contemplates antibodies comprising one or more of the polypeptide sequences of SEQ ID NO: 316; SEQ ID NO: 317; and SEQ ID NO: 318 which correspond to the complementarity-determining regions (CDRs, or hypervariable regions) of the variable light chain sequence of SEQ ID NO: 314, and/or one or more of the polypeptide sequences of SEQ ID NO: 319; SEQ ID NO: 320; and SEQ ID NO: 321 which correspond to the complementarity-determining regions (CDRs, or hypervariable regions) of the variable heavy chain sequence of SEQ ID NO: 315, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 316; SEQ ID NO: 317; and SEQ ID NO: 318 which correspond to the complementarity-determining regions (CDRs, or hypervariable regions) of the variable light chain sequence of SEQ ID NO: 314, and/or one or more of the polypeptide sequences of SEQ ID NO: 319; SEQ ID NO: 320; and SEQ ID NO: 321 which correspond to the complementarity-determining regions (CDRs, or hypervariable regions) of the variable heavy chain sequence of SEQ ID NO: 315, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 314. In another embodiment of the invention, antibody fragments of the invention comprise, or alternatively consist of, the polypeptide sequence of SEQ ID NO: 315.

In a further embodiment of the invention, fragments of the antibody having binding specificity to IL-6 comprise, or alternatively consist of, one or more of the polypeptide sequences of SEQ ID NO: 316; SEQ ID NO: 317; and SEQ ID NO: 318 which correspond to the complementarity-determining regions (CDRs, or hypervariable regions) of the variable light chain sequence of SEQ ID NO: 314.

In a further embodiment of the invention, fragments of the antibody having binding specificity to IL-6 comprise, or alternatively consist of, one or more of the polypeptide sequences of SEQ ID NO: 319; SEQ ID NO: 320; and SEQ ID NO: 321 which correspond to the complementarity-determining regions (CDRs; or hypervariable regions) of the variable heavy chain sequence of SEQ ID NO: 315.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 314; the variable heavy chain region of SEQ ID NO: 315; the complementarity-determining regions (SEQ ID NO: 316; SEQ ID NO: 317; and SEQ ID NO: 318) of the variable light chain region of SEQ ID NO: 314; and the complementarity-determining regions (SEQ ID NO: 319; SEQ ID NO: 320; and SEQ ID NO: 321) of the variable heavy chain region of SEQ ID NO: 315.

In a preferred embodiment of the invention, the anti-IL-6 antibody is Ab20, comprising SEQ ID NO: 314 and SEQ ID NO: 315, and having at least one of the biological activities set forth herein.

In another embodiment, the invention includes antibodies having binding specificity to IL-6 and possessing a variable light chain sequence comprising the sequence set forth below:

(SEQ ID NO: 330)
MDTRAPTQLLGLLLLWLPGARCAYDMTQTPASVEVAVGGTVTIKCQASQS

VYNWLSWYQQKPGQPPKLLIYTASSLASGVPSRFSGSGSGTEFTLTISGV

ECADAATYYCQQGYTSDVDNV

The invention also includes antibodies having binding specificity to IL-6 and possessing a variable heavy chain sequence comprising the sequence set forth below:

(SEQ ID NO: 331)
METGLRWLLLVAVLKGVQCQSLEEAGGRLVTPGTPLTLTCTVSGIDLSSY

AMGWVRQAPGKGLEYIGIISSSGSTYYATWAKGRFTISQASSTTVDLKIT

SPTTEDSATYFCARGGAGSGGVWLLDGFDP.

The invention further contemplates antibodies comprising one or more of the polypeptide sequences of SEQ ID NO: 332; SEQ ID NO: 333; and SEQ ID NO: 334 which correspond to the complementarity-determining regions (CDRs, or hypervariable regions) of the variable light chain sequence of SEQ ID NO: 330, and/or one or more of the polypeptide sequences of SEQ ID NO: 335; SEQ ID NO: 336; and SEQ ID NO: 337 which correspond to the complementarity-determining regions (CDRs, or hypervariable regions) of the variable heavy chain sequence of SEQ ID NO: 331, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 332; SEQ ID NO: 333; and SEQ ID NO: 334 which correspond to the complementarity-determining regions (CDRs, or hypervariable regions) of the variable light chain sequence of SEQ ID NO: 330, and/or one or more of the polypeptide sequences of SEQ ID NO: 335; SEQ ID NO: 336; and SEQ ID NO: 337 which correspond to the complementarity-determining regions (CDRs, or hypervariable regions) of the variable heavy chain sequence of SEQ ID NO: 331, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 330. In another embodiment of the invention, antibody fragments of the invention comprise, or alternatively consist of, the polypeptide sequence of SEQ ID NO: 331.

In a further embodiment of the invention, fragments of the antibody having binding specificity to IL-6 comprise, or alternatively consist of, one or more of the polypeptide sequences of SEQ ID NO: 332; SEQ ID NO: 333; and SEQ ID NO: 334 which correspond to the complementarity-determining regions (CDRs, or hypervariable regions) of the variable light chain sequence of SEQ ID NO: 330.

In a further embodiment of the invention, fragments of the antibody having binding specificity to IL-6 comprise, or alternatively consist of, one or more of the polypeptide sequences of SEQ ID NO: 335; SEQ ID NO: 336; and SEQ ID NO: 337 which correspond to the complementarity-determining regions (CDRs, or hypervariable regions) of the variable heavy chain sequence of SEQ ID NO: 331.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 330; the variable heavy chain region of SEQ ID NO: 331; the complementarity-determining regions (SEQ ID NO: 332; SEQ ID NO: 333; and SEQ ID NO: 334) of the variable light chain region of SEQ ID NO: 330; and the complementarity-determining regions (SEQ ID NO: 335; SEQ ID NO: 336; and SEQ ID NO: 337) of the variable heavy chain region of SEQ ID NO: 331.

In a preferred embodiment of the invention, the anti-IL-6 antibody is Ab21, comprising SEQ ID NO: 330 and SEQ ID NO: 331, and having at least one of the biological activities set forth herein.

In another embodiment, the invention includes antibodies having binding specificity to IL-6 and possessing a variable light chain sequence comprising the sequence set forth below:

```
                                         (SEQ ID NO: 346)
MDTRAPTQLLGLLLLWLPGAKCADVVMTQTPASVSAAVGGTVTINCQASE

NIYNWLAWYQQKPGQPPKLLIYTVGDLASGVSSRFKGSGSGTEFTLTISD

LECADAATYYCQQGYSSSYVDNV
```

The invention also includes antibodies having binding specificity to IL-6 and possessing a variable heavy chain sequence comprising the sequence set forth below:

```
                                         (SEQ ID NO: 347)
METGLRWLLLVAVLKGVQCQEQLKESGGRLVTPGTPLTLTCTVSGFSLND

YAVGWFRQAPGKGLEWIGYIRSSGTTAYATWAKGRFTISATSTTVDLKIT

SPTTEDTATYFCARGGAGSSGVWILDGFAP.
```

The invention further contemplates antibodies comprising one or more of the polypeptide sequences of SEQ ID NO: 348; SEQ ID NO: 349; and SEQ ID NO: 350 which correspond to the complementarity-determining regions (CDRs, or hypervariable regions) of the variable light chain sequence of SEQ ID NO: 346, and/or one or more of the polypeptide sequences of SEQ ID NO: 351; SEQ ID NO: 352; and SEQ ID NO: 353 which correspond to the complementarity-determining regions (CDRs, or hypervariable regions) of the variable heavy chain sequence of SEQ ID NO: 347, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 348; SEQ ID NO: 349; and SEQ ID NO: 350 which correspond to the complementarity-determining regions (CDRs, or hypervariable regions) of the variable light chain sequence of SEQ ID NO: 346, and/or one or more of the polypeptide sequences of SEQ ID NO: 351; SEQ ID NO: 352; and SEQ ID NO: 353 which correspond to the complementarity-determining regions (CDRs, or hypervariable regions) of the variable heavy chain sequence of SEQ ID NO: 347, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 346. In another embodiment of the invention, antibody fragments of the invention comprise, or alternatively consist of, the polypeptide sequence of SEQ ID NO: 347.

In a further embodiment of the invention, fragments of the antibody having binding specificity to IL-6 comprise, or alternatively consist of, one or more of the polypeptide sequences of SEQ ID NO: 348; SEQ ID NO: 349; and SEQ ID NO: 350 which correspond to the complementarity-determining regions (CDRs, or hypervariable regions) of the variable light chain sequence of SEQ ID NO: 346.

In a further embodiment of the invention, fragments of the antibody having binding specificity to IL-6 comprise, or alternatively consist of, one or more of the polypeptide sequences of SEQ ID NO: 351; SEQ ID NO: 352; and SEQ ID NO: 353 which correspond to the complementarity-determining regions (CDRs, or hypervariable regions) of the variable heavy chain sequence of SEQ ID NO: 347.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 346; the variable heavy chain region of SEQ ID NO: 347; the complementarity-determining regions (SEQ ID NO: 348; SEQ ID NO: 349; and SEQ ID NO: 350) of the variable light chain region of SEQ ID NO: 346; and the complementarity-determining regions (SEQ ID NO: 351; SEQ ID NO: 352; and SEQ ID NO: 353) of the variable heavy chain region of SEQ ID NO: 347.

In a preferred embodiment of the invention, the anti-IL-6 antibody is Ab22, comprising SEQ ID NO: 346 and SEQ ID NO: 347, and having at least one of the biological activities set forth herein.

In another embodiment, the invention includes antibodies having binding specificity to IL-6 and possessing a variable light chain sequence comprising the sequence set forth below:

```
                                         (SEQ ID NO: 362)
MDTRAPTQLLGLLLLWLPGATFAQVLTQTPSSVSAAVGGTVTINCQASQS

VYQNNYLSWFQQKPGQPPKLLIYGAATLASGVPSRFKGSGSGTQFTLTIS

DLECDDAATYYCAGAYRDVDS
```

The invention also includes antibodies having binding specificity to IL-6 and possessing a variable heavy chain sequence comprising the sequence set forth below:

```
                                         (SEQ ID NO: 363)
METGLRWLLLVAVLKGVQCQSLEESGGDLVKPGASLTLTCTASGFSFTST

YYIYWVRQAPGKGLEWIACIDAGSSGSTYYATWVNGRFTISKTSSTTVTL

QMTSLTAADTATYFCAKWDYGGNVGWGYDL.
```

The invention further contemplates antibodies comprising one or more of the polypeptide sequences of SEQ ID NO: 364; SEQ ID NO: 365; and SEQ ID NO: 366 which correspond to the complementarity-determining regions (CDRs, or hypervariable regions) of the variable light chain sequence of SEQ ID NO: 362, and/or one or more of the polypeptide sequences of SEQ ID NO: 367; SEQ ID NO: 368; and SEQ ID NO: 369 which correspond to the complementarity-determining regions (CDRs, or hypervariable regions) of the variable heavy chain sequence of SEQ ID NO: 363, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 364; SEQ ID NO: 365; and SEQ ID NO: 366 which correspond to the complementarity-determining regions (CDRs, or hypervariable regions) of the variable light chain sequence of SEQ ID NO: 362, and/or one or more of the polypeptide sequences of SEQ ID NO: 367; SEQ ID NO: 368; and SEQ ID NO: 369 which correspond to the complementarity-determining regions (CDRs, or hypervariable regions) of the variable heavy chain sequence of SEQ ID NO: 363, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 362. In another embodiment of the invention, antibody fragments of the invention comprise, or alternatively consist of, the polypeptide sequence of SEQ ID NO: 363.

In a further embodiment of the invention, fragments of the antibody having binding specificity to IL-6 comprise, or alternatively consist of, one or more of the polypeptide sequences of SEQ ID NO: 364; SEQ ID NO: 365; and SEQ ID NO: 366 which correspond to the complementarity-determining regions (CDRs, or hypervariable regions) of the variable light chain sequence of SEQ ID NO: 362.

In a further embodiment of the invention, fragments of the antibody having binding specificity to IL-6 comprise, or alternatively consist of, one or more of the polypeptide sequences of SEQ ID NO: 367; SEQ ID NO: 368; and SEQ ID NO: 369 which correspond to-the complementarity-determining regions (CDRs, or hypervariable regions) of the variable heavy chain sequence of SEQ ID NO: 363.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 362; the variable heavy chain region of SEQ ID NO: 363; the complementarity-determining regions (SEQ ID NO: 364; SEQ ID NO: 365; and SEQ ID NO: 366) of the variable light chain region of SEQ ID NO: 362; and the complementarity-determining regions (SEQ ID NO: 367; SEQ ID NO: 368; and SEQ ID NO: 369) of the variable heavy chain region of SEQ ID NO: 363.

In a preferred embodiment of the invention, the anti-IL-6 antibody is Ab23, comprising SEQ ID NO: 362 and SEQ ID NO: 363, and having at least one of the biological activities set forth herein.

In another embodiment, the invention includes antibodies having binding specificity to IL-6 and possessing a variable light chain sequence comprising the sequence set forth below:

(SEQ ID NO: 378)
MDTRAPTQLLGLLLLWLPGARCAFELTQTPSSVEAAVGGTVTIKCQASQS

ISSYLAWYQQKPGQPPKFLIYRASTLASGVPSRFKGSGSGTEFTLTISDL

ECADAATYYCQSYYDSVSNP

The invention also includes antibodies having binding specificity to IL-6 and possessing a variable heavy chain sequence comprising the sequence set forth below:

(SEQ ID NO: 379)
METGLRWLLLVAVLKGVQCQSLEESGGDLVKPEGSLTLTCKASGLDLGTY

WFMCWVRQAPGKGLEWIACIYTGSSGSTFYASWVNGRFTISKTSSTTVTL

QMTSLTAADTATYFCARGYSGYGYFKL.

The invention further contemplates antibodies comprising one or more of the polypeptide sequences of SEQ ID NO: 380; SEQ ID NO: 381; and SEQ ID NO: 382 which correspond to the complementarity-determining regions (CDRs, or hypervariable regions) of the variable light chain sequence of SEQ ID NO: 378, and/or one or more of the polypeptide sequences of SEQ ID NO: 383; SEQ ID NO: 384; and SEQ ID NO: 385 which correspond to the complementarity-determining regions (CDRs, or hypervariable regions) of the variable heavy chain sequence of SEQ ID NO: 379, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 380; SEQ ID NO: 381; and SEQ ID NO: 382 which correspond to the complementarity-determining regions (CDRs, or hypervariable regions) of the variable light chain sequence of SEQ ID NO: 378, and/or one or more of the polypeptide sequences of SEQ ID NO: 383; SEQ ID NO: 384; and SEQ ID NO: 385 which correspond to the complementarity-determining regions (CDRs, or hypervariable regions) of the variable heavy chain sequence of SEQ ID NO: 379, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 378. In another embodiment of the invention, antibody fragments of the invention comprise, or alternatively consist of, the polypeptide sequence of SEQ ID NO: 379.

In a further embodiment of the invention, fragments of the antibody having binding specificity to IL-6 comprise, or alternatively consist of, one or more of the polypeptide sequences of SEQ ID NO: 380; SEQ ID NO: 381; and SEQ ID NO: 382 which correspond to the complementarity-determining regions (CDRs, or hypervariable regions) of the variable light chain sequence of SEQ ID NO: 378.

In a further embodiment of the invention, fragments of the antibody having binding specificity to IL-6 comprise, or alternatively consist of, one or more of the polypeptide sequences of SEQ ID NO: 383; SEQ ID NO: 384; and SEQ ID NO: 385 which correspond to the complementarity-determining regions (CDRs, -or hypervariable regions) of the variable heavy chain sequence of SEQ ID NO: 379.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 378; the variable heavy chain region of SEQ ID NO: 379; the complementarity-determining regions (SEQ ID NO: 380; SEQ ID NO:

381; and SEQ ID NO: 382) of the variable light chain region of SEQ ID NO: 378; and the complementarity-determining regions (SEQ ID NO: 383; SEQ ID NO: 384; and SEQ ID NO: 385) of the variable heavy chain region of SEQ ID NO: 379.

In a preferred embodiment of the invention, the anti-IL-6 antibody is Ab24, comprising SEQ ID NO: 378 and SEQ ID NO: 379, and having at least one of the biological activities set forth herein.

In another embodiment, the invention includes antibodies having binding specificity to IL-6 and possessing a variable light chain sequence comprising the sequence set forth below:

(SEQ ID NO: 394)
MDTRAPTQLLGLLLLWLPGVTFAIEMTQSPFSVSAAVGGTVSISCQASQS

VYKNNQLSWYQQKSGQPPKLLIYGASALASGVPSRFKGSGSGTEFTLTIS

DVQCDDAATYYCAGAITGSIDTDG

The invention also includes antibodies having binding specificity to IL-6 and possessing a variable heavy chain sequence comprising the sequence set forth below:

(SEQ ID NO: 395)
METGLRWLLLVAVLKGVQCQSLEESGGDLVKPGASLTLTCTTSGFSFSSS

YFICWVRQAPGKGLEWIACIYGGDGSTYYASWAKGRFTISKTSSTTVTLQ

MTSLTAADTATYFCAREWAYSQGYFGAFDL.

The invention further contemplates antibodies comprising one or more of the polypeptide sequences of SEQ ID NO: 396; SEQ ID NO: 397; and SEQ ID NO: 398 which correspond to the complementarity-determining regions (CDRs, or hypervariable regions) of the variable light chain sequence of SEQ ID NO: 394, and/or one or more of the polypeptide sequences of SEQ ID NO: 399; SEQ ID NO: 400; and SEQ ID NO: 401 which correspond to the complementarity-determining regions (CDRs, or hypervariable regions) of the variable heavy chain sequence of SEQ ID NO: 395, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 396; SEQ ID NO: 397; and SEQ ID NO: 398 which correspond to the complementarity-determining regions (CDRs, or hypervariable regions) of the variable light chain sequence of SEQ ID NO: 394, and/or one or more of the polypeptide sequences of SEQ ID NO: 399; SEQ ID NO: 400; and SEQ ID NO: 401 which correspond to the complementarity-determining regions (CDRs, or hypervariable regions) of the variable heavy chain sequence of SEQ ID NO: 395, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 394. In another embodiment of the invention, antibody fragments of the invention comprise, or alternatively consist of, the polypeptide sequence of SEQ ID NO: 395.

In a further embodiment of the invention, fragments of the antibody having binding specificity to IL-6 comprise, or alternatively consist of, one or more of the polypeptide sequences of SEQ ID NO: 396; SEQ ID NO: 397; and SEQ ID NO: 398 which correspond to the complementarity-determining regions (CDRs, or hypervariable regions) of the variable light chain sequence of SEQ ID NO: 394.

In a further embodiment of the invention, fragments of the antibody having binding specificity to IL-6 comprise, or alternatively consist of, one or more of the polypeptide sequences of SEQ ID NO: 399; SEQ ID NO: 400; and SEQ ID NO: 401 which correspond to the complementarity-determining regions (CDRs, or hypervariable regions) of the variable heavy chain sequence of SEQ ID NO: 395.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 394; the variable heavy chain region of SEQ 1D NO: 395; the complementarity-determining regions (SEQ ID NO: 396; SEQ ID NO: 397; and SEQ ID NO: 398) of the variable light chain region of SEQ ID NO: 394; and the complementarity-determining regions (SEQ ID NO: 399; SEQ ID NO: 400; and SEQ ID NO: 401) of the variable heavy chain region of SEQ ID NO: 395.

In a preferred embodiment of the invention, the anti-IL-6 antibody is Ab25, comprising SEQ ID NO: 394 and SEQ ID NO: 395, and having at least one of the biological activities set forth herein.

In another embodiment, the invention includes antibodies having binding specificity to IL-6 and possessing a variable light chain sequence comprising the sequence set forth below:

(SEQ ID NO: 410)
MDTRAPTQLLGLLLLWLPGARCDVVMTQTPASVEAAVGGTVTIKCQASED

ISSYLAWYQQKPGQPPKLLIYAASNLESGVSSRFKGSGSGTEYTLTISDL

ECADAATYYCQCTYGTISISDGNA

The invention also includes antibodies having binding specificity to IL-6 and possessing a variable heavy chain sequence comprising the sequence set forth below:

(SEQ ID NO: 411)
METGLRWLLLVAVLKGVQCQSVEESGGRLVTPGTPLTLTCTVSGFSLSSY

FMTWVRQAPGEGLEYIGFINPGGSAYYASWVKGRFTISKSSTTVDLKITS

PTTEDTATYFCARVLIVSYGAFTI.

The invention further contemplates antibodies comprising one or more of the polypeptide sequences of SEQ ID NO: 412; SEQ 1D NO: 413; and SEQ ID NO: 414 which correspond to the complementarity-determining regions (CDRs, or hypervariable regions) of the variable light chain sequence of SEQ ID NO: 410, and/or one or more of the polypeptide sequences of SEQ ID NO: 415; SEQ ID NO: 416; and SEQ ID NO: 417 which correspond to the complementarity-determining regions (CDRs, or hypervariable regions) of the variable heavy chain sequence of SEQ ID NO: 411, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 412; SEQ ID NO: 413; and SEQ ID NO: 414 which correspond to the complementarity-determining regions (CDRs, or hypervariable regions) of the variable light chain sequence of SEQ ID NO: 410, and/or one or more of the polypeptide sequences of SEQ ID NO: 415; SEQ ID NO: 416; and SEQ ID NO: 417 which correspond to the complementarity-determining regions (CDRs, or hypervariable regions) of the variable heavy chain sequence of SEQ ID NO: 411, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 410. In another embodiment of the invention, antibody fragments of the invention comprise, or alternatively consist of, the polypeptide sequence of SEQ ID NO: 411.

In a further embodiment of the invention, fragments of the antibody having binding specificity to IL-6 comprise, or alternatively consist of, one or more of the polypeptide sequences of SEQ ID NO: 412; SEQ ID NO: 413; and SEQ ID NO: 414 which correspond to the complementarity-determining regions (CDRs, or hypervariable regions) of the variable light chain sequence of SEQ ID NO: 410.

In a further embodiment of the invention, fragments of the antibody having binding specificity to IL-6 comprise, or alternatively consist of, one or more of the polypeptide sequences of SEQ ID NO: 415; SEQ ID NO: 416; and SEQ ID NO: 417 which correspond to the complementarity-determining regions (CDRs, or hypervariable regions) of the variable heavy chain sequence of SEQ ID NO: 411.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 410; the variable heavy chain region of SEQ ID NO: 411; the complementarity-determining regions (SEQ ID NO: 412; SEQ ID NO: 413; and SEQ ID NO: 414) of the variable light chain region of SEQ ID NO: 410; and the complementarity-determining regions (SEQ ID NO: 415; SEQ ID NO: 416; and SEQ ID NO: 417) of the variable heavy chain region of SEQ ID NO: 411.

In a preferred embodiment of the invention, the anti-IL-6 antibody is Ab26, comprising SEQ ID NO: 410 and SEQ ID NO: 411, and having at least one of the biological activities set forth herein.

In another embodiment, the invention includes antibodies having binding specificity to IL-6 and possessing a variable light chain sequence comprising the sequence set forth below:

```
                                          (SEQ ID NO: 426)
MDTRAPTQLLGLLLLWLPGARCDVVMTQTPASVSAAVGGTVTIKCQASED

IESYLAWYQQKPGQPPKLLIYGASNLESGVSSRFKGSGSGTEFTLTISDL

ECADAATYYCQCTYGIISISDGNA
```

The invention also includes antibodies having binding specificity to IL-6 and possessing a variable heavy chain sequence comprising the sequence set forth below:

```
                                          (SEQ ID NO: 427)
METGLRWLLLVAVLKGVQCQSVEESGGRLVTPGTPLTLTCTVSGFSLSSY

FMTWVRQAPGEGLEYIGFMNTGDNAYYASWAKGRFTISKTSTTVDLKITS

PTTEDTATYFCARVLVVAYGAFNI.
```

The invention further contemplates antibodies comprising one or more of the polypeptide sequences of SEQ ID NO: 428; SEQ ID NO: 429; and SEQ ID NO: 430 which correspond to the complementarity-determining regions (CDRs, or hypervariable regions) of the variable light chain sequence of SEQ ID NO: 426, and/or one or more of the polypeptide sequences of SEQ ID NO: 431; SEQ ID NO: 432; and SEQ ID NO: 433 which correspond to the complementarity-determining regions (CDRs, or hypervariable regions) of the variable heavy chain sequence of SEQ ID NO: 427, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 428; SEQ ID NO: 429; and SEQ ID NO: 430 which correspond to the complementarity-determining regions (CDRs, or hypervariable regions) of the variable light chain sequence of SEQ ID NO: 426, and/or one or more of the polypeptide sequences of SEQ ID NO: 431; SEQ ID NO: 432; and SEQ ID NO: 433 which correspond to the complementarity-determining regions (CDRs, or hypervariable regions) of the variable heavy chain sequence of SEQ ID NO: 427, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 426. In another embodiment of the invention, antibody fragments of the invention comprise, or alternatively consist of, the polypeptide sequence of SEQ ID NO: 427.

In a further embodiment of the invention, fragments of the antibody having binding specificity to IL-6 comprise, or alternatively consist of, one or more of the polypeptide sequences of SEQ ID NO: 428; SEQ ID NO: 429; and SEQ ID NO: 430 which correspond to the complementarity-determining regions (CDRs, or hypervariable regions) of the variable light chain sequence of SEQ ID NO: 426.

In a further embodiment of the invention, fragments of the antibody having binding specificity to IL-6 comprise, or alternatively consist of, one or more of the polypeptide sequences of SEQ ID NO: 431; SEQ ID NO: 432; and SEQ ID NO: 433 which correspond to the complementarity-determining regions (CDRs, or hypervariable regions) of the variable heavy chain sequence of SEQ ID NO: 427.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 426; the variable heavy chain region of SEQ ID NO: 427; the complementarity-determining regions (SEQ ID NO: 428; SEQ ID NO: 429; and SEQ ID NO: 430) of the variable light chain region of SEQ ID NO: 426; and the complementarity-determining regions (SEQ ID NO: 431; SEQ ID NO: 432; and SEQ ID NO: 433) of the variable heavy chain region of SEQ ID NO: 427.

In a preferred embodiment of the invention, the anti-IL-6 antibody is Ab27, comprising SEQ ID NO: 426 and SEQ ID NO: 427, and having at least one of the biological activities set forth herein.

In another embodiment, the invention includes antibodies having binding specificity to IL-6 and possessing a variable light chain sequence comprising the sequence set forth below:

(SEQ ID NO: 442)
MDTRAPTQLLGLLLLWLPGATFAAVLTQTPSPVSEPVGGTVSISCQSSKS

VMNNNYLAWYQQKPGQPPKLLIYGASNLASGVPSRFSGSGSGTQFTLTIS

DVQCDDAATYYCQGGYTGYSDHGT

The invention also includes antibodies having binding specificity to IL-6 and possessing a variable heavy chain sequence comprising the sequence set forth below:

(SEQ ID NO: 443)
METGLRWLLLVAVLKGVQCQSVEESGGRLVKPDETLTLTCTVSGIDLSSY

PMNWVRQAPGKGLEWIGFINTGGTIVYASWAKGRFTISKTSTTVDLKMTS

PTTEDTATYFCARGSYVSSGYAYYFNV.

The invention further contemplates antibodies comprising one or more of the polypeptide sequences of SEQ ID NO: 444; SEQ ID NO: 445; and SEQ ID NO: 446 which correspond to the complementarity-determining regions (CDRs, or hypervariable regions) of the variable light chain sequence of SEQ ID NO: 442, and/or one or more of the polypeptide sequences of SEQ ID NO: 447; SEQ ID NO: 448; and SEQ ID NO: 449 which correspond to the complementarity-determining regions (CDRs, or hypervariable regions) of the variable heavy chain sequence of SEQ ID NO: 443, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 444; SEQ ID NO: 445; and SEQ ID NO: 446 which correspond to the complementarity-determining regions (CDRs, or hypervariable regions) of the variable light chain sequence of SEQ ID NO: 442, and/or one or more of the polypeptide sequences of SEQ ID NO: 447; SEQ ID NO: 448; and SEQ ID NO: 449 which correspond to the complementarity-determining regions (CDRs, or hypervariable regions) of the variable heavy chain sequence of SEQ ID NO: 443, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 442. In another embodiment of the invention, antibody fragments of the invention comprise, or alternatively consist of, the polypeptide sequence of SEQ ID NO: 443.

In a further embodiment of the invention, fragments of the antibody having binding specificity to IL-6 comprise, or alternatively consist of, one or more of the polypeptide sequences of SEQ ID NO: 444; SEQ ID NO: 445; and SEQ ID NO: 446 which correspond to the complementarity-determining regions (CDRs, or hypervariable regions) of the variable light chain sequence of SEQ ID NO: 442.

In a further embodiment of the invention, fragments of the antibody having binding specificity to IL-6 comprise, or alternatively consist of, one or more of the polypeptide sequences of SEQ ID NO: 447; SEQ ID NO: 448; and SEQ ID NO: 449 which correspond to the complementarity-determining regions (CDRs, or hypervariable regions) of the variable heavy chain sequence of SEQ ID NO: 443.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 442; the variable heavy chain region of SEQ ID NO: 443; the complementarity-determining regions (SEQ ID NO: 444; SEQ ID NO: 445; and SEQ ID NO: 446) of the variable light chain region of SEQ ID NO: 442; and the complementarity-determining regions (SEQ ID NO: 447; SEQ ID NO: 448; and SEQ ID NO: 449) of the variable heavy chain region of SEQ ID NO: 443.

In a preferred embodiment of the invention, the anti-IL-6 antibody is Ab28, comprising SEQ ID NO: 442 and SEQ ID NO: 443, and having at least one of the biological activities set forth herein.

In another embodiment, the invention includes antibodies having binding specificity to IL-6 and possessing a variable light chain sequence comprising the sequence set forth below:

(SEQ ID NO: 458)
MDTRAPTQLLGLLLLWLPGATFAAVLTQTPSPVSAAVGGTVSISCQSSQS

VYNNNWLSWFQQKPGQPPKLLIYKASTLASGVPSRFKGSGSGTQFTLTIS

DVQCDDVATYYCAGGYLDSVI

The invention also includes antibodies having binding specificity to IL-6 and possessing a variable heavy chain sequence comprising the sequence set forth below:

(SEQ ID NO: 459)
METGLRWLLLVAVLKGVQCQSVEESGGRLVTPGTPLTLTCTVSGFSLSTY

SINWVRQAPGKGLEWIGIIANSGTTFYANWAKGRFTVSKTSTTVDLKITS

PTTEDTATYFCARESGMYNEYGKFNI.

The invention further contemplates antibodies comprising one or more of the polypeptide sequences of SEQ ID NO: 460; SEQ ID NO: 461; and SEQ ID NO: 462 which correspond to the complementarity-determining regions (CDRs, or hypervariable regions) of the variable light chain sequence of SEQ ID NO: 458, and/or one or more of the polypeptide sequences of SEQ ID NO: 463; SEQ ID NO: 464; and SEQ ID NO: 465 which correspond to the complementarity-determining regions (CDRs, or hypervariable regions) of the variable heavy chain sequence of SEQ ID NO: 459, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 460; SEQ ID NO: 461; and SEQ ID NO: 462 which correspond to the complementarity-determining regions (CDRs, or hypervariable regions) of the variable light chain sequence of SEQ ID NO: 458, and/or one or more of the polypeptide sequences of SEQ ID NO: 463; SEQ ID NO: 464; and SEQ ID NO: 465 which correspond to the complementarity-determining regions (CDRs, or hypervariable regions) of the variable heavy chain sequence of SEQ ID NO: 459, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 458. In another embodiment of the invention, antibody fragments of the invention comprise, or alternatively consist of, the polypeptide sequence of SEQ ID NO: 459.

In a further embodiment of the invention, fragments of the antibody having binding specificity to IL-6 comprise, or alternatively consist of, one or more of the polypeptide sequences of SEQ ID NO: 460; SEQ ID NO: 461; and SEQ ID NO: 462 which correspond to the complementarity-determining regions (CDRs, or hypervariable regions) of the variable light chain sequence of SEQ ID NO: 458.

In a further embodiment of the invention, fragments of the antibody having binding specificity to IL-6 comprise, or alternatively consist of, one or more of the polypeptide sequences of SEQ ID NO: 463; SEQ ID NO: 464; and SEQ ID NO: 465 which correspond to the complementarity-determining regions (CDRs, or hypervariable regions) of the variable heavy chain sequence of SEQ ID NO: 459.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 458; the variable heavy chain region of SEQ ID NO: 459; the complementarity-determining regions (SEQ ID NO: 460; SEQ ID NO: 461; and SEQ ID NO: 462) of the variable light chain region of SEQ ID NO: 458; and the complementarity-determining regions (SEQ ID NO: 463; SEQ ID NO: 464; and SEQ ID NO: 465) of the variable heavy chain region of SEQ ID NO: 459.

In a preferred embodiment of the invention, the anti-IL-6 antibody is Ab29, comprising SEQ ID NO: 458 and SEQ ID NO: 459, and having at least one of the biological activities set forth herein.

In another embodiment, the invention includes antibodies having binding specificity to IL-6 and possessing a variable light chain sequence comprising the sequence set forth below:

(SEQ ID NO: 474)
MDTRAPTQLLGLLLLWLPGARCASDMTQTPSSVSAAVGGTVTINCQASEN

IYSFLAWYQQKPGQPPKLLIFKASTLASGVSSRFKGSGSGTQFTLTISDL

ECDDAATYYCQQGATVYDIDNN

The invention also includes antibodies having binding specificity to IL-6 and possessing a variable heavy chain sequence comprising the sequence set forth below:

(SEQ ID NO: 475)
METGLRWLLLVAVLKGVQCQSLEESGGRLVTPGTPLTLTCTVSGIDLSAY

AMIWVRQAPGEGLEWITIIYPNGITYYANWAKGRFTVSKTSTAMDLKITS

PTTEDTATYFCARDAESSKNAYWGYFNV.

The invention further contemplates antibodies comprising one or more of the polypeptide sequences of SEQ ID NO: 476; SEQ ID NO: 477; and SEQ ID NO: 478 which correspond to the complementarity-determining regions (CDRs, or hypervariable regions) of the variable light chain sequence of SEQ ID NO: 474, and/or one or more of the polypeptide sequences of SEQ ID NO: 479; SEQ ID NO: 480; and SEQ ID NO: 481 which correspond to the complementarity-determining regions (CDRs, or hypervariable regions) of the variable heavy chain sequence of SEQ ID NO: 475, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 476; SEQ ID NO: 477; and SEQ ID NO: 478 which correspond to the complementarity-determining regions (CDRs, or hypervariable regions) of the variable light chain sequence of SEQ ID NO: 474, and/or one or more of the polypeptide sequences of SEQ ID NO: 479; SEQ ID NO: 480; and SEQ ID NO: 481 which correspond to the complementarity-determining regions (CDRs, or hypervariable regions) of the variable heavy chain sequence of SEQ ID NO: 475, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 474. In another embodiment of the invention, antibody fragments of the invention comprise, or alternatively consist of, the polypeptide sequence of SEQ ID NO: 475.

In a further embodiment of the invention, fragments of the antibody having binding specificity to IL-6 comprise, or alternatively consist of, one or more of the polypeptide sequences of SEQ ID NO: 476; SEQ ID NO: 477; and SEQ ID NO: 478 which correspond to the complementarity-determining regions (CDRs, or hypervariable regions) of the variable light chain sequence of SEQ ID NO: 474.

In a further embodiment of the invention, fragments of the antibody having binding specificity to IL-6 comprise, or alternatively consist of, one or more of the polypeptide sequences of SEQ ID NO: 479; SEQ ID NO: 480; and SEQ ID NO: 481 which correspond to the complementarity-determining regions (CDRs, or hypervariable regions) of the variable heavy chain sequence of SEQ ID NO: 475.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 474; the variable heavy chain region of SEQ ID NO: 475; the complementarity-determining regions (SEQ ID NO: 476; SEQ ID NO: 477; and SEQ ID NO: 478) of the variable light chain region of SEQ ID NO: 474; and the complementarity-determining regions (SEQ ID NO: 479; SEQ ID NO: 480; and SEQ ID NO: 481) of the variable heavy chain region of SEQ ID NO: 475.

In a preferred embodiment of the invention, the anti-IL-6 antibody is Ab30, comprising SEQ ID NO: 474 and SEQ ID NO: 475, and having at least one of the biological activities set forth herein.

In another embodiment, the invention includes antibodies having binding specificity to IL-6 and possessing a variable light chain sequence comprising the sequence set forth below:

(SEQ ID NO: 490)
MDTRAPTQLLGLLLLWLPGARCASDMTQTPSSVSAAVGGTVTINCQASEN

IYSFLAWYQQKPGQPPKLLIFRASTLASGVSSRFKGSGSGTQFTLTISDL

ECDDAATYYCQQGATVYDIDNN

The invention also includes antibodies having binding specificity to IL-6 and possessing a variable heavy chain sequence comprising the sequence set forth below:

(SEQ ID NO: 491)
METGLRWLLLVAVLKGVQCQSLEESGGRLVTPGTPLTLTCTVSGIDLSAY

AMIWVRQAPGEGLEWITIIYPNGITYYANWAKGRFTVSKTSTAMDLKITS

PTTEDTATYFCARDAESSKNAYWGYFNV.

The invention further contemplates antibodies comprising one or more of the polypeptide sequences of SEQ ID NO: 492; SEQ ID NO: 493; and SEQ ID NO: 494 which correspond to the complementarity-determining regions (CDRs, or hypervariable regions) of the variable light chain sequence of SEQ ID NO: 490, and/or one or more of the polypeptide sequences of SEQ ID NO: 495; SEQ ID NO: 496; and SEQ ID NO: 497 which correspond to the complementarity-determining regions (CDRs, or hypervariable regions) of the variable heavy chain sequence of SEQ ID NO: 491, or combinations of these polypeptide sequences.

In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 492; SEQ ID NO: 493; and SEQ ID NO: 494 which correspond to the complementarity-determining regions (CDRs, or hypervariable regions) of the variable light chain sequence of SEQ ID NO: 490, and/or one or more of the polypeptide sequences of SEQ ID NO: 495; SEQ ID NO: 496; and SEQ ID NO: 497 which correspond to the complementarity-determining regions (CDRs, or hypervariable regions) of the variable heavy chain sequence of SEQ ID NO: 491, or combinations of these polypeptide sequences.

In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 490. In another embodiment of the invention, antibody fragments of the invention comprise, or alternatively consist of, the polypeptide sequence of SEQ ID NO: 491.

In a further embodiment of the invention, fragments of the antibody having binding specificity to IL-6 comprise, or alternatively consist of, one or more of the polypeptide sequences of SEQ ID NO: 492; SEQ ID NO: 493; and SEQ ID NO: 494 which correspond to the complementarity-determining regions (CDRs, or hypervariable regions) of the variable light chain sequence of SEQ ID NO: 490.

In a further embodiment of the invention, fragments of the antibody having binding specificity to IL-6 comprise, or alternatively consist of, one or more of the polypeptide sequences of SEQ ID NO: 495; SEQ ID NO: 496; and SEQ ID NO: 497 which correspond to the complementarity-determining regions (CDRs, or hypervariable regions) of the variable heavy chain sequence of SEQ ID NO: 491.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 490; the variable heavy chain region of SEQ ID NO: 491; the complementarity-determining regions (SEQ ID NO: 492; SEQ ID NO: 493; and SEQ ID NO: 494) of the variable light chain region of SEQ ID NO: 490; and the complementarity-determining regions (SEQ ID NO: 495; SEQ ID NO: 496; and SEQ ID NO: 497) of the variable heavy chain region of SEQ ID NO: 491.

In a preferred embodiment of the invention, the anti-IL-6 antibody is Ab31, comprising SEQ ID NO: 490 and SEQ ID NO: 491, and having at least one of the biological activities set forth herein.

In another embodiment, the invention includes antibodies having binding specificity to IL-6 and possessing a variable light chain sequence comprising the sequence set forth below:

(SEQ ID NO: 506)
MDTRAPTQLLGLLLLWLPGATFAIEMTQTPSPVSAAVGGTVTINCQASES

VFNNMLSWYQQKPGHSPKLLIYDASDLASGVPSRFKGSGSGTQFTLTISG

VECDDAATYYCAGYKSDSNDGDNV

The invention also includes antibodies having binding specificity to IL-6 and possessing a variable heavy chain sequence comprising the sequence set forth below:

```
                                                        (SEQ ID NO: 507)
METGLRWLLLVAVLKGVQCQSLEESGGRLVTPGTPLTLTCTVSGFSLNRN

SITWVRQAPGEGLEWIGIITGSGRTYYANWAKGRFTISKTSTTVDLKMTS

PTTEDTATYFCARGHPGLGSGNI.
```

The invention further contemplates antibodies comprising one or more of the polypeptide sequences of SEQ ID NO: 508; SEQ ID NO: 509; and SEQ ID NO: 510 which correspond to the complementarity-determining regions (CDRs, or hypervariable regions) of the variable light chain sequence of SEQ ID NO: 506, and/or one or more of the polypeptide sequences of SEQ ID NO: 511; SEQ ID NO: 512; and SEQ ID NO: 513 which correspond to the complementarity-determining regions (CDRs, or hypervariable regions) of the variable heavy chain sequence of SEQ ID NO: 507, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 508; SEQ ID NO: 509; and SEQ ID NO: 510 which correspond to the complementarity-determining regions (CDRs, or hypervariable regions) of the variable light chain sequence of SEQ ID NO: 506, and/or one or more of the polypeptide sequences of SEQ ID NO: 511; SEQ ID NO: 512; and SEQ ID NO: 513 which correspond to the complementarity-determining regions (CDRs, or hypervariable regions) of the variable heavy chain sequence of SEQ ID NO: 507, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 506. In another embodiment of the invention, antibody fragments of the invention comprise, or alternatively consist of, the polypeptide sequence of SEQ ID NO: 507.

In a further embodiment of the invention, fragments of the antibody having binding specificity to IL-6 comprise, or alternatively consist of, one or more of the polypeptide sequences of SEQ ID NO: 508; SEQ ID NO: 509; and SEQ ID NO: 510 which correspond to the complementarity-determining regions (CDRs, or hypervariable regions) of the variable light chain sequence of SEQ ID NO: 506.

In a further embodiment of the invention, fragments of the antibody having binding specificity to IL-6 comprise, or alternatively consist of, one or more of the polypeptide sequences of SEQ ID NO: 511; SEQ ID NO: 512; and SEQ ID NO: 513 which correspond to the complementarity-determinin-g regions (CDRs, or hypervariable regions) of the variable heavy chain sequence of SEQ ID NO: 507.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 506; the variable heavy chain region of SEQ ID NO: 507; the complementarity-determining regions (SEQ ID NO: 508; SEQ ID NO: 509; and SEQ ID NO: 510) of the variable light chain region of SEQ ID NO: 506; and the complementarity-determining regions (SEQ ID NO: 511; SEQ ID NO: 512; and SEQ ID NO: 513) of the variable heavy chain region of SEQ ID NO: 507.

In a preferred embodiment of the invention, the anti-IL-6 antibody is Ab32, comprising SEQ ID NO: 506 and SEQ ID NO: 507, and having at least one of the biological activities set forth herein.

In another embodiment, the invention includes antibodies having binding specificity to IL-6 and possessing a variable light chain sequence comprising the sequence set forth below:

```
                                                        (SEQ ID NO: 522)
MDTRAPTQLLGLLLLWLPGATFAQVLTQTASSVSAAVGGTVTINCQSSQS

VYNNYLSWYQQKPGQPPKLLIYTASSLASGVPSRFKGSGSGTQFTLTISE

VQCDDAATYYCQGYYSGPIIT
```

The invention also includes antibodies having binding specificity to IL-6 and possessing a variable heavy chain sequence comprising the sequence set forth below:

```
                                                        (SEQ ID NO: 523)
METGLRWLLLVAVLKGVQCQSLEESGGRLVTPGTPLTLTCTASGFSLNNY

YIQWVRQAPGEGLEWIGIIYAGGSAYYATWANGRFTIAKTSSTTVDLKMT

SLTTEDTATYFCARGTFDGYEL.
```

The invention further contemplates antibodies comprising one or more of the polypeptide sequences of SEQ ID NO: 524; SEQ ID NO: 525; and SEQ ID NO: 526 which correspond to the complementarity-determining regions (CDRs, or hypervariable regions) of the variable light chain sequence of SEQ ID NO: 522, and/or one or more of the polypeptide sequences of SEQ ID NO: 527; SEQ ID NO: 528; and SEQ ID NO: 529 which correspond to the complementarity-determining regions (CDRs, or hypervariable regions) of the variable heavy chain sequence of SEQ ID NO: 523, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 524; SEQ ID NO: 525; and SEQ ID NO: 526 which correspond to the complementarity-determining regions (CDRs, or hypervariable regions) of the variable light chain sequence of SEQ ID NO: 522, and/or one or more of the polypeptide sequences of SEQ ID NO: 527; SEQ ID NO: 528; and SEQ ID NO: 529 which correspond to the complementarity-determining regions (CDRs, or hypervariable regions) of the variable heavy chain sequence of SEQ ID NO: 523, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 522. In another embodiment of the invention, antibody fragments of the invention comprise, or alternatively consist of, the polypeptide sequence of SEQ ID NO: 523.

In a further embodiment of the invention, fragments of the antibody having binding specificity to IL-6 comprise, or alternatively consist of, one or more of the polypeptide sequences of SEQ ID NO: 524; SEQ ID NO: 525; and SEQ ID NO: 526 which correspond to the complementarity-determining regions (CDRs, or hypervariable regions) of the variable light chain sequence of SEQ ID NO: 522.

In a further embodiment of the invention, fragments of the antibody having binding specificity to IL-6 comprise, or alternatively consist of, one or more of the polypeptide sequences of SEQ ID NO: 527; SEQ ID NO: 528; and SEQ ID NO: 529 which correspond to the complementarity-determining regions (CDRs, or hypervariable regions) of the variable heavy chain sequence of SEQ ID NO: 523.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 522; the variable heavy chain region of SEQ ID NO: 523; the complementarity-determining regions (SEQ ID NO: 524; SEQ ID NO: 525; and SEQ ID NO: 526) of the variable light chain region of SEQ ID NO: 522; and the complementarity-determining regions (SEQ ID NO: 527; SEQ ID NO: 528; and SEQ ID NO: 529) of the variable heavy chain region of SEQ ID NO: 523.

In a preferred embodiment of the invention, the anti-IL-6 antibody is Ab33, comprising SEQ ID NO: 522 and SEQ ID NO: 523, and having at least one of the biological activities set forth herein.

In another embodiment, the invention includes antibodies having binding specificity to IL-6 and possessing a variable light chain sequence comprising the sequence set forth below:

(SEQ ID NO: 538)
MDTRAPTQLLGLLLLWLPGATFAQVLTQTPSPVSVPVGDTVTISCQSSES

VYSNNLLSWYQQKPGQPPKLLIYRASNLASGVPSRFKGSGSGTQFTLTIS

GAQCDDAATYYCQGYYSGVINS

The invention also includes antibodies having binding specificity to IL-6 and possessing a variable heavy chain sequence comprising the sequence set forth below:

(SEQ ID NO: 539)
METGLRWLLLVAVLKGVQCQSVEESGGRLVTPGTPLTLTCTVSGFSLSSY

FMSWVRQAPGEGLEYIGFINPGGSAYYASWASGRLTISKTSTTVDLKITS

PTTEDTATYFCARILIVSYGAFTI.

The invention further contemplates antibodies comprising one or more of the polypeptide sequences of SEQ ID NO: 540; SEQ ID NO: 541; and SEQ ID NO: 542 which correspond to the complementarity-determining regions (CDRs, or hypervariable regions) of the variable light chain sequence of SEQ ID NO: 538, and/or one or more of the polypeptide sequences of SEQ ID NO: 543; SEQ ID NO: 544; and SEQ ID NO: 545 which correspond to the complementarity-determining regions (CDRs, or hypervariable regions) of the variable heavy chain sequence of SEQ ID NO: 539, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 540; SEQ ID NO: 541; and SEQ ID NO: 542 which correspond to the complementarity-determining regions (CDRs, or hypervariable regions) of the variable light chain sequence of SEQ ID NO: 538, and/or one or more of the polypeptide sequences of SEQ ID NO: 543; SEQ ID NO: 544; and SEQ ID NO: 545 which correspond to the complementarity-determining regions (CDRs, or hypervariable regions) of the variable heavy chain sequence of SEQ ID NO: 539, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 538. In another embodiment of the invention, antibody fragments of the invention comprise, or alternatively consist of, the polypeptide sequence of SEQ ID NO: 539.

In a further embodiment of the invention, fragments of the antibody having binding specificity to IL-6 comprise, or alternatively consist of, one or more of the polypeptide sequences of SEQ ID NO: 540; SEQ ID NO: 541; and SEQ ID NO: 542 which correspond to the complementarity-determining regions (CDRs, or hypervariable regions) of the variable light chain sequence of SEQ ID NO: 538.

In a further embodiment of the invention, fragments of the antibody having binding specificity to IL-6 comprise, or alternatively consist of, one or more of the polypeptide sequences of SEQ ID NO: 543; SEQ ID NO: 544; and SEQ ID NO: 545 which correspond to the complementarity-determining regions (CDRs, or hypervariable regions) of the variable heavy chain sequence of SEQ ID NO: 539.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 538; the variable heavy chain region of SEQ ID NO: 539; the complementarity-determining regions (SEQ ID NO: 540; SEQ ID NO: 541; and SEQ ID NO: 542) of the variable light chain region of SEQ ID NO: 538; and the complementarity-determining regions (SEQ ID NO: 543; SEQ ID NO: 544; and SEQ ID NO: 545) of the variable heavy chain region of SEQ ID NO: 539.

In a preferred embodiment of the invention, the anti-IL-6 antibody is Ab34, comprising SEQ ID NO: 538 and SEQ ID NO: 539, and having at least one of the biological activities set forth herein.

In another embodiment, the invention includes antibodies having binding specificity to IL-6 and possessing a variable light chain sequence comprising the sequence set forth below:

(SEQ ID NO: 554)
MDTRAPTQLLGLLLLWLPGARCAYDMTQTPASVEVAVGGTVTIKCQATES

IGNELSWYQQKPGQAPKLLIYSASTLASGVPSRFKGSGSGTQFTLTITGV

ECDDAATYYCQQGYSSANIDNA

The invention also includes antibodies having binding specificity to IL-6 and possessing a variable heavy chain sequence comprising the sequence set forth below:

(SEQ ID NO: 555)
METGLRWLLLVAVLKGVQCQSLEESGGRLVTPGTPLTLTCTVSGFSLSKY

YMSWVRQAPEKGLKYIGYIDSTTVNTYYATWARGRFTISKTSTTVDLKIT

SPTSEDTATYFCARGSTYFTDGGHRLDL.

The invention further contemplates antibodies comprising one or more of the polypeptide sequences of SEQ ID NO: 556; SEQ ID NO: 557; and SEQ ID NO: 558 which correspond to the complementarity-determining regions (CDRs, or hypervariable regions) of the variable light chain sequence of SEQ ID NO: 554, and/or one or more of the polypeptide sequences of SEQ ID NO: 559; SEQ ID NO: 560; and SEQ ID NO: 561 which correspond to the- complementarity-determining regions (CDRs, or hypervariable regions) of the variable heavy chain sequence of SEQ ID NO: 555, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 556; SEQ ID NO: 557; and SEQ ID NO: 558 which correspond to the complementarity-determining regions (CDRs, or hypervariable regions) of the variable light chain sequence of SEQ ID NO: 554, and/or one or more of the polypeptide sequences of SEQ ID NO: 559; SEQ ID NO: 560; and SEQ ID NO: 561 which correspond to the complementarity-determining regions (CDRs, or hypervariable regions) of the variable heavy chain sequence of SEQ ID NO: 555, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 554. In another embodiment of the invention, antibody fragments of the invention comprise, or alternatively consist of, the polypeptide sequence of SEQ ID NO: 555.

In a further embodiment of the invention, fragments of the antibody having binding specificity to IL-6 comprise, or alternatively consist of, one or more of the polypeptide sequences of SEQ ID NO: 556; SEQ ID NO: 557; and SEQ ID NO: 558 which correspond to the complementarity-determining regions (CDRs, or hypervariable regions) of the variable light chain sequence of SEQ ID NO: 554.

In a further embodiment of the invention, fragments of the antibody having binding specificity to IL-6 comprise, or alternatively consist of, one or more of the polypeptide sequences of SEQ ID NO: 559; SEQ ID NO: 560; and SEQ ID NO: 561 which correspond to the complementarity-determining regions (CDRs, or hypervariable regions) of the variable heavy chain sequence of SEQ ID NO: 555.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 554; the variable heavy chain region of SEQ ID NO: 555; the complementarity-determining regions (SEQ ID NO: 556; SEQ ID NO: 557; and SEQ ID NO: 558) of the variable light chain region of SEQ ID NO: 554; and the complementarity-determining regions (SEQ ID NO: 559; SEQ ID NO: 560; and SEQ ID NO: 561) of the variable heavy chain region of SEQ ID NO: 555.

In a preferred embodiment of the invention, the anti-IL-6 antibody is Ab35, comprising SEQ ID NO: 554 and SEQ ID NO: 555, and having at least one of the biological activities set forth herein.

In another embodiment, the invention includes antibodies having binding specificity to IL-6 and possessing a variable light chain sequence comprising the sequence set forth below:

(SEQ ID NO: 570)
MDTRAPTQLLGLLLLWLPGARCAYDMTQTPASVEVAVGGTVTIKCQATES

IGNELSWYQQKPGQAPKLLIYSASTLASGVPSRFKGSGSGTQFTLTITGV

ECDDAATYYCQQGYSSANIDNA

The invention also includes antibodies having binding specificity to IL-6 and possessing a variable heavy chain sequence comprising the sequence set forth below:

(SEQ ID NO: 571)
METGLRWLLLVAVLKGVQCQSLEESGGRLVTPGTPLTLTCTVSGFSLSTY

NMGWVRQAPGKGLEWIGSITIDGRTYYASWAKGRFTVSKSSTTVDLKMTS

LTTGDTATYFCARILIVSYGAFTI.

The invention further contemplates antibodies comprising one or more of the polypeptide sequences of SEQ ID NO: 572; SEQ ID NO: 573; and SEQ ID NO: 574 which correspond to the complementarity-determining regions (CDRs, or hypervariable regions) of the variable light chain sequence of SEQ ID NO: 570, and/or one or more of the polypeptide sequences of SEQ ID NO: 575; SEQ ID NO: 576; and SEQ ID NO: 577 which correspond to the complementarity-determining regions (CDRs, or-hypervariable regions) of the variable heavy chain sequence of SEQ ID NO: 571, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 572; SEQ ID NO: 573; and SEQ ID NO: 574 which correspond to the complementarity-determining regions (CDRs, or hypervariable regions) of the variable light chain sequence of SEQ ID NO: 570, and/or one or more of the polypeptide sequences of SEQ ID NO: 575; SEQ ID NO: 576; and SEQ ID NO: 577 which correspond to the complementarity-determining regions (CDRs, or hypervariable regions) of the variable heavy chain sequence of SEQ ID NO: 571, or combinations of these polypeptide sequences. In another embodiment of the invention, the antibodies of the invention include combinations of the CDRs and the variable heavy and light chain sequences set forth above.

The invention also contemplates fragments of the antibody having binding specificity to IL-6. In one embodiment of the invention, antibody fragments of the invention comprise, or alternatively consist of, the polypeptide sequence of SEQ ID NO: 570. In another embodiment of the invention, antibody fragments of the invention comprise, or alternatively consist of, the polypeptide sequence of SEQ ID NO: 571.

In a further embodiment of the invention, fragments of the antibody having binding specificity to IL-6 comprise, or alternatively consist of, one or more of the polypeptide sequences of SEQ ID NO: 572; SEQ ID NO: 573; and SEQ ID NO: 574 which correspond to the complementarity-determining regions (CDRs, or hypervariable regions) of the variable light chain sequence of SEQ ID NO: 570.

In a further embodiment of the invention, fragments of the antibody having binding specificity to IL-6 comprise, or alternatively consist of, one or more of the polypeptide sequences of SEQ ID NO: 575; SEQ ID NO: 576; and SEQ ID NO: 577 which correspond to the complementarity-determining-regions (CDRs, or hypervariable regions) of the variable heavy chain sequence of SEQ ID NO: 571.

The invention also contemplates antibody fragments which include one or more of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 570; the variable heavy chain region of SEQ ID NO: 571; the complementarity-determining regions (SEQ ID NO: 572; SEQ ID NO: 573; and SEQ ID NO: 574) of the variable light chain region of SEQ ID NO: 570; and the complementarity-determining regions (SEQ ID NO: 575; SEQ ID NO: 576; and SEQ ID NO: 577) of the variable heavy chain region of SEQ ID NO: 571.

In a preferred embodiment of the invention, the anti-IL-6 antibody is Ab36, comprising SEQ ID NO: 570 and SEQ ID NO: 571, and having at least one of the biological activities set forth herein.

Such antibody fragments may be present in one or more of the following non-limiting forms: Fab, Fab', F(ab')$_2$, Fv and single chain Fv antibody forms. In a preferred embodiment, the anti-IL-6 antibodies described herein further comprises the kappa constant light chain sequence comprising the sequence set forth below:

(SEQ ID NO: 586)
VAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSF

NRGEC.

In another preferred embodiment, the anti-IL-6 antibodies described herein further comprises and the gamma-1 constant heavy chain polypeptide sequence comprising the sequence set forth below:

(SEQ ID NO: 588)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

-continued
KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In another embodiment, the invention contemplates an isolated anti-IL-6 antibody comprising a V$_H$ polypeptide sequence selected from the group consisting of: SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555 and SEQ ID NO: 571; and further comprising a V$_L$ polypeptide sequence selected from the group consisting of: SEQ ID NO: 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554 and SEQ ID NO: 570 or a variant thereof wherein one or more of the framework residues (FR residues) in said V$_H$ or V$_L$ polypeptide has been substituted with another amino acid residue resulting in an anti-IL-6 antibody that specifically binds IL-6. The invention contemplates humanized and chimeric forms of these antibodies. The chimeric antibodies may include an Fc derived from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions.

In one embodiment of the invention, the antibodies or V$_H$ or V$_L$ polypeptides originate or are selected from one or more rabbit B cell populations prior to initiation of the humanization process referenced herein.

In another embodiment of the invention, the anti-IL-6 antibodies and fragments thereof have binding specificity for primate homologs of the human IL-6 protein. Non-limiting examples of primate homologs of the human IL-6 protein are IL-6 obtained from Macaca fascicularis (also known as the cynomolgus monkey) and the Rhesus monkey. In another embodiment of the invention, the anti-IL-6 antibodies and fragments thereof inhibits the association of IL-6 with IL-6R, and/or the production of IL-6/IL-6R/gp130 complexes and/or the production of IL-6/IL-6R/gp130 multimers and/or antagonizes the biological effects of one or more of the foregoing.

As stated herein, antibodies and fragments thereof may be modified post-translationally to add effector moieties such as chemical linkers, detectable moieties-- such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Regarding detectable moieties, further exemplary enzymes include, but are not limited to, horseradish peroxidase, acetylcholinesterase, alkaline phosphatase, beta-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent moieties include, but are not limited to, luminol. Further exemplary bioluminescent materials include, but are not limited to, luciferin and aequorin. Further exemplary radioactive materials include, but are not limited to, Iodine 125 ($^{125}$I), Carbon 14 ($^{14}$C), Sulfur 35 ($^{35}$S), Tritium ($^{3}$H) and Phosphorus 32 ($^{32}$P).

Regarding functional moieties, exemplary cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine and bleomycin. Toxic enzymes from plants and bacteria such as ricin, diphtheria toxin and *Pseudomonas* toxin may be conjugated to the humanized antibodies, or binding fragments thereof, to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof, with or without the use of a complex-forming agent. Such radionuclides include beta-emitters such as Phosphorus-32 ($^{32}$P), Scandium-47 ($^{47}$Sc), Copper-67 ($^{67}$Cu), Gallium-67 ($^{67}$Ga), Yttrium-88 ($^{88}$Y), Yttrium-90 ($^{90}$Y), Iodine-125 ($^{125}$I), Iodine-131 ($^{131}$I), Samarium-153 ($^{153}$Sm), Lutetium-177 ($^{177}$Lu), Rhenium-186 ($^{186}$Re) or Rhenium-188 ($^{188}$Re), and alpha-emitters such as Astatine-211 (211 ($^{211}$At), Lead-212 ($^{212}$Pb), Bismuth-212 ($^{212}$Bi) or -213 ($^{213}$Bi) or Actinium-225 ($^{225}$Ac).

Methods are known in the art for conjugating an antibody or binding fragment thereof to a detectable moiety and the like, such as for example those methods described by Hunter et al, Nature 144:945 (1962); David et al, Biochemistry 13:1014 (1974); Pain et al, J. Immunol. Meth. 40:219 (1981); and Nygren, J., Histochem. and Cytochem. 30:407 (1982).

Embodiments described herein further include variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

In another embodiment, the invention contemplates polypeptide sequences having at least 90% or greater sequence homology to any one or more of the polypeptide sequences of antibody fragments, variable regions and CDRs set forth herein. More preferably, the invention contemplates polypeptide sequences having at least 95% or greater sequence homology, even more preferably at least 98% or greater sequence homology, and still more preferably at least 99% or greater sequence homology to any one or more of the polypeptide sequences of antibody fragments, variable regions and CDRs set forth herein. Methods for determining homology between nucleic acid and amino acid sequences are well known to those of ordinary skill in the art.

In another embodiment, the invention further contemplates the above-recited polypeptide homologs of the antibody fragments, variable regions and CDRs set forth herein further having anti-IL-6 activity. Non-limiting examples of anti-IL-6 activity are set forth herein.

In another embodiment, the invention further contemplates the generation and use of anti-idiotypic antibodies that bind any of the foregoing sequences. In an exemplary embodiment, such an anti-idiotypic antibody could be administered to a subject who has received an anti-IL-6 antibody to modulate, reduce, or neutralize, the effect of the anti-IL-6 antibody. Such anti-idiotypic antibodies could also be useful for treatment of an autoimmune disease characterized by the presence of anti-IL-6 antibodies. A further exemplary use of such anti-idiotypic antibodies is for detection of the anti-IL-6 antibodies of the present invention, for example to monitor the levels of the anti-IL-6 antibodies present in a subject's blood or other bodily fluids.

The present invention also contemplates anti-IL-6 antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein.

Additional Exemplary Embodiments of the Invention

In another embodiment, the invention contemplates one or more anti-human IL-6 antibodies or antibody fragment which specifically bind to the same linear or conformational epitope(s) and/or competes for binding to the same linear or conformational epitope(s) on an intact human IL-6 polypeptide or fragment thereof as an anti-human IL-6 antibody selected from the group consisting of Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, and Ab36. In a preferred embodiment, the anti-human IL-6 antibody or fragment specifically binds to the same linear or conformational epitope(s) and/or competes for binding to the same linear or conformational epitope(s) on an intact human IL-6 polypeptide or a fragment thereof as Ab1.

In another embodiment of the invention, the anti-human IL-6 antibody which specifically binds to the same linear or conformational epitopes on an intact IL-6 polypeptide or fragment thereof that is (are) specifically bound by Ab1 binds to a IL-6 epitope(s) ascertained by epitopic mapping using overlapping linear peptide fragments which span the full length of the native human IL-6 polypeptide. In one embodiment of the invention, the IL-6 epitope comprises, or alternatively consists of, one or more residues comprised in IL-6 fragments selected from those respectively encompassing amino acid residues 37-51, amino acid residues 70-84, amino acid residues 169-183, amino acid residues 31-45 and/or amino acid residues 58-72.

The invention is also directed to an anti-IL-6 antibody that binds with the same IL-6 epitope and/or competes with an anti-IL-6 antibody for binding to IL-6 as an antibody or antibody fragment disclosed herein, including but not limited to an anti-IL-6 antibody selected from Ab1, Ab2, Ab3, Ab4, Abs, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, and Ab36.

In another embodiment, the invention is also directed to an isolated anti-IL-6 antibody or antibody fragment comprising one or more of the CDRs contained in the $V_H$ polypeptide sequences selected from the group consisting of: SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555 and SEQ ID NO: 571 and/or one or more of the CDRs contained in the $V_L$ polypeptide sequence consisting of: 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554 and SEQ ID NO: 570.

In one embodiment of the invention, the anti-human IL-6 antibody discussed in the two prior paragraphs comprises at least 2 complementarity determining regions (CDRs) in each the variable light and the variable heavy regions which are identical to those contained in an anti-human IL-6 antibody selected from the group consisting of Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, and Ab36.

In a preferred embodiment, the anti-human IL-6 antibody discussed above comprises at least 2 complementarity determining regions (CDRs) in each the variable light and the variable heavy regions which are identical to those contained in Ab1. In another embodiment, all of the CDRs of the anti-human IL-6 antibody discussed above are identical to the CDRs contained in an anti-human IL-6 antibody selected from the group consisting of Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, and Ab36. In a preferred embodiment of the invention, all of the CDRs of the anti-human IL-6 antibody discussed above are identical to the CDRs contained in Ab1.

The invention further contemplates that the one or more anti-human IL-6 antibodies discussed above are aglycosylated; that contain an Fc region that has been modified to alter effector function, half-life, proteolysis, and/or glycosylation; are human, humanized, single chain or chimeric; and are a humanized antibody derived from a rabbit (parent) anti-human IL-6 antibody.

The invention further contemplates one or more anti-human IL-6 antibodies wherein the framework regions (FRs) in the variable light region and the variable heavy regions of said antibody respectively are human FRs which are unmodified or which have been modified by the substitution of at most 2 or 3 human FR residues in the variable light or heavy chain region with the corresponding FR residues of the parent rabbit antibody, and wherein said human FRs have been derived from human variable heavy and light chain antibody sequences which have been selected from a library of human germline antibody sequences based on their high level of homology to the corresponding rabbit variable heavy or light chain regions relative to other human germline antibody sequences contained in the library.

In one embodiment of the invention, the anti-human IL-6 antibody or fragment specifically binds to IL-6 expressing human cells and/or to circulating soluble IL-6 molecules in vivo, including IL-6 expressed on or by human cells in a patient with a disease associated with cells that express IL-6.

In another embodiment, the disease is selected from general fatigue, exercise-induced fatigue, cancer-related fatigue, inflammatory disease-related fatigue, chronic fatigue syndrome, cancer-related cachexia, cardiac-related cachexia, respiratory-related cachexia, renal-related cachexia, age-related cachexia, rheumatoid arthritis, systemic lupus erythematosus (SLE), systemic juvenile idiopathic arthritis, psoriasis, psoriatic arthropathy, ankylosing spondylitis, inflammatory bowel disease (IBD), polymyalgia rheumatica, giant cell arteritis, autoimmune vasculitis, graft versus host disease (GVHD), Sjogren's syndrome, adult onset Still's disease, rheumatoid arthritis, systemic juvenile idiopathic arthritis, osteoarthritis, osteoporosis, Paget's disease of bone, osteoarthritis, multiple myeloma, Hodgkin's lymphoma, non-Hodgkin's lymphoma, prostate cancer, leukemia, renal cell cancer, multicentric Castleman's disease, ovarian cancer, drug resistance in cancer chemotherapy, cancer chemotherapy toxicity, ischemic heart disease, atherosclerosis, obesity, diabetes, asthma, multiple sclerosis, Alzheimer's disease, cerebrovascular disease, fever, acute phase response, allergies, anemia, anemia of inflammation (anemia of chronic disease), hypertension, depression, depression associated with a chronic illness, thrombosis, thrombocytosis, acute heart failure, metabolic syndrome, miscarriage, obesity, chronic prostatitis, glomerulonephritis, pelvic inflammatory disease, reperfusion injury, transplant rejection, graft versus host disease (GVHD), avian influenza, smallpox, pandemic influenza, adult respiratory distress syndrome (ARDS), severe acute respiratory syndrome (SARS), sepsis, and systemic inflammatory response syndrome (SIRS). In a preferred embodiment, the disease is selected from a cancer, inflammatory disorder, viral disorder, or autoimmune disorder. In a particularly preferred embodiment, the disease is arthritis, cachexia, and wasting syndrome The invention further contemplates anti-human IL-6 antibodies or fragments directly or indirectly attached to a detectable label or therapeutic agent.

The invention also contemplates one or more nucleic acid sequences which result in the expression of an anti-human IL-6 antibody or antibody fragment as set forth above, including those comprising, or alternatively consisting of, yeast or human preferred codons. The invention also contemplates vectors (including plasmids or recombinant viral vectors) comprising said nucleic acid sequence(s). The invention also contemplates host cells or recombinant host cells expressing at least one of the antibodies set forth above, including a mammalian, yeast, bacterial, and insect cells. In a preferred embodiment, the host cell is a yeast cell. In a further preferred embodiment, the yeast cell is a diploidal yeast cell. In a more preferred embodiment, the yeast cell is a *Pichia* yeast.

The invention also contemplates a method of treatment comprising administering to a patient with a disease or condition associated with IL-6 expressing cells a therapeutically effective amount of at least one anti-human IL-6 antibody or fragment. The diseases that may be treated are presented in the non-limiting list set forth above. In a preferred embodiment, the disease is selected from a cancer, autoimmune disease, or inflammatory condition. In a particularly preferred embodiment, the disease is cancer or viral infection. In another embodiment the treatment further includes the administration of another therapeutic agent or regimen selected from chemotherapy, radiotherapy, cytokine administration or gene therapy.

The invention further contemplates a method of in vivo imaging which detects the presence of cells which express IL-6 comprising administering a diagnostically effective amount of at least one anti-human IL-6 antibody. In one embodiment, said administration further includes the administration of a radionuclide or fluorophore that facilitates detection of the antibody at IL-6 expressing disease sites. In another embodiment of the invention, the method of in vivo imaging is used to detect IL-6 expressing tumors or metastases or is used to detect the presence of sites of autoimmune disorders associated with IL-6 expressing cells. In a further embodiment, the results of said in vivo imaging method are used to facilitate design of an appropriate therapeutic regimen, including therapeutic regimens including radiotherapy, chemotherapy or a combination thereof.

Polynucleotides Encoding Anti-IL-6 Antibody Polypeptides

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 2:

```
                                        (SEQ ID NO: 10)
ATGGACACGAGGGCCCCCACTCAGCTGCTGGGGCTCCTGCTGCTCTGGCT

CCCAGGTGCCAGATGTGCCTATGATATGACCCAGACTCCAGCCTCGGTGT

CTGCAGCTGTGGGAGGCACAGTCACCATCAAGTGCCAGGCCAGTCAGAGC

ATTAACAATGAATTATCCTGGTATCAGCAGAAACCAGGGCAGCGTCCCAA

GCTCCTGATCTATAGGGCATCCACTCTGGCATCTGGGGTCTCATCGCGGT

TCAAAGGCAGTGGATCTGGGACAGAGTTCACTCTCACCATCAGCGACCTG

GAGTGTGCCGATGCTGCCACTTACTACTGTCAACAGGGTTATAGTCTGAG

GAATATTGATAATGCTTTCGGCGGAGGGACCGAGGTGGTGGTCAAACGTA

CGGTAGCGGCCCCATCTGTCTTCATCTTCCCGCCATCTGATGAGCAGTTG

AAATCTGGAACTGCCTCTGTTGTGTGCCTGCTGAATAACTT
```

In another embodiment of the invention, polynucleotides of the invention comprise, or alternatively consist of, the following polynucleotide sequence encoding the variable heavy chain polypeptide sequence of SEQ ID NO: 3:

```
                                        (SEQ ID NO: 11)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCACGCCTGGGA
```

```
-continued
CACCCCTGACACTCACCTGCACAGCCTCTGGATTCTCCCTCAGTAACTAC

TACGTGACCTGGGTCCGCCAGGCTCCAGGGAAGGGGCTGGAATGGATCGG

AATCATTTATGGTAGTGATGAAACGGCCTACGCGACCTGGGCGATAGGCC

GATTCACCATCTCCAAAACCTCGACCACGGTGGATCTGAAAATGACCAGT

CTGACAGCCGCGGACACGGCCACCTATTTCTGTGCCAGAGATGATAGTAG

TGACTGGGATGCAAAATTTAACTTGTGGGGCCAAGGCACCCTGGTCACCG

TCTCGAGCGCCTCCACCAAGGGCCCATCGGTCTTCCCCCTGGCACCCTCC

TCCAAGAGCACCTCTGGGGGCACAGCGGCCCTGGGCTGCCTGGTCAAGG.
```

In a further embodiment of the invention, polynucleotides encoding fragments of the antibody having binding specificity to IL-6 comprise, or alternatively consist of, one or more of the polynucleotide sequences of SEQ ID NO: 12; SEQ ID NO: 13; and SEQ ID NO: 14 which correspond to polynucleotides encoding the complementarity-determining regions (CDRs, or hypervariable regions) of the light chain variable sequence of SEQ ID NO: 2.

In a further embodiment of the invention, polynucleotides encoding fragments of the antibody having binding specificity to IL-6 comprise, or alternatively consist of, one or more of the polynucleotide sequences of SEQ ID NO: 15; SEQ ID NO: 16; and SEQ ID NO: 17 which correspond to polynucleotides encoding the complementarity-determining regions (CDRs, or hypervariable regions) of the heavy chain variable sequence of SEQ ID NO: 3.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 10 encoding the light chain variable region of SEQ ID NO: 2; the polynucleotide SEQ ID NO: 11 encoding the heavy chain variable region of SEQ ID NO: 3; polynucleotides encoding the complementarity-determining regions (SEQ ID NO: 12; SEQ ID NO: 13; and SEQ ID NO: 14) of the light chain variable region of SEQ ID NO: 10; and polynucleotides encoding the complementarity-determining regions (SEQ ID NO: 15; SEQ ID NO: 16; and SEQ ID-NO: 17) of the heavy chain variable region of SEQ ID NO: 11.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 21:

```
                                        (SEQ ID NO: 29)
ATGGACACGAGGGCCCCCACTCAGCTGCTGGGGCTCCTGCTGCTCTGGCT

CCCAGGTGCCAGATGTGCCTATGATATGACCCAGACTCCAGCCTCTGTGG

AGGTAGCTGTGGGAGGCACAGTCACCATCAATTGCCAGGCCAGTGAGACC

ATTTACAGTTGGTTATCCTGGTATCAGCAGAAGCCAGGGCAGCCTCCCAA

GCTCCTGATCTACCAGGCATCCGATCTGGCATCTGGGGTCCCATCGCGAT
```

-continued

```
TCAGCGGCAGTGGGGCTGGGACAGAGTACACTCTCACCATCAGCGGCGTG

CAGTGTGACGATGCTGCCACTTACTACTGTCAACAGGGTTATAGTGGTAG

TAATGTTGATAATGTTTTCGGCGGAGGGACCGAGGTGGTGGTCAAACGTA

CGGTAGCGGCCCCATCTGTCTTCATCTTCCCGCCATCTGATGAGCAGTTG

AAATCTGGAACTGCCTCTGTTGTGTGCCTGCTGAATAACTTCTATCCCAG

AGAGGCCAAAG
```

In another embodiment of the invention, polynucleotides of the invention comprise, or alternatively consist of, the following polynucleotide sequence encoding the variable heavy chain polypeptide sequence of SEQ ID NO: 22:

```
(SEQ ID NO: 30)
ATGGAGACTGGGCTGCGCTGGCTTCTCCTGGTCGCTGTGCTCAAAGGTGT

CCAGTGTCAGGAGCAGCTGAAGGAGTCCGGGGGTCGCCTGGTCACGCCTG

GGACACCCCTGACACTTACCTGCACAGCCTCTGGATTCTCCCTCAATGAC

CATGCAATGGGCTGGGTCCGCCAGGCTCCAGGGAAGGGGCTGGAATACAT

CGGATTCATTAATAGTGGTGGTAGCGCACGCTACGCGAGCTGGGCAGAAG

GCCGATTCACCATCTCCAGAACCTCGACCACGGTGGATCTGAAAATGACC

AGTCTGACAACCGAGGACACGGCCACCTATTTCTGTGTCAGAGGGGTGC

TGTTTGGAGTATTCATAGTTTTGATCCCTGGGGCCCAGGGACCCTGGTCA

CCGTCTCGAGCGCCTCCACCAAGGGCCCATCGGTCTTCCCCCTGGCACCC

TCCTCCAAGAGCACCTCTGGGGGCACAGCGGCCCTGGGCTGCCTGGTCAA

G.
```

In a further embodiment of the invention, polynucleotides encoding fragments of the antibody having binding specificity to IL-6 comprise, or alternatively consist of, one or more of the polynucleotide sequences of SEQ ID NO: 31; SEQ ID NO: 32; and SEQ ID NO: 33 which correspond to polynucleotides encoding the complementarity-determining regions (CDRs, or hypervariable regions) of the light chain variable sequence of SEQ ID NO: 21.

In a further embodiment of the invention, polynucleotides encoding fragments of the antibody having binding specificity to IL-6 comprise, or alternatively consist of, one or more of the polynucleotide sequences of SEQ ID NO: 34; SEQ ID NO: 35; and SEQ ID NO: 36 which correspond to polynucleotides encoding the complementarity-determining regions (CDRs, or hypervariable regions) of the heavy chain variable sequence of SEQ ID NO: 22.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 29 encoding the light chain variable region of SEQ ID NO: 21; the polynucleotide SEQ ID NO: 30 encoding the heavy chain variable region of SEQ ID NO: 22; polynucleotides encoding the complementarity-determining regions (SEQ ID NO: 31; SEQ ID NO: 32; and SEQ ID NO: 33) of the light chain variable region of SEQ ID NO: 29; and polynucleotides encoding the complementarity-determining regions (SEQ ID NO: 34; SEQ ID NO: 35; and SEQ ID NO: 36) of the heavy chain variable region of SEQ ID NO: 30.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 37:

```
(SEQ ID NO: 45)
ATGGACACGAGGGCCCCCACTCAGCTGCTGGGGCTCCTGCTGCTCTGGCT

CCCAGGTGCCACATTTGCCGCCGTGCTGACCCAGACTCCATCTCCCGTGT

CTGCAGCTGTGGGAGGCACAGTCAGCATCAGTTGCCAGGCCAGTCAGAGT

GTTTATGACAACAACTACTTATCCTGGTTTCAGCAGAAACCAGGGCAGCC

TCCCAAGCTCCTGATCTATGGTGCATCCACTCTGGCATCTGGGGTCCCAT

CGCGGTTCGTGGGCAGTGGATCTGGGACACAGTTCACTCTCACCATCACA

GACGTGCAGTGTGACGATGCTGCCACTTACTATTGTGCAGGCGTTTATGA

TGATGATAGTGATAATGCCTTCGGCGGAGGGACCGAGGTGGTGGTCAAAC

GTACGGTAGCGGCCCCATCTGTCTTCATCTTCCCGCCATCTGATGAGCAG

TTGAAATCTGGAACTGCCTCTGTTGTGTGCCTGCTGAATAACTTCT
```

In another embodiment of the invention, polynucleotides of the invention comprise, or alternatively consist of, the following polynucleotide sequence encoding the variable heavy chain polypeptide sequence of SEQ ID NO: 38:

```
(SEQ ID NO: 46)
ATGGAGACTGGGCTGCGCTGGCTTCTCCTGGTGGCTGTGCTCAAAGGTGT

CCAGTGTCAGTCGCTGGAGGAGTCCGGGGGTCGCCTGGTCACCCCTGGGA

CACCCCTGACACTCACCTGCACAGCCTCTGGATTCTCCCTCAGTGTCTAC

TACATGAACTGGGTCCGCCAGGCTCCAGGGAAGGGGCTGGAATGGATCGG

ATTCATTACAATGAGTGATAATATAAATTACGCGAGCTGGGCGAAAGGCC

GATTCACCATCTCCAAAACCTCGACCACGGTGGATCTGAAAATGACCAGT

CCGACAACCGAGGACACGGCCACCTATTTCTGTGCCAGGAGTCGTGGCTG

GGGTACAATGGGTCGGTTGGATCTCTGGGGCCCAGGCACCCTCGTCACCG

TCTCGAGCGCCTCCACCAAGGGCCCATCGGTCTTCCCCCTGGCACCCTCC

TCCAAGAGCACCTCTGGGGGCACAGCGGCCCTGGGCTGCCTGGTCAAGG.
```

In a further embodiment of the invention, polynucleotides encoding fragments of the antibody having binding specificity to IL-6 comprise, or alternatively consist of, one or more of the polynucleotide sequences of SEQ ID NO: 47; SEQ ID NO: 48; and SEQ ID NO: 49 which correspond to polynucleotides encoding the complementarity-determining regions (CDRs, or hypervariable regions) of the light chain variable sequence of SEQ ID NO: 37.

In a further embodiment of the invention, polynucleotides encoding fragments of the antibody having binding specificity to IL-6 comprise, or alternatively consist of, one or more of the polynucleotide sequences of SEQ ID NO: 50; SEQ ID NO: 51; and SEQ ID NO: 52 which correspond to polynucleotides encoding the complementarity-determining regions (CDRs, or hypervariable regions) of the heavy chain variable sequence of SEQ ID NO: 38.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 45 encoding the light chain variable region of SEQ ID NO: 37; the polynucleotide SEQ ID NO: 46 encoding the heavy chain variable region of SEQ ID NO: 38; polynucleotides encoding the complementarity-determining regions (SEQ ID NO: 47; SEQ ID NO: 48; and SEQ ID NO: 49) of the light chain variable region of SEQ ID NO: 37; and polynucleotides encoding the complementarity-determining regions (SEQ ID NO: 50; SEQ ID NO: 51; and SEQ ID NO: 52) of the heavy chain variable region of SEQ ID NO: 38.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 53:

```
                                           (SEQ ID NO: 61)
ATGGACACGAGGGCCCCCACTCAGCTGCTGGGGCTCCTGCTGCTCTGGCT

CCCAGGTGCCATATGTGACCCTGTGCTGACCCAGACTCCATCTCCCGTAT

CTGCACCTGTGGGAGGCACAGTCAGCATCAGTTGCCAGGCCAGTCAGAGT

GTTTATGAGAACAACTATTTATCCTGGTTTCAGCAGAAACCAGGGCAGCC

TCCCAAGCTCCTGATCTATGGTGCATCCACTCTGGATTCTGGGGTCCCAT

CGCGGTTCAAAGGCAGTGGATCTGGGACACAGTTCACTCTCACCATTACA

GACGTGCAGTGTGACGATGCTGCCACTTACTATTGTGCAGGCGTTTATGA

TGATGATAGTGATGATGCCTTCGGCGGAGGGACCGAGGTGGTGGTCAAAC

GTACGGTAGCGGCCCCATCTGTCTTCATCTTCCCGCCATCTGATGAGCAG

TTGAAATCTGGAACTGCCTCTGTTGTGTGCCTGCTGAATAACTT
```

In another embodiment of the invention, polynucleotides of the invention comprise, or alternatively consist of, the following polynucleotide sequence encoding the variable heavy chain polypeptide sequence of SEQ ID NO: 54:

```
                                           (SEQ ID NO: 62)
ATGGAGACTGGGCTGCGCTGGCTTCTCCTGGTGGCTGTGCTCAAAGGTGT

CCAGTGTCAGGAGCAGCTGAAGGAGTCCGGAGGAGGCCTGGTAACGCCTG

GAGGAACCCTGACACTCACCTGCACAGCCTCTGGATTCTCCCTCAATGCC

TACTACATGAACTGGGTCCGCCAGGCTCCAGGGAAGGGGCTGGAATGGAT

CGGATTCATTACTCTGAATAATAATGTAGCTTACGCGAACTGGGCGAAAG

GCCGATTCACCTTCTCCAAAACCTCGACCACGGTGGATCTGAAAATGACC

AGTCCGACACCCGAGGACACGGCCACCTATTTCTGTGCCAGGAGTCGTGG

CTGGGGTGCAATGGGTCGGTTGGATCTCTGGGGCATGGCACCCTGGTCA

CCGTCTCGAGCGCCTCCACCAAGGGCCCATCGGTCTTCCCCCTGGCACCC
```

TCCTCCAAGAGCACCTCTGGGGGCACAGCGGCCCTGGGCTGCCTGGTCAA

GG.

In a further embodiment of the invention, polynucleotides encoding fragments of the antibody having binding specificity to IL-6 comprise, or alternatively consist of, one or more of the polynucleotide sequences of SEQ ID NO: 63; SEQ ID NO: 64; and SEQ ID NO: 65 which correspond to polynucleotides encoding the complementarity-determining regions (CDRs, or hypervariable regions) of the light chain variable sequence of SEQ ID NO: 53.

In a further embodiment of the invention, polynucleotides encoding fragments of the antibody having binding specificity to IL-6 comprise, or alternatively consist of, one or more of the polynucleotide sequences of SEQ 1D NO: 66; SEQ ID NO: 67; and SEQ ID NO: 68 which correspond to polynucleotides encoding the complementarity-determining regions (CDRs, or hypervariable regions) of the heavy chain variable sequence of SEQ ID NO: 54.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 61 encoding the light chain variable region of SEQ ID NO: 53; the polynucleotide SEQ ID NO: 62 encoding the heavy chain variable region of SEQ ID NO: 54; polynucleotides encoding the complementarity-determining regions (SEQ ID NO: 63; SEQ ID NO: 64; and SEQ ID NO: 65) of the light chain variable region of SEQ ID NO: 53; and polynucleotides encoding the complementarity-determining regions (SEQ ID NO: 66; SEQ ID NO: 67; and SEQ ID NO: 68) of the heavy chain variable region of SEQ ID NO: 54.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 69:

```
                                           (SEQ ID NO: 77)
ATGGACACGAGGGCCCCCACTCAGCTGCTGGGGCTCCTGCTGCTCTGGCT

CCCAGGTGCCACATTTGCCCAAGTGCTGACCCAGACTCCATCGCCTGTGT

CTGCAGCTGTGGGAGGCACAGTCACCATCAACTGCCAGGCCAGTCAGAGT

GTTGATGATAACAACTGGTTAGGCTGGTATCAGCAGAAACGAGGGCAGCC

TCCCAAGTACCTGATCTATTCTGCATCCACTCTGGCATCTGGGGTCCCAT

CGCGGTTCAAAGGCAGTGGATCTGGGACACAGTTCACTCTCACCATCAGC

GACCTGGAGTGTGACGATGCTGCCACTTACTACTGTGCAGGCGGTTTTAG

TGGTAATATCTTTGCTTTCGGCGGAGGGACCGAGGTGGTGGTCAAACGTA

CGGTAGCGGCCCCATCTGTCTTCATCTTCCCGCCATCTGATGAGCAGTTG

AAATCTGGAACTGCCTCTGTTGTGTGCCTGCTGAATAACTTCT
```

In another embodiment of the invention, polynucleotides of the invention comprise, or alternatively consist of, the following polynucleotide sequence encoding the variable heavy chain polypeptide sequence of SEQ ID NO: 70:

(SEQ ID NO: 78)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGCTTCTCCCTCAGTAGCTAT

GCAATGAGCTGGGTCCGCCAGGCTCCAGGAAAGGGGCTGGAGTGGATCGG

AATCATTGGTGGTTTTGGTACCACATACTACGCGACCTGGGCGAAAGGCC

GATTCACCATCTCCAAAACCTCGACCACGGTGGATCTGAGAATCACCAGT

CCGACAACCGAGGACACGGCCACCTATTTCTGTGCCAGAGGTGGTCCTGG

TAATGGTGGTGACATCTGGGGCCAAGGGACCCTGGTCACCGTCTCGAGCG

CCTCCACCAAGGGCCCATCGGTCTTCCCCCTGGCACCCTCCTCCAAGAGC

ACCTCTGGGGGCACAGCGGCCCTGGGCTGCCTGGTCAAGGACT.

In a further embodiment of the invention, polynucleotides encoding fragments of the antibody having binding specificity to IL-6 comprise, or alternatively consist of, one or more of the polynucleotide sequences of SEQ ID NO: 79; SEQ ID NO: 80; and SEQ ID NO: 81 which correspond to polynucleotides encoding the complementarity-determining regions (CDRs, or hypervariable regions) of the light chain variable sequence of SEQ ID NO: 69.

In a further embodiment of the invention, polynucleotides encoding fragments of the antibody having binding specificity to IL-6 comprise, or alternatively consist of, one or more of the polynucleotide sequences of SEQ ID NO: 82; SEQ ID NO: 83; and SEQ ID NO: 84 which correspond to polynucleotides encoding the complementarity-determining regions (CDRs, or hypervariable regions) of the heavy chain variable sequence of SEQ ID NO: 70.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 77 encoding the light chain variable region of SEQ ID NO: 69; the polynucleotide SEQ ID NO: 78 encoding the heavy chain variable region of SEQ ID NO: 70; polynucleotides encoding the complementarity-determining regions (SEQ ID NO: 79; SEQ ID NO: 80; and SEQ ID NO: 81) of the light chain variable region of SEQ ID NO: 69; and polynucleotides encoding the complementarity-determining regions (SEQ ID NO: 82; SEQ ID NO: 83; and SEQ ID NO: 84) of the heavy chain variable region of SEQ ID NO: 70.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 85:

(SEQ ID NO: 93)
ATGGACACGAGGGCCCCCACTCAGCTGCTGGGGCTCCTGCTGCTCTGGCT

CCCAGGTGCCACATTTGCAGCCGTGCTGACCCAGACACCATCGCCCGTGT

CTGTACCTGTGGGAGGCACAGTCACCATCAAGTGCCAGTCCAGTCAGAGT

-continued
GTTTATAATAATTTCTTATCGTGGTATCAGCAGAAACCAGGGCAGCCTCC

CAAGCTCCTGATCTACCAGGCATCCAAACTGGCATCTGGGGTCCCAGATA

GGTTCAGCGGCAGTGGATCTGGGACACAGTTCACTCTCACCATCAGCGGC

GTGCAGTGTGACGATGCTGCCACTTACTACTGTCTAGGCGGTTATGATGA

TGATGCTGATAATGCTTTCGGCGGAGGGACCGAGGTGGTGGTCAAACGTA

CGGTAGCGGCCCCATCTGTCTTCATCTTCCCGCCATCTGATGAGCAGTTG

AAATCTGGAACTGCCTCTGTTGTGTGCCTGCTGAATAACTTC

In another embodiment of the invention, polynucleotides of the invention comprise, or alternatively consist of, the following polynucleotide sequence encoding the variable heavy chain polypeptide sequence of SEQ ID NO: 86:

(SEQ ID NO: 94)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACGCTCACCTGCACAGTCTCTGGAATCGACCTCAGTGACTAT

GCAATGAGCTGGGTCCGCCAGGCTCCAGGGAAGGGGCTGGAATGGATCGG

AATCATTTATGCTGGTAGTGGTAGCACATGGTACGCGAGCTGGGCGAAAG

GCCGATTCACCATCTCCAAAACCTCGACCACGGTGGATCTGAAAATCACC

AGTCCGACAACCGAGGACACGGCCACCTATTTCTGTGCCAGAGATGGATA

CGATGACTATGGTGATTTCGATCGATTGGATCTCTGGGGCCCAGGCACCC

TCGTCACCGTCTCGAGCGCCTCCACCAAGGGCCCATCGGTCTTCCCCCTG

GCACCCTCCTCCAAGAGCACCTCTGGGGGCACAGCGGCCCTGGGCTGCCT

GGTCAAGGACT.

In a further embodiment of the invention, polynucleotides encoding fragments of the antibody having binding specificity, to IL-6 comprise, or alternatively consist of, one or more of the polynucleotide sequences of SEQ ID NO: 95; SEQ ID NO: 96; and SEQ ID NO: 97 which correspond to polynucleotides encoding the complementarity-determining regions (CDRs, or hypervariable regions) of the light chain variable sequence of SEQ ID NO: 85.

In a further embodiment of the invention, polynucleotides encoding fragments of the antibody having binding specificity to IL-6 comprise, or alternatively consist of, one or more of the polynucleotide sequences of SEQ ID NO: 98; SEQ ID NO: 99; and SEQ ID NO: 100 which correspond to polynucleotides encoding the complementarity-determining regions (CDRs, or hypervariable regions) of the heavy chain variable sequence of SEQ ID NO: 86.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 93 encoding the light chain variable region of SEQ ID NO: 85; the polynucleotide SEQ ID NO: 94 encoding the heavy chain variable region of SEQ ID NO: 86; polynucleotides encoding the complementarity-determining regions (SEQ ID NO: 95; SEQ ID NO: 96; and SEQ ID NO: 97) of the light chain variable region of SEQ ID NO: 85; and polynucleotides encoding the complementarity-determining regions (SEQ ID NO: 98; SEQ ID NO: 99; and SEQ ID NO: 100) of the heavy chain variable region of SEQ ID NO: 86.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 101:

(SEQ ID NO: 109)
ATGGACACGAGGGCCCCCACTCAGCTGCTGGGGCTCCTGCTGCTCTGGCT

CCCAGGTGCCAGATGTGCCTATGATATGACCCAGACTCCAGCCTCGGTGT

CTGCAGCTGTGGGAGGCACAGTCACCATCAAATGCCAGGCCAGTCAGAGC

ATTAACAATGAATTATCCTGGTATCAGCAGAAATCAGGGCAGCGTCCCAA

GCTCCTGATCTATAGGGCATCCACTCTGGCATCTGGGGTCTCATCGCGGT

TCAAAGGCAGTGGATCTGGGACAGAGTTCACTCTCACCATCAGCGACCTG

GAGTGTGCCGATGCTGCCACTTACTACTGTCAACAGGGTTATAGTCTGAG

GAATATTGATAATGCTTTCGGCGGAGGGACCGAGGTGGTGGTCAAACGTA

CGGTAGCGGCCCCATCTGTCTTCATCTTCCCGCCATCTGATGAGCAGTTG

AAATCTGGAACTGCCTCTGTTGTGTGCCTGCTGAATAACTTC

In another embodiment of the invention, polynucleotides of the invention comprise, or alternatively consist of, the following polynucleotide sequence encoding the variable heavy chain polypeptide sequence of SEQ ID NO: 102:

(SEQ ID NO: 110)
ATGGAGACTGGGCTGCGCTGGCTTCTCCTGGTCGCTGTGCTCTCAGGTGT

CCAGTGTCAGTCGCTGGAGGAGTCCGGGGGTCGCCTGGTCACGCCTGGGA

CACCCCTGACACTCACCTGCACAGCCTCTGGATTCTCCCTCAGTAACTAC

TACATGACCTGGGTCCGCCAGGCTCCAGGGAAGGGGCTGGAATGGATCGG

AATGATTTATGGTAGTGATGAAACAGCCTACGCGAACTGGGCGATAGGCC

GATTCACCATCTCCAAAACCTCGACCACGGTGGATCTGAAAATGACCAGT

CTGACAGCCGCGGACACGGCCACCTATTTCTGTGCCAGAGATGATAGTAG

TGACTGGGATGCAAAATTTAACTTGTGGGGCCAAGGGACCCTCGTCACCG

TCTCGAGCGCCTCCACCAAGGGCCCATCGGTCTTCCCCCTGGCACCCTCC

TCCAAGAGCACCTCTGGGGGCACAGCGGCCCTGGGCTGCCTGGTCAAGG.

In a further embodiment of the invention, polynucleotides encoding fragments of the antibody having binding specificity to IL-6 comprise, or alternatively consist of, one or more of the polynucleotide sequences of SEQ ID NO: 111; SEQ ID NO: 112; and SEQ ID NO: 113 which correspond to polynucleotides encoding the complementarity-determining regions (CDRs, or hypervariable regions) of the light chain variable sequence of SEQ ID NO: 101.

In a further embodiment of the invention, polynucleotides encoding fragments of the antibody having binding specificity to IL-6 comprise, or alternatively consist of, one or more of the polynucleotide sequences of SEQ ID NO: 114; SEQ ID NO: 115; and SEQ ID NO: 116 which correspond to polynucleotides encoding the complementarity-determining regions (CDRs, or hypervariable regions) of the heavy chain variable sequence of SEQ ID NO: 102.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 109 encoding the light chain variable region of SEQ ID NO: 101; the polynucleotide SEQ ID NO: 110 encoding the heavy chain variable region of SEQ ID NO: 102; polynucleotides encoding the complementarity-determining regions (SEQ ID NO: 111; SEQ ID NO: 112; and SEQ ID NO: 113) of the light chain variable region of SEQ ID NO: 101; and polynucleotides encoding the complementarity-determining regions (SEQ ID NO: 114; SEQ ID NO: 115; and SEQ ID NO: 116) of the heavy chain variable region of SEQ ID NO: 102.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 122:

(SEQ ID NO: 130)
ATGGACACGAGGGCCCCCACTCAGCTGCTGGGGCTCCTGCTGCTCTGGCT

CCCAGGTGCCACATTTGCAGCCGTGCTGACCCAGACACCATCACCCGTGT

CTGCAGCTGTGGGAGGCACAGTCACCATCAGTTGCCAGTCCAGTCAGAGT

GTTGGTAATAACCAGGACTTATCCTGGTTTCAGCAGAGACCAGGGCAGCC

TCCCAAGCTCCTGATCTACGAAATATCCAAACTGGAATCTGGGGTCCCAT

CGCGGTTCAGCGGCAGTGGATCTGGGACACACTTCACTCTCACCATCAGC

GGCGTACAGTGTGACGATGCTGCCACTTACTACTGTCTAGGCGGTTATGA

TGATGATGCTGATAATGCT

In another embodiment of the invention, polynucleotides of the invention comprise, or alternatively consist of, the following polynucleotide sequence encoding the variable heavy chain polypeptide sequence of SEQ ID NO: 123:

(SEQ ID NO: 131)
ATGGAGACTGGGCTGCGCTGGCTTCTCCTGGTCGCTGTGCTCAAAGGTGT

CCAGTGTCACTCGGTGGAGGAGTCCGGGGGTCGCCTGGTCACGCCTGGGA

CACCCCTGACACTCACCTGCACAGTCTCTGGATTCTCCCTCAGTAGTCGT

ACAATGTCCTGGGTCCGCCAGGCTCCAGGGAAGGGGCTGGAGTGGATCGG

ATACATTTGGAGTGGTGGTAGCACATACTACGCGACCTGGGCGAAAGGCC

GATTCACCATCTCCAAAACCTCGACCACGGTGGATCTGAAAATCACCAGT

CCGACAACCGAGGACACGGCCACCTATTTCTGTGCCAGATTGGGCGATAC

TGGTGGTCACGCTTATGCTACTCGCTTAAATCTC.

In a further embodiment of the invention, polynucleotides encoding fragments of the antibody having binding specificity to IL-6 comprise, or alternatively consist of, one or more of the polynucleotide sequences of SEQ ID NO: 132; SEQ ID NO: 133; and SEQ ID NO: 134 which correspond to polynucleotides encoding the complementarity-determining regions (CDRs, or hypervariable regions) of the light chain variable sequence of SEQ ID NO: 122.

In a further embodiment of the invention, polynucleotides encoding fragments of the antibody having binding specificity to IL-6 comprise, or alternatively consist of, one or more of the polynucleotide sequences of SEQ ID NO: 135; SEQ ID NO: 136; and SEQ ID NO: 137 which correspond to polynucleotides encoding the complementarity-determining regions (CDRs, or hypervariable regions) of the heavy chain variable sequence of SEQ ID NO: 123.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 130 encoding the light chain variable region of SEQ ID NO: 122; the polynucleotide SEQ ID NO: 131 encoding the heavy chain variable region of SEQ ID NO: 123; polynucleotides encoding the complementarity-determining regions (SEQ ID NO: 132; SEQ ID NO: 133; and SEQ ID NO: 134) of the light chain variable region of SEQ ID NO: 122; and polynucleotides encoding the complementarity-determining regions (SEQ ID NO: 135; SEQ ID NO: 136; and SEQ ID NO: 137) of the heavy chain variable region of SEQ ID NO: 123.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 138:

```
                                            (SEQ ID NO: 146)
ATGGACACGAGGGCCCCCACTCAGCTGCTGGGGCTCCTGCTGCTCTGGCT

CCCAGGTGCCACATTTGCAGCCGTGCTGACCCAGACACCATCGTCCGTGT

CTGCAGCTGTGGGAGGCACAGTCAGCATCAGTTGCCAGTCCAGTCAGAGT

GTTTATAGTAATAAGTACCTAGCCTGGTATCAGCAGAAACCAGGGCAGCC

TCCCAAGCTCCTGATCTACTGGACATCCAAACTGGCATCTGGGGCCCCAT

CACGGTTCAGCGGCAGTGGATCTGGGACACAATTCACTCTCACCATCAGC

GGCGTGCAGTGTGACGATGCTGCCACTTACTACTGTCTAGGCGCTTATGA

TGATGATGCTGATAATGCT
```

In another embodiment of the invention, polynucleotides of the invention comprise, or alternatively consist of, the following polynucleotide sequence encoding the variable heavy chain polypeptide sequence of SEQ ID NO: 139:

```
                                            (SEQ ID NO: 147)
ATGGAGACTGGGCTGCGCTGGCTTCTCCTGGTCGCTGTGCTCAAAGGTGT

CCAGTGTCAGTCGGTGGAAGAGTCCGGGGGTCGCCTGGTCAAGCCTGACG

AAACCCTGACACTCACCTGCACAGCCTCTGGATTCTCCCTGGAGGGCGGC

TACATGACCTGGGTCCGCCAGGCTCCAGGGAAGGGGCTGGAATGGATCGG

AATCAGTTATGATAGTGGTAGCACATACTACGCGAGCTGGGCGAAAGGCC

GATTCACCATCTCCAAGACCTCGTCGACCACGGTGGATCTGAAAATGACC
```

-continued
```
AGTCTGACAACCGAGGACACGGCCACCTATTTCTGCGTCAGATCACTAAA

ATATCCTACTGTTACTTCTGATGACTTG.
```

In a further embodiment of the invention, polynucleotides encoding fragments of the antibody having binding specificity to IL-6 comprise, or alternatively consist of, one or more of the polynucleotide sequences of SEQ ID NO: 148; SEQ ID NO: 149; and SEQ ID NO: 150 which correspond to polynucleotides encoding the complementarity-determining regions (CDRs, or hypervariable regions) of the light chain variable sequence of SEQ ID NO: 138.

In a further embodiment of the invention, polynucleotides encoding fragments of the antibody having binding specificity to IL-6 comprise, or alternatively consist of, one or more of the polynucleotide sequences of SEQ ID NO: 151; SEQ ID NO: 152; and SEQ ID NO: 153 which correspond to polynucleotides encoding the complementarity-determining regions (CDRs, or hypervariable regions) of the heavy chain variable sequence of SEQ ID NO: 139.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 146 encoding the light chain variable region of SEQ ID NO: 138; the polynucleotide SEQ ID NO: 147 encoding the heavy chain variable region of SEQ ID NO: 139; polynucleotides encoding the complementarity-determining regions (SEQ ID NO: 148; SEQ ID NO: 149; and SEQ ID NO: 150) of the light chain variable region of SEQ ID NO: 138; and polynucleotides encoding the complementarity-determining regions (SEQ ID NO: 151; SEQ ID NO: 152; and SEQ ID NO: 153) of the heavy chain variable region of SEQ ID NO: 139.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 154:

```
                                            (SEQ ID NO: 162)
ATGGACACGAGGGCCCCCACTCAGCTGCTGGGGCTCCTGCTGCTCTGGCT

CCCAGGTGCCACATTTGCAGCCGTGCTGACCCAGACACCATCACCCGTGT

CTGCAGCTGTGGGAGGCACAGTCACCATCAGTTGCCAGTCCAGTCAGAGT

GTTTATAATAATAACGACTTAGCCTGGTATCAGCAGAAACCAGGGCAGCC

TCCTAAACTCCTGATCTATTATGCATCCACTCTGGCATCTGGGGTCCCAT

CGCGGTTCAAAGGCAGTGGATCTGGGACACAGTTCACTCTCACCATCAGC

GGCGTGCAGTGTGACGATGCTGCCGCTTACTACTGTCTAGGCGGTTATGA

TGATGATGCTGATAATGCT
```

In another embodiment of the invention, polynucleotides of the invention comprise, or alternatively consist of, the following polynucleotide sequence encoding the variable heavy chain polypeptide sequence of SEQ ID NO: 155:

(SEQ ID NO: 163)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTATCTGGATTATCCCTCAGTAGCAAT

ACAATAAACTGGGTCCGCCAGGCTCCAGGGAAGGGGCTGGAGTGGATCGG

ATACATTTGGAGTGGTGGTAGTACATACTACGCGAGCTGGGTGAATGGTC

GATTCACCATCTCCAAAACCTCGACCACGGTGGATCTGAAAATCACCAGT

CCGACAACCGAGGACACGGCCACCTATTTCTGTGCCAGAGGGGGTTACGC

TAGTGGTGGTTATCCTTATGCCACTCGGTTGGATCTC.

In a further embodiment of the invention, polynucleotides encoding fragments of the antibody having binding specificity to IL-6 comprise, or alternatively consist of, one or more of the polynucleotide sequences of SEQ ID NO: 164; SEQ ID NO: 165; and SEQ ID NO: 166 which correspond to polynucleotides encoding the complementarity-determining regions (CDRs, or hypervariable regions) of the light chain variable sequence of SEQ ID NO: 154.

In a further embodiment of the invention, polynucleotides encoding fragments of the antibody having binding specificity to IL-6 comprise, or alternatively consist of, one or more of the polynucleotide sequences of SEQ ID NO: 167; SEQ ID NO: 168; and SEQ ID NO: 169 which correspond to polynucleotides encoding the complementarity-determining regions (CDRs, or hypervariable regions) of the heavy chain variable sequence of SEQ ID NO: 155.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 162 encoding the light chain variable region of SEQ ID NO: 154; the polynucleotide SEQ ID NO: 163 encoding the heavy chain variable region of SEQ ID NO: 155; polynucleotides encoding the complementarity-determining regions (SEQ ID NO: 164; SEQ ID NO: 165; and SEQ ID NO: 166) of the light chain variable region of SEQ ID NO: 154; and polynucleotides encoding the complementarity-determining regions (SEQ ID NO: 167; SEQ ID NO: 168; and SEQ ID NO: 169) of the heavy chain variable region of SEQ ID NO: 155.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 170:

(SEQ ID NO: 178)
ATGGACACGAGGGCCCCCACTCAGCTGCTGGGGCTCCTGCTGCTCTGGCT

CCCAGGTGCCACATTTGCAGCCGTGCTGACCCAGACACCATCCTCCGTGT

CTGCAGCTGTGGGAGGCACAGTCACCATCAATTGCCAGTCCAGTCAGAGT

GTTTATAATAACGACTACTTATCCTGGTATCAACAGAGGCCAGGGCAACG

TCCCAAGCTCCTAATCTATGGTGCTTCCAAACTGGCATCTGGGGTCCCGT

CACGGTTCAAAGGCAGTGGATCTGGGAAACAGTTTACTCTCACCATCAGC

GGCGTGCAGTGTGACGATGCTGCCACTTACTACTGTCTGGGCGATTATGA

TGATGATGCTGATAATACT

In another embodiment of the invention, polynucleotides of the invention comprise, or alternatively consist of, the following polynucleotide sequence encoding the variable heavy chain polypeptide sequence of SEQ ID NO: 171:

(SEQ ID NO: 179)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCACGCCTGGGA

CACCCCTGACACTCACTTGCACAGTCTCTGGATTCACCCTCAGTACCAAC

TACTACCTGAGCTGGGTCCGCCAGGCTCCAGGGAAGGGGCTAGAATGGAT

CGGAATCATTTATCCTAGTGGTAACACATATTGCGCGAAGTGGGCGAAAG

GCCGATTCACCATCTCCAAAACCTCGTCGACCACGGTGGATCTGAAAATG

ACCAGTCCGACAACCGAGGACACAGCCACGTATTTCTGTGCCAGAAATTA

TGGTGGTGATGAAAGTTTG.

In a further embodiment of the invention, polynucleotides encoding fragments of the antibody having binding specificity to IL-6 comprise, or alternatively consist of, one or more of the polynucleotide sequences of SEQ ID NO: 180; SEQ ID NO: 181; and SEQ ID NO: 182 which correspond to polynucleotides encoding the complementarity-determining regions (CDRs, or hypervariable regions) of the light chain variable sequence of SEQ ID NO: 170.

In a further embodiment of the invention, polynucleotides encoding fragments of the antibody having binding specificity to IL-6 comprise, or alternatively consist of, one or more of the polynucleotide sequences of SEQ ID NO: 183; SEQ ID NO: 184; and SEQ ID NO: 185 which correspond to polynucleotides encoding the complementarity-determining regions (CDRs, or hypervariable regions) of the heavy chain variable sequence of SEQ ID NO: 171.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 178 encoding the light chain variable region of SEQ ID NO: 170; the polynucleotide SEQ ID NO: 179 encoding the heavy chain variable region of SEQ ID NO: 171; polynucleotides encoding the complementarity-determining regions (SEQ ID NO: 180; SEQ ID NO: 181; and SEQ ID NO: 182) of the light chain variable region of SEQ ID NO: 170; and polynucleotides encoding the complementarity-determining regions (SEQ ID NO: 183; SEQ ID NO: 184; and SEQ ID NO: 185) of the heavy chain variable region of SEQ ID NO: 171.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 186:

(SEQ ID NO: 194)
ATGGACACGAGGGCCCCCACTCAGCTGCTGGGGCTCCTGCTGCTCTGGCT

CCCAGGTGCCAGATGTGATGTTGTGATGACCCAGACTCCAGCCTCCGTGG

AGGCAGCTGTGGGAGGCACAGTCACCATCAAGTGCCAGGCCAGTGAGACC

ATTGGCAATGCATTAGCCTGGTATCAGCAGAAATCAGGGCAGCCTCCCAA

GCTCCTGATCTACAAGGCATCCAAACTGGCATCTGGGGTCCCATCGCGGT

TCAAAGGCAGTGGATCTGGGACAGAGTACACTCTCACCATCAGCGACCTG

GAGTGTGCCGATGCTGCCACTTACTACTGTCAATGGTGTTATTTTGGTGA

TAGTGTT

In another embodiment of the invention, polynucleotides of the invention comprise, or alternatively consist of, the following polynucleotide sequence encoding the variable heavy chain polypeptide sequence of SEQ ID NO: 187:

(SEQ ID NO: 195)
ATGGAGACTGGGCTGCGCTGGCTTCTCCTGGTCACTGTGCTCAAAGGTGT

CCAGTGTCAGGAGCAGCTGGTGGAGTCCGGGGGAGGCCTGGTCCAGCCTG

AGGGATCCCTGACACTCACCTGCACAGCCTCTGGATTCGACTTCAGTAGC

GGCTACTACATGTGCTGGGTCCGCCAGGCTCCAGGGAAGGGGCTGGAGTG

GATCGCGTGTATTTTCACTATTACTACTAACACTTACTACGCGAGCTGGG

CGAAAGGCCGATTCACCATCTCCAAGACCTCGTCGACCACGGTGACTCTG

CAAATGACCAGTCTGACAGCCGCGGACACGGCCACCTATCTCTGTGCGAG

AGGGATTTATTCTGATAATAATTATTATGCCTTG.

In a further embodiment of the invention, polynucleotides encoding fragments of the antibody having binding specificity to IL-6 comprise, or alternatively consist of, one or more of the polynucleotide sequences of SEQ ID NO: 196; SEQ ID NO: 197; and SEQ ID NO: 198 which correspond to polynucleotides encoding the complementarity-determining regions (CDRs, or hypervariable regions) of the light chain variable sequence of SEQ ID NO: 186.

In a further embodiment of the invention, polynucleotides encoding fragments of the antibody having binding specificity to IL-6 comprise, or alternatively consist of, one or more of the polynucleotide sequences of SEQ ID NO: 199; SEQ ID NO: 200; and SEQ ID NO: 201 which correspond to polynucleotides encoding the complementarity-determining regions (CDRs, or hypervariable regions) of the heavy chain variable sequence of SEQ ID NO: 187.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 194 encoding the light chain variable region of SEQ ID NO: 186; the polynucleotide SEQ ID NO: 195 encoding the heavy chain variable region of SEQ ID NO: 187; polynucleotides encoding the complementarity-determining regions (SEQ ID NO: 196; SEQ ID NO: 197; and SEQ ID NO: 198) of the light chain variable region of SEQ ID NO: 186; and polynucleotides encoding the complementarity-determining regions (SEQ ID NO: 199; SEQ ID NO: 200; and SEQ ID NO: 201) of the heavy chain variable region of SEQ ID NO: 187.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 202:

(SEQ ID NO: 210)
ATGGACACGAGGGCCCCCACTCAGCTGCTGGGGCTCCTGCTGCTCTGGCT

CCCAGGTGCCAGATGTGATGTTGTGATGACCCAGACTCCAGCCTCCGTGG

AGGCAGCTGTGGGAGGCACAGTCACCATCAAGTGCCAGGCCAGTGAGAGC

ATTGGCAATGCATTAGCCTGGTATCAGCAGAAACCAGGGCAGCCTCCCAA

GCTCCTGATCTACAAGGCATCCACTCTGGCATCTGGGGTCCCATCGCGGT

TCAGCGGCAGTGGATCTGGGACAGAGTTCACTCTCACCATCAGCGGCGTG

CAGTGTGCCGATGCTGCCGCTTACTACTGTCAATGGTGTTATTTTGGTGA

TAGTGTT

In another embodiment of the invention, polynucleotides of the invention comprise, or alternatively consist of, the following polynucleotide sequence encoding the variable heavy chain polypeptide sequence of SEQ ID NO: 203:

(SEQ ID NO: 211)
ATGGAGACTGGGCTGCGCTGGCTTCTCCTGGTCGCTGTGCTCAAAGGTGT

CCAGTGTCAGCAGCAGCTGGTGGAGTCCGGGGGAGGCCTGGTCAAGCCGG

GGGCATCCCTGACACTCACCTGCAAAGCCTCTGGATTCTCCTTCAGTAGC

GGCTACTACATGTGCTGGGTCCGCCAGGCTCCAGGGAAGGGGCTGGAGTC

GATCGCATGCATTTTTACTATTACTGATAACACTTACTACGCGAACTGGG

CGAAAGGCCGATTCACCATCTCCAAGCCCTCGTCGCCCACGGTGACTCTG

CAAATGACCAGTCTGACAGCCGCGGACACGGCCACCTATTTCTGTGCGAG

GGGGATTTATTCTACTGATAATTATTATGCCTTG.

In a further embodiment of the invention, polynucleotides encoding fragments of the antibody having binding specificity to IL-6 comprise, or alternatively consist of, one or more of the polynucleotide sequences of SEQ ID NO: 212; SEQ ID NO: 213; and SEQ ID NO: 214 which correspond to polynucleotides encoding the complementarity-determining regions (CDRs, or hypervariable regions) of the light chain variable sequence of SEQ ID NO: 202.

In a further embodiment of the invention, polynucleotides encoding fragments of the antibody having binding specificity to IL-6 comprise, or alternatively consist of, one or more of the polynucleotide sequences of SEQ ID NO: 215; SEQ ID NO: 216; and SEQ ID NO: 217 which correspond to polynucleotides encoding the complementarity-determining regions (CDRs, or hypervariable regions) of the heavy chain variable sequence of SEQ ID NO: 203.

The invention also contemplates polynucleotide sequences including one or more of the polynucleotide sequences encoding antibody fragments described herein. In one embodiment of the invention, polynucleotides- encoding fragments of the antibody having binding specificity to IL-6 comprise, or alternatively consist of, one, two, three or more, including all of the following polynucleotides encoding antibody fragments: the polynucleotide SEQ ID NO: 210 encoding the light chain variable region of SEQ ID NO: 202;

the polynucleotide SEQ ID NO: 211 encoding the heavy chain variable region of SEQ ID NO: 203; polynucleotides encoding the complementarity-determining regions (SEQ ID NO: 212; SEQ ID NO: 213; and SEQ ID NO: 214) of the light chain variable region of SEQ ID NO: 202; and polynucleotides encoding the complementarity-determining regions (SEQ ID NO: 215; SEQ ID NO: 216; and SEQ ID NO: 217) of the heavy chain variable region of SEQ ID NO: 203.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 218:

(SEQ ID NO: 226)
ATGGACACGAGGGCCCCCACTCAGCTGCTGGGGCTCCTGCTGCTCTGGCT

CCCAGGTGCCAGATGTGATGTTGTGATGACCCAGACTCCAGCCTCCGTGG

AGGCAGCTGTGGGAGGCACAGTCACCATCAAGTGCCAGGCCAGTCAGAGC

GTTAGTAGCTACTTAAACTGGTATCAGCAGAAACCAGGGCAGCCTCCCAA

GCTCCTGATCTACAGGGCATCCACTCTGGAATCTGGGGTCCCATCGCGGT

TCAAAGGCAGTGGATCTGGGACAGAGTTCACTCTCACCATCAGCGACCTG

GAGTGTGCCGATGCTGCCACTTACTACTGTCAATGTACTTATGGTACTAG

TAGTAGTTATGGTGCTGCT

In another embodiment of the invention, polynucleotides of the invention comprise, or alternatively consist of, the following polynucleotide sequence encoding the variable heavy chain polypeptide sequence of SEQ ID NO: 219:

(SEQ ID NO: 227)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACCGTCTCTGGTATCTCCCTCAGTAGCAAT

GCAATAAGCTGGGTCCGCCAGGCTCCAGGGAAGGGGCTGGAATGGATCGG

AATCATTAGTTATAGTGGTACCACATACTACGCGAGCTGGGCGAAAGGCC

GATTCACCATCTCCAAAACCTCGTCGACCACGGTGGATCTGAAAATCACT

AGTCCGACAACCGAGGACACGGCCACCTACTTCTGTGCCAGAGATGACCC

TACGACAGTTATGGTTATGTTGATACCTTTTGGAGCCGGCATGGACCTC.

In a further embodiment of the invention, polynucleotides encoding fragments of the antibody having binding specificity to IL-6 comprise, or alternatively consist of, one or more of the polynucleotide sequences of SEQ ID NO: 228; SEQ ID NO: 229; and SEQ ID NO: 230 which correspond to polynucleotides encoding the complementarity-determining regions (CDRs, or hypervariable regions) of the light chain variable sequence of SEQ ID NO: 218.

In a further embodiment of the invention, polynucleotides encoding fragments of the antibody having binding specificity to IL-6 comprise, or alternatively consist of, one or more of the polynucleotide sequences of SEQ ID NO: 231; SEQ ID NO: 232; and SEQ ID NO: 233 which correspond to polynucleotides encoding the complementarity-determining regions (CDRs, or hypervariable regions) of the heavy chain variable sequence of SEQ ID NO: 219.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 226 encoding the light chain variable region of SEQ ID NO: 218; the polynucleotide SEQ ID NO: 227 encoding the heavy chain variable region of SEQ ID NO: 219; polynucleotides encoding the complementarity-determining regions (SEQ ID NO: 228; SEQ ID NO: 229; and SEQ ID NO: 230) of the light chain variable region of SEQ ID NO: 218; and polynucleotides encoding the complementarity-determining regions (SEQ ID NO: 231; SEQ ID NO: 232; and SEQ ID NO: 233) of the heavy chain variable region of SEQ ID NO: 219.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 234:

(SEQ ID NO: 242)
ATGGACACGAGGGCCCCCACTCAGCTGCTGGGGCTCCTGCTGCTCTGGCT

CCCAGGTGCCACATTTGCCCAAGTGCTGACCCAGACTGCATCGCCCGTGT

CTGCAGCTGTGGGAGGCACAGTCACCATCAACTGCCAGGCCAGTCAGAGT

GTTTATAAGAACAACTACTTATCCTGGTATCAGCAGAAACCAGGGCAGCC

TCCCAAAGGCCTGATCTATTCTGCATCGACTCTAGATTCTGGGGTCCCAT

TGCGGTTCAGCGGCAGTGGATCTGGGACACAGTTCACTCTCACCATCAGC

GACGTGCAGTGTGACGATGCTGCCACTTACTACTGTCTAGGCAGTTATGA

TTGTAGTAGTGGTGATTGTTATGCT

In another embodiment of the invention, polynucleotides of the invention comprise, or alternatively consist of, the following polynucleotide sequence encoding the variable heavy chain polypeptide sequence of SEQ ID NO: 235:

(SEQ ID NO: 243)
ATGGAGACTGGGCTGCGCTGGCTTCTCCTGGTCGCTGTGCTCAAAGGTGT

CCAGTGTCAGTCGTTGGAGGAGTCCGGGGGAGACCTGGTCAAGCCTGAGG

GATCCCTGACACTCACCTGCACAGCCTCTGGATTCTCCTTCAGTAGCTAC

TGGATGTGCTGGGTCCGCCAGGCTCCAGGGAAGGGGCTGGAGTGGATCGC

ATGCATTGTTACTGGTAATGGTAACACTTACTACGCGAACTGGGCGAAAG

GCCGATTCACCATCTCCAAAACCTCGTCGACCACGGTGACTCTGCAAATG

ACCAGTCTGACAGCCGCGGACACGGCCACCTATTTTTGTGCGAAAGCCTA

TGACTTG.

In a further embodiment of the invention, polynucleotides encoding fragments of the antibody having binding specificity to IL-6 comprise, or alternatively consist of, one or more of the polynucleotide sequences of SEQ ID NO: 244; SEQ ID NO: 245; and SEQ ID NO: 246 which correspond to polynucleotides encoding the complementarity-determining regions (CDRs, or hypervariable regions) of the light chain variable sequence of SEQ ID NO: 234.

In a further embodiment of the invention, polynucleotides encoding fragments of the antibody having binding specificity to IL-6 comprise, or alternatively consist of, one or more of the polynucleotide sequences of SEQ ID NO: 247; SEQ ID NO: 248; and SEQ ID NO: 249 which correspond to polynucleotides encoding the complementarity-determining regions (CDRs, or hypervariable regions) of the heavy chain variable sequence of SEQ ID NO: 235.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 242 encoding the light chain variable region of SEQ ID NO: 234; the polynucleotide SEQ ID NO: 243 encoding the heavy chain variable region of SEQ ID NO: 235; polynucleotides encoding the complementarity-determining regions (SEQ ID NO: 244; SEQ ID NO: 245; and SEQ ID NO: 246) of the light chain variable region of SEQ ID NO: 234; and polynucleotides encoding the complementarity-determining regions (SEQ ID NO: 247; SEQ ID NO: 248; and SEQ ID NO: 249) of the heavy chain variable region of SEQ ID NO: 235.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 250:

```
                                        (SEQ ID NO: 258)
ATGGACACGAGGGCCCCCACTCAGCTGCTGGGGCTCCTGCTGCTCTGGCT

CCCAGGTTCCACATTTGCCGCCGTGCTGACCCAGACTCCATCTCCCGTGT

CTGCAGCTGTGGGAGGCACAGTCAGCATCAGTTGCCAGGCCAGTCAGAGT

GTTTATGACAACAACTATTTATCCTGGTATCAGCAGAAACCAGGACAGCC

TCCCAAGCTCCTGATCTATGGTGCATCCACTCTGGCATCTGGGGTCCCAT

CGCGGTTCAAAGGCACGGGATCTGGGACACAGTTCACTCTCACCATCACA

GACGTGCAGTGTGACGATGCTGCCACTTACTATTGTGCAGGCGTTTTTAA

TGATGATAGTGATGATGCC
```

In another embodiment of the invention, polynucleotides of the invention comprise, or alternatively consist of, the following polynucleotide sequence encoding the variable heavy chain polypeptide sequence of SEQ ID NO: 251:

```
                                        (SEQ ID NO: 259)
ATGGAGACTGGGCTGCGCTGGCTTCTCCTGGTCGCTGTGCCCAAAGGTGT

CCAGTGTCAGTCGCTGGAGGAGTCCGGGGGTCGCCTGGTCACGCCTGGGA

CACCCCTGACACTCACCTGCACACTCTCTGGATTCTCCCTCAGTGCATAC

TATATGAGCTGGGTCCGCCAGGCTCCAGGGAAGGGGCTGGAATGGATCGG

ATTCATTACTCTGAGTGATCATATATCTTACGCGAGGTGGGCGAAAGGCC

GATTCACCATCTCCAAAACCTCGACCACGGTGGATCTGAAAATGACCAGT
```

CCGACAACCGAGGACACGGCCACCTATTTCTGTGCCAGGAGTCGTGGCTG

GGGTGCAATGGGTCGGTTGGATCTC.

In a further embodiment of the invention, polynucleotides encoding fragments of the antibody having binding specificity to IL-6 comprise, or alternatively consist of, one or more of the polynucleotide sequences of SEQ ID NO: 260; SEQ ID NO: 261; and SEQ ID NO: 262 which correspond to polynucleotides encoding the complementarity-determining regions (CDRs, or hypervariable regions) of the light chain variable sequence of SEQ ID NO: 250.

In a further embodiment of the invention, polynucleotides encoding fragments of the antibody having binding specificity to IL-6 comprise, or alternatively consist of, one or more of the polynucleotide sequences of SEQ ID NO: 263; SEQ ID NO: 264; and SEQ ID NO: 265 which correspond to polynucleotides encoding the complementarity-determining regions (CDRs, or hypervariable regions) of the heavy chain variable sequence of SEQ ID NO: 251.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 258 encoding the light chain variable region of SEQ ID NO: 250; the polynucleotide SEQ ID NO: 259 encoding the heavy chain variable region of SEQ ID NO: 251; polynucleotides encoding the complementarity-determining regions (SEQ ID NO: 260; SEQ ID NO: 261; and SEQ ID NO: 262) of the light chain variable region of SEQ ID NO: 250; and polynucleotides encoding the complementarity-determining regions (SEQ ID NO: 263; SEQ ID NO: 264; and SEQ ID NO: 265) of the heavy chain variable region of SEQ ID NO: 251.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 266:

```
                                        (SEQ ID NO: 274)
ATGGACACGAGGGCCCCCACTCAGCTGCTGGGGCTCCTGCTGCTCTGGCT

CCCAGGTGCCACATTCGCAGCCGTGCTGACCCAGACACCATCGCCCGTGT

CTGCGGCTGTGGGAGGCACAGTCACCATCAGTTGCCAGGCCAGTCAGAGT

GTTTATAACAACAAAAATTTAGCCTGGTATCAGCAGAAATCAGGGCAGCC

TCCCAAGCTCCTGATCTACTGGGCATCCACTCTGGCATCTGGGGTCTCAT

CGCGGTTCAGCGGCAGTGGATCTGGGACACAGTTCACTCTCACCGTCAGC

GGCGTGCAGTGTGACGATGCTGCCACTTACTACTGTCTAGGCGTTTTTGA

TGATGATGCTGATAATGCT
```

In another embodiment of the invention, polynucleotides of the invention comprise, or alternatively consist of, the following polynucleotide sequence encoding the variable heavy chain polypeptide sequence of SEQ ID NO: 267:

(SEQ ID NO: 275)
ATGGAGACTGGGCTGCGCTGGCTTCTCCTGGTCGCTGTGCTCAAAGGTGT

CCAATGTCAGTCGGTGGAGGAGTCCGGGGGTCGCCTGGTCACGCCTGGGA

CACCCCTGACACTCACCTGCACAGCCTCTGGATTCTCCCTCAGTAGCTAC

TCCATGACCTGGGTCCGCCAGGCTCCAGGGAAGGGGCTGGAATATATCGG

AGTCATTGGTACTAGTGGTAGCACATACTACGCGACCTGGGCGAAAGGCC

GATTCACCATCTCCAGAACCTCGACCACGGTGGCTCTGAAAATCACCAGT

CCGACAACCGAGGACACGGCCACCTATTTCTGTGTCAGGAGTCTTTCTTC

TATTACTTTCTTG.

In a further embodiment of the invention, polynucleotides encoding fragments of the antibody having binding specificity to IL-6 comprise, or alternatively consist of, one or more of the polynucleotide sequences of SEQ ID NO: 276; SEQ ID NO: 277; and SEQ ID NO: 278 which correspond to polynucleotides encoding the complementarity-determining regions (CDRs, or hypervariable regions) of the light chain variable sequence of SEQ ID NO: 266.

In a further embodiment of the invention, polynucleotides encoding fragments of the antibody having binding specificity to IL-6 comprise, or alternatively consist of, one or more of the polynucleotide sequences of SEQ ID NO: 279; SEQ ID NO: 280; and SEQ ID NO: 281 which correspond to polynucleotides encoding the complementarity-determining regions (CDRs, or hypervariable regions) of the heavy chain variable sequence of SEQ ID NO: 267.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 274 encoding the light chain variable region of SEQ ID NO: 266; the polynucleotide SEQ ID NO: 275 encoding the heavy chain variable region of SEQ ID NO: 267; polynucleotides encoding the complementarity-determining regions (SEQ ID NO: 276; SEQ ID NO: 277; and SEQ ID NO: 278) of the light chain variable region of SEQ ID NO: 266; and polynucleotides encoding the complementarity-determining regions (SEQ ID NO: 279; SEQ ID NO: 280; and SEQ ID NO: 281) of the heavy chain variable region of SEQ ID NO: 267.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 282:

(SEQ ID NO: 290)
ATGGACACGAGGGCCCCCACTCAGCTGCTGGGGCTCCTGCTGCTCTGGCT

CCCAGGTGCCAGATGTGCATTCGAATTGACCCAGACTCCAGCCTCCGTGG

AGGCAGCTGTGGGAGGCACAGTCACCATCAATTGCCAGGCCAGTCAGAAC

ATTTATAGATACTTAGCCTGGTATCAGCAGAAACCAGGGCAGCCTCCCAA

GTTCCTGATCTATCTGGCATCTACTCTGGCATCTGGGGTCCCATCGCGGT

TTAAAGGCAGTGGATCTGGGACAGAGTTCACTCTCACCATCAGCGACCTG

GAGTGTGCCGATGCTGCCACTTACTACTGTCAAAGTTATTATAGTAGTAA

TAGTGTCGCT

In another embodiment of the invention, polynucleotides of the invention comprise, or alternatively consist of, the following polynucleotide sequence encoding the variable heavy chain polypeptide sequence of SEQ ID NO: 283:

(SEQ ID NO: 291)
ATGGAGACTGGGCTGCGCTGGCTTCTCCTGGTCGCTGTGCTCAAAGGTGT

CCAGTGTCAGGAGCAGCTGGTGGAGTCCGGGGGAGACCTGGTCCAGCCTG

AGGGATCCCTGACACTCACCTGCACAGCTTCTGAGTTAGACTTCAGTAGC

GGCTACTGGATATGCTGGGTCCGCCAGGTTCCAGGGAAGGGGCTGGAGTG

GATCGGATGCATTTATACTGGTAGTAGTGGTAGCACTTTTTACGCGAGTT

GGGCGAAAGGCCGATTCACCATCTCCAAAACCTCGTCGACCACGGTGACT

CTGCAAATGACCAGTCTGACAGCCGCGGACACGGCCACCTATTTCTGTGC

GAGAGGTTATAGTGGCTTTGGTTACTTTAAGTTG.

In a further embodiment of the invention, polynucleotides encoding fragments of the antibody having binding specificity to IL-6 comprise, or alternatively consist of, one or more of the polynucleotide sequences of SEQ ID NO: 292; SEQ ID NO: 293; and SEQ ID NO: 294 which correspond to polynucleotides encoding the complementarity-determining regions (CDRs, or hypervariable regions) of the light chain variable sequence of SEQ ID NO: 282.

In a further embodiment of the invention, polynucleotides encoding fragments of the antibody having binding specificity to IL-6 comprise, or alternatively consist of, one or more of the polynucleotide sequences of SEQ ID NO: 295; SEQ ID NO: 296; and SEQ ID NO: 297 which correspond to polynucleotides encoding the complementarity-determining regions (CDRs, or hypervariable regions) of the heavy chain variable sequence of SEQ ID NO: 283.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 290 encoding the light chain variable region of SEQ ID NO: 282; the polynucleotide SEQ ID NO: 291 encoding the heavy chain variable region of SEQ ID NO: 283; polynucleotides encoding the complementarity-determining regions (SEQ ID NO: 292; SEQ ID NO: 293; and SEQ ID NO: 294) of the light chain variable region of SEQ ID NO: 282; and polynucleotides encoding the complementarity-determining regions (SEQ ID NO: 295; SEQ ID NO: 296; and SEQ ID NO: 297) of the heavy chain variable region of SEQ ID NO: 283.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 298:

(SEQ ID NO: 306)
ATGGACACGAGGGCCCCCACTCAGCTGCTGGGGCTCCTGCTGCTCTGGCT

CCCAGGTGCCAGATGTGCCTATGATATGACCCAGACTCCAGCCTCTGTGG

AGGTAGCTGTGGGAGGCACAGTCACCATCAAGTGCCAGGCCAGTGAGGAC

ATTTATAGGTTATTGGCCTGGTATCAACAGAAACCAGGGCAGCCTCCCAA

GCTCCTGATCTATGATTCATCCGATCTGGCATCTGGGGTCCCATCGCGGT

TCAAAGGCAGTGGATCTGGGACAGAGTTCACTCTCGCCATCAGCGGTGTG

CAGTGTGACGATGCTGCCACTTACTACTGTCAACAGGCTTGGAGTTATAG

TGATATTGATAATGCT

In another embodiment of the invention, polynucleotides of the invention comprise, or alternatively consist of, the following polynucleotide sequence encoding the variable heavy chain polypeptide-sequence of SEQ ID NO: 299:

(SEQ ID NO: 307)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCGGGGA

CACCCCTGACACTCACCTGCACAGCCTCTGGATTCTCCCTCAGTAGCTAC

TACATGAGCTGGGTCCGCCAGGCTCCAGGGAAGGGGCTGGAATGGATCGG

AATCATTACTACTAGTGGTAATACATTTTACGCGAGCTGGGCGAAAGGCC

GGCTCACCATCTCCAGAACCTCGACCACGGTGGATCTGAAAATCACCAGT

CCGACAACCGAGGACACGGCCACCTATTTCTGTGCCAGAACTTCTGATAT

TTTTTATTATCGTAACTTG.

In a further embodiment of the invention, polynucleotides encoding fragments of the antibody having binding specificity to IL-6 comprise, or alternatively consist of, one or more of the polynucleotide sequences of SEQ ID NO: 308; SEQ ID NO: 309; and SEQ ID NO: 310 which correspond to polynucleotides encoding the complementarity-determining regions (CDRs, or hypervariable regions) of the light chain variable sequence of SEQ ID NO: 298.

In a further embodiment of the invention, polynucleotides encoding fragments of the antibody having binding specificity to IL-6 comprise, or alternatively consist of, one or more of the polynucleotide sequences of SEQ ID NO: 311; SEQ ID NO: 312; and SEQ ID NO: 313 which correspond to polynucleotides encoding the complementarity-determining regions (CDRs, or hypervariable regions) of the heavy chain variable sequence of SEQ ID NO: 299.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 306 encoding the light chain variable region of SEQ ID NO: 298; the polynucleotide SEQ ID NO: 307 encoding the heavy chain variable region of SEQ ID NO: 299; polynucleotides encoding the complementarity-determining regions (SEQ ID NO: 308; SEQ ID NO: 309; and SEQ ID NO: 310) of the light chain variable region of SEQ ID NO: 298; and polynucleotides encoding the complementarity-determining regions (SEQ ID NO: 311; SEQ ID NO: 312; and SEQ ID NO: 313) of the heavy chain variable region of SEQ ID NO: 299.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 314:

(SEQ ID NO: 322)
ATGGACACGAGGGCCCCCACTCAGCTGCTGGGGCTCCTGCTGCTCTGGCT

CCCAGGTGCCACGTTTGCAGCCGTGCTGACCCAGACTGCATCACCCGTGT

CTGCCGCTGTGGGAGCCACAGTCACCATCAACTGCCAGTCCAGTCAGAGT

GTTTATAATGACATGGACTTAGCCTGGTTTCAGCAGAAACCAGGGCAGCC

TCCCAAGCTCCTGATCTATTCTGCATCCACTCTGGCATCTGGGGTCCCAT

CGCGGTTCAGCGGCAGTGGATCTGGGACAGAGTTCACTCTCACCATCAGC

GGCGTGCAGTGTGACGATGCTGCCACTTACTACTGTCTAGGCGCTTTTGA

TGATGATGCTGATAATACT

In another embodiment of the invention, polynucleotides of the invention comprise, or alternatively consist of, the following polynucleotide sequence encoding the variable heavy chain polypeptide sequence of SEQ ID NO: 315:

(SEQ ID NO: 323)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGATTCTCCCTCACTAGGCAT

GCAATAACCTGGGTCCGCCAGGCTCCAGGGAAGGGGCTGGAATGGATCGG

ATGCATTTGGAGTGGTGGTAGCACATACTACGCGACCTGGGCGAAAGGCC

GATTCACCATCTCCAAAACCTCGACCACGGTGGATCTCAGAATCACCAGT

CCGACAACCGAGGACACGGCCACCTACTTCTGTGCCAGAGTCATTGGCGA

TACTGCTGGTTATGCTTATTTTACGGGGCTTGACTTG.

In a further embodiment of the invention, polynucleotides encoding fragments of the antibody having binding specificity to IL-6 comprise, or alternatively consist of, one or more of the polynucleotide sequences of SEQ ID NO: 324; SEQ ID NO: 325; and SEQ ID NO: 326 which correspond to polynucleotides encoding the complementarity-determining regions (CDRs, or hypervariable regions) of the light chain variable sequence of SEQ ID NO: 314.

In a further embodiment of the invention, polynucleotides encoding fragments of the antibody having binding specificity to IL-6 comprise, or alternatively consist of, one or more of the polynucleotide sequences of SEQ ID NO: 327; SEQ ID NO: 328; and SEQ ID NO: 329 which correspond to polynucleotides encoding the complementarity-determining regions (CDRs, or hypervariable regions) of the heavy chain variable sequence of SEQ ID NO: 315.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 322 encoding the light chain variable region of SEQ ID NO: 314;

the polynucleotide SEQ ID NO: 323 encoding the heavy chain variable region of SEQ ID NO: 315; polynucleotides encoding the complementarity-determining regions (SEQ ID NO: 324; SEQ ID NO: 325; and SEQ ID NO: 326) of the light chain variable region of SEQ ID NO: 314; and polynucleotides encoding the complementarity-determining regions (SEQ ID NO: 327; SEQ ID NO: 328; and SEQ ID NO: 329) of the heavy chain variable region of SEQ ID NO: 315.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 330:

(SEQ ID NO: 338)
ATGGACACGAGGGCCCCCACTCAGCTGCTGGGGCTCCTGCTGCTCTGGCT

CCCAGGTGCCAGATGTGCCTATGATATGACCCAGACTCCAGCCTCTGTGG

AGGTAGCTGTGGGAGGCACAGTCACCATCAAGTGCCAGGCCAGTCAGAGT

GTTTATAATTGGTTATCCTGGTATCAGCAGAAACCAGGGCAGCCTCCCAA

GCTCCTGATCTATACTGCATCCAGTCTGGCATCTGGGGTCCCATCGCGGT

TCAGTGGCAGTGGATCTGGGACAGAGTTCACTCTCACCATCAGCGGCGTG

GAGTGTGCCGATGCTGCCACTTACTACTGTCAACAGGGTTATACTAGTGA

TGTTGATAATGTT

In another embodiment of the invention, polynucleotides of the invention comprise, or alternatively consist of, the following polynucleotide sequence encoding the variable heavy chain polypeptide sequence of SEQ ID NO: 331:

(SEQ ID NO: 339)
ATGGAGACTGGGCTGCGCTGGCTTCTCCTGGTCGCTGTGCTCAAAGGTGT

CCAGTGTCAGTCGCTGGAGGAGGCCGGGGGTCGCCTGGTCACGCCTGGGA

CACCCCTGACACTCACCTGCACAGTCTCTGGAATCGACCTCAGTAGCTAT

GCAATGGGCTGGGTCCGCCAGGCTCCAGGGAAGGGGCTGGAATACATCGG

AATCATTAGTAGTAGTGGTAGCACATACTACGCGACCTGGGCGAAAGGCC

GATTCACCATCTCACAAGCCTCGTCGACCACGGTGGATCTGAAAATTACC

AGTCCGACAACCGAGGACTCGGCCACATATTTCTGTGCCAGAGGGGTGC

TGGTAGTGGTGGTGTTTGGCTGCTTGATGGTTTTGATCCC.

In a further embodiment of the invention, polynucleotides encoding fragments of the antibody having binding specificity to IL-6 comprise, or alternatively consist of, one or more of the polynucleotide sequences of SEQ ID NO: 340; SEQ ID NO: 341; and SEQ ID NO: 342 which correspond to polynucleotides encoding the complementarity-determining regions (CDRs, or hypervariable regions) of the light chain variable sequence of SEQ ID NO: 330.

In a further embodiment of the invention, polynucleotides encoding fragments of the antibody having binding specificity to IL-6 comprise, or alternatively consist of, one or more of the polynucleotide sequences of SEQ ID NO: 343; SEQ ID NO: 344; and SEQ ID NO: 345 which correspond to polynucleotides encoding the complementarity-determining regions (CDRs, or hypervariable regions) of the heavy chain variable sequence of SEQ ID NO: 331.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 338 encoding the light chain variable region of SEQ ID NO: 330; the polynucleotide SEQ ID NO: 339 encoding the heavy chain variable region of SEQ ID NO: 331; polynucleotides encoding the complementarity-determining regions (SEQ ID NO: 340; SEQ ID NO: 341; and SEQ ID NO: 342) of the light chain variable region of SEQ ID NO: 330; and polynucleotides encoding the complementarity-determining regions (SEQ ID NO: 343; SEQ ID NO: 344; and SEQ ID NO: 345) of the heavy chain variable region of SEQ ID NO: 331.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 346:

(SEQ ID NO: 354)
ATGGACACGAGGGCCCCCACTCAGCTGCTGGGGCTCCTGCTGCTCTGGCT

CCCAGGTGCCAAATGTGCCGATGTTGTGATGACCCAGACTCCAGCCTCCG

TGTCTGCAGCTGTGGGAGGCACAGTCACCATCAATTGCCAGGCCAGTGAG

AACATTTATAATTGGTTAGCCTGGTATCAGCAGAAACCAGGGCAGCCTCC

CAAGCTCCTGATCTATACTGTAGGCGATCTGGCATCTGGGGTCTCATCGC

GGTTCAAAGGCAGTGGATCTGGGACAGAGTTCACTCTCACCATCAGCGAC

CTGGAGTGTGCCGATGCTGCCACTTACTATTGTCAACAGGGTTATAGTAG

TAGTTATGTTGATAATGTT

In another embodiment of the invention, polynucleotides of the invention comprise, or alternatively consist of, the following polynucleotide sequence encoding the variable heavy chain polypeptide sequence of SEQ ID NO: 347:

(SEQ ID NO: 355)
ATGGAGACTGGGCTGCGCTGGCTTCTCCTGGTCGCTGTGCTCAAAGGTGT

CCAGTGTCAGGAGCAGCTGAAGGAGTCCGGGGGTCGCCTGGTCACGCCTG

GGACACCCCTGACACTCACCTGCACAGTCTCTGGATTCTCCCTCAATGAC

TATGCAGTGGGCTGGTTCCGCCAGGCTCCAGGGAAGGGGCTGGAATGGAT

CGGATACATTCGTAGTAGTGGTACCACAGCCTACGCGACCTGGGCGAAAG

GCCGATTCACCATCTCCGCTACCTCGACCACGGTGGATCTGAAAATCACC

AGTCCGACAACCGAGGACACGGCCACCTATTTCTGTGCCAGAGGGGGTGC

TGGTAGTAGTGGTGTGTGGATCCTTGATGGTTTTGCTCCC.

In a further embodiment of the invention, polynucleotides encoding fragments of the antibody having binding specificity to IL-6 comprise, or alternatively consist of, one or more of the polynucleotide sequences of SEQ ID NO: 356; SEQ ID NO: 357; and SEQ ID NO: 358 which correspond to polynucleotides encoding the complementarity-determining regions (CDRs, or hypervariable regions) of the light chain variable sequence of SEQ ID NO: 346.

In a further embodiment of the invention, polynucleotides encoding fragments of the antibody having binding specificity to IL-6 comprise, or alternatively consist of, one or more of the polynucleotide sequences of SEQ ID NO: 359; SEQ ID NO: 360; and SEQ ID NO: 361 which correspond to polynucleotides encoding the complementarity-determining regions (CDRs, or hypervariable regions) of the heavy chain variable sequence of SEQ ID NO: 347.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 354 encoding the light chain variable region of SEQ ID NO: 346; the polynucleotide SEQ ID NO: 355 encoding the heavy chain variable region of SEQ ID NO: 347; polynucleotides encoding the complementarity-determining regions (SEQ ID NO: 356; SEQ ID NO: 357; and SEQ ID NO: 358) of the light chain variable region of SEQ ID NO: 346; and polynucleotides encoding the complementarity-determining regions (SEQ ID NO: 359; SEQ ID NO: 360; and SEQ ID NO: 361) of the heavy chain variable region of SEQ ID NO: 347.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 362:

```
                                       (SEQ ID NO: 370)
ATGGACACGAGGGCCCCCACTCAGCTGCTGGGGCTCCTGCTGCTCTGGCT

CCCAGGTGCCACATTTGCTCAAGTGCTGACCCAGACTCCATCCTCCGTGT

CTGCAGCTGTGGGAGGCACAGTCACCATCAATTGCCAGGCCAGTCAGAGT

GTTTATCAGAACAACTACTTATCCTGGTTTCAGCAGAAACCAGGGCAGCC

TCCCAAGCTCCTGATCTATGGTGCGGCCACTCTGGCATCTGGGGTCCCAT

CGCGGTTCAAAGGCAGTGGATCTGGGACACAGTTCACTCTCACCATCAGC

GACCTGGAGTGTGACGATGCTGCCACTTACTACTGTGCAGGCGCTTATAG

GGATGTGGATTCT
```

In another embodiment of the invention, polynucleotides of the invention comprise, or alternatively consist of, the following polynucleotide sequence encoding the variable heavy chain polypeptide sequence of SEQ ID NO: 363:

```
                                       (SEQ ID NO: 371)
ATGGAGACTGGGCTGCGCTGGCTTCTCCTGGTCGCTGTGCTCAAAGGTGT

CCAGTGTCAGTCGTTGGAGGAGTCCGGGGGAGACCTGGTCAAGCCTGGGG

CATCCCTGACACTCACCTGCACAGCCTCTGGATTCTCCTTTACTAGTACC

TACTACATCTACTGGGTCCGCCAGGCTCCAGGGAAGGGGCTGGAGTGGAT

CGCATGTATTGATGCTGGTAGTAGTGGTAGCACTTACTACGCGACCTGGG

TGAATGGCCGATTCACCATCTCCAAAACCTCGTCGACCACGGTGACTCTG
```

```
                                      -continued
CAAATGACCAGTCTGACAGCCGCGGACACGGCCACCTATTTCTGTGCGAA

ATGGGATTATGGTGGTAATGTTGGTTGGGGTTATGACTTG.
```

In a further embodiment of the invention, polynucleotides encoding fragments of the antibody having binding specificity to IL-6 comprise, or alternatively consist of, one or more of the polynucleotide sequences of SEQ ID NO: 372; SEQ ID NO: 373; and SEQ ID NO: 374 which correspond to polynucleotides encoding the complementarity-determining regions (CDRs, or hypervariable regions) of the light chain variable sequence of SEQ ID NO: 362.

In a further embodiment of the invention, polynucleotides encoding fragments of the antibody having binding specificity to IL-6 comprise, or alternatively consist of, one or more of the polynucleotide sequences of SEQ ID NO: 375; SEQ ID NO: 376; and SEQ ID NO: 377 which correspond to polynucleotides encoding the complementarity-determining regions (CDRs, or hypervariable regions) of the heavy chain variable sequence of SEQ ID NO: 363.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 370 encoding the light chain variable region of SEQ ID NO: 362; the polynucleotide SEQ ID NO: 371 encoding the heavy chain variable region of SEQ ID NO: 363; polynucleotides encoding the complementarity-determining regions (SEQ ID NO: 372; SEQ ID NO: 373; and SEQ ID NO: 374) of the light chain variable region of SEQ ID NO: 362; and polynucleotides encoding the complementarity-determining regions (SEQ ID NO: 375; SEQ ID NO: 376; and SEQ ID NO: 377) of the heavy chain variable region of SEQ ID NO: 363.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 378:

```
                                       (SEQ ID NO: 386)
ATGGACACGAGGGCCCCCACTCAGCTGCTGGGGCTCCTGCTGCTCTGGCT

CCCAGGTGCCAGATGTGCATTCGAATTGACCCAGACTCCATCCTCCGTGG

AGGCAGCTGTGGGAGGCACAGTCACCATCAAGTGCCAGGCCAGTCAGAGC

ATTAGTAGTTACTTAGCCTGGTATCAGCAGAAACCAGGGCAGCCTCCCAA

GTTCCTGATCTACAGGGCGTCCACTCTGGCATCTGGGGTCCCATCGCGAT

TCAAAGGCAGTGGATCTGGGACAGAGTTCACTCTCACCATCAGCGACCTG

GAGTGTGCCGATGCTGCCACTTACTACTGTCAAAGCTATTATGATAGTGT

TTCAAATCCT
```

In -another embodiment of the invention, polynucleotides of the invention comprise, or alternatively consist of, the following polynucleotide sequence encoding the variable heavy chain polypeptide sequence of SEQ ID NO: 379:

(SEQ ID NO: 387)
ATGGAGACTGGGCTGCGCTGGCTTCTCCTGGTCGCTGTGCTCAAAGGTGT

CCAGTGTCAGTCGTTGGAGGAGTCCGGGGGAGACCTGGTCAAGCCTGAGG

GATCCCTGACACTCACCTGCAAAGCCTCTGGACTCGACCTCGGTACCTAC

TGGTTCATGTGCTGGGTCCGCCAGGCTCCAGGGAAGGGGCTGGAGTGGAT

CGCTTGTATTTATACTGGTAGTAGTGGTTCCACTTTCTACGCGAGCTGGG

TGAATGGCCGATTCACCATCTCCAAAACCTCGTCGACCACGGTGACTCTG

CAAATGACCAGTCTGACAGCCGCGGACACGGCCACTTATTTTGTGCGAG

AGGTTATAGTGGTTATGGTTATTTTAAGTTG.

In a further embodiment of the invention, polynucleotides encoding fragments of the antibody having binding specificity to IL-6 comprise, or alternatively consist of, one or more of the polynucleotide sequences of SEQ ID NO: 388; SEQ ID NO: 389; and SEQ ID NO: 390 which correspond to polynucleotides encoding the complementarity-determining regions (CDRs, or hypervariable regions) of the light chain variable sequence of SEQ ID NO: 378.

In a further embodiment of the invention, polynucleotides encoding fragments of the antibody having binding specificity to IL-6 comprise, or alternatively consist of, one or more of the polynucleotide sequences of SEQ ID NO: 391; SEQ ID NO: 392; and SEQ ID NO: 393 which correspond to polynucleotides encoding the complementarity-determining regions (CDRs, or hypervariable regions) of the heavy chain variable sequence of SEQ ID NO: 379.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 386 encoding the light chain variable region of SEQ ID NO: 378; the polynucleotide SEQ ID NO: 387 encoding the heavy chain variable region of SEQ ID NO: 379; polynucleotides encoding the complementarity-determining regions (SEQ ID NO: 388; SEQ ID NO: 389; and SEQ ID NO: 390) of the light chain variable region of SEQ ID NO: 378; and polynucleotides encoding the complementarity-determining regions (SEQ ID NO: 391; SEQ ID NO: 392; and SEQ ID NO: 393) of the heavy chain variable region of SEQ ID NO: 379.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 394:

(SEQ ID NO: 402)
ATGGACACGAGGGCCCCCACTCAGCTGCTGGGGCTCCTGCTGCTCTGGCT

CCCAGGTGTCACATTTGCCATCGAAATGACCCAGAGTCCATTCTCCGTGT

CTGCAGCTGTGGGAGGCACAGTCAGCATCAGTTGCCAGGCCAGTCAGAGT

GTTTATAAGAACAACCAATTATCCTGGTATCAGCAGAAATCAGGGCAGCC

TCCCAAGCTCCTGATCTATGGTGCATCGGCTCTGGCATCTGGGGTCCCAT

CGCGGTTCAAAGGCAGTGGATCTGGGACAGAGTTCACTCTCACCATCAGC

GACGTGCAGTGTGACGATGCTGCCACTTACTACTGTGCAGGCGCTATTAC

TGGTAGTATTGATACGGATGGT

In another embodiment of the invention, polynucleotides of the invention comprise, or alternatively consist of, the following polynucleotide sequence encoding the variable heavy chain polypeptide sequence of SEQ ID NO: 395:

(SEQ ID NO: 403)
ATGGAGACTGGGCTGCGCTGGCTTCTCCTGGTCGCTGTGCTCAAAGGTGT

CCAGTGTCAGTCGTTGGAGGAGTCCGGGGGAGACCTGGTCAAGCCTGGGG

CATCCCTGACACTCACCTGCACAACTTCTGGATTCTCCTTCAGTAGCAGC

TACTTCATTTGCTGGGTCCGCCAGGCTCCAGGGAAGGGGCTGGAGTGGAT

CGCATGCATTTATGGTGGTGATGGCAGCACATACTACGCGAGCTGGGCGA

AAGGCCGATTCACCATCTCCAAAACCTCGTCGACCACGGTGACGCTGCAA

ATGACCAGTCTGACAGCCGCGGACACGGCCACCTATTTCTGTGCGAGAGA

ATGGGCATATAGTCAAGGTTATTTTGGTGCTTTTGATCTC.

In a further embodiment of the invention, polynucleotides encoding fragments of the antibody having binding specificity to IL-6 comprise, or alternatively consist of, one or more of the polynucleotide sequences of SEQ ID NO: 404; SEQ ID NO: 405; and SEQ ID NO: 406 which correspond to polynucleotides encoding the complementarity-determining regions (CDRs, or hypervariable regions) of the light chain variable sequence of SEQ ID NO: 394.

In a further embodiment of the invention, polynucleotides encoding fragments of the antibody having binding specificity to IL-6 comprise, or alternatively consist of, one or more of the polynucleotide sequences of SEQ ID NO: 407; SEQ ID NO: 408; and SEQ ID NO: 409 which correspond to polynucleotides encoding the complementarity-determining regions (CDRs, or hypervariable regions) of the heavy chain variable sequence of SEQ ID NO: 395.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 402 encoding the light chain variable region of SEQ ID NO: 394; the polynucleotide SEQ ID NO: 403 encoding the heavy chain variable region of SEQ ID NO: 395; polynucleotides encoding the complementarity-determining regions (SEQ ID NO: 404; SEQ ID NO: 405; and SEQ ID NO: 406) of the light chain variable region of SEQ ID NO: 394; and polynucleotides encoding the complementarity-determining regions (SEQ ID NO: 407; SEQ ID NO: 408; and SEQ ID NO: 409) of the heavy chain variable region of SEQ ID NO: 395.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 410:

(SEQ ID NO: 418)
ATGGACACGAGGGCCCCCACTCAGCTGCTGGGGCTCCTGCTGCTCTGGCT

CCCAGGTGCCAGATGTGATGTTGTGATGACCCAGACTCCAGCCTCCGTGG

AGGCAGCTGTGGGAGGCACAGTCACCATCAAGTGCCAGGCCAGTGAGGAT

ATTAGTAGCTACTTAGCCTGGTATCAGCAGAAACCAGGGCAGCCTCCCAA

GCTCCTGATCTATGCTGCATCCAATCTGGAATCTGGGGTCTCATCGCGAT

TCAAAGGCAGTGGATCTGGGACAGAGTACACTCTCACCATCAGCGACCTG

GAGTGTGCCGATGCTGCCACCTATTACTGTCAATGTACTTATGGTACTAT

TTCTATTAGTGATGGTAATGCT

In another embodiment of the invention, polynucleotides of the invention comprise, or alternatively consist of, the following polynucleotide sequence encoding the variable heavy chain polypeptide sequence of SEQ ID NO: 411:

(SEQ ID NO: 419)
ATGGAGACTGGGCTGCGCTGGCTTCTCCTGGTCGCTGTGCTCAAAGGTGT

CCAATGTCAGTCGGTGGAGGAGTCCGGGGGTCGCCTGGTCACGCCTGGGA

CACCCCTGACACTCACCTGCACAGTCTCTGGATTCTCCCTCAGTAGCTAC

TTCATGACCTGGGTCCGCCAGGCTCCAGGGGAGGGGCTGGAATACATCGG

ATTCATTAATCCTGGTGGTAGCGCTTACTACGCGAGCTGGGTGAAAGGCC

GATTCACCATCTCCAAGTCCTCGACCACGGTAGATCTGAAAATCACCAGT

CCGACAACCGAGGACACGGCCACCTATTTCTGTGCCAGGGTTCTGATTGT

TTCTTATGGAGCCTTTACCATC.

In a further embodiment of the invention, polynucleotides encoding fragments of the antibody having binding specificity to IL-6 comprise, or alternatively consist of, one or more of the polynucleotide sequences of SEQ ID NO: 420; SEQ ID NO: 421; and SEQ ID NO: 422 which correspond to polynucleotides encoding the complementarity-determining regions (CDRs, or hypervariable regions) of the light chain variable sequence of SEQ ID NO: 410.

In a further embodiment of the invention, polynucleotides encoding fragments of the antibody having binding specificity to IL-6 comprise, or alternatively consist of, one or more of the polynucleotide sequences of SEQ ID NO: 423; SEQ ID NO: 424; and SEQ ID NO: 425 which correspond to polynucleotides encoding the complementarity-determining regions (CDRs, or hypervariable regions) of the heavy chain variable sequence of SEQ ID NO: 411.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 418 encoding the light chain variable region of SEQ ID NO: 410; the polynucleotide SEQ ID NO: 419 encoding the heavy chain variable region of SEQ ID NO: 411; polynucleotides encoding the complementarity-determining regions (SEQ ID NO: 420; SEQ ID NO: 421; and SEQ ID NO: 422) of the light chain variable region of SEQ ID NO: 410; and polynucleotides encoding the complementarity-determining regions (SEQ ID NO: 423; SEQ ID NO: 424; and SEQ ID NO: 425) of the heavy chain variable region of SEQ ID NO: 411.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 426:

(SEQ ID NO: 434)
ATGGACACGAGGGCCCCCACTCAGCTGCTGGGGCTCCTGCTGCTCTGGCT

CCCAGGTGCCAGATGTGATGTTGTGATGACCCAGACTCCAGCCTCCGTGT

CTGCAGCTGTGGGAGGCACAGTCACCATCAAGTGCCAGGCCAGTGAGGAC

ATTGAAAGCTATCTAGCCTGGTATCAGCAGAAACCAGGGCAGCCTCCCAA

GCTCCTGATCTATGGTGCATCCAATCTGGAATCTGGGGTCTCATCGCGGT

TCAAAGGCAGTGGATCTGGGACAGAGTTCACTCTCACCATCAGCGACCTG

GAGTGTGCCGATGCTGCCACTTACTATTGTCAATGCACTTATGGTATTAT

TAGTATTAGTGATGGTAATGCT

In another embodiment of the invention, polynucleotides of the invention comprise, or alternatively consist of, the following polynucleotide sequence encoding the variable heavy chain polypeptide sequence of SEQ ID NO: 427:

(SEQ ID NO: 435)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTGTCTGGATTCTCCCTCAGTAGCTAC

TTCATGACCTGGGTCCGCCAGGCTCCAGGGGAGGGGCTGGAATACATCGG

ATTCATGAATACTGGTGATAACGCATACTACGCGAGCTGGGCGAAAGGCC

GATTCACCATCTCCAAAACCTCGACCACGGTGGATCTGAAAATCACCAGT

CCGACAACCGAGGACACGGCCACCTATTTCTGTGCCAGGGTTCTTGTTGT

TGCTTATGGAGCCTTTAACATC.

In a further embodiment of the invention, polynucleotides encoding fragments of the antibody having binding specificity to IL-6 comprise, or alternatively consist of, one or more of the polynucleotide sequences of SEQ ID NO: 436; SEQ ID NO: 437; and SEQ ID NO: 438 which correspond to polynucleotides encoding the complementarity-determining regions (CDRs, or hypervariable regions) of the light chain variable sequence of SEQ ID NO: 426.

In a further embodiment of the invention, polynucleotides encoding fragments of the antibody having binding specificity to IL-6 comprise, or alternatively consist of, one or more of the polynucleotide sequences of SEQ ID NO: 439; SEQ ID NO: 440; and SEQ ID NO: 441 which correspond to polynucleotides encoding the complementarity-determining regions (CDRs, or hypervariable regions) of the heavy chain variable sequence of SEQ ID NO: 427.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 434 encoding the light chain variable region of SEQ ID NO: 426;

the polynucleotide SEQ ID NO: 435 encoding the heavy chain variable region of SEQ ID NO: 427; polynucleotides encoding the complementarity-determining regions (SEQ ID NO: 436; SEQ ID NO: 437; and SEQ ID NO: 438) of the light chain variable region of SEQ ID NO: 426; and polynucleotides encoding the complementarity-determining regions (SEQ ID NO: 439; SEQ ID NO: 440; and SEQ ID NO: 441) of the heavy chain variable region of SEQ ID NO: 427.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 442:

(SEQ ID NO: 450)
ATGGACACGAGGGCCCCCACTCAGCTGCTGGGGCTCCTGCTGCTCTGGCT

CCCAGGTGCCACATTTGCCGCCGTGCTGACCCAGACTCCATCTCCCGTGT

CTGAACCTGTGGGAGGCACAGTCAGCATCAGTTGCCAGTCCAGTAAGAGT

GTTATGAATAACAACTACTTAGCCTGGTATCAGCAGAAACCAGGGCAGCC

TCCCAAGCTCCTGATCTATGGTGCATCCAATCTGGCATCTGGGGTCCCAT

CACGGTTCAGCGGCAGTGGATCTGGGACACAGTTCACTCTCACCATCAGC

GACGTGCAGTGTGACGATGCTGCCACTTACTACTGTCAAGGCGGTTATAC

TGGTTATAGTGATCATGGGACT

In another embodiment of the invention, polynucleotides of the invention comprise, or alternatively consist of, the following polynucleotide sequence encoding the variable heavy chain polypeptide sequence of SEQ ID NO: 443:

(SEQ ID NO: 451)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCAAGCCTGACG

AAACCCTGACACTCACCTGCACAGTCTCTGGAATCGACCTCAGTAGCTAT

CCAATGAACTGGGTCCGCCAGGCTCCAGGGAAGGGGCTGGAATGGATCGG

ATTCATTAATACTGGTGGTACCATAGTCTACGCGAGCTGGGCAAAAGGCC

GATTCACCATCTCCAAAACCTCGACCACGGTGGATCTGAAAATGACCAGT

CCGACAACCGAGGACACGGCCACCTATTTCTGTGCCAGAGGCAGTTATGT

TTCATCTGGTTATGCCTACTATTTTAATGTC.

In a further embodiment of the invention, polynucleotides encoding fragments of the antibody having binding specificity to IL-6 comprise, or alternatively consist of, one or more of the polynucleotide sequences of SEQ ID NO: 452; SEQ ID NO: 453; and SEQ ID NO: 454 which correspond to polynucleotides encoding the complementarity-determining regions (CDRs, or hypervariable regions) of the light chain variable sequence of SEQ ID NO: 442.

In a further embodiment of the invention, polynucleotides encoding fragments of the antibody having binding specificity to IL-6 comprise, or alternatively consist of, one or more of the polynucleotide sequences of SEQ ID NO: 455; SEQ ID NO: 456; and SEQ ID NO: 457 which correspond to polynucleotides encoding the complementarity-determining regions (CDRs, or hypervariable regions) of the heavy chain variable sequence of SEQ ID NO: 443.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 450 encoding the light chain variable region of SEQ ID NO: 442; the polynucleotide SEQ ID NO: 451 encoding the heavy chain variable region of SEQ ID NO: 443; polynucleotides encoding the complementarity-determining regions (SEQ ID NO: 452; SEQ ID NO: 453; and SEQ ID NO: 454) of the light chain variable region of SEQ ID NO: 442; and polynucleotides encoding the complementarity-determining regions (SEQ ID NO: 455; SEQ ID NO: 456; and SEQ ID NO: 457) of the heavy chain variable region of SEQ ID NO: 443.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 458:

(SEQ ID NO: 466)
ATGGACACGAGGGCCCCCACTCAGCTGCTGGGGCTCCTGCTGCTCTGGCT

CCCAGGTGCCACATTTGCCGCCGTGCTGACCCAGACTCCATCTCCCGTGT

CTGCAGCTGTGGGAGGCACAGTCAGCATCAGTTGCCAGTCCAGTCAGAGT

GTTTATAATAACAACTGGTTATCCTGGTTTCAGCAGAAACCAGGGCAGCC

TCCCAAGCTCCTGATCTACAAGGCATCCACTCTGGCATCTGGGGTCCCAT

CGCGGTTCAAAGGCAGTGGATCTGGGACACAGTTCACTCTCACCATCAGC

GACGTGCAGTGTGACGATGTTGCCACTTACTACTGTGCGGGCGGTTATCT

TGATAGTGTTATT

In another embodiment of the invention, polynucleotides of the invention comprise, or alternatively consist of, the following polynucleotide sequence encoding the variable heavy chain polypeptide sequence of SEQ ID NO: 459:

(SEQ ID NO: 467)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGATTCTCCCTCAGTACCTAT

TCAATAAACTGGGTCCGCCAGGCTCCAGGGAAGGGCCTGGAATGGATCGG

AATCATTGCTAATAGTGGTACCACATTCTACGCGAACTGGGCGAAAGGCC

GATTCACCGTCTCCAAAACCTCGACCACGGTGGATCTGAAAATCACCAGT

CCGACAACCGAGGACACGGCCACCTATTTCTGTGCCAGAGAGAGTGGAAT

GTACAATGAATATGGTAAATTTAACATC.

In a further embodiment of the invention, polynucleotides encoding fragments of the antibody having binding specificity to IL-6 comprise, or alternatively consist of, one or more of the polynucleotide sequences of SEQ ID NO: 468; SEQ ID NO: 469; and SEQ ID NO: 470 which correspond to polynucleotides encoding the complementarity-determining regions (CDRs, or hypervariable regions) of the light chain variable sequence of SEQ ID NO: 458.

In a further embodiment of the invention, polynucleotides encoding fragments of the antibody having binding specificity to IL-6 comprise, or alternatively consist of, one or more of the polynucleotide sequences of SEQ ID NO: 471; SEQ ID NO: 472; and SEQ ID NO: 473 which correspond to polynucleotides encoding the complementarity-determining regions (CDRs, or hypervariable regions) of the heavy chain variable sequence of SEQ ID NO: 459.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 466 encoding the light chain variable region of SEQ ID NO: 458; the polynucleotide SEQ ID NO: 467 encoding the heavy chain variable region of SEQ ID NO: 459; polynucleotides encoding the complementarity-determining regions (SEQ ID NO: 468; SEQ ID NO: 469; and SEQ ID NO: 470) of the light chain variable region of SEQ ID NO: 458; and polynucleotides encoding the complementarity-determining regions (SEQ ID NO: 471; SEQ ID NO: 472; and SEQ ID NO: 473) of the heavy chain variable region of SEQ ID NO: 459.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 474:

```
(SEQ ID NO: 482)
ATGGACACGAGGGCCCCCACTCAGCTGCTGGGGCTCCTGCTGCTCTGGCT

CCCAGGTGCCAGATGTGCCTCTGATATGACCCAGACTCCATCCTCCGTGT

CTGCAGCTGTGGGAGGCACAGTCACCATCAATTGCCAGGCCAGTGAGAAC

ATTTATAGCTTTTTGGCCTGGTATCAGCAGAAACCAGGGCAGCCTCCCAA

GCTCCTGATCTTCAAGGCTTCCACTCTGGCATCTGGGGTCTCATCGCGGT

TCAAAGGCAGTGGATCTGGGACACAGTTCACTCTCACCATCAGCGACCTG

GAGTGTGACGATGCTGCCACTTACTACTGTCAACAGGGTGCTACTGTGTA

TGATATTGATAATAAT
```

In another embodiment of the invention, polynucleotides of the invention comprise, or alternatively consist of, the following polynucleotide sequence encoding the variable heavy chain polypeptide sequence of SEQ ID NO: 475:

```
(SEQ ID NO: 483)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCACGCCTGGGA

CACCCCTGACACTCACCTGCACAGTTTCTGGAATCGACCTCAGTGCCTAT

GCAATGATCTGGGTCCGCCAGGCTCCAGGGGAGGGGCTGGAATGGATCAC

AATCATTTATCCTAATGGTATCACATACTACGCGAACTGGGCGAAAGGCC

GATTCACCGTCTCCAAAACCTCGACCGCGATGGATCTGAAAATCACCAGT
```

-continued
```
CCGACAACCGAGGACACGGCCACCTATTTCTGTGCCAGAGATGCAGAAAG

TAGTAAGAATGCTTATTGGGGCTACTTTAACGTC.
```

In a further embodiment of the invention, polynucleotides encoding fragments of the antibody having binding specificity to IL-6 comprise, or alternatively consist of, one or more of the polynucleotide sequences of SEQ ID NO: 484; SEQ ID NO: 485; and SEQ ID NO: 486 which correspond to polynucleotides encoding the complementarity-determining regions (CDRs, or hypervariable regions) of the light chain variable sequence of SEQ ID NO: 474.

In a further embodiment of the invention, polynucleotides encoding fragments of the antibody having binding specificity to IL-6 comprise, or alternatively consist of, one or more of the polynucleotide sequences of SEQ ID NO: 487; SEQ ID NO: 488; and SEQ ID NO: 489 which correspond to polynucleotides encoding the complementarity-determining regions (CDRs, or hypervariable regions) of the heavy chain variable sequence of SEQ ID NO: 475.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 482 encoding the light chain variable region of SEQ ID NO: 474; the polynucleotide SEQ ID NO: 483 encoding the heavy chain variable region of SEQ ID NO: 475; polynucleotides encoding the complementarity-determining regions (SEQ ID NO: 484; SEQ ID NO: 485; and SEQ ID NO: 486) of the light chain variable region of SEQ ID NO: 474; and polynucleotides encoding the complementarity-determining regions (SEQ ID NO: 487; SEQ ID NO: 488; and SEQ ID NO: 489) of the heavy chain variable region of SEQ ID NO: 475.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 490:

```
(SEQ ID NO: 498)
ATGGACACGAGGGCCCCCACTCAGCTGCTGGGGCTCCTGCTGCTCTGGCT

CCCAGGTGCCAGATGTGCCTCTGATATGACCCAGACTCCATCCTCCGTGT

CTGCAGCTGTGGGAGGCACAGTCACCATCAATTGCCAGGCCAGTGAGAAC

ATTTATAGCTTTTTGGCCTGGTATCAGCAGAAACCAGGGCAGCCTCCCAA

GCTCCTGATCTTCAGGGCTTCCACTCTGGCATCTGGGGTCTCATCGCGGT

TCAAAGGCAGTGGATCTGGGACACAGTTCACTCTCACCATCAGCGACCTG

GAGTGTGACGATGCTGCCACTTACTACTGTCAACAGGGTGCTACTGTGTA

TGATATTGATAATAAT
```

In another embodiment of the invention, polynucleotides of the invention comprise, or alternatively consist of, the following polynucleotide sequence encoding the variable heavy chain polypeptide sequence of SEQ ID NO: 491:

(SEQ ID NO: 499)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCACGCCTGGGA

CACCCCTGACACTCACCTGCACAGTTTCTGGAATCGACCTCAGTGCCTAT

GCAATGATCTGGGTCCGCCAGGCTCCAGGGGAGGGGCTGGAATGGATCAC

AATCATTTATCCTAATGGTATCACATACTACGCGAACTGGGCGAAAGGCC

GATTCACCGTCTCCAAAACCTCGACCGCGATGGATCTGAAAATCACCAGT

CCGACAACCGAGGACACGGCCACCTATTTCTGTGCCAGAGATGCAGAAAG

TAGTAAGAATGCTTATTGGGGCTACTTTAACGTC.

In a further embodiment of the invention, polynucleotides encoding fragments of the antibody having binding specificity to IL-6 comprise, or alternatively consist of, one or more of the polynucleotide sequences of SEQ ID NO: 500; SEQ ID NO: 501; and SEQ ID NO: 502 which correspond to polynucleotides encoding the complementarity-determining regions (CDRs, or hypervariable regions) of the light chain variable sequence of SEQ ID NO: 490.

In a further embodiment of the invention, polynucleotides encoding fragments of the antibody having binding specificity to IL-6 comprise, or alternatively consist of, one or more of the polynucleotide sequences of SEQ ID NO: 503; SEQ ID NO: 504; and SEQ ID NO: 505 which correspond to polynucleotides encoding the complementarity-determining regions (CDRs, or hypervariable regions) of the heavy chain variable sequence of SEQ ID NO: 491.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 498 encoding the light chain variable region of SEQ ID NO: 490; the polynucleotide SEQ ID NO: 499 encoding the heavy chain variable region of SEQ ID NO: 491; polynucleotides encoding the complementarity-determining regions (SEQ ID NO: 500; SEQ ID NO: 501; and SEQ ID NO: 502) of the light chain variable region of SEQ ID NO: 490; and polynucleotides encoding the complementarity-determining regions (SEQ ID NO: 503; SEQ ID NO: 504; and SEQ ID NO: 505) of the heavy chain variable region of SEQ ID NO: 491.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 506:

(SEQ ID NO: 514)
ATGGACACGAGGGCCCCCACTCAGCTGCTGGGGCTCCTGCTGCTCTGGCT

CCCAGGTGCCACATTTGCCATTGAAATGACCCAGACTCCATCCCCCGTGT

CTGCCGCTGTGGGAGGCACAGTCACCATCAATTGCCAGGCCAGTGAGAGT

GTTTTTAATAATATGTTATCCTGGTATCAGCAGAAACCAGGGCACTCTCC

TAAGCTCCTGATCTATGATGCATCCGATCTGGCATCTGGGGTCCCATCGC

GGTTCAAAGGCAGTGGATCTGGGACACAGTTCACTCTCACCATCAGTGGC

GTGGAGTGTGACGATGCTGCCACTTACTATTGTGCAGGGTATAAAAGTGA

TAGTAATGATGGCGATAATGTT

In another embodiment of the invention, polynucleotides of the invention comprise, or alternatively consist of, the following polynucleotide sequence encoding the variable heavy chain polypeptide sequence of SEQ ID NO: 507:

(SEQ ID NO: 515)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCACGCCTGGGA

CACCCCTGACACTCACCTGCACAGTCTCTGGATTCTCCCTCAACAGGAAT

TCAATAACCTGGGTCCGCCAGGCTCCAGGGGAGGGGCTGGAATGGATCGG

AATCATTACTGGTAGTGGTAGAACGTACTACGCGAACTGGGCAAAAGGCC

GATTCACCATCTCCAAAACCTCGACCACGGTGGATCTGAAAATGACCAGT

CCGACAACCGAGGACACGGCCACCTATTTCTGTGCCAGAGGCCATCCTGG

TCTTGGTAGTGGTAACATC.

In a further embodiment of the invention, polynucleotides encoding fragments of the antibody having binding specificity to IL-6 comprise, or alternatively consist of, one or more of the polynucleotide sequences of SEQ ID NO: 516; SEQ ID NO: 517; and SEQ ID NO: 518 which correspond to polynucleotides encoding the complementarity-determining regions (CDRs, or hypervariable regions) of the light chain variable sequence of SEQ ID NO: 506.

In a further embodiment of the invention, polynucleotides encoding fragments of the antibody having binding specificity to IL-6 comprise, or alternatively consist of, one or more of the polynucleotide sequences of SEQ ID NO: 519; SEQ ID NO: 520; and SEQ ID NO: 521 which correspond to polynucleotides encoding the complementarity-determining regions (CDRs, or hypervariable regions) of the heavy chain variable sequence of SEQ ID NO: 507.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 514 encoding the light chain variable region of SEQ ID NO: 506; the polynucleotide SEQ ID NO: 515 encoding the heavy chain variable region of SEQ ID NO: 507; polynucleotides encoding the complementarity-determining regions (SEQ ID NO: 516; SEQ ID NO: 517; and SEQ ID NO: 518) of the light chain variable region of SEQ ID NO: 506; and polynucleotides encoding the complementarity-determining regions (SEQ ID NO: 519; SEQ ID NO: 520; and SEQ ID NO: 521) of the heavy chain variable region of SEQ ID NO: 507.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 522:

(SEQ ID NO: 530)
ATGGACACGAGGGCCCCCACTCAGCTGCTGGGGCTCCTGCTGCTCTGGCT

CCCAGGTGCCACATTTGCGCAAGTGCTGACCCAGACTGCATCGTCCGTGT

CTGCAGCTGTGGGAGGCACAGTCACCATCAATTGCCAGTCCAGTCAGAGT

GTTTATAATAACTACTTATCCTGGTATCAGCAGAAACCAGGGCAGCCTCC

CAAGCTCCTGATCTATACTGCATCCAGCCTGGCATCTGGGGTCCCATCGC

GGTTCAAAGGCAGTGGATCTGGGACACAGTTCACTCTCACCATCAGCGAA

GTGCAGTGTGACGATGCTGCCACTTACTACTGTCAAGGCTATTATAGTGG

TCCTATAATTACT

In another embodiment of the invention, polynucleotides of the invention comprise, or alternatively consist of, the following polynucleotide sequence encoding the variable heavy chain polypeptide sequence of SEQ ID NO: 523:

(SEQ ID NO: 531)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCACGCCTGGGA

CACCCCTGACACTCACCTGCACAGCCTCTGGATTCTCCCTCAATAACTAC

TACATACAATGGGTCCGCCAGGCTCCAGGGGAGGGGCTGGAATGGATCGG

GATCATTTATGCTGGTGGTAGCGCATACTACGCGACCTGGGCAAACGGCC

GATTCACCATCGCCAAAACCTCGTCGACCACGGTGGATCTGAAGATGACC

AGTCTGACAACCGAGGACACGGCCACCTATTTCTGTGCCAGAGGGACATT

TGATGGTTATGAGTTG.

In a further embodiment of the invention, polynucleotides encoding fragments of the antibody having binding specificity to IL-6 comprise, or alternatively consist of, one or more of the polynucleotide sequences of SEQ ID NO: 532; SEQ ID NO: 533; and SEQ ID NO: 534 which correspond to polynucleotides encoding the complementarity-determining regions (CDRs, or hypervariable regions) of the light chain variable sequence of SEQ ID NO: 522.

In a further embodiment of the invention, polynucleotides encoding fragments of the antibody having binding specificity to IL-6 comprise, or alternatively consist of, one or more of the polynucleotide sequences of SEQ ID NO: 535; SEQ ID NO: 536; and SEQ ID NO: 537 which correspond to polynucleotides encoding the complementarity-determining regions (CDRs, or hypervariable regions) of the heavy chain variable sequence of SEQ ID NO: 523.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 530 encoding the light chain variable region of SEQ ID NO: 522; the polynucleotide SEQ ID NO: 531 encoding the heavy chain variable region of SEQ ID NO: 523; polynucleotides encoding the complementarity-determining regions (SEQ ID NO: 532; SEQ ID NO: 533; and SEQ ID NO: 534) of the light chain variable region of SEQ ID NO: 522; and polynucleotides encoding the complementarity-determining regions (SEQ ID NO: 535; SEQ ID NO: 536; and SEQ ID NO: 537) of the heavy chain variable region of SEQ ID NO: 523.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 538:

(SEQ ID NO: 546)
ATGGACACGAGGGCCCCCACTCAGCTGCTGGGGCTCCTGCTGCTCTGGCT

CCCAGGTGCCACATTTGCCCAAGTGCTGACCCAGACTCCATCCCCTGTGT

CTGTCCCTGTGGGAGACACAGTCACCATCAGTTGCCAGTCCAGTGAGAGC

GTTTATAGTAATAACCTCTTATCCTGGTATCAGCAGAAACCAGGGCAGCC

TCCCAAGCTCCTGATCTACAGGGCATCCAATCTGGCATCTGGTGTCCCAT

CGCGGTTCAAAGGCAGTGGATCTGGGACACAGTTCACTCTCACCATCAGC

GGCGCACAGTGTGACGATGCTGCCACTTACTACTGTCAAGGCTATTATAG

TGGTGTCATTAATAGT

In another embodiment of the invention, polynucleotides of the invention comprise, or alternatively consist of, the following polynucleotide sequence encoding the variable heavy chain polypeptide sequence of SEQ ID NO: 539:

(SEQ ID NO: 547)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTGTCTGGATTCTCCCTCAGTAGCTAC

TTCATGAGCTGGGTCCGCCAGGCTCCAGGGGAGGGGCTGGAATACATCGG

ATTCATTAATCCTGGTGGTAGCGCATACTACGCGAGCTGGGCGAGTGGCC

GACTCACCATCTCCAAAACCTCGACCACGGTAGATCTGAAAATCACCAGT

CCGACAACCGAGGACACGGCCACCTATTTCTGTGCCAGGATTCTTATTGT

TTCTTATGGAGCCTTTACCATC.

In a further embodiment of the invention, polynucleotides encoding fragments of the antibody having binding specificity to IL-6 comprise, or alternatively consist of, one or more of the polynucleotide sequences of SEQ ID NO: 548; SEQ ID NO: 549; and SEQ ID NO: 550 which correspond to polynucleotides encoding the complementarity-determining regions (CDRs, or hypervariable regions) of the light chain variable sequence of SEQ ID NO: 538.

In a further embodiment of the invention, polynucleotides encoding fragments of the antibody having binding specificity to IL-6 comprise, or alternatively consist of, one or more of the polynucleotide sequences of SEQ ID NO: 551; SEQ ID NO: 552; and SEQ ID NO: 553 which correspond to polynucleotides encoding the complementarity-determining regions (CDRs, or hypervariable regions) of the heavy chain variable sequence of SEQ ID NO: 539.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 546 encoding the light chain variable region of SEQ ID NO: 538;

the polynucleotide SEQ ID NO: 547 encoding the heavy chain variable region of SEQ ID NO: 539; polynucleotides encoding the complementarity-determining regions (SEQ ID NO: 548; SEQ ID NO: 549; and SEQ ID NO: 550) of the light chain variable region of SEQ ID NO: 538; and polynucleotides encoding the complementarity-determining regions (SEQ ID NO: 551; SEQ ID NO: 552; and SEQ ID NO: 553) of the heavy chain variable region of SEQ ID NO: 539.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 554:

```
                                          (SEQ ID NO: 562)
ATGGACACGAGGGCCCCCACTCAGCTGCTGGGGCTCCTGCTGCTCTGGCT

CCCAGGTGCCAGATGTGCCTATGATATGACCCAGACTCCAGCCTCTGTGG

AGGTAGCTGTGGGAGGCACAGTCACCATCAAGTGCCAGGCCACTGAGAGC

ATTGGCAATGAGTTATCCTGGTATCAGCAGAAACCAGGGCAGGCTCCCAA

GCTCCTGATCTATTCTGCATCCACTCTGGCATCTGGGGTCCCATCGCGGT

TCAAAGGCAGTGGATCTGGGACACAGTTCACTCTCACCATCACCGGCGTG

GAGTGTGATGATGCTGCCACTTACTACTGTCAACAGGGTTATAGTAGTGC

TAATATTGATAATGCT
```

In another embodiment of the invention, polynucleotides of the invention comprise, or alternatively consist of, the following polynucleotide sequence encoding the variable heavy chain polypeptide sequence of SEQ ID NO: 555:

```
                                          (SEQ ID NO: 563)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCACGCCTGGGA

CACCCCTGACACTCACCTGCACCGTCTCTGGATTCTCCCTCAGTAAGTAC

TACATGAGCTGGGTCCGCCAGGCTCCAGAGAAGGGGCTGAAATACATCGG

ATACATTGATAGTACTACTGTTAATACATACTACGCGACCTGGGCGAGAG

GCCGATTCACCATCTCCAAAACCTCGACCACGGTGGATCTGAAGATCACC

AGTCCGACAAGTGAGGACACGGCCACCTATTTCTGTGCCAGAGGAAGTAC

TTATTTTACTGATGGAGGCCATCGGTTGGATCTC.
```

In a further embodiment of the invention, polynucleotides encoding fragments of the antibody having binding specificity to IL-6 comprise, or alternatively consist of, one or more of the polynucleotide sequences of SEQ ID NO: 564; SEQ ID NO: 565; and SEQ ID NO: 566 which correspond to polynucleotides encoding the complementarity-determining regions (CDRs, or hypervariable regions) of the light chain variable sequence of SEQ ID NO: 554.

In a further embodiment of the invention, polynucleotides encoding fragments of the antibody having binding specificity to IL-6 comprise, or alternatively consist of, one or more of the polynucleotide sequences of SEQ ID NO: 567; SEQ ID NO: 568; and SEQ ID NO: 569 which correspond to polynucleotides encoding the complementarity-determining regions (CDRs, or hypervariable regions) of the heavy chain variable sequence of SEQ ID NO: 555.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 562 encoding the light chain variable region of SEQ ID NO: 554; the polynucleotide SEQ ID NO: 563 encoding the heavy chain variable region of SEQ ID NO: 555; polynucleotides encoding the complementarity-determining regions (SEQ ID NO: 564; SEQ ID NO: 565; and SEQ ID NO: 566) of the light chain variable region of SEQ ID NO: 554; and polynucleotides encoding the complementarity-determining regions (SEQ ID NO: 567; SEQ ID NO: 568; and SEQ ID NO: 569) of the heavy chain variable region of SEQ ID NO: 555.

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 570:

```
                                          (SEQ ID NO: 578)
ATGGACACGAGGGCCCCCACTCAGCTGCTGGGGCTCCTGCTGCTCTGGCT

CCCAGGTGCCAGATGTGCCTATGATATGACCCAGACTCCAGCCTCTGTGG

AGGTAGCTGTGGGAGGCACAGTCACCATCAAGTGCCAGGCCACTGAGAGC

ATTGGCAATGAGTTATCCTGGTATCAGCAGAAACCAGGGCAGGCTCCCAA

GCTCCTGATCTATTCTGCATCCACTCTGGCATCTGGGGTCCCATCGCGGT

TCAAAGGCAGTGGATCTGGGACACAGTTCACTCTCACCATCACCGGCGTG

GAGTGTGATGATGCTGCCACTTACTACTGTCAACAGGGTTATAGTAGTGC

TAATATTGATAATGCT
```

In another embodiment of the invention, polynucleotides of the invention comprise, or alternatively consist of, the following polynucleotide sequence encoding the variable heavy chain polypeptide sequence of SEQ ID NO: 571:

```
                                          (SEQ ID NO: 579)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTAACGCCTGGGA

CACCCCTGACACTCACCTGCACAGTCTCTGGATTCTCCCTCAGTACCTAC

AACATGGGCTGGGTCCGCCAGGCTCCAGGGAAGGGGCTGGAATGGATCGG

AAGTATTACTATTGATGGTCGCACATACTACGCGAGCTGGGCGAAAGGCC

GATTCACCGTCTCCAAAAGCTCGACCACGGTGGATCTGAAAATGACCAGT

CTGACAACCGGGGACACGGCCACCTATTTCTGTGCCAGGATTCTTATTGT

TTCTTATGGGCCTTTACCATC.
```

In a further embodiment of the invention, polynucleotides encoding fragments of the antibody having binding specificity to IL-6 comprise, or alternatively consist of, one or more of the polynucleotide sequences of SEQ ID NO: 580; SEQ ID NO: 581; and SEQ ID NO: 582 which correspond to polynucleotides encoding the complementarity-determining regions (CDRs, or hypervariable regions) of the light chain variable sequence of SEQ ID NO: 570.

In a further embodiment of the invention, polynucleotides encoding fragments of the antibody having binding specificity to IL-6 comprise, or alternatively consist of, one or more of the polynucleotide sequences of SEQ ID NO: 583; SEQ ID NO: 584; and SEQ ID NO: 585 which correspond to polynucleotides encoding the complementarity-determining regions (CDRs, or hypervariable regions) of the heavy chain variable sequence of SEQ ID NO: 571.

The invention also contemplates polynucleotide sequences including one or more of the polynucleotide sequences encoding antibody fragments described herein. In one embodiment of the invention, polynucleotides encoding fragments of the antibody having binding specificity to IL-6 comprise, or alternatively consist of, one, two, three or more, including all of the following polynucleotides encoding antibody fragments: the polynucleotide SEQ ID NO: 578 encoding the light chain variable region of SEQ ID NO: 570; the polynucleotide SEQ ID NO: 579 encoding the heavy chain variable region of SEQ ID NO: 571; polynucleotides encoding the complementarity-determining regions (SEQ ID NO: 580; SEQ ID NO: 581; and SEQ ID NO: 582) of the light chain variable region of SEQ ID NO: 570; and polynucleotides encoding the complementarity-determining regions (SEQ ID NO: 583; SEQ ID NO: 584; and SEQ ID NO: 585) of the heavy chain variable region of SEQ ID NO: 571.

In another embodiment of the invention, polynucleotides of the invention further comprise, the following polynucleotide sequence encoding the kappa constant light chain sequence of SEQ ID NO: 586:

(SEQ ID NO: 587)
GTGGCTGCACCATCTGTCTTCATCTTCCCGCCATCTGATGAGCAGTTGAA

ATCTGGAACTGCCTCTGTTGTGTGCCTGCTGAATAACTTCTATCCCAGAG

AGGCCAAAGTACAGTGGAAGGTGGATAACGCCCTCCAATCGGGTAACTCC

CAGGAGAGTGTCACAGAGCAGGACAGCAAGGACAGCACCTACAGCCTCAG

CAGCACCCTGACGCTGAGCAAAGCAGACTACGAGAAACACAAAGTCTACG

CCTGCGAAGTCACCCATCAGGGCCTGAGCTCGCCCGTCACAAAGAGCTTC

AACAGGGGAGAGTGT.

In another embodiment of the invention, polynucleotides of the invention further comprise, the following polynucleotide sequence encoding the gamma-1 constant heavy chain polypeptide sequence of SEQ ID NO: 588:

(SEQ ID NO: 589)
GCCTCCACCAAGGGCCCATCGGTCTTCCCCCTGGCACCCTCCTCCAAGAG

CACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAG

CGTGGTGACCGTGCCCTCCAGCAGCTTGGGCACCCAGACCTACATCTGCA

ACGTGAATCACAAGCCCAGCAACACCAAGGTGGACAAGAGAGTTGAGCCC

AAATCTTGTGACAAAACTCACACATGCCCACCGTGCCCAGCACCTGAACT

CCTGGGGGGACCGTCAGTCTTCCTCTTCCCCCCAAAACCCAAGGACACCC

TCATGATCTCCCGGACCCCTGAGGTCACATGCGTGGTGGTGGACGTGAGC

CACGAAGACCCTGAGGTCAAGTTCAACTGGTACGTGGACGGCGTGGAGGT

GCATAATGCCAAGACAAAGCCGCGGGAGGAGCAGTACGCCAGCACGTACC

GTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAA

AACCATCTCCAAAGCCAAAGGGCAGCCCCGAGAACCACAGGTGTACACCC

TGCCCCCATCCCGGGAGGAGATGACCAAGAACCAGGTCAGCCTGACCTGC

CTGGTCAAAGGCTTCTATCCCAGCGACATCGCCGTGGAGTGGGAGAGCAA

TGGGCAGCCGGAGAACAACTACAAGACCACGCCTCCCGTGCTGGACTCCG

ACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAA

CCACTACACGCAGAAGAGCCTCTCCCTGTCTCCGGGTAAA.

In one embodiment, the invention is directed to an isolated polynucleotide comprising a polynucleotide encoding an anti-IL-6 $V_H$ antibody amino acid sequence selected from SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555 and SEQ ID NO: 571 or encoding a variant thereof wherein at least one framework residue (FR residue) has been substituted with an amino acid present at the corresponding position in a rabbit anti-IL-6 antibody $V_H$ polypeptide or a conservative amino acid substitution.

In another embodiment, the invention is directed to an isolated polynucleotide comprising the polynucleotide sequence encoding an anti-IL-6 $V_L$ antibody amino acid sequence of 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554 and SEQ ID NO: 570 or encoding a variant thereof wherein at least one framework residue (FR residue) has been substituted with an amino acid present at the corresponding position in a rabbit anti-IL-6 antibody $V_L$ polypeptide or a conservative amino acid substitution.

In yet another embodiment, the invention is directed to one or more heterologous polynucleotides comprising a sequence encoding the polypeptides contained in SEQ ID NO:2 and SEQ ID NO:3; SEQ ID NO:2 and SEQ ID NO:18; SEQ NO:2 and SEQ ID NO:19; SEQ ID NO:20 and SEQ ID NO:3; SEQ ID NO:20 and SEQ ID NO:18; SEQ ID NO:20 and SEQ ID NO:19; SEQ ID NO:21 and SEQ ID NO:22; SEQ ID NO:37 and SEQ ID NO:38; SEQ ID NO:53 and SEQ ID NO:54; SEQ ID NO:69 and SEQ ID NO:70; SEQ ID NO:85 and SEQ ID NO:86; SEQ ID NO:101 and SEQ ID NO:102; SEQ ID NO:101 and SEQ ID NO:117; SEQ ID NO:101 and SEQ ID NO:118; SEQ ID NO:119 and SEQ ID NO:102; SEQ ID NO:119 and SEQ ID NO:117; SEQ ID NO:119 and SEQ ID NO:118; SEQ ID NO:122 and SEQ ID NO:123; SEQ ID NO:138 and SEQ ID NO:139; SEQ ID NO:154 and SEQ ID NO:155; SEQ ID NO:170 and SEQ ID NO:171; SEQ ID NO:186 and SEQ ID NO:187; SEQ ID NO:202 and SEQ ID NO:203; SEQ ID NO:218 and SEQ ID NO:219; SEQ ID NO:234 and SEQ ID NO:235; SEQ ID NO:250 and SEQ ID NO:251; SEQ ID NO:266 and SEQ ID NO:267; SEQ ID NO:282 and SEQ ID NO:283; SEQ ID NO:298 and SEQ ID NO:299; SEQ ID NO:314 and SEQ ID NO:315; SEQ ID NO:330 and SEQ ID NO:331; SEQ ID NO:346 and SEQ ID NO:347; SEQ ID NO:362 and SEQ ID NO:363; SEQ ID NO:378 and SEQ ID NO:379; SEQ ID NO:394 and SEQ ID NO:395; SEQ ID NO:410 and SEQ ID NO:411; SEQ ID NO:426 and SEQ ID NO:427; SEQ ID NO:442 and SEQ ID NO:443; SEQ ID NO:458 and SEQ ID NO:459; SEQ ID NO:474 and SEQ ID NO:475; SEQ ID NO:490-and SEQ ID NO:491; SEQ ID NO:506 and SEQ ID NO:507; SEQ ID NO:522 and SEQ ID NO:523; SEQ ID NO:538 and SEQ ID NO:539; SEQ ID NO:554 and SEQ ID NO:555; or SEQ 1D NO:570 and SEQ ID NO:571.

In another embodiment, the invention is directed to an isolated isolated polynucleotide that expresses a polypeptide containing at least one CDR polypeptide derived from an anti-IL-6 antibody wherein said expressed polypeptide alone specifically binds IL-6 or specifically binds IL-6 when expressed in association with another polynucleotide sequence that expresses a polypeptide containing at least one CDR polypeptide derived from an anti-IL-6 antibody wherein said at least one CDR is selected from those contained in the $V_L$ or $V_H$ polypeptides contained in SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555; 571; 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554 and SEQ ID NO: 570.

Host cells and vectors comprising said polynucleotides are also contemplated.

The invention further contemplates vectors comprising the polynucleotide sequences encoding the variable heavy and light chain polypeptide sequences, as well as the individual complementarity determining regions (CDRs, or hypervariable regions) set forth herein, as well as host cells comprising said sequences. In one embodiment of the invention, the host cell is a yeast cell. In another embodiment of the invention, the yeast host cell belongs to the genus *Pichia*.

Anti-IL-6 Activity

As stated previously, IL-6 is a member of a family of cytokines that promote cellular responses through a receptor complex consisting of at least one subunit of the signal-transducing glycoprotein gp130 and the IL-6 receptor (IL-6R). The IL-6R may also be present in a soluble form (sIL-6R). IL-6 binds to IL-6R, which then dimerizes the signal-transducing receptor gp130.

It is believed that the anti-IL-6 antibodies of the invention, or IL-6 binding fragments thereof, are useful by exhibiting anti-IL-6 activity. In one non-limiting embodiment of the invention, the anti-IL-6 antibodies of the invention, or IL-6 binding fragments thereof, exhibit anti-IL-6 activity by binding to IL-6 which may be soluble IL-6 or cell surface expressed IL-6 and/or may prevent or inhibit the binding of IL-6 to IL-6R and/or activation (dimerization) of the gp130 signal-transducing glycoprotein and the formation of IL-6/IL-6R/gp130 multimers and the biological effects of any of the foregoing. The subject IL-6 antibodies may possess different antagonistic activities based on where (i.e., epitope) the particular antibody binds IL-6 and/or how it affects the formation of the foregoing IL-6 complexes and/or multimers and the biological effects thereof. Consequently, different IL-6 antibodies according to the invention e.g., may be better suited for preventing or treating conditions involving the formation and accumulation of substantial soluble IL-6 such as rheumatoid arthritis whereas other antibodies may be favored in treatments wherein the prevention of IL-6/IL-6R/gp130 or IL-6/IL-6R/gp130 multimers is a desired therapeutic outcome. This can be determined in binding and other assays.

The anti-IL-6 activity of the anti-IL-6 antibody of the present invention, and fragments thereof having binding specificity to IL-6, may also be described by their strength of binding or their affinity for IL-6. This also may affect their therapeutic properties. In one embodiment of the invention, the anti-IL-6 antibodies of the present invention, and fragments thereof having binding specificity to IL-6, bind to IL-6 with a dissociation constant ($K_D$) of less than or equal to $5\times10^{-7}$, $10^{-7}$, $5\times10^{-8}$, $10^{-8}$, $5\times10^{-9}$, $10^{-9}$, $5\times10^{-10}$, $10^{-10}$, $5\times10^{-11}$, $10^{-11}$, $5\times10^{-12}$, $10^{-12}$, $5\times10^{-13}$, $10^{-13}$, $5\times10^{-14}$, $10^{-14}$, $5\times10^{-15}$ or $10^{-15}$. Preferably, the anti-IL-6 antibodies and fragments thereof bind IL-6 with a dissociation constant of less than or equal to $5\times10^{-10}$.

In another embodiment of the invention, the anti-IL-6 activity of the anti-IL-6 antibodies of the present invention, and fragments thereof having binding specificity to IL-6, bind to IL-6 with an off-rate of less than or equal to $10^{-4}$ $S^{-1}$, $5\times10^{-5}$ $S^{-1}$, $10^{-5}$ $S^{-1}$, $5\times10$ $S^{-1}$, $10^{-6}$ $S^{-1}$, $5\times10^{-7}$ $S^{-1}$, or $10^{-7}$ $S^{-1}$. In one embodiment of the invention, the anti-IL-6 antibodies of the invention, and fragments thereof having binding specificity to IL-6, bind to a linear or conformational IL-6 epitope.

In a further embodiment of the invention, the anti-IL-6 activity of the anti-IL-6 antibodies of the present invention, and fragments thereof having binding specificity to IL-6, exhibit anti-IL-6 activity by ameliorating or reducing the symptoms of, or alternatively treating, or preventing, diseases and disorders associated with IL-6. Non-limiting examples of diseases and disorders associated with IL-6 are set forth infra. As noted cancer-related fatigue, cachexia and rheumatoid arthritis are preferred indications for the subject IL-6 antibodies.

In another embodiment of the invention, the anti-IL-6 antibodies described herein, or IL-6 binding fragments thereof, do not have binding specificity for IL-6R or the gp-130 signal-transducing glycoprotein.

B-cell Screening and Isolation

In one embodiment, the present invention provides methods of isolating a clonal population of antigen-specific B cells that may be used for isolating at least one antigen-specific cell. As described and exemplified infra, these methods contain a series of culture and selection steps that can be used separately, in combination, sequentially, repetitively, or periodically. Preferably, these methods are used for isolating at least one antigen-specific cell, which can be used to produce a monoclonal antibody, which is specific to a desired antigen, or a nucleic acid sequence corresponding to such an antibody.

In one embodiment, the present invention provides a method comprising the steps of:

a. preparing a cell population comprising at least one antigen-specific B cell;

b. enriching the cell population, e.g., by chromatography, to form an enriched cell population comprising at least one antigen-specific B cell;

c. isolating a single B cell from the enriched B cell population; and d. determining whether the single B cell produces an antibody specific to the antigen.

In another embodiment, the present invention provides an improvement to a method of isolating a single, antibody-producing B cell, the improvement comprising enriching a B cell population obtained from a host that has been immunized or naturally exposed to an antigen, wherein the enriching step precedes any selection steps, comprises at least one culturing step, and results in a clonal population of B cells that produces a single monoclonal antibody specific to said antigen.

Throughout this application, a "clonal population of B cells" refers to a population of B cells that only secrete a single antibody specific to a desired antigen. That is to say that these cells produce only one type of monoclonal antibody specific to the desired antigen.

In the present application, "enriching" a cell population cells means increasing the frequency of desired cells, typically antigen-specific cells, contained in a mixed cell population, e.g., a B cell-containing isolate derived from a host that is immunized against a desired antigen. Thus, an enriched cell population encompasses a cell population having a higher frequency of antigen-specific cells as a result of an enrichment step, but this population of cells may contain and produce different antibodies.

The general term "cell population" encompasses pre- and a post-enrichment cell populations, keeping in mind that when multiple enrichment steps are performed, a cell population can be both pre- and post-enrichment. For example, in one embodiment, the present invention provides a method:

a. harvesting a cell population from an immunized host to obtain a harvested cell population;

b. creating at least one single cell suspension from the harvested cell population;

c. enriching at least one single cell suspension to form a first enriched cell population;

d. enriching the first enriched cell population to form a second enriched cell population;

e. enriching the second enriched cell population to form a third enriched cell population; and f. selecting an antibody produced by an antigen-specific cell of the third enriched cell population.

Each cell population may be used directly in the next step, or it can be partially or wholly frozen for long --or short-term storage or for later steps. Also, cells from a cell population can be individually suspended to yield single cell suspensions. The single cell suspension can be enriched, such that a single cell suspension serves as the pre-enrichment cell population. Then, one or more antigen-specific single cell suspensions together form the enriched cell population; the antigen-specific single cell suspensions can be grouped together, e.g., re-plated for further analysis and/or antibody production.

In one embodiment, the present invention provides a method of enriching a cell population to yield an enriched cell population having an antigen-specific cell frequency that is about 50% to about 100%, or increments therein. Preferably, the enriched cell population has an antigen-specific cell frequency greater than or equal to about 50%, 60%, 70%, 75%, 80%, 90%, 95%, 99%, or 100%.

In another embodiment, the present invention provides a method of enriching a cell population whereby the frequency of antigen-specific cells is increased by at least about 2-fold, 5-fold, 10-fold, 20-fold, 50-fold, 100-fold, or increments therein.

Throughout this application, the term "increment" is used to define a numerical value in varying degrees of precision, e.g., to the nearest 10, 1, 0.1, 0.01, etc. The increment can be rounded to any measurable degree of precision, and the increment need not be rounded to the same degree of precision on both sides of a range. For example, the range 1 to 100 or increments therein includes ranges such as 20 to 80, 5 to 50, and 0.4 to 98. When a range is open-ended, e.g., a range of less than 100, increments therein means increments between 100 and the measurable limit. For example, less than 100 or increments therein means 0 to 100 or increments therein unless the feature, e.g., temperature, is not limited by 0.

Antigen-specificity can be measured with respect to any antigen. The antigen can be any substance to which an antibody can bind including, but not limited to, peptides, proteins or fragments thereof; carbohydrates; organic and inorganic molecules; receptors produced by animal cells, bacterial cells, and viruses; enzymes; agonists and antagonists of biological pathways; hormones; and cytokines. Exemplary antigens include, but are not limited to, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF) and Hepcidin. Preferred antigens include IL-6, IL-13, TNF-α, VEGF-α, Hepatocyte Growth Factor (HGF) and Hepcidin. In a method utilizing more than one enrichment step, the antigen used in each enrichment step can be the same as or different from one another. Multiple enrichment steps with the same antigen may yield a large and/or diverse population of antigen-specific cells; multiple enrichment steps with different antigens may yield an enriched cell population with cross-specificity to the different antigens.

Enriching a cell population can be performed by any cell-selection means known in the art for isolating antigen-specific cells. For example, a cell population can be enriched by chromatographic techniques, e.g., Miltenyi bead or magnetic bead technology. The beads can be directly or indirectly attached to the antigen of interest. In a preferred embodiment, the method of enriching a cell population includes at least one chromatographic enrichment step.

A cell population can also be enriched by performed by any antigen-specificity assay technique known in the art, e.g., an ELISA assay or a halo assay. ELISA assays include, but are not limited to, selective antigen immobilization (e.g., biotinylated antigen capture by streptavidin, avidin, or neutravidin coated plate), non-specific antigen plate coating, and through an antigen build-up strategy (e.g., selective antigen capture followed by binding partner addition to generate a heteromeric protein-antigen complex). The antigen can be directly or indirectly attached to a solid matrix or support, e.g., a column. A halo assay comprises contacting the cells with antigen-loaded beads and labeled anti-host antibody specific to the host used to harvest the B cells. The label can be, e.g., a fluorophore. In one embodiment, at least one assay enrichment step is performed on at least one single cell suspension. In another embodiment, the method of enriching a cell population includes at least one chromatographic enrichment step and at least one assay enrichment step.

Methods of "enriching" a cell population by size or density are known in the art. See, e.g., U.S. Pat. No. 5,627,052. These steps can be used in the present method in addition to enriching the cell population by antigen-specificity.

The cell populations of the present invention contain at least one cell capable of recognizing an antigen. Antigen-recognizing cells include, but are not limited to, B cells, plasma cells, and progeny thereof. In one embodiment, the present invention provides a clonal cell population containing a single type of antigen-specific B-cell, i.e., the cell population produces a single monoclonal antibody specific to a desired antigen.

In such embodiment, it is believed that the clonal antigen-specific population of B cells consists predominantly of antigen-specific, antibody-secreting cells, which are obtained by the novel culture and selection protocol provided herein. Accordingly, the present invention also provides methods for obtaining an enriched cell population containing at least one antigen-specific, antibody-secreting cell. In one embodiment, the present invention provides an enriched cell population containing about 50% to about 100%, or increments therein, or greater than or equal to about 60%, 70%, 80%, 90%, or 100% of antigen-specific, antibody-secreting cells.

In one embodiment, the present invention provides a method of isolating a single B cell by enriching a cell population obtained from a host before any selection steps, e.g., selecting a particular B cell from a cell population and/or selecting an antibody produced by a particular cell. The enrichment step can be performed as one, two, three, or more steps. In one embodiment, a single B cell is isolated from an enriched cell population before confirming whether the single B cell secretes an antibody with antigen-specificity and/or a desired property.

In one embodiment, a method of enriching a cell population is used in a method for antibody production and/or selection. Thus, the present invention provides a method comprising enriching a cell population before selecting an antibody. The method can include the steps of: preparing a cell population comprising at least one antigen-specific cell, enriching the cell population by isolating at least one antigen-specific cell to form an enriched cell population, and inducing antibody production from at least one antigen-specific cell. In a preferred embodiment, the enriched cell population contains more than one antigen-specific cell. In one embodiment, each antigen-specific cell of the enriched population is cultured under conditions that yield a clonal antigen-specific B cell population before isolating an antibody producing cell therefrom and/or producing an antibody using said B cell, or a nucleic acid sequence corresponding to such an antibody. In contrast to prior techniques where antibodies are produced from a cell population with a low frequency of antigen-specific cells, the present invention allows antibody selection from among a high frequency of antigen-specific cells. Because an enrichment step is used prior to antibody selection, the majority of the cells, preferably virtually all of the cells, used for antibody production are antigen-specific. By producing antibodies from a population of cells with an increased frequency of antigen specificity, the quantity and variety of antibodies are increased.

In the antibody selection methods of the present invention, an antibody is preferably selected after an enrichment step and a culture step that results in a clonal population of antigen-specific B cells. The methods can further comprise a step of sequencing a selected antibody or portions thereof from one or more isolated, antigen-specific cells. Any method known in the art for sequencing can be employed and can include sequencing the heavy chain, light chain, variable region(s), and/or complementarity determining region(s) (CDR).

In addition to the enrichment step, the method for antibody selection can also include one or more steps of screening a cell population for antigen recognition and/or antibody functionality. For example, the desired antibodies may have specific structural features, such as binding to a particular epitope or mimicry of a particular structure; antagonist or agonist activity; or neutralizing activity, e.g., inhibiting binding between the antigen and a ligand. In one embodiment, the antibody functionality screen is ligand-dependent. Screening for antibody functionality includes, but is not limited to, an in vitro protein-protein interaction assay that recreates the natural interaction of the antigen ligand with recombinant receptor protein; and a cell-based response that is ligand dependent and easily monitored (e.g., proliferation response). In one embodiment, the method for antibody selection includes a step of screening the cell population for antibody functionality by measuring the inhibitory concentration (IC50). In one embodiment, at least one of the isolated, antigen-specific cells produces an antibody having an IC50 of less than about 100, 50, 30, 25, 10 µg/mL, or increments therein.

In addition to the enrichment step, the method for antibody selection can also include one or more steps of screening a cell population for antibody binding strength. Antibody binding strength can be measured by any method known in the art (e.g., Biacore). In one embodiment, at least one of the isolated, antigen-specific cells produces an antibody having a high antigen affinity, e.g., a dissociation constant (Kd) of less than about $5\times10^{-10}$ M-1, preferably about $1\times10^{-13}$ to $5\times10^{-10}$, $1\times10^{-12}$ to $1\times10^{-10}$, $1\times10^{-12}$ to $7.5\times10^{-11}$, $1\times10^{-11}$ to $2\times10^{-11}$, about $1.5\times10^{-11}$ or less, or increments therein. In this embodiment, the antibodies are said to be affinity mature. In a preferred embodiment, the affinity of the antibodies is comparable to or higher than the affinity of any one of Panorex® (edrecolomab), Rituxan® (rituximab), Herceptin® (traztuzumab), Mylotarg® (gentuzumab), Campath® (alemtuzumab), Zevalin™ (ibritumomab), Erbitux™ (cetuximab), Avastin™ (bevicizumab), Raptiva™ (efalizumab), Remicade® (infliximab), Humira™ (adalimumab), and Xolair™ (omalizumab). Preferably, the affinity of the antibodies is comparable to or higher than the affinity of Humira™. The affinity of an antibody can also be increased by known affinity maturation techniques. In one embodiment, at least one cell population is screened for at least one of, preferably both, antibody functionality and antibody binding strength.

In addition to the enrichment step, the method for antibody selection can also include one or more steps of screening a cell population for antibody sequence homology, especially human homology. In one embodiment, at least one of the isolated, antigen-specific cells produces an antibody that has a homology to a human antibody of about 50% to about 100%, or increments therein, or greater than about 60%, 70%, 80%, 85%, 90%, or 95% homologous. The antibodies can be humanized to increase the homology to a human sequence by techniques known in the art such as CDR grafting or selectivity determining residue grafting (SDR).

In another embodiment, the present invention also provides the antibodies themselves according to any of the embodiments described above in terms of IC50, Kd, and/or homology.

The B cell selection protocol disclosed herein has a number of intrinsic advantages versus other methods for obtaining antibody-secreting B cells and monoclonal antibodies specific to desired target antigens. These advantages include, but are not restricted to, the following:

First, it has been found that when these selection procedures are utilized with a desired antigen such as IL-6 or TNF-α, the methods reproducibly result in antigen-specific B cells capable of generating what appears to be a substantially comprehensive complement of antibodies, i.e., antibodies that bind to the various different epitopes of the antigen. Without being bound by theory, it is hypothesized that the comprehensive complement is attributable to the antigen enrichment step that is performed prior to initial B cell recovery. Moreover, this advantage allows for the isolation and selection of antibodies with different properties as these properties may vary depending on the epitopic specificity of the particular antibody.

Second, it has been found that the B cell selection protocol reproducibly yields a clonal B cell culture containing a single B cell, or its progeny, secreting a single monoclonal antibody that generally binds to the desired antigen with a relatively high binding affinity, i.e. picomolar or better antigen binding affinities. By contrast, prior antibody selection methods tend to yield relatively few high affinity antibodies and therefore require extensive screening procedures to isolate an antibody with therapeutic potential. Without being bound by theory, it is hypothesized that the protocol results in both in vivo B cell immunization of the host (primary immunization) followed by a second in vitro B cell stimulation (secondary antigen priming step) that may enhance the ability and propensity of the recovered clonal B cells to secrete a single high affinity monoclonal antibody specific to the antigen target.

Third, it has been observed (as shown herein with IL-6 specific B cells) that the B cell selection protocol reproducibly yields enriched B cells producing IgG's that are, on average, highly selective (antigen specific) to the desired target. Antigen-enriched B cells recovered by these methods are believed to contain B cells capable of yielding the desired full complement of epitopic specificities as discussed above.

Fourth, it has been observed that the B cell selection protocols, even when used with small antigens, i.e., peptides of 100 amino acids or less, e.g., 5-50 amino acids long, reproducibly give rise to a clonal B cell culture that secretes a single high affinity antibody to the small antigen, e.g., a peptide. This is highly surprising as it is generally quite difficult, labor intensive, and sometimes not even feasible to produce high affinity antibodies to small peptides. Accordingly, the invention can- be used to produce therapeutic antibodies to desired peptide targets, e.g., viral, bacterial or autoantigen peptides, thereby allowing for the production of monoclonal antibodies with very discrete binding properties or even the production of a cocktail of monoclonal antibodies to different peptide targets, e.g., different viral strains. This advantage may especially be useful in the context of the production of a therapeutic or prophylactic vaccine having a desired valency, such as an HPV vaccine that induces protective immunity to different HPV strains.

Fifth, the B cell selection protocol, particularly when used with B cells derived from rabbits, tends to reproducibly yield antigen-specific antibody sequences that are very similar to endogenous human immunoglobulins (around 90% similar at the amino acid level) and that contain CDRs that possess a length very analogous to human immunoglobulins and therefore require little or no sequence modification (typically at most only a few CDR residues may be modified in the parent antibody sequence and no framework exogenous residues introduced) in order to eliminate potential immunogenicity concerns. In particular, preferably the recombinant antibody will contain only the host (rabbit) CDR1 and CDR2 residues required for antigen recognition and the entire CDR3. Thereby, the high antigen binding affinity of the recovered antibody sequences produced according to the B cell and antibody selection protocol remains intact or substantially intact even with humanization.

In sum, these method can be used to produce antibodies exhibiting higher binding affinities to more distinct epitopes by the use of a more efficient protocol than was previously known.

In a specific embodiment, the present invention provides a method for identifying a single B cell that secretes an antibody specific to a desired antigen and that optionally possesses at least one desired functional property such as affinity, avidity, cytolytic activity, and the like by a process including the following steps:

a. immunizing a host against an antigen;
b. harvesting B cells from the host;
c. enriching the harvested B cells to increase the frequency of antigen-specific cells;
d. creating at least one single cell suspension;
e. culturing a sub-population from the single cell suspension under conditions that favor the survival of a single antigen-specific B cell per culture well;
f. isolating B cells from the sub-population; and
g. determining whether the single B cell produces an antibody specific to the antigen.

Typically, these methods will further comprise an additional step of isolating and sequencing, in whole or in part, the polypeptide and nucleic acid sequences encoding the desired antibody. These sequences or modified versions or portions thereof can be expressed in desired host cells in order to produce recombinant antibodies to a desired antigen.

As noted previously, it is believed that the clonal population of B cells predominantly comprises antibody-secreting B cells producing antibody against the desired antigen. It is also believed based on experimental results obtained with several antigens and with different B cell populations that the clonally produced B cells and the isolated antigen-specific B cells derived therefrom produced according to the invention secrete a monoclonal antibody that is typically of relatively high affinity and moreover is capable of efficiently and reproducibly producing a selection of monoclonal antibodies of greater epitopic variability as compared to other methods of deriving monoclonal antibodies from cultured antigen-specific B cells. In an exemplary embodiment the population of immune cells used in such B cell selection methods will be derived from a rabbit. However, other hosts that produce antibodies, including non-human and human hosts, can alternatively be used as a source of immune B cells. It is believed that the use of rabbits as a source of B cells may enhance the diversity of monoclonal antibodies that may be derived by the methods. Also, the antibody sequences derived from rabbits according to the invention typically possess sequences having a high degree of sequence identity to human antibody sequences making them favored for use in humans since they should possess little antigenicity. In the course of humanization, the final humanized antibody contains a much lower foreign/host residue content, usually restricted to a subset of the host CDR residues that differ dramatically due-to their nature versus the human target sequence used in the grafting. This enhances the probability of complete activity recovery in the humanized antibody protein.

The methods of antibody selection using an enrichment step disclosed herein include a step of obtaining a immune cell-containing cell population from an immunized host. Methods of obtaining an immune cell-containing cell population from an immunized host are known in the art and generally include inducing an immune response in a host and harvesting cells from the host to obtain one or more cell populations. The response can be elicited by immunizing the host against a desired antigen. Alternatively, the host used as a source of such immune cells can be naturally exposed to the desired antigen such as an individual who has been infected with a particular pathogen such as a bacterium or virus or alternatively has mounted a specific antibody response to a cancer that the individual is afflicted with.

Host animals are well-known in the art and include, but are not limited to, guinea pig, rabbit, mouse, rat, non-human primate, human, as well as other mammals and rodents, chicken, cow, pig, goat, and sheep. Preferably the host is a mammal, more preferably, rabbit, mouse, rat, or human. When exposed to an antigen, the host produces antibodies as part of the native immune response to the antigen. As mentioned, the immune response can occur naturally, as a result of disease, or it can be induced by immunization with the antigen. Immunization can be performed by any method known in the art, such as, by one or more injections of the antigen with or without an agent to enhance immune response, such as complete or incomplete Freund's adjuvant. In another embodiment, the invention also contemplates intrasplenic immunization. As an alternative to immunizing a host animal in vivo, the method can comprise immunizing a host cell culture in vitro.

After allowing time for the immune response (e.g., as measured by serum antibody detection), host animal cells are harvested to obtain one or more cell populations. In a preferred embodiment, a harvested cell population is screened for antibody binding strength and/or antibody functionality. A harvested cell population is preferably from at least one of the spleen, lymph nodes, bone marrow, and/or peripheral blood mononuclear cells (PBMCs). The cells can be harvested from more than one source and pooled. Certain sources may be preferred for certain antigens. For example, the spleen, lymph nodes, and PBMCs are preferred for IL-6; and the lymph nodes are preferred for TNF. The cell population is harvested about 20 to about 90 days or increments therein after immunization, preferably about 50 to about 60 days. A harvested cell population and/or a single cell suspension therefrom can be enriched, screened, and/or cultured for antibody selection. The frequency of antigen-specific cells within a harvested cell population is usually about 1% to about 5%, or increments therein.

In one embodiment, a single cell suspension from a harvested cell population is enriched, preferably by using Miltenyi beads. From the harvested cell population having a frequency of antigen-specific cells of about 1% to about 5%, an enriched cell population is thus derived having a frequency of antigen-specific cells approaching 100%.

Figure 3:
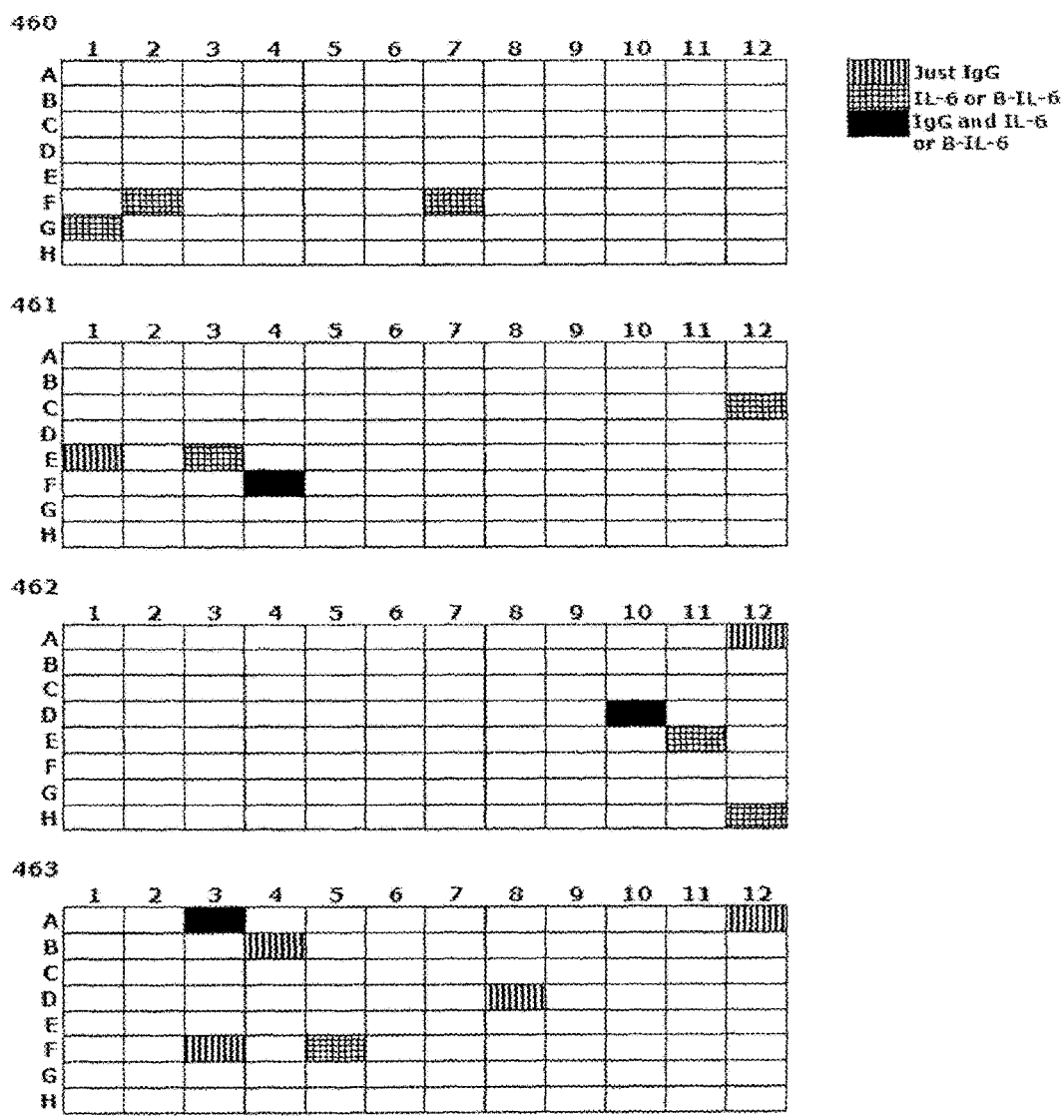
FIG. 3 demonstrates the high correlation between the IgG produced and antigen specificity for an exemplary IL-6 protocol. 9 of 11 wells showed specific IgG correlation with antigen recognition.

The method of antibody selection using an enrichment step includes a step of producing antibodies from at least one antigen-specific cell from an enriched cell population. Methods of producing antibodies in vitro are well known in the art, and any suitable method can be employed. In one embodiment, an enriched cell population, such as an antigen-specific single cell suspension from a harvested cell population, is plated at various cell densities, such as 50, 100, 250, 500, or other increments between 1 and 1000 cells per well. Preferably, the sub-population comprises no more than about 10,000 antigen-specific, antibody-secreting cells, more preferably about 50-10,000, about 50-5,000, about 50-1,000, about 50-500, about 50-250 antigen-specific, antibody-secreting cells, or increments therein. Then, these sub-populations are cultured with suitable medium (e.g., an activated T cell conditioned medium, particularly 1-5% activated rabbit T cell conditioned medium) on a feeder layer, preferably under conditions that favor the survival of a single proliferating antibody-secreting cell per culture well. The feeder layer, generally comprised of irradiated cell matter, e.g., EL4B cells, does not constitute part of the cell population. The cells are cultured in a suitable media for a time sufficient for antibody production, for example about 1 day to about 2 weeks, about 1 day to about 10 days, at least about 3 days, about 3 to about 5 days, about 5 days to about 7 days, at least about 7 days, or other increments therein. In one embodiment, more than one sub-population is cultured simultaneously. Preferably, a single antibody-producing cell and progeny thereof survives in each well, thereby providing a clonal population of antigen-specific B cells in each well. At this stage, the immunoglobulin G (IgG) produced by the clonal population is highly correlative with antigen specificity. In a preferred embodiment, the IgGs exhibit a correlation with antigen specificity that is greater than about 50%, more preferably greater than 70%, 85%, 90%, 95%, 99%, or increments therein. See FIG. 3, which demonstrates an exemplary correlation for IL-6. The correlations were demonstrated by setting up B cell cultures under limiting conditions to establish single antigen-specific antibody products per well. Antigen-specific versus general IgG synthesis was compared. Three populations were observed: IgG that recognized a single format of antigen (biotinylated and direct coating), detectable IgG and antigen recognition irrespective of immobilization, and IgG production alone. IgG production was highly correlated with antigen-specificity.

A supernatant containing the antibodies is optionally collected, which can be can be enriched, screened, and/or cultured for antibody selection according to the steps described above. In one embodiment, the supernatant is enriched (preferably by an antigen-specificity assay, especially an ELISA assay) and/or screened for antibody functionality.

In another embodiment, the enriched, preferably clonal, antigen-specific B cell population from which a supernatant described above is optionally screened in order to detect the presence of the desired secreted monoclonal antibody is used for the isolation of a few B cells, preferably a single B cell, which is then tested in an appropriate assay in order to confirm the presence of a single antibody-producing B cell in the clonal B cell population. In one embodiment about 1 to about 20 cells are isolated from the clonal B cell population, preferably less than about 15, 12, 10, 5, or 3 cells, or increments therein, most preferably a single cell. The screen is preferably effected by an antigen-specificity assay, especially a halo assay. The halo assay can be performed with the full length protein, or a fragment thereof. The antibody-containing supernatant can also be screened for at least one of: antigen binding affinity; agonism or antagonism of antigen-ligand binding, induction or inhibition of the proliferation of a specific target cell type; induction or inhibition of lysis of a target cell, and induction or inhibition of a biological pathway involving the antigen.

The identified antigen-specific cell can be used to derive the corresponding nucleic acid sequences encoding the desired monoclonal antibody. (An AluI digest can confirm that only a single monoclonal antibody type is produced per well.) As mentioned above, these sequences can be mutated, such as by humanization, in order to render them suitable for use in human medicaments.

As mentioned, the enriched B cell population used in the process can also be further enriched, screened, and/or cultured for antibody selection according to the steps described above which can be repeated or performed in a different order. In a preferred embodiment, at least one cell of an enriched, preferably clonal, antigen-specific cell population is isolated, cultured, and used for antibody selection.

Thus, in one embodiment, the present invention provides a method comprising:

a. harvesting a cell population from an immunized host to obtain a harvested cell population;

b. creating at least one single cell suspension from a harvested cell population;

c. enriching at least one single cell suspension, preferably by chromatography, to form a first enriched cell population;

d. enriching the first enriched cell population, preferably by ELISA assay, to form a second enriched cell population which preferably is clonal, i.e., it contains only a single type of antigen-specific B cell;

e. enriching the second enriched cell population, preferably by halo assay, to form a third enriched cell population containing a single or a few number of B cells that produce an antibody specific to a desired antigen; and f. selecting an antibody produced by an antigen-specific cell isolated from the third enriched cell population.

The method can further include one or more steps of screening the harvested cell population for antibody binding strength (affinity, avidity) and/or antibody functionality. Suitable screening steps include, but are not limited to, assay methods that detect: whether the antibody produced by the identified antigen-specific B cell produces an antibody possessing a minimal antigen binding affinity, whether the antibody agonizes or antagonizes the binding of a desired antigen to a ligand; whether the antibody induces or inhibits the proliferation of a specific cell type; whether the antibody induces or elicits a cytolytic reaction against target cells; whether the antibody binds to a specific epitope; and whether the antibody modulates (inhibits or agonizes) a specific biological pathway or pathways involving the antigen.

Similarly, the method can include one or more steps of screening the second enriched cell population for antibody binding strength and/or antibody functionality.

The method can further include a step of sequencing the polypeptide sequence or the corresponding nucleic acid sequence of the selected antibody. The method can also include a step of producing a recombinant antibody using the sequence, a fragment thereof, or a genetically modified version of the selected antibody. Methods for mutating antibody sequences in order to retain desired properties are well known to those skilled in the art and include humanization, chimerisation, production of single chain antibodies; these mutation methods can yield recombinant antibodies possessing desired effector function, immunogenicity, stability, removal or addition of glycosylation, and the like. The recombinant antibody can be produced by any suitable recombinant cell, including, but not limited to mammalian cells such as CHO, COS, BHK, HEK-293, bacterial cells, yeast cells, plant cells, insect cells, and amphibian cells. In one embodiment, the antibodies are expressed in polyploidal yeast cells, i.e., diploid yeast cells, particularly *Pichia*.

In one embodiment, the method comprises:

a. immunizing a host against an antigen to yield host antibodies;

b. screening the host antibodies for antigen specificity and neutralization;

c. harvesting B cells from the host;

d. enriching the harvested B cells to create an enriched cell population having an increased frequency of antigen-specific cells;

e. culturing one or more sub-populations from the enriched cell population under conditions that favor the survival of a single B cell to produce a clonal population in at least one culture well;

f. determining whether the clonal population produces an antibody specific to the antigen;

g. isolating a single B cell; and h. sequencing the nucleic acid sequence of the antibody produced by the single B cell.

Methods of Humanizing Antibodies

In another embodiment of the invention, there is provided a method for humanizing antibody heavy and light chains. In this embodiment, the following method is followed for the humanization of the heavy and light chains:

Light Chain

1. Identify the amino acid that is the first one following the signal peptide sequence. This is the start of Framework 1. The signal peptide starts at the first initiation methionine and is typically, but not necessarily 22 amino acids in length for rabbit light chain protein sequences. The start of the mature polypeptide can also be determined experimentally by N-terminal protein sequencing, or can be predicted using a prediction algorithm. This is also the start of Framework 1 as classically defined by those in the field.

Example: RbtVL Amino acid residue 1 in FIG. 2, starting 'AYDM . . . .'

2. Identify the end of Framework 3. This is typically 86-90 amino acids following the start of Framework 1 and is typically a cysteine residue preceded by two tyrosine residues. This is the end of the Framework 3 as classically defined by those in the field.

Example: RbtVL amino acid residue 88 in FIG. 2, ending as 'TYYC'

3. Use the rabbit light chain sequence of the polypeptide starting from the beginning of Framework 1 to the end of Framework 3 as defined above and perform a sequence homology search for the most similar human antibody protein sequences. This will typically be a search against human germline sequences prior to antibody maturation in order to reduce the possibility of immunogenicity, however any human sequences can be used. Typically a program like BLAST can be used to search a database of sequences for the most homologous. Databases of human antibody sequences can be found from various sources such as NCBI (National Center for Biotechnology Information).

Example: RbtVL amino acid sequence from residues numbered 1 through 88 in FIG. 2 is BLASTed against a human antibody germline database. The top three unique returned sequences are shown in FIG. 2 as L12A, V1 and Vx02.

4. Generally the most homologous human germline variable light chain sequence is then used as the basis for humanization. However those skilled in the art may decide to use another sequence that wasn't the highest homology as determined by the homology algorithm, based on other factors including sequence gaps and framework similarities.

Example: In FIG. 2, L12A was the most homologous human germline variable light chain sequence and is used as the basis for the humanization of RbtVL.

5. Determine the framework and CDR arrangement (FR1, FR2, FR3, CDR1 & CDR2) for the human homolog being used for the light chain humanization. This is using the traditional layout as described in the field. Align the rabbit variable light chain sequence with the human homolog, while maintaining the layout of the framework and CDR regions.

Example: In FIG. 2, the RbtVL sequence is aligned with the human homologous sequence L12A, and the framework and CDR domains are indicated.

6. Replace the human homologous light chain sequence CDR1 and CDR2 regions with the CDR1 and CDR2 sequences from the rabbit sequence. If there are differences in length between the rabbit and human CDR sequences then use the entire rabbit CDR sequences and their lengths. It is possible that the specificity, affinity and/or immunogenicity of the resulting humanized antibody may be unaltered if smaller or larger sequence exchanges are performed, or if specific residue(s) are altered, however the exchanges as described have been used successfully, but do not exclude the possibility that other changes may be permitted.

Example: In FIG. 2, the CDR1 and CDR2 amino acid residues of the human homologous variable light chain L12A are replaced with the CDR1 and CDR2 amino acid sequences from the RbtVL rabbit antibody light chain sequence. The human L12A frameworks 1, 2 and 3 are unaltered. The resulting humanized sequence is shown below as VLh from residues numbered 1 through 88. Note that the only residues that are different from the L12A human sequence are underlined, and are thus rabbit-derived amino acid residues. In this example only 8 of the 88 residues are different than the human sequence.

7. After framework 3 of the new hybrid sequence created in Step 6, attach the entire CDR3 of the rabbit light chain antibody sequence. The CDR3 sequence can be of various lengths, but is typically 9 to 15 amino acid residues in length. The CDR3 region and the beginning of the following framework 4 region are defined classically and identifiable by those skilled in the art. Typically the beginning of Framework 4, and thus after the end of CDR3 consists of the sequence 'FGGG . . . ', however some variation may exist in these residues.

Example: In FIG. 2, the CDR3 of RbtVL (amino acid residues numbered 89-100) is added after the end of framework 3 in the humanized sequence indicated as VLh.

8. The rabbit light chain framework 4, which is typically the final 11 amino acid residues of the variable light chain and begins as indicated in Step 7 above and typically ends with the amino acid sequence ' . . . VVKR' is replaced with the nearest human light chain framework 4 homolog, usually from germline sequence. Frequently this human light chain framework 4 is of the sequence 'FGGGTKVEIKR'. It is possible that other human light chain framework 4 sequences that are not the most homologous or otherwise different may be used without affecting the specificity, affinity and/or immunogenicity of the resulting humanized antibody. This human light chain framework 4 sequence is added to the end of the variable light chain humanized sequence immediately following the CDR3 sequence from Step 7 above. This is now the end of the variable light chain humanized amino acid sequence.

Example: In FIG. 2, Framework 4 (FR4) of the RbtVL rabbit light chain sequence is shown above a homologous human FR4 sequence. The human FR4 sequence is added to the humanized variable light chain sequence (VLh) right after the end of the CD3 region added in Step 7 above.

Heavy Chain

1. Identify the amino acid that is the first one following the signal peptide sequence. This is the start of Framework 1. The signal peptide starts at the first initiation methionine and is typically 19 amino acids in length for rabbit heavy chain protein sequences. Typically, but not necessarily always, the final 3 amino acid residues of a rabbit heavy chain signal peptide are ' . . . VQC', followed by the start of Framework 1. The start of the mature polypeptide can also be determined experimentally by N-terminal protein sequencing, or can be predicted using a prediction algorithm. This is also the start of Framework 1 as classically defined by those in the field.

Example: RbtVH Amino acid residue 1 in FIG. 2, starting 'QEQL . . . '

2. Identify the end of Framework 3. This is typically 95-100 amino acids following the start of Framework 1 and typically has the final sequence of ' . . . CAR' (although the alanine can also be a valine). This is the end of the Framework 3 as classically defined by those in the field.

Example: RbtVH amino acid residue 98 in FIG. 2, ending as ' . . . FCVR'.

3. Use the rabbit heavy chain sequence of the polypeptide starting from the beginning of Framework 1 to the end of Framework 3 as defined above and perform a sequence homology search for the most similar human antibody protein sequences. This will typically be against a database of human germline sequences prior to antibody maturation in order to reduce the possibility of immunogenicity, however any human sequences can be used. Typically a program like BLAST can be used to search a database of sequences for the most homologous. Databases of human antibody sequences can be found from various sources such as NCBI (National Center for Biotechnology Information).

Example: RbtVH amino acid sequence from residues numbered 1 through 98 in FIG. 2 is BLASTed against a human antibody germline database. The top three unique returned sequences are shown in FIGS. 2 as 3-64-04, 3-66-04, and 3-53-02.

4. Generally the most homologous human germline variable heavy chain sequence is then used as the basis for humanization. However those skilled in the art may decide to use another sequence that wasn't the most homologous as determined by the homology algorithm, based on other factors including sequence gaps and framework similarities.

Example: 3-64-04 in FIG. 2 was the most homologous human germline variable heavy chain sequence and is used as the basis for the humanization of RbtVH.

5. Determine the framework and CDR arrangement (FR1, FR2, FR3, CDR1 & CDR2) for the human homolog being used for the heavy chain humanization. This is using the traditional layout as described in the field. Align the rabbit variable heavy chain sequence with the human homolog, while maintaining the layout of the framework and CDR regions.

Example: In FIG. 2, the RbtVH sequence is aligned with the human homologous sequence 3-64-04, and the framework and CDR domains are indicated.

6. Replace the human homologous heavy chain sequence CDR1 and CDR2 regions with the CDR1 and CDR2 sequences from the rabbit sequence. If there are differences in length between the rabbit and human CDR sequences then use the entire rabbit CDR sequences and their lengths. In addition, it may be necessary to replace the final three amino acids of the human heavy chain Framework 1 region with the final three amino acids of the rabbit heavy chain Framework 1. Typically but not always, in rabbit heavy chain Framework 1 these three residues follow a Glycine residue preceded by a Serine residue. In addition, it may be necessary replace the final amino acid of the human heavy chain Framework 2 region with the final amino acid of the rabbit heavy chain Framework 2. Typically, but not necessarily always, this is a Glycine residue preceded by an Isoleucine residue in the rabbit heavy chain Framework 2. It is possible that the specificity, affinity and/or immunogenicity of the resulting humanized antibody may be unaltered if smaller or larger sequence exchanges are performed, or if specific residue(s) are altered, however the exchanges as described have been used successfully, but do not exclude the possibility that other changes may be permitted. For example, a tryptophan amino acid residue typically occurs four residues prior to the end of the rabbit heavy chain CDR2 region, whereas in human heavy chain CDR2 this residue is typically a Serine residue. Changing this rabbit tryptophan residue to a human Serine residue at this position has been demonstrated to have minimal to no effect on the humanized antibody's specificity or affinity, and thus further minimizes the content of rabbit sequence-derived amino acid residues in the humanized sequence.

Example: In FIG. 2, The CDR1 and CDR2 amino acid residues of the human homologous variable heavy chain are replaced with the CDR1 and CDR2 amino acid sequences from the RbtVH rabbit antibody light chain sequence, except for the boxed residue, which is tryptophan in the rabbit sequence (position number 63) and Serine at the same position in the human sequence, and is kept as the human Serine residue. In addition to the CDR1 and CDR2 changes, the final three amino acids of Framework 1 (positions 28-30) as well as the final residue of Framework 2 (position 49) are retained as rabbit amino acid residues instead of human. The resulting humanized sequence is shown below as. VHh from residues numbered 1 through 98. Note that the only residues that are different from the 3-64-04 human sequence are underlined, and are thus rabbit-derived amino acid residues. In this example only 15 of the 98 residues are different than the human sequence.

7. After framework 3 of the new hybrid sequence created in Step 6, attach the entire CDR3 of the rabbit heavy chain antibody sequence. The CDR3 sequence can be of various lengths, but is typically 5 to 19 amino acid residues in length. The CDR3 region and the beginning of the following framework 4 region are defined classically and are identifiable by those skilled in the art. Typically the beginning of framework 4, and thus after the end of CDR3 consists of the sequence WGXG . . . (where X is usually Q or P), however some variation may exist in these residues.

Example: The CDR3 of RbtVH (amino acid residues numbered 99-110) is added after the end of framework 3 in the humanized sequence indicated as VHh.

8. The rabbit heavy chain framework 4, which is typically the final 11 amino acid residues of the variable heavy chain and begins as indicated in Step 7 above and typically ends with the amino acid sequence ' . . . TVSS ' is replaced with the nearest human heavy chain framework 4 homolog, usually from germline sequence. Frequently this human heavy chain framework 4 is of the sequence 'WGQGTLVT-VSS'. It is possible that other human heavy chain framework 4 sequences that are not the most homologous or otherwise different may be used without affecting the specificity, affinity and/or immunogenicity of the resulting humanized antibody. This human heavy chain framework 4 sequence is added to the end of the variable heavy chain humanized sequence immediately following the CDR3 sequence from Step 7 above. This is now the end of the variable heavy chain humanized amino-acid sequence.

Example: In FIG. 2, framework 4 (FR4) of the RbtVH rabbit heavy chain sequence is shown above a homologous human heavy FR4 sequence. The human FR4 sequence is added to the humanized variable heavy chain sequence (VHh) right after the end of the CD3 region added in Step 7 above.

Methods of Producing Antibodies and Fragments thereof

The invention is also directed to the production of the antibodies described herein or fragments thereof. Recombinant polypeptides corresponding to the antibodies described herein or fragments thereof are secreted from polyploidal, preferably diploid or tetraploid strains of mating competent yeast. In an exemplary embodiment, the invention is directed to methods for producing these recombinant polypeptides in secreted form for prolonged periods using cultures comprising polyploid yeast, i.e., at least several days to a week, more preferably at least a month or several months, and even more preferably at least 6 months to a year or longer. These polyploid yeast cultures will express at least 10-25 mg/liter of the polypeptide, more preferably at least 50-250 mg/liter, still more preferably at least 500-1000 mg/liter, and most preferably a gram per liter or more of the recombinant polypeptide(s).

In one embodiment of the invention a pair of genetically marked yeast haploid cells are transformed with expression vectors comprising subunits of a desired heteromultimeric protein. One haploid cell comprises a first expression vector, and a second haploid cell comprises a second expression vector. In another embodiment diploid yeast cells will be transformed with one or more expression vectors that provide for the expression and secretion of one or more of the recombinant polypeptides. In still another embodiment a single haploid cell may be transformed with one or more vectors and used to produce a polyploidal yeast by fusion or mating strategies. In yet another embodiment a diploid yeast culture may be transformed with one or more vectors providing for the expression and secretion of a desired polypeptide or polypeptides. These vectors may comprise vectors e.g., linearized plasmids or other linear DNA products that integrate into the yeast cell's genome randomly, through homologous recombination, or using a recombinase such-as Cre/Lox or Flp/Frt. Optionally, additional expression vectors may be introduced into the haploid or diploid cells; or the first or second expression vectors may comprise additional coding sequences; for the synthesis of heterotrimers; heterotetramers; etc. The expression levels of the non-identical polypeptides may be individually calibrated, and adjusted through appropriate selection, vector copy number, promoter strength and/or induction and the like. The transformed haploid cells are genetically crossed or fused. The resulting diploid or tetraploid strains are utilized to produce and secrete fully assembled and biologically functional proteins, humanized antibodies described herein or fragments thereof.

The use of diploid or tetraploid cells for protein production provides for unexpected benefits. The cells can be grown for production purposes, i.e. scaled up, and for extended periods of time, in conditions that can be deleterious to the growth of haploid cells, which conditions may include high cell density; growth in minimal media; growth at low temperatures; stable growth in the absence of selective pressure; and which may provide for maintenance of heterologous gene sequence integrity and maintenance of high level expression over time. Without wishing to be bound thereby, the inventors theorize that these benefits may arise, at least in part, from the creation of diploid strains from two distinct parental haploid strains. Such haploid strains can comprise numerous minor autotrophic mutations, which mutations are complemented in the diploid or tetraploid, enabling growth and enhanced production under highly selective conditions.

Transformed mating competent haploid yeast cells provide a genetic method that enables subunit pairing of a desired protein. Haploid yeast strains are transformed with each of two expression vectors, a first vector to direct the synthesis of one polypeptide chain and a second vector to direct the synthesis of a second, non-identical polypeptide chain. The two haploid strains are mated to provide a diploid host where optimized target protein production can be obtained.

Optionally, additional non-identical coding sequence(s) are provided. Such sequences may be present on additional expression vectors or in the first or the second expression vectors. As is known in the art, multiple coding sequences may be independently expressed from individual promoters; or may be coordinately expressed through the inclusion of an "internal ribosome entry site" or "IRES", which is an element that promotes direct internal ribosome entry to the initiation codon, such as ATG, of a cistron (a protein encoding region), thereby leading to the cap-independent translation of the gene. IRES elements functional in yeast are described by Thompson et al. (2001) P.N.A.S. 98:12866-12868.

In one embodiment of the invention, antibody sequences are produced in combination with a secretory J chain, which provides for enhanced stability of IgA (see U.S. Pat. Nos. 5,959,177; and 5,202,422).

In a preferred embodiment the two haploid yeast strains are each auxotrophic, and require supplementation of media for growth of the haploid cells. The pair of auxotrophs are complementary, such that the diploid product will grow in the absence of the supplements required for the haploid cells. Many such genetic markers are known in yeast, including requirements for amino acids (e.g. met, lys, his, arg, etc.), nucleosides (e.g. ura3, ade1, etc.); and the like. Amino acid markers may be preferred for the methods of the invention. Alternatively diploid cells which contain the desired vectors can be selected by other means, e.g., by use of other markers, such as green fluorescent protein, antibiotic resistance genes, various dominant selectable markers, and the like.

Two transformed haploid cells may be genetically crossed and diploid strains arising from this mating event selected by their hybrid nutritional requirements and/or antibiotic resistance spectra. Alternatively, populations of the two transformed haploid strains are spheroplasted and fused, and diploid progeny regenerated and selected. By either method, diploid strains can be identified and selectively grown based on their ability to grow in different media than their parents. For example, the diploid cells may be grown in minimal medium that may include antibiotics. The diploid synthesis strategy has certain advantages. Diploid strains have the potential to produce enhanced levels of heterologous protein through broader complementation to underlying mutations, which may impact the production and/or secretion of recombinant protein. Furthermore, once stable strains have been obtained, any antibiotics used to select those strains do not necessarily need to be continuously present in the growth media.

As noted above, in some embodiments a haploid yeast may be transformed with a single or multiple vectors and mated or fused with a non-transformed cell to produce a diploid cell containing the vector or vectors. In other embodiments, a diploid yeast cell may be transformed with one or more vectors that provide for the expression and secretion of a desired heterologous polypeptide by the diploid yeast cell.

In one embodiment of the invention, two haploid strains are transformed with a library of polypeptides, e.g. a library of antibody heavy or light chains. Transformed haploid cells that synthesize the polypeptides are mated with the complementary haploid cells. The resulting diploid cells are screened for functional protein. The diploid cells provide a means of rapidly, conveniently and inexpensively bringing together a large number of combinations of polypeptides for functional testing. This technology is especially applicable for the generation of heterodimeric protein products, where optimized subunit synthesis levels are critical for functional protein expression and secretion.

In another embodiment of the invention, the expression level ratio of the two subunits is regulated in order to maximize product generation. Heterodimer subunit protein levels have been shown previously to impact the final product generation (Simmons L C, J lmmunol Methods. 2002 May 1;263(1-2):133-47). Regulation can be achieved prior to the mating step by selection for a marker present on the expression vector. By stably increasing the copy number of the vector, the expression level can be increased. In some cases, it may be desirable to increase the level of one chain relative to the other, so as to reach a balanced proportion between the subunits of the polypeptide. Antibiotic resistance markers are useful for this purpose, e.g. Zeocin resistance marker, G418 resistance, etc. and provide a means of enrichment for strains that contain multiple integrated copies of an expression vector in a strain by selecting for transformants that are resistant to higher levels of Zeocin or G418. The proper ratio, e.g. 1:1; 1:2; etc. of the subunit genes may be important for efficient protein production. Even when the same promoter is used to transcribe both subunits, many other factors contribute to the final level of protein expressed and therefore, it can be useful to increase the number of copies of one encoded gene relative to the other. Alternatively, diploid strains that produce higher levels of a polypeptide, relative to single copy vector strains, are created by mating two haploid strains, both of which have multiple copies of the expression vectors.

Host cells are transformed with the above-described expression vectors, mated to form diploid strains, and cultured in conventional nutrient media modified as appropriate for inducing promoters, selecting transformants or amplifying the genes encoding the desired sequences. A number of minimal media suitable for the growth of yeast are known in the art. Any of these media may be supplemented as necessary with salts (such as sodium chloride, calcium, magnesium, and phosphate), buffers (such as phosphate, HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Secreted proteins are recovered from the culture medium. A protease inhibitor, such as phenyl methyl sulfonyl fluoride (PMSF) may be useful to inhibit proteolytic degradation during purification, and antibiotics may be included to prevent the growth of adventitious contaminants. The composition may be concentrated, filtered, dialyzed, etc., using methods known in the art.

The diploid cells of the invention are grown for production purposes. Such production purposes desirably include growth in minimal media, which media lacks pre-formed amino acids and other complex biomolecules, e.g., media comprising ammonia as a nitrogen source, and glucose as an energy and carbon source, and salts as a source of phosphate, calcium and the like. Preferably such production media lacks selective agents such as antibiotics, amino acids, purines, pyrimidines, etc. The diploid cells can be grown to high cell density, for example at least about 50 g/L; more usually at least about 100 g/L; and may be at least about 300, about 400, about 500 g/L or more.

In one embodiment of the invention, the growth of the subject cells for production purposes is performed at low temperatures, which temperatures may be lowered during log phase, during stationary phase, or both. The term "low temperature" refers to temperatures of at least about 15° C., more usually at least about 17° C., and may be about 20° C., and is usually not more than about 25° C., more usually not more than about 22° C. In another embodiment of the invention, the low temperature is usually not more than about 28° C. Growth temperature can impact the production of full-length secreted proteins in production cultures, and decreasing the culture growth temperature can strongly enhance the intact product yield. The decreased temperature appears to assist intracellular trafficking through the folding and post-translational processing pathways used by the host to generate the target product, along with reduction of cellular protease degradation.

The methods of the invention provide for expression of secreted, active protein, preferably a mammalian protein. In one embodiment, secreted, "active antibodies", as used herein, refers to a correctly folded multimer of at least two properly paired chains, which accurately binds to its cognate antigen. Expression levels of active protein are usually at least about 10-50 mg/liter culture, more usually at least about 100 mg/liter, preferably at least about 500 mg/liter, and may be 1000 mg/liter or more.

The methods of the invention can provide for increased stability of the host and heterologous coding sequences during production. The stability is evidenced, for example, by maintenance of high levels of expression of time, where the starting level of expression is decreased by not more than about 20%, usually not more than 10%, and may be decreased by not more than about 5% over about 20 doublings, 50 doublings, 100 doublings, or more.

The strain stability also provides for maintenance of heterologous gene sequence integrity over time, where the sequence of the active coding sequence and requisite transcriptional regulatory elements are maintained in at least about 99% of the diploid cells, usually in at least about 99.9% of the diploid cells, and preferably in at least about 99.99% of the diploid cells over about 20 doublings, 50 doublings, 100 doublings, or more. Preferably, substantially all of the diploid cells maintain the sequence of the active coding sequence and requisite transcriptional regulatory elements.

Other methods of producing antibodies are well known to those of ordinary skill in the art. For example, methods of producing chimeric antibodies are now well known in the art (See, for example, U.S. Pat. No. 4,816,567 to Cabilly et al.; Morrison et al., P.N.A.S. USA, 81:8651-55 (1984); Neuberger, M. S. et al., Nature, 314:268-270 (1985); Boulianne, G. L. et al., Nature, 312:643-46 (1984), the disclosures of each of which are herein incorporated by reference in their entireties).

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al, Nature, 321:522-525 (1986); Reichmann, L., et al, Nature, 332:323-327 (1988); Verhoeyen, M, et al, Science, 239:1534-36 (1988), the disclosures of each of which are herein incorporated by reference in their entireties).

Antibody polypeptides of the invention having IL-6 binding specificity may also be produced by constructing, using conventional techniques well known to those of ordinary skill in the art, an expression vector containing an operon and a DNA sequence encoding an antibody heavy chain in which the DNA sequence encoding the CDRs required for antibody specificity is derived from a non-human cell source, preferably a rabbit B-cell source, while the DNA sequence encoding the remaining parts of the antibody chain is derived from a human cell source.

A second expression vector is produced using the same conventional means well known to those of ordinary skill in the art, said expression vector containing an operon and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding an operon and a light chain-derived polypeptide and the second vector containing DNA encoding an operon and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA.

The host cells used to express the antibody polypeptides may be either a bacterial cell such as E. coli, or a eukaryotic cell. In a particularly preferred embodiment of the invention, a mammalian cell of a well-defined type for this purpose, such as a myeloma cell or a Chinese hamster ovary (CHO) cell line may be used.

The general methods by which the vectors may be constructed, transfection methods required to produce the host cell and culturing methods required to produce the antibody polypeptides from said host cells all include conventional techniques. Although preferably the cell line used to produce the antibody is a mammalian cell line, any other suitable cell line, such as a bacterial cell line such as an E. coli-derived bacterial strain, or a yeast cell line, may alternatively be used.

Similarly, once produced the antibody polypeptides may be purified according to standard procedures in the art, such as for example cross-flow filtration, ammonium sulphate precipitation, affinity column chromatography and the like.

The antibody polypeptides described herein may also be used for the design and synthesis of either peptide or non-peptide mimetics that would be useful for the same therapeutic applications as the antibody polypeptides of the invention. See, for example, Saragobi et al, Science, 253: 792-795 (1991), the contents of which is herein incorporated by reference in its entirety.

Screening Assays

The invention also includes screening assays designed to assist in the identification of diseases and disorders associated with IL-6 in patients exhibiting symptoms of an IL-6 associated disease or disorder.

In one embodiment of the invention, the anti-IL-6 antibodies of the invention, or IL-6 binding fragments thereof, are used to detect the presence of IL-6 in a biological sample obtained from a patient exhibiting symptoms of a disease or disorder associated with IL-6. The presence of IL-6, or elevated levels thereof when compared to pre-disease levels of IL-6 in a comparable biological sample, may be beneficial in diagnosing a disease or disorder associated with IL-6.

Another embodiment of the invention provides a diagnostic or screening assay to assist in diagnosis of diseases or disorders associated with IL-6 in patients exhibiting symptoms of an IL-6 associated disease or disorder identified herein, comprising assaying the level of IL-6 expression in a biological sample from said patient using a post-translationally modified anti-IL-6 antibody or binding fragment thereof. The anti-IL-6 antibody or binding fragment thereof may be post-translationally modified to include a detectable moiety such as set forth previously in the disclosure.

The IL-6 level in the biological sample is determined using a modified anti-IL-6 antibody or binding fragment thereof as set forth herein, and comparing the level of IL-6 in the biological sample against a standard level of IL-6 (e.g., the level in normal biological samples). The skilled clinician would understand that some variability may exist between normal biological samples, and would take that into consideration when evaluating results.

The above-recited assay may also be useful in monitoring a disease or disorder, where the level of IL-6 obtained in a biological sample from a patient believed to have an IL-6 associated disease or disorder is compared with the level of IL-6 in prior biological samples from the same patient, in order to ascertain whether the IL-6 level in said patient has changed with, for example, a treatment regimen.

The invention is also directed to a method of in vivo imaging which detects the presence of cells which express IL-6 comprising administering a diagnostically effective amount of a diagnostic composition. Said in vivo imaging is useful for the detection and imaging of IL-6 expressing tumors or metastases and IL-6 expressing inflammatory sites, for example, and can be used as part of a planning regimen for design of an effective cancer or arthritis treatment protocol. The treatment protocol may include, for example, one or more of radiation, chemotherapy, cytokine therapy, gene therapy, and antibody therapy, as well as an anti-IL-6 antibody or fragment thereof.

A skilled clinician would understand that a biological sample includes, but is not limited to, sera, plasma, urine, saliva, mucous, pleural fluid, synovial fluid and spinal fluid.

Methods of Ameliorating or Reducing Symptoms of, or Treating, or Preventing, Diseases and Disorders Associated with, IL-6

In another embodiment of the invention, anti-IL-6 antibodies described herein, or fragments thereof, are useful for ameliorating or reducing the symptoms of, or treating, or preventing, diseases and disorders associated with IL-6. Anti-IL-6 antibodies described herein, or fragments thereof, can also be administered in a therapeutically effective amount to patients in need of treatment of diseases and disorders associated with IL-6 in the form of a pharmaceutical composition as described in greater detail below.

In one embodiment of the invention, anti-IL-6 antibodies described herein, or fragments thereof, are useful for ameliorating or reducing the symptoms of, or treating, or preventing, diseases and disorders associated with fatigue. Diseases and disorders associated with fatigue include, but are not limited to, general fatigue, exercise-induced fatigue, cancer-related fatigue, inflammatory disease-related fatigue and chronic fatigue syndrome. See, for example, Esper D H, et al, The cancer cachexia syndrome: a review of metabolic and clinical manifestations, Nutr Clin Pract., 2005 August; 20 (4):369-76; Vgontzas A N, et al, IL-6 and its circadian secretion in humans, Neuroimmunomodulation, 2005; 12(3):131-40; Robson-Ansley, P J, et al, Acute interleukin-6 administration impairs athletic performance in healthy, trained male runners, Can J Appl Physiol., 2004 August; 29(4):411-8; Shephard R J., Cytokine responses to physical activity, with particular reference to IL-6: sources, actions, and clinical implications, Crit Rev Immunol., 2002; 22(3): 165-82; Arnold, M C, et al, Using an interleukin-6 challenge to evaluate neuropsychological performance in chronic fatigue syndrome, Psychol Med., 2002 August; 32(6):1075-89; Kurzrock R., The role of cytokines in cancer-related fatigue, Cancer, 2001 Sep. 15; 92(6 Suppl):1684-8; Nishimoto N, et al, Improvement in Castleman's disease by humanized anti-interleukin-6 receptor antibody therapy, Blood, 2000 Jan. 1; 95 (1):56-61; Vgontzas A N, et al, Circadian interleukin-6 secretion and quantity and depth of sleep, J Clin Endocrinol Metab., 1999 August; 84(8):2603-7; and Spath-Schwalbe E, et al, Acute effects of recombinant human interleukin 6 on endocrine and central nervous sleep functions in healthy men, J Clin Endocrinol Metab., 1998 May; 83(5):1573-9; the disclosures of each of which are herein incorporated by reference in their entireties.

In a preferred embodiment of the invention, anti-IL-6 antibodies described herein, or fragments thereof, are useful for ameliorating or reducing the symptoms of, or treating, or preventing, cachexia. Diseases and disorders associated with cachexia include, but are not limited to, cancer-related cachexia, cardiac-related cachexia, respiratory-related cachexia, renal-related cachexia and age-related cachexia. See, for example, Barton, B E., Interleukin-6 and new strategies for the treatment of cancer, hyperproliferative diseases and paraneoplastic syndromes, Expert Opin Ther Targets, 2005 August; 9(4):737-52; Zaki M H, et al, CNTO 328, a monoclonal antibody to IL-6, inhibits human tumor-induced cachexia in nude mice, Int J Cancer, 2004 Sep. 10; 111(4):592-5; Trikha M, et al, Targeted anti-interleukin-6 monoclonal antibody therapy for cancer: a review of the rationale and clinical evidence, Clin Cancer Res., 2003 Oct. 15; 9(13):4653-65; Lelli G, et al, Treatment of the cancer anorexia-cachexia syndrome: a critical reappraisal, J Chemother., 2003 June; 15(3):220-5; Argiles J M, et al, Cytokines in the pathogenesis of cancer cachexia, Curr Opin Clin Nutr Metab Care, 2003 July; 6(4):401-6; Barton B E., IL-6-like cytokines and cancer cachexia: consequences of chronic inflammation, Immunol Res., 2001; 23(1):41-58; Yamashita J I, et al, Medroxyprogesterone acetate and cancer cachexia: interleukin-6 involvement, Breast Cancer, 2000; 7(2):130-5; Yeh S S, et al, Geriatric cachexia: the role of cytokines, Am J Clin Nutr., 1999 August; 70(2):183-97; Strassmann G, et al, Inhibition of experimental cancer cachexia by anti-cytokine and anti-cytokine-receptor therapy, Cytokines Mol Ther., 1995 June; 1(2):107-13; Fujita J, et al, Anti-interleukin-6 receptor antibody prevents muscle atrophy in colon-26 adenocarcinoma-bearing mice with modulation of lysosomal and ATP-ubiquitin-dependent proteolytic pathways, Int J Cancer, 1996 Nov. 27; 68(5): 637-43; Tsujinaka T, et al, Interleukin 6 receptor antibody inhibits muscle atrophy and modulates proteolytic systems in interleukin 6 transgenic mice, J Clin Invest., 1996 Jan. 1; 97(1):244-9; Emilie D, et al, Administration of an anti-interleukin-6 monoclonal antibody to patients with acquired immunodeficiency syndrome and lymphoma: effect on lymphoma growth and on B clinical Symptoms, Blood, 1994 Oct. 15; 84 (8):2472-9; and Strassmann G, et al, Evidence for the involvement of interleukin 6 in experimental cancer cachexia, J Clin Invest., 1992 May; 89(5):1681-4; the disclosures of each of which are herein incorporated by reference in their entireties.

In another embodiment of the invention, anti-IL-6 antibodies described herein, or fragments thereof, are useful for ameliorating or-reducing the symptoms of, or treating, or preventing, autoimmune diseases and disorders. Diseases and disorders associated with autoimmunity include, but are not limited to, rheumatoid arthritis, systemic lupus erythematosus (SLE), systemic juvenile idiopathic arthritis, psoriasis, psoriatic arthropathy, ankylosing spondylitis, inflammatory bowel disease (IBD), polymyalgia rheumatica, giant cell arteritis, autoimmune vasculitis, graft versus host disease (GVHD), Sjogren's syndrome, adult onset Still's disease. In a preferred embodiment of the invention, humanized anti-IL-6 antibodies described herein, or fragments thereof, are useful for ameliorating or reducing the symptoms of, or treating, or preventing, rheumatoid arthritis and systemic juvenile idiopathic arthritis. See, for example, Nishimoto N., Clinical studies in patients with Castleman's disease, Crohn's disease, and rheumatoid arthritis in Japan, Clin Rev Allergy Immunol., 2005 June; 28(3):221-30; Nishimoto N, et al, Treatment of rheumatoid arthritis with humanized anti-interleukin-6 receptor antibody: a multicenter, double-blind, placebo-controlled trial, Arthritis Rheum., 2004 June; 50(6):1761-9; Choy E., Interleukin 6 receptor as a target for the treatment of rheumatoid arthritis, Ann Rheum Dis., 2003 November; 62 Suppl 2:ii68-9; Nishimoto N, et al, Toxicity, pharmacokinetics, and dose-finding study of repetitive treatment with the humanized anti-interleukin 6 receptor antibody MRA in rheumatoid arthritis. Phase I/II clinical study, J Rheumatol., 2003 July; 30(7):1426-35; Mihara M, et al, Humanized antibody to human interleukin-6 receptor inhibits the development of collagen arthritis in cynomolgus monkeys, Clin Immunol., 2001 March; 98(3):319-26; Nishimoto N, et al, Anti-interleukin 6 receptor antibody treatment in rheumatic disease, Ann Rheum Dis., 2000 November; 59 Suppl 1:i21-7; Tackey E, et al, Rationale for interleukin-6 blockade in systemic lupus erythematosus, Lupus, 2004; 13(5):339-43; Finck B K, et al, Interleukin 6 promotes murine lupus in NZB/NZW F1 mice, J Clin Invest., 1994 August; 94 (2):585-91; Kitani A, et al, Autostimulatory effects of IL-6 on excessive B cell differentiation in patients with systemic lupus erythematosus: analysis of IL-6 production and IL-6R expression, Clin Exp Immunol., 1992 April; 88(1):75-83; Stuart R A, et al, Elevated serum interleukin-6 levels associated with active disease in systemic connective tissue disorders, Clin Exp Rheumatol., 1995 Jan-February; 13 (1):17-22; Mihara M, et al, IL-6 receptor blockage inhibits the onset of autoimmune kidney disease in NZB/W F1 mice, Clin Exp Immunol., 1998 June; 12(3):397-402; Woo P, et al, Open label phase II trial of single, ascending doses of MRA in Caucasian children with severe systemic juvenile idiopathic arthritis: proof of principle of the efficacy of IL-6 receptor blockade in this type of arthritis and demonstration of prolonged clinical improvement, Arthritis Res Ther., 2005; 7(6):RI281-8. Epub 2005 Sep. 15; Yokota S, et al, Clinical study of tocilizumab in children with systemic-onset juvenile idiopathic arthritis, Clin Rev Allergy Immunol., 2005 June; 28(3):231-8; Yokota S, et al, Therapeutic efficacy of humanized recombinant anti-interleukin-6 receptor antibody in children with systemic-onset juvenile idiopathic arthritis, Arthritis Rheum., 2005 March; 52(3):818-25; de Benedetti F, et al, Targeting the interleukin-6 receptor: a new treatment for systemic juvenile idiopathic arthritis?, Arthritis Rheum., 2005 March; 52(3):687-93; De Benedetti F, et al, Is systemic juvenile rheumatoid arthritis an interleukin 6 mediated disease?, J Rheumatol., 1998 February; 25(2):203-7; Ishihara K, et al, IL-6 in autoimmune disease and chronic inflammatory proliferative disease, Cytokine Growth Factor Rev., 2002 August-October; 13 (4-5):357- 68; Gilhar A, et al, In vivo effects of cytokines on psoriatic skin grafted on nude mice: involvement of the tumor necrosis factor (TNF) receptor, Clin Exp Immunol., 1996 October; 106(1):134-42; Spadaro A, et al, Interleukin-6 and soluble interleukin-2 receptor in psoriatic arthritis: correlations with clinical and laboratory parameters, Clin Exp Rheumatol., 1996 July-August; 14 (4):413-6; Ameglio F, et al, Interleukin-6 and tumor necrosis factor levels decrease in the suction blister fluids of psoriatic patients during effective therapy, Dermatology, 1994; 189 (4):359-63; Wendling D, et al, Combination therapy of anti-CD4 and anti-IL-6 monoclonal antibodies in a case of severe spondylarthropathy, Br J Rheumatol., 1996 December; 35(12):1330; Gratacos J, et al, Serum cytokines (IL-6, TNF-alpha, IL-1 beta and IFN-gamma) in ankylosing spondylitis: a close correlation between serum IL-6 and disease activity and severity, Br J Rheumatol., 1994 October; 33(10):927-31; Ito H., Treatment of Crohn's disease with anti-IL-6 receptor antibody, J Gastroenterol., 2005 March; 40 Suppl 16:32-4; Ito H, et al, A pilot randomized trial of a human anti-interleukin-6 receptor monoclonal antibody in active Crohn's disease, Gastroenterology, 2004 April; 126 (4):989-96; discussion 947; Ito H., IL-6 and Crohn's disease, Curr Drug Targets Inflamm Allergy, 2003 June; 2(2): 12530; Ito H, et al, Anti-IL-6 receptor monoclonal antibody inhibits leukocyte recruitment and promotes T-cell apoptosis in a murine model of Crohn's disease, J Gastroenterol., 2002 November; 37 Suppl 14:56-61; Ito H., Anti-interleukin-6 therapy for Crohn's disease, Curr Pharm Des., 2003; 9(4): 295-305; Salvarani C, et al, Acute-phase reactants and the risk of relapse/recurrence in polymyalgia rheumatica: a prospective follow-up study, Arthritis Rheum., 2005 Feb. 15; 53(1):33-8; Roche N E, et al, Correlation of interleukin-6 production and disease activity in polymyalgia rheumatica and giant cell arteritis, Arthritis Rheum., 1993 September; 36(9):1286-94; Gupta M, et al, Cytokine modulation with immune gamma-globulin in peripheral blood of normal children and its implications in Kawasaki disease treatment, J Clin Immunol., 2001 May; 21(3):193-9; Noris M, et al, Interleukin-6 and RANTES in Takayasu arteritis: a guide for therapeutic decisions?, Circulation, 1999 Jul. 6; 100(1):55-60; Besbas N, et al, The role of cytokines in Henoch Schonlein purpura, Scand J Rheumatol., 1997; 26(6):456-60; Hirohata S, et al, Cerebrospinal fluid interleukin-6 in progressive Neuro-Behcet's syndrome, Clin Immunol Immunopathol., 1997 January; 82(1):12-7; Yamakawa Y, et al, Interleukin-6 (IL-6) in patients with Behcet's disease, J Dermatol Sci., 1996 March; 11(3):189-95; Kim D S., Serum interleukin-6 in Kawasaki disease, Yonsei Med J., 1992 June; 33(2):183-8; Lange, A., et al, Cytokines, adhesion molecules (E-selectin and VCAM-1) and graft-versus-host disease, Arch. Immunol Ther Exp., 1995, 43(2):99-105; Tanaka, J., et al, Cytokine gene expression after allogeneic bone marrow transplantation, Leuk. Lymphoma, 1995 16(5-6):413-418; Dickenson, A M, et al, Predicting outcome in hematological stem cell transplantation, Arch Immunol Ther Exp., 2002 50(6):371-8; Zeiser, R, et al, Immunopathogenesis of acute graft-versus-host disease: implications for novel preventive and therapeutic strategies, Ann Hematol., 2004 83(9):551-65; Dickinson, A M, et al, Genetic polymorphisms predicting the outcome of bone marrow transplants, Br. J Haematol., 2004 127(5):479-90; and Scheinberg M A, et al, Interleukin 6: a possible marker of disease activity in adult onset Still's disease, Clin Exp Rheumatol., 1996 November-December; 14 (6):653-5, the disclosures of each of which are herein incorporated by reference in their entireties.

In another embodiment of the invention, anti-IL-6 antibodies described herein, or fragments thereof, are useful for ameliorating or reducing the symptoms of, or treating, or preventing, diseases and disorders associated with the skeletal system. Diseases and disorders associated with the skeletal system include, but are not limited to, osteoarthritis, osteoporosis and Paget's disease of bone. In a preferred embodiment of the invention, humanized anti-IL-6 antibodies described herein, or fragments thereof, are useful for ameliorating or reducing the symptoms of, or treating, or preventing, osteoarthritis. See, for example, Malemud C J., Cytokines as therapeutic targets for osteoarthritis, BioDrugs, 2004; 18(1):23-35; Westacott C I, et al, Cytokines in osteoarthritis: mediators or markers of joint destruction?, Semin Arthritis Rheum., 1996 February; 25(4):254-72; Sugiyama T., Involvement of interleukin-6 and prostaglandin E2 in particular osteoporosis of postmenopausal women with rheumatoid arthritis, J Bone Miner Metab., 2001; 19(2):89-96; Abrahamsen B, et al, Cytokines and bone loss in a 5-year longitudinal study—hormone replacement therapy suppresses serum soluble interleukin-6 receptor and increases interleukin-1-receptor antagonist: the Danish Osteoporosis Prevention Study, J Bone Miner Res., 2000 August; 15(8):1545-54; Straub R H, et al, Hormone replacement therapy and interrelation between serum interleukin-6 and body mass index in postmenopausal women: a population-based study, J Clin Endocrinol Metab., 2000 March; 85(3):1340-4; Manolagas S C, The role of IL-6 type cytokines and their receptors in bone, Ann NY Acad Sci., 1998 May 1; 840:194-204; Ershler W B, et al, Immunologic aspects of osteoporosis, Dev Comp Immunol., 1997 November-December; 21(6):487-99; Jilka R L, et al, Increased osteoclast development after estrogen loss: mediation by interleukin-6, Science, 1992 Jul. 3; 257(5066):88-91; Kallen K J, et al, New developments in IL-6 dependent biology and therapy: where do we stand and what are the options?, Expert Opin Investig Drugs, 1999 September; 8(9):1327-49; Neale SD, et al, The influence of serum cytokines and growth factors on osteoclast formation in Paget's disease, QJM, 2002 April; 95 (4):233 - 40; Roodman G D, Osteoclast function In Paget's disease and multiple myeloma, Bone, 1995 August; 17(2 Suppl):57S-61S; Hoyland J A, et al, Interleukin-6, IL-6 receptor, and IL-6 nuclear factor gene expression in Paget's disease, J Bone Miner Res., 1994 January; 9(1):75-80; and Roodman G D, et al, Interleukin 6. A potential autocrine/paracrine factor in Paget's disease of bone, J Clin Invest., 1992 January; 89(1):46-52; the disclosures of each of which are herein incorporated by reference in their entireties.

In another embodiment of the invention, anti-IL-6 antibodies described herein, or fragments thereof, are useful for ameliorating or reducing the symptoms of, or treating, or preventing, diseases and disorders associated with cancer. Diseases and disorders associated with cancer include, but are not limited to, multiple myeloma, Hodgkin's lymphoma, non-Hodgkin's lymphoma, prostate cancer, leukemia, renal cell cancer, multicentric Castleman's disease, ovarian cancer, drug resistance in cancer chemotherapy and cancer chemotherapy toxicity. See, for example, Hirata T, et al, Humanized anti-interleukin-6 receptor monoclonal antibody induced apoptosis of fresh and cloned human myeloma cells in vitro, Leuk Res., 2003 April; 27(4):343-9, Bataille R, et al, Biologic effects of anti-interleukin-6 murine monoclonal antibody in advanced multiple myeloma, Blood, 1995 Jul. 15;86 (2):685-91; Goto H, et al, Mouse anti-human interleukin-6 receptor monoclonal antibody inhibits proliferation of fresh human myeloma cells in vitro, Jpn J Cancer Res., 1994 September; 85(9):958-65; Klein B, et al, Murine anti-interleukin-6 monoclonal antibody therapy for a patient with plasma cell leukemia, Blood, 1991 Sep. 1;78(5):1198-204; Mauray S, et al, Epstein-Barr virus-dependent lymphoproliferative disease: critical role of IL-6, Eur J Immunol., 2000 July; 30(7):2065-73; Tsunenari T, et al, New xenograft model of multiple myeloma and efficacy of a humanized antibody against human interleukin-6 receptor, Blood, 1997 Sep. 15; 90(6):2437-44; Emilie D, et al, Interleukin-6 production in high-grade B lymphomas: correlation with the presence of malignant immunoblasts in acquired immunodeficiency syndrome and in human immunodeficiency virus-seronegative patients, Blood, 1992 Jul. 15; 80(2):498-504; Emilie D, et al, Administration of an anti-interleukin-6 monoclonal antibody to patients with acquired immunodeficiency syndrome and lymphoma: effect on lymphoma growth and on B clinical Symptoms, Blood, 1994 Oct. 15; 84(8):2472-9; Smith P C, et al, Anti-interleukin-6 monoclonal antibody induces regression of human prostate cancer xenografts in nude mice, Prostate, 2001 Jun. 15; 48(1):47-53; Smith P C, et al, Interleukin-6 and prostate cancer progression, Cytokine Growth Factor Rev., 2001 March; 12(1):33-40; Chung T D, et al, Characterization of the role of IL-6 in the progression of prostate cancer, Prostate, 1999 Feb. 15; 38(3):199-207; Okamoto M, et al, Interleukin-6 as a paracrine and autocrine growth factor in human prostatic carcinoma cells in vitro, Cancer Res., 1997 Jan. 1; 57(1):141-6; Reittie J E, et al, Interleukin-6 inhibits apoptosis and tumor necrosis factor induced proliferation of B-chronic lymphocytic leukemia, Leuk Lymphoma, 1996 June; 22(1-2):83-90, follow 186, color plate VI; Sugiyama H, et al, The expression of IL-6 and its related genes in acute leukemia, Leuk Lymphoma, 1996 March; 21(1-2):49-52; Bataille R, et al, Effects of an anti-interleukin-6 (IL-6) murine monoclonal antibody in a patient with acute monoblastic leukemia, Med Oncol Tumor Pharmacother., 1993; 10(4):185-8; Kedar 1, et al, Thalidomide reduces serum C-reactive protein and interleukin-6 and induces response to IL-2 in a fraction of metastatic renal cell cancer patients who failed IL-2-based therapy, Int J Cancer, 2004 Jun. 10; 110(2):260-5; Angelo L S, Talpaz M, Kurzrock R, Autocrine interleukin-6 production in renal cell carcinoma: evidence for the involvement of p53, Cancer Res., 2002 Feb. 1; 62(3):932-40; Nishimoto N, Humanized anti-interleukin-6 receptor antibody treatment of multicentric Castleman disease, Blood, 2005 Oct. 15; 106(8):2627-32, Epub 2005 Jul. 5; Katsume A, et al, Anti-interleukin 6 (IL-6) receptor antibody suppresses Castleman's disease like symptoms emerged in IL-6 transgenic mice, Cytokine, 2002 Dec. 21; 20(6):304-11; Nishimoto N, et al, Improvement in Castleman's disease by humanized anti-interleukin-6 receptor antibody therapy, Blood, 2000 Jan. 1; 95(1):56-61; Screpanti I, Inactivation of the IL-6 gene prevents development of multicentric Castleman's disease in C/EBP beta-deficient mice, J Exp Med., 1996 Oct. 1; 184(4):1561-6; Hsu S M, et al, Expression of interleukin-6 in Castleman's disease, Hum Pathol., 1993 August; 24(8):833-9; Yoshizaki K, et al, Pathogenic significance of interleukin-6 (IL 6/BSF-2) in Castleman's disease, Blood, 1989 September; 74(4):1360-7; Nilsson M B, et al, Interleukin-6, secreted by human ovarian carcinoma cells, is a potent proangiogenic cytokine, Cancer Res., 2005 Dec, 1; 65(23):10794-800; Toutirais O, et al, Constitutive expression of TGF-beta1, interleukin-6 and interleukin-8 by tumor cells as a major component of immune escape in human ovarian carcinoma, Eur Cytokine Netw., 2003 October-December; 14(4):246-55; Obata N H, et al, Effects of interleukin 6 on in vitro cell attachment, migration and invasion of human ovarian carcinoma, Anticancer Res., 1997 January-February; 17 (1A):337-42;

Dedoussis G V, et al, Endogenous interleukin 6 conveys resistance to cis-diamminedichloroplatinum-mediated apoptosis of the K562 human leukemic cell line, Exp Cell Res., 1999 Jun. 15; 249(2):269-78; Borsellino N, et al, Blocking signaling through the Gp130 receptor chain by interleukin-6 and oncostatin M inhibits PC-3 cell growth and sensitizes the tumor cells to etoposide and cisplatin-mediated cytotoxicity, Cancer, 1999 Jan. 1; 85(1):134-44; Borsellino N, et al, Endogenous interleukin 6 is a resistance factor for cis-diamminedichloroplatinum and etoposide-mediated cytotoxicity of human prostate carcinoma cell lines, Cancer Res., 1995 Oct. 15; 55(20):4633-9; Mizutani Y, et al, Sensitization of human renal cell carcinoma cells to cis-diamminedichloroplatinum(II) by anti-interleukin 6 monoclonal antibody or anti-interleukin 6 receptor monoclonal antibody; Cancer Res., 1995 February 1; 55(3):590-6; Yusuf R Z, et al, Paclitaxel resistance: molecular mechanisms and pharmacologic manipulation, Curr Cancer Drug Targets, 2003 February; 3(1):1-19; Duan Z, et al, Overexpression of IL-6 but not IL-8 increases paclitaxel resistance of U-20S human osteosarcoma cells, Cytokine, 2002 Mar. 7; 17(5):234-42; Conze D, et al, Autocrine production of interleukin 6 causes multidrug resistance in breast cancer cells, Cancer Res., 2001 Dec. 15; 61(24):8851-8; Rossi J F, et al, Optimizing the use of anti-interleukin-6 monoclonal antibody with dexamethasone and 140 mg/m2 of melphalan in multiple myeloma: results of a pilot study including biological aspects, Bone Marrow Transplant, 2005 November; 36(9):771-9; and Tonini G, et al, Oxaliplatin may induce cytokine-release syndrome in colorectal cancer patients, J Biol Regul Homeost Agents, 2002 April-June; 16 (2):105-9; the disclosures of each of which are herein incorporated by reference in their entireties.

In another embodiment of the invention, anti-IL-6 antibodies described herein, or fragments thereof, are useful for ameliorating or reducing the symptoms of, or treating, or preventing, ischemic heart disease, atherosclerosis, obesity, diabetes, asthma, multiple sclerosis, Alzheimer's disease, cerebrovascular disease, fever, acute phase response, allergies, anemia, anemia of inflammation (anemia of chronic disease), hypertension, depression, depression associated with a chronic illness, thrombosis, thrombocytosis, acute heart failure, metabolic syndrome, miscarriage, obesity, chronic prostatitis, glomerulonephritis, pelvic inflammatory disease, reperfusion injury, and transplant rejection. See, for example, Tzoulaki I, et al, C-reactive protein, interleukin-6, and soluble adhesion molecules as predictors of progressive peripheral atherosclerosis in the general population: Edinburgh Artery Study, Circulation, 2005 Aug. 16; 112(7):976-83, Epub 2005 Aug. 8; Rattazzi M, et al, C-reactive protein and interleukin-6 in vascular disease: culprits or passive bystanders?, J Hypertens., 2003 October; 21(10):1787-803; Ito T, et al, HMG-CoA reductase inhibitors reduce interleukin-6 synthesis in human vascular smooth muscle cells, Cardiovasc Drugs Ther., 2002 March; 16(2):121-6; Stenvinkel P, et al, Mortality, malnutrition, and atherosclerosis in ESRD: what is the role of interleukin-6?, Kidney Int Suppl., 2002 May; (80):103-8; Yudkin J S, et al, Inflammation, obesity, stress and coronary heart disease: is interleukin-6 the link?, Atherosclerosis, 2000 February; 148(2):209-14; Huber S A, et al, Interleukin-6 exacerbates early atherosclerosis in mice, Arterioscler Thromb Vasc Biol., 1999 October; 19(10):2364-7; Kado S, et al, Circulating levels of interleukin-6, its soluble receptor and interleukin-6/interleukin-6 receptor complexes in patients with type 2 diabetes mellitus, Acta Diabetol.,1999 June; 36(1-2):67-72; Sukovich D A, et al, Expression of interleukin-6 in atherosclerotic lesions of male ApoE-knockout mice: inhibition by 17beta-estradiol, Arterioscler Thromb Vasc Biol.,1998 September; 8(9):1498-505; Klover P J, et al, Interleukin-6 depletion selectively improves hepatic insulin action in obesity, Endocrinology, 2005 August; 146(8):3417-27, Epub 2005 Apr. 21; Lee Y H, et al, The evolving role of inflammation in obesity and the metabolic syndrome, Curr Diab Rep., 2005 February; 5(1): 70-5; Diamant M, et al, The association between abdominal visceral fat and carotid stiffness is mediated by circulating inflammatory markers in uncomplicated type 2 diabetes, J Clin Endocrinol Metab., 2005 March; 90(3):1495-501, Epub 2004 Dec. 21; Bray G A, Medical consequences of obesity, J Clin Endocrinol Metab., 2004 June; 89(6):2583 9; Klover P J, et al, Chronic exposure to interleukin-6 causes hepatic insulin resistance in mice, Diabetes, 2003 November; 52 (11):2784-9; Yudkin J S, et al, Inflammation, obesity, stress and coronary heart disease: is interleukin-6 the link?, Atherosclerosis, 2000 February; 148(2):209-14; Doganci A, et al, Pathological role of IL-6 in the experimental allergic bronchial asthma in mice, Clin Rev Allergy Immunol., 2005 June; 28(3):257-70; Doganci A, et al, The IL-6R alpha chain controls lung CD4+CD25+ Treg development and function during allergic airway inflammation in vivo, J Clin Invest., 2005 February; 115(2):313 25, (Erratum in: J Clin Invest., 2005 May; 115(5):1388, Lehr, Hans A [added]); Stelmasiak Z, et al, IL 6 and sIL-6R concentration in the cerebrospinal fluid and serum of MS patients, Med Sci Monit., 2001 September-October; 7(5):914-8; Tilgner J, et al, Continuous interleukin-6 application in vivo via macroencapsulation of interleukin-6-expressing COS-7 cells induces massive gliosis, Glia, 2001 September; 35(3):234-45, Brunello A G, et al, Astrocytic alterations in interleukin-6 Soluble interleukin-6 receptor alpha double-transgenic mice, Am J Pathol., 2000 November; 157(5):1485-93; Hampel H, et al, Pattern of interleukin-6 receptor complex immunoreactivity between cortical regions of rapid autopsy normal and Alzheimer's disease brain, Eur Arch Psychiatry Clin Neurosci., 2005 August; 255(4):269-78, Epub 2004 Nov. 26; Cacquevel M, et al, Cytokines in neuroinflammation and Alzheimer's disease, Curr Drug Targets, 2004 August; 5(6):529-34; Quintanilla R A, et al, Interleukin 6 induces Alzheimer-type phosphorylation of tau protein by deregulating the cdk5/p35 pathway, Exp Cell Res., 2004 Apr. 15; 295 (1):245-57; Gadient R A, et al, Interleukin-6 (IL-6)—a molecule with both beneficial and destructive potentials, Prog Neurobiol., 1997 August; 52(5):379-90; Hull M, et al, Occurrence of interleukin-6 in cortical plaques of Alzheimer's disease patients may precede transformation of diffuse into neuritic plaques, Ann NY Acad Sci., 1996 Jan. 17; 777:205-12; Rallidis L S, et al, Inflammatory markers and in-hospital mortality in acute ischaemic stroke, Atherosclerosis, 2005 Dec. 30; Emsley H C, et al, Interleukin-6 and acute ischaemic stroke, Acta Neurol Scand., 2005 October; 112(4):273-4; Smith C J, et al, Peak plasma interleukin-6 and other peripheral markers of inflammation in the first week of ischaemic stroke correlate with brain infarct volume, stroke severity and long-term outcome, BMC Neurol., 2004 Jan. 15; 4:2; Vila N, et al, Proinflammatory cytokines and early neurological worsening in ischemic stroke, Stroke, 2000 October; 31(10):2325-9; and Tarkowski E, et al, Early intrathecal production of interleukin-6 predicts the size of brain lesion in stroke, Stroke, 1995 August; 26(8):1393-8; the disclosures of each of which are herein incorporated by reference in their entireties.

In another embodiment of the invention, anti-IL-6 antibodies described herein, or fragments thereof, are useful for ameliorating or reducing the symptoms of, or treating, or preventing, diseases and disorders associated with cytokine storm. Diseases and disorders associated with cytokine storm include, but are not limited to, graft versus host disease (GVHD), avian influenza, smallpox, pandemic influenza, adult respiratory distress syndrome (ARDS), severe acute respiratory syndrome (SARS), sepsis, and systemic inflammatory response syndrome (SIRS). See, for example, Cecil, R. L., Goldman, L., & Bennett, J. C. (2000). Cecil textbook of medicine. Philadelphia: W. B. Saunders; Ferrara J L, et al., Cytokine storm of graft- versus-host disease: a critical effector role for interleukin-1, Transplant Proc. 1993 February; 25(1 Pt 2):1216-7; Osterholm M T, Preparing for the Next Pandemic, N Engl J Med. 2005 May 5; 352(18): 1839-42; Huang K J, et al., An interferon-gamma-related cytokine storm in SARS patients, J Med Virol. 2005 February; 75(2):185-94; and Cheung C Y, et al., Induction of proinflammatory cytokines in human macrophages by influenza A (H5N1) viruses: a mechanism for the unusual severity of human disease? Lancet. 2002 Dec. 7; 360(9348):1831-7.

In another embodiment of the invention, anti-IL-6 antibodies described herein, or fragments thereof, are useful as a wakefulness aid.

Administration

In one embodiment of the invention, the anti-IL-6 antibodies described herein, or IL-6 binding fragments thereof, as well as combinations of said antibody fragments, are administered to a subject at a concentration of between about 0.1 and 20 mg/kg, such as about 0.4 mg/kg, about 0.8 mg/kg, about 1.6 mg/kg, or about 4 mg/kg, of body weight of recipient subject. In a preferred embodiment of the invention, the anti-IL-6 antibodies described herein, or IL-6 binding fragments thereof, as well as combinations of said antibody fragments, are administered to a subject at a concentration of about 0.4 mg/kg of body weight of recipient subject. In a preferred embodiment of the invention, the anti-IL-6 antibodies described herein, or IL-6 binding fragments thereof, as well as combinations of said antibody fragments, are administered to a recipient subject with a frequency of once every twenty-six weeks or less, such as once every sixteen weeks or less, once every eight weeks or less, or once every four weeks, or less.

It is understood that the effective dosage may depend on recipient subject attributes, such as, for example, age, gender, pregnancy status, body mass index, lean body mass, condition or conditions for which the composition is given, other health conditions of the recipient subject that may affect metabolism or tolerance of the composition, levels of IL-6 in the recipient subject, and resistance to the composition (for example, arising from the patient developing antibodies against the composition). A person of skill in the art would be able to determine an effective dosage and frequency of administration through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Pharmacology. Lippincott's illustrated reviews. Philadelphia: Lippincott Williams & Wilkins; and Golan, D. E. (2008). Principles of pharmacology: the pathophysiologic basis of drug therapy. Philadelphia, Pa., [etc.]: Lippincott Williams & Wilkins.

In another embodiment of the invention, the anti-IL-6 antibodies described herein, or IL-6 binding fragments thereof, as well as combinations of said antibody fragments, are administered to a subject in a pharmaceutical formulation.

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration.

In one embodiment of the invention, the anti-IL-6 antibodies described herein, or IL-6 binding fragments thereof, as well as combinations of said antibody fragments, may be optionally administered in combination with one or more active agents. Such active agents include analgesic, antipyretic, anti-inflammatory, antibiotic, antiviral, and anti-cytokine agents. Active agents include agonists, antagonists, and modulators of TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors. Active agents also include 2-Arylpropionic acids, Aceclofenac, Acemetacin, Acetylsalicylic acid (Aspirin), Alclofenac, Alminoprofen, Amoxiprin, Ampyrone, Arylalkanoic acids, Azapropazone, Benorylate/Benorilate, Benoxaprofen, Bromfenac, Carprofen, Celecoxib, Choline magnesium salicylate, Clofezone, COX-2 inhibitors, Dexibuprofen, Dexketoprofen, Diclofenac, Diflunisal, Droxicam, Ethenzamide, Etodolac, Etoricoxib, Faislamine, fenamic acids, Fenbufen, Fenoprofen, Flufenamic acid, Flunoxaprofen, Flurbiprofen, Ibuprofen, Ibuproxam, Indometacin, Indoprofen, Kebuzone, Ketoprofen, Ketorolac, Lornoxicam, Loxoprofen, Lumiracoxib, Magnesium salicylate, Meclofenamic acid, Mefenamic acid, Meloxicam, Metamizole, Methyl salicylate, Mofebutazone, Nabumetone, Naproxen, N-Arylanthranilic acids, Oxametacin, Oxaprozin, Oxicams, Oxyphenbutazone, Parecoxib, Phenazone, Phenylbutazone, Phenylbutazone, Piroxicam, Pirprofen, profens, Proglumetacin, Pyrazolidine derivatives, Rofecoxib, Salicyl salicylate, Salicylamide, Salicylates, Sulfinpyrazone, Sulindac, Suprofen, Tenoxicam, Tiaprofenic acid, Tolfenamic acid, Tolmetin, and Valdecoxib. Antibiotics include Amikacin, Aminoglycosides, Amoxicillin, Ampicillin, Ansamycins, Arsphenamine, Azithromycin, Azlocillin, Aztreonam, Bacitracin, Carbacephem, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftazidime, Ceftibuten, Ceftizoxime, Ceftobiprole, Ceftriaxone, Cefuroxime, Cephalosporins, Chloramphenicol, Cilastatin, Ciprofloxacin, Clarithromycin, Clindamycin, Cloxacillin, Colistin, Co-trimoxazole, Dalfopristin, Demeclocycline, Dicloxacillin, Dirithromycin, Doripenem, Doxycycline, Enoxacin, Ertapenem, Erythromycin, Ethambutol, Flucloxacillin, Fosfomycin, Furazolidone, Fusidic acid, Gatifloxacin, Geldanamycin, Gentamicin, Glycopeptides, Herbimycin, Imipenem, Isoniazid, Kanamycin, Levofloxacin, Lincomycin, Linezolid, Lomefloxacin, Loracarbef, Macrolides, Mafenide, Meropenem, Meticillin, Metronidazole, Mezlocillin, Minocycline, Monobactams, Moxifloxacin, Mupirocin, Nafcillin, Neomycin, Netilmicin, Nitrofurantoin, Norfloxacin, Ofloxacin, Oxacillin, Oxytetracycline, Paromomycin, Penicillin, Penicillins, Piperacillin, Platensimycin, Polymyxin B, Polypeptides, Prontosil, Pyrazinamide, Quinolones, Quinupristin, Rifampicin, Rifampin, Roxithromycin, Spectinomycin, Streptomycin, Sulfacetamide, Sulfamethizole, Sulfanilimide, Sulfasalazine, Sulfisoxazole, Sulfonamides, Teicoplanin, Telithromycin, Tetracycline, Tetracyclines, Ticarcillin, Tinidazole, Tobramycin, Trimethoprim, Trimethoprim-Sulfamethoxazole, Troleandomycin, Trovafloxacin, and Vancomycin. Active agents also include Aldosterone, Beclometasone, Betamethasone, Corticosteroids, Cortisol, Cortisone acetate, Deoxycorticosterone acetate, Dexamethasone, Fludrocortisone acetate, Glucocorticoids, Hydrocortisone, Methylprednisolone, Prednisolone, Prednisone, Steroids, and Triamcinolone. Antiviral agents include abacavir, aciclovir, acyclovir, adefovir, amantadine, amprenavir, an antiretroviral fixed dose combination, an antiretroviral synergistic enhancer, arbidol, atazanavir, atripla, brivudine, cidofovir, combivir, darunavir, delavirdine, didanosine, docosanol, edoxudine, efavirenz, emtricitabine, enfuvirtide, entecavir, entry inhibitors, famciclovir, fomivirsen, fosamprenavir, foscarnet, fosfonet, fusion inhibitor, ganciclovir, gardasil, ibacitabine, idoxuridine, imiquimod, imunovir, indinavir, inosine, integrase inhibitor, interferon, interferon type I, interferon type II, interferon type III, lamivudine, lopinavir, loviride, maraviroc, MK-0518, moroxydine, nelfmavir, nevirapine, nexavir, nucleoside analogues, oseltamivir, penciclovir, peramivir, pleconaril, podophyllotoxin, protease inhibitor, reverse transcriptase inhibitor, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine. Any suitable combination of these active agents is also contemplated.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations can be found, for example, in Remington's Pharmaceutical Sciences, 19$^{th}$ Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the alkaline polypeptide can be formulated in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to methods for obtaining a clonal population of antigen-specific B cells were disclosed in U.S. Provisional patent application No. 60/801,412, filed May 19, 2006, the disclosure of which is herein incorporated by reference in its entirety.

Certain teachings related to humanization of rabbit-derived monoclonal antibodies and preferred sequence modifications to maintain antigen binding affinity were disclosed in International Application No. PCT/U.S. 08/64432, entitled "Novel Rabbit Antibody Humanization Method and Humanized Rabbit Antibodies", filed May 21, 2008, the disclosure of which is herein incorporated by reference in its entirety.

Certain teachings related to producing antibodies or fragments thereof using mating competent yeast and corresponding methods were disclosed in U.S. patent application Ser. No. 11/429,053, filed May 8, 2006, (U.S. Patent Application Publication No. US2006/0270045), the disclosure of which is herein incorporated by reference in its entirety.

Certain teachings related to IL-6 antibodies, methods of producing antibodies or fragments thereof using mating competent yeast and corresponding methods were disclosed in U.S. provisional patent application No. 60/924,550, filed May 21, 2007, the disclosure of which is herein incorporated by reference in its entirety.

Certain anti-IL-6 antibody polynucleotides and polypeptides are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1

Production of Enriched Antigen-Specific B Cell Antibody Culture

Panels of antibodies are derived by immunizing traditional antibody host animals to exploit the native immune response to a target antigen of interest. Typically, the host used for immunization is a rabbit or other host that produces antibodies using a similar maturation process and provides for a population of antigen-specific B cells producing antibodies of comparable diversity, e.g., epitopic diversity. The initial antigen immunization can be conducted using complete Freund's adjuvant (CFA), and the subsequent boosts effected with incomplete adjuvant. At about 50-60 days after immunization, preferably at day 55, antibody titers are tested, and the Antibody Selection (ABS) process is initiated if appropriate titers are established. The two key criteria for ABS initiation are potent antigen recognition and function-modifying activity in the polyclonal sera.

At the time positive antibody titers are established, animals are sacrificed and B cell sources isolated. These sources include: the spleen, lymph nodes, bone marrow, and peripheral blood mononuclear cells (PBMCs). Single cell suspensions are generated, and the cell suspensions are washed to make them compatible for low temperature long term storage. The cells are then typically frozen.

To initiate the antibody identification process, a small fraction of the frozen cell suspensions are thawed, washed, and placed in tissue culture media. These suspensions are then mixed with a biotinylated form of the antigen that was used to generate the animal immune response, and antigen-specific cells are recovered using the Miltenyi magnetic bead cell selection methodology. Specific enrichment is conducted using streptavidin beads. The enriched population is recovered and progressed in the next phase of specific B cell isolation.

Example 2

Production of Clonal, Antigen-Specific B Cell-Containing Culture

Enriched B cells produced according to Example 1 are then plated at varying cell densities per well in a 96 well microtiter plate. Generally, this is at 50, 100, 250, or 500 cells per well with 10 plates per group. The media is supplemented with 4% activated rabbit T cell conditioned media along with 50K frozen irradiated EL4B feeder cells. These cultures are left undisturbed for 5-7 days at which time supernatant-containing secreted antibody is collected and evaluated for target properties in a separate assay setting. The remaining supernatant is left intact, and the plate is frozen at −70° C. Under these conditions, the culture process typically results in wells containing a mixed cell population that comprises a clonal population of antigen-specific B cells, i.e., a single well will only contain a single monoclonal antibody specific to the desired antigen.

Example 3

Screening of Antibody Supernatants for Monoclonal Antibody of Desired Specificity and/or Functional Properties Antibody-containing supernatants derived from the well containing a clonal antigen-specific B cell population produced according to Example 2 are initially screened for antigen recognition using ELISA methods. This includes selective antigen immobilization (e.g., biotinylated antigen capture by streptavidin coated plate), non-specific antigen plate coating, or alternatively, through an antigen build-up strategy (e.g., selective antigen capture followed by binding partner addition to generate a heteromeric protein-antigen complex). Antigen-positive well supernatants are then optionally tested in a function-modifying assay that is strictly dependant on the ligand. One such example is an in vitro protein-protein interaction assay that recreates the natural interaction of the antigen ligand with recombinant receptor protein. Alternatively, a cell-based response that is ligand dependent and easily monitored (e.g., proliferation response) is utilized. Supernatant that displays significant antigen recognition and potency is deemed a positive well. Cells derived from the original positive well are then transitioned to the antibody recovery phase.

Example 4

Recovery of Single, Antibody-Producing B Cell of Desired Antigen Specificity

Cells are isolated from a well that contains a clonal population of antigen-specific B cells (produced according to Example 2 or 3), which secrete a single antibody sequence. The isolated cells are then assayed to isolate a single, antibody-secreting cell. Dynal streptavidin beads are coated with biotinylated target antigen under buffered medium to prepare antigen-containing microbeads compatible with cell viability. Next antigen-loaded beads, antibody-producing cells from the positive well, and a fluorescein isothiocyanate (FITC)-labeled anti-host H&L IgG antibody (as noted, the host can be any mammalian host, e.g., rabbit, mouse, rat, etc.) are incubated together at 37° C. This mixture is then re-pipetted in aliquots onto a glass slide such that each aliquot has on average a single, antibody-producing B-cell. The antigen-specific, antibody-secreting cells are then detected through fluorescence microscopy. Secreted antibody is locally concentrated onto the adjacent beads due to the bound antigen and provides localization information based on the strong fluorescent signal. Antibody-secreting cells are identified via FITC detection of antibody-antigen complexes formed adjacent to the secreting cell. The single cell found in the center of this complex is then recovered using a micromanipulator. The cell is snap-frozen in an eppendorf PCR tube for storage at −80° C. until antibody sequence recovery is initiated.

Example 5

Isolation of Antibody Sequences From Antigen-Specific B Cell

Antibody sequences are recovered using a combined RT-PCR based method from a single isolated B-cell produced according to Example 4 or an antigenic specific B cell isolated from the clonal B cell population obtained according to Example 2. Primers are designed to anneal in conserved and constant regions of the target immunoglobulin genes (heavy and light), such as rabbit immunoglobulin sequences, and a two-step nested PCR recovery step is used to obtain the antibody sequence. Amplicons from each well are analyzed for recovery and size integrity. The resulting fragments are then digested with AluI to fingerprint the sequence clonality. Identical sequences display a common fragmentation pattern in their electrophoretic analysis. Significantly, this common fragmentation pattern which proves cell clonality is generally observed even in the wells originally plated up to 1000 cells/well. The original heavy and light chain amplicon fragments are then restriction enzyme digested with HindIII and XhoI or HindIII and BsiWI to prepare the respective pieces of DNA for cloning. The resulting digestions are then ligated into an expression vector and transformed into bacteria for plasmid propagation and production. Colonies are selected for sequence characterization.

Example 6

Recombinant Production of Monoclonal Antibody of Desired Antigen Specificity and/or Functional Properties Correct full-length antibody sequences for each well containing a single monoclonal antibody is established and miniprep DNA is prepared using Qiagen solid-phase methodology. This DNA is then used to transfect mammalian cells to produce recombinant full-length antibody. Crude antibody product is tested for antigen recognition and functional properties to confirm the original characteristics are found in the recombinant antibody protein. Where appropriate, large-scale transient mammalian transfections are completed, and antibody is purified through Protein A affinity chromatography. Kd is assessed using standard methods (e.g., Biacore) as well as IC50 in a potency assay.

Example 7

Preparation of Antibodies that Bind Human IL-6

By using the antibody selection protocol described herein, one can generate an extensive panel of antibodies. The antibodies have high affinity towards IL-6 (single to double digit pM Kd) and demonstrate potent antagonism of IL-6 in multiple cell-based screening systems (T1165 and HepG2). Furthermore, the collection of antibodies display distinct modes of antagonism toward IL-6-driven processes.

Immunization Strategy

Rabbits were immunized with huIL-6 (R&R). Immunization consisted of a first subcutaneous (sc) injection of 100 µg in complete Freund's adjuvant (CFA) (Sigma) followed by two boosts, two weeks apart, of 50 µg each in incomplete Freund's adjuvant (IFA) (Sigma). Animals were bled on day 55, and serum titers were determined by ELISA (antigen recognition) and by non-radioactive proliferation assay (Promega) using the T1165 cell line.

Antibody Selection Titer Assessment

Antigen recognition was determined by coating Immulon 4 plates (Thermo) with 1 µg/ml of huIL-6 (50 µl/well) in phosphate buffered saline (PBS, Hyclone) overnight at 4° C. On the day of the assay, plates were washed 3 times with PBS /Tween 20 (PBST tablets, Calbiochem). Plates were then blocked with 200 µl/well of 0.5% fish skin gelatin (FSG, Sigma) in PBS for 30 minutes at 37° C. Blocking solution was removed, and plates were blotted. Serum samples were made (bleeds and pre-bleeds) at a starting dilution of 1:100 (all dilutions were made in FSG 50 µl/well) followed by 1:10 dilutions across the plate (column 12 was left blank for background control). Plates were incubated for 30 minutes at 37° C. Plates were washed 3 times with PBS/Tween 20. Goat anti-rabbit FC-HRP (Pierce) diluted 1:5000 was added to all wells (50 µl/well), and plates were incubated for 30 minutes at 37° C. Plates were washed as described above. 50 µl/well of TMB-Stable stop (Fitzgerald Industries) was added to plates, and color was allowed to develop, generally for 3 to 5 minutes. The development reaction was stopped with 50 µl/well 0.5 M HCl. Plates were read at 450 nm. Optical density (OD) versus dilution was plotted using Graph Pad Prizm software, and titers were determined.

Functional Titer Assessment

The functional activity of the samples was determined by a T1165 proliferation assay. T1165 cells were routinely maintained in modified RPMI medium (Hyclone) supplemented with Hepes, sodium pyruvate, sodium bicarbonate, L-glutamine, high glucose, penicillin/streptomycin, 10% heat inactivated fetal bovine serum (FBS) (all supplements from Hyclone), 2-mercaptoethanol (Sigma), and 10 ng/ml of huIL-6 (R&D). On the day of the assay, cell viability was determined by trypan blue (Invitrogen), and cells were seeded at a fixed density of 20,000 cells/well. Prior to seeding, cells were washed twice in the medium described above without human-IL-6 (by centrifuging at 13000 rpm for 5 minutes and discarding the supernatant). After the last wash, cells were resuspended in the same medium used for washing in a volume equivalent to 50 µl/well. Cells were set aside at room temperature.

In a round-bottom, 96-well plate (Costar), serum samples were added starting at 1:100, followed by a 1:10 dilution across the plate (columns 2 to 10) at 30 μl/well in replicates of 5 (rows B to F: dilution made in the medium described above with no huIL-6). Column 11 was medium only for IL-6 control. 30 μl/well of huIL-6 at 4× concentration of the final EC50 (concentration previously determined) were added to all wells (huIL-6 was diluted in the medium described above). Wells were incubated for 1 hour at 37° C. to allow antibody binding to occur. After 1 hour, 50 μl/well of antibody-antigen (Ab-Ag) complex were transferred to a flat-bottom, 96-well plate (Costar) following the plate map format laid out in the round-bottom plate. On Row G, 50 μl/well of medium were added to all wells (columns 2 to 11) for background control. 50 μl/well of the cell suspension set aside were added to all wells (columns 2 to 11, rows B to G). On Columns 1 and 12 and on rows A and H, 200 μl/well of medium was added to prevent evaporation of test wells and to minimize edge effect. Plates were incubated for 72 h at 37° C. in 4% CO2. At 72 h, 20 μl/well of CellTiter96 (Promega) reagents was added to all test wells per manufacturer protocol, and plates were incubated for 2 h at 37° C. At 2 h, plates were gently mixed on an orbital shaker to disperse cells and to allow homogeneity in the test wells. Plates were read at 490 nm wavelength. Optical density (OD) versus dilution was plotted using Graph Pad Prizm software, and functional titer was determined. A positive assay control plate was conducted as described above using MAB2061 (R&D Systems) at a starting concentration of 1 μg/ml (final concentration) followed by 1:3 dilutions across the plate.

Tissue Harvesting

Once acceptable titers were established, the rabbit(s) were sacrificed. Spleen, lymph nodes, and whole blood were harvested and processed as follows:

Spleen and lymph nodes were processed into a single cell suspension by disassociating the tissue and pushing through sterile wire mesh at 70 μm (Fisher) with a plunger of a 20 cc syringe. Cells were collected in the modified RPMI medium described above without huIL-6, but with low glucose. Cells were washed twice by centrifugation. After the last wash, cell density was determined by trypan blue. Cells were centrifuged at 1500 rpm for 10 minutes; the supernatant was discarded. Cells were resuspended in the appropriate volume of 10% dimethyl sulfoxide (DMSO, Sigma) in FBS (Hyclone) and dispensed at 1 ml/vial. Vials were then stored at −70° C. for 24 h prior to being placed in a liquid nitrogen (LN2) tank for long-term storage.

Peripheral blood mononuclear cells (PBMCs) were isolated by mixing whole blood with equal parts of the low glucose medium described above without FBS. 35 ml of the whole blood mixture was carefully layered onto 8 ml of Lympholyte Rabbit (Cedarlane) into a 45 ml conical tube (Corning) and centrifuged 30 minutes at 2500 rpm at room temperature without brakes. After centrifugation, the PBMC layers were carefully removed using a glass Pasteur pipette (VWR), combined, and placed into a clean 50 ml vial. Cells were washed twice with the modified medium described above by centrifugation at 1500 rpm for 10 minutes at room temperature, and cell density was determined by trypan blue staining. After the last wash, cells were resuspended in an appropriate volume of 10% DMSO/FBS medium and frozen as described above.

B Cell Culture

On the day of setting up B cell culture, PBMC, splenocyte, or lymph node vials were thawed for use. Vials were removed from LN2 tank and placed in a 37° C. water bath until thawed. Contents of vials were transferred into 15 ml conical centrifuge tube (Corning) and 10 ml of modified RPMI described above was slowly added to the tube. Cells were centrifuged for 5 minutes at 1.5K rpm, and the supernatant was discarded. Cells were resuspended in 10 ml of fresh media. Cell density and viability was determined by trypan blue. Cells were washed again and resuspended at 1E07 cells/80 ul medium. Biotinylated huIL-6 (B huIL-6) was added to the cell suspension at the final concentration of 3 ug/mL and incubated for 30 minutes at 4° C. Unbound B huIL-6 was removed with two 10 ml washes of phosphate-buffered (PBF):Ca/Mg free PBS (Hyclone), 2 mM ethylene-diamine tetraacetic acid (EDTA), 0.5% bovine serum albumin (BSA) (Sigma-biotin free). After the second wash, cells were resuspended at 1E07 cells/80 μl PBF. 20 of MACS® streptavidin beads (Milteni)/10E7 cells were added to the cell suspension. Cells were incubated at 4° C. for 15 minutes. Cells were washed once with 2 ml of PBF/10E7 cells. After washing, the cells were resuspended at 1E08 cells/500 μl of PBF and set aside. A MACS® MS column (Milteni) was pre-rinsed with 500 ml of PBF on a magnetic stand (Milteni). Cell suspension was applied to the column through a pre-filter, and unbound fraction was collected. The column was washed with 1.5 ml of PBF buffer. The column was removed from the magnet stand and placed onto a clean, sterile 5 ml Polypropylene Falcon tube. 1 ml of PBF buffer was added to the top of the column, and positive selected cells were collected. The yield and viability of positive and negative cell fraction was determined by trypan blue staining. Positive selection yielded an average of 1% of the starting cell concentration.

A pilot cell screen was established to provide information on seeding levels for the culture. Three 10-plate groups (a total of 30 plates) were seeded at 50, 100, and 200 enriched B cells/well. In addition, each well contained 50K cells/well of irradiated EL-4.B5 cells (5,000 Rads) and an appropriate level of T cell supernatant (ranging from 1-5% depending on preparation) in high glucose modified RPMI medium at a final volume of 250 μl/well. Cultures were incubated for 5 to 7 days at 37° C. in 4% CO2.

Identification of Selective Antibody Secreting B Cells

Cultures were tested for antigen recognition and functional activity between days 5 and 7.

Antigen Recognition Screening

The ELISA format used is as described above except 50 μl of supernatant from the B cell cultures (BCC) wells (all 30 plates) was used as the source of the antibody. The conditioned medium was transferred to antigen-coated plates. After positive wells were identified, the supernatant was removed and transferred to a 96-well master plate(s). The original culture plates were then frozen by removing all the supernatant except 40 μl/well and adding 60 μl/well of 16% DMSO in FBS. Plates were wrapped in paper towels to slow freezing and placed at −70° C.

Functional Activity Screening

Master plates were then screened for functional activity in the T1165 proliferation assay as described before, except row B was media only for background control, row C was media+IL-6 for positive proliferation control, and rows D-G and columns 2-11 were the wells from the BCC (50 μl/well, single points). 40 μl of IL-6 was added to all wells except the media row at 2.5 times the EC50 concentration determined for the assay. After 1 h incubation, the Ab/Ag complex was transferred to a tissue culture (TC) treated, 96-well, flat-bottom plate. 20 μl of cell suspension in modified RPMI medium without huIL-6 (T1165 at 20,000 cells/well) was added to all wells (100 µl final volume per well). Background was subtracted, and observed OD values were transformed into % of inhibition.

B Cell Recovery

Plates containing wells of interest were removed from −70° C., and the cells from each well were recovered with 5-200 µl washes of medium/well. The washes were pooled in a 1.5 ml sterile centrifuge tube, and cells were pelleted for 2 minutes at 1500 rpm.

The tube was inverted, the spin repeated, and the supernatant carefully removed. Cells were resuspended in 100 µl/tube of medium. 100 µl biotinylated IL-6 coated streptavidin M280 dynabeads (Invitrogen) and 16 µl of goat anti-rabbit H&L IgG-FITC diluted 1:100 in medium was added to the cell suspension.

20 µl of cell/beads/FITC suspension was removed, and 5 µl droplets were prepared on a glass slide (Corning) previously treated with Sigmacote (Sigma), 35 to 40 droplets/slide. An impermeable barrier of parafin oil (JT Baker) was added to submerge the droplets, and the slide was incubated for 90 minutes at 37° C., 4% CO2 in the dark.

Specific B cells that produce antibody can be identified by the fluorescent ring around them due to antibody secretion, recognition of the bead-associated biotinylated antigen, and subsequent detection by the fluorescent-IgG detection reagent. Once a cell of interest was identified, the cell in the center of the fluorescent ring was recovered via a micromanipulator (Eppendorf). The single cell synthesizing and exporting the antibody was transferred into a 250 µl microcentrifuge tube and placed in dry ice. After recovering all cells of interest, these were transferred to −70° C. for long-term storage.

Example 8

Yeast Cell Expression

Antibody genes: Genes were cloned and constructed that directed the synthesis of a chimeric humanized rabbit monoclonal antibody.

Expression vector: The vector contains the following functional components: 1) a mutant ColE1 origin of replication, which facilitates the replication of the plasmid vector in cells of the bacterium *Escherichia coli;* 2) a bacterial Sh ble gene, which confers resistance to the antibiotic Zeocin and serves as the selectable marker for transformations of both *E. coli* and *P. pastoris;* 3) an expression cassette composed of the glyceraldehyde dehydrogenase gene (GAP gene) promoter, fused to sequences encoding the *Saccharomyces cerevisiae* alpha mating factor pre pro secretion leader sequence, followed by sequences encoding a *P. pastoris* transcriptional termination signal from the *P. pastoris* alcohol oxidase I gene (AOX1). The Zeocin resistance marker gene provides a means of enrichment for strains that contain multiple integrated copies of an expression vector in a strain by selecting for transformants that are resistant to higher levels of Zeocin.

*P. pastoris* strains: *P. pastoris* strains met1, lys3, ura3 and ade1 may be used. Although any two complementing sets of auxotrophic strains could be used for the construction and maintenance of diploid strains, these two strains are especially suited for this method for two reasons. First, they grow more slowly than diploid strains that are the result of their mating or fusion. Thus, if a small number of haploid ade1 or ura3 cells remain present in a culture or arise through meiosis or other mechanism, the diploid strain should outgrow them in culture.

The second is that it is easy to monitor the sexual state of these strains since diploid Ade+ colonies arising from their mating are a normal white or cream color, whereas cells of any strains that are haploid ade1 mutants will form a colony with a distinct pink color. In addition, any strains that are haploid ura3 mutants are resistant to the drug 5-fluoro-orotic acid (FOA) and can be sensitively identified by plating samples of a culture on minimal medium+uracil plates with FOA. On these plates, only uracil-requiring ura3 mutant (presumably haploid) strains can grow and form colonies. Thus, with haploid parent strains marked with ade1 and ura3, one can readily monitor the sexual state of the resulting antibody-producing diploid strains (haploid versus diploid).

Methods

Construction of pGAPZ-alpha expression vectors for transcription of light and heavy chain antibody genes. The humanized light and heavy chain fragments were cloned into the pGAPZ expression vectors through a PCR directed process. The recovered humanized constructs were subjected to amplification under standard KOD polymerase (Novagen) kit conditions ((1) 94° C., 2 minutes; (2) 94° C., 30 seconds; (3) 55° C., 30 seconds; (4) 72° C., 30 seconds-cycling through steps 2-4 for 35 times; (5) 72° C. 2 minutes) employing the following primers (1)

```
light chain forward
                                    [SEQ ID NO. 647]
AGCGCTTATTCCGCTATCCAGATGACCCAGTC
``` the AfeI site is single underlined. The end of the HSA signal sequence is double underlined, followed by the sequence for the mature variable light chain (not underlined); the reverse CGTACGTTTGATTCCACCTTG [SEQ ID NO. 6481].

Variable light chain reverse primer. BsiWI site is underlined, followed by the reverse compliment for the 3' end of the variable light chain. Upon restriction enzyme digest with AfeI and BsiWI this enable insertion in-frame with the pGAPZ vector using the human HAS leader sequence in frame with the human kapp light chain constant region for export. (2) A similar strategy is performed for the heavy chain.

```
The forward primer employed is
                                    [SEQ ID NO. 649]
AGCGCTTATTCCGAGGTGCAGCTGGTGGAGTC.
```

The AfeI site is single underlined. The end of the HSA signal sequence is double underlined, followed by the sequence for the mature variable heavy chain (not underlined). The reverse heavy chain primer is CTCGAGACGGTGAC-GAGGGT [SEQ ID NO. 650]. The XhoI site is underlined, followed by the reverse complement for the 3' end of the variable heavy chain. This enables cloning of the heavy chain in-frame with IgG-γ1 CH1-CH2-CH3 region previous inserted within pGAPZ using a comparable directional cloning strategy.

Transformation of expression vectors into haploid ode1 ura3, met1 and lys3 host strains of *P. pastoris*. All methods used for transformation of haploid *P. pastoris* strains and genetic manipulation of the *P. pastoris* sexual cycle are as described in Higgins, D. R., and Cregg, J. M., Eds. 1998. *Pichia Protocols. Methods in Molecular Biology*. Humana Press, Totowa, N.J.

Prior to transformation, each expression vector is linearized within the GAP promoter sequences with AvrII to direct the integration of the vectors into the GAP promoter locus of the *P. pastoris* genome. Samples of each vector are then individually transformed into electrocompetent cultures of the ade1, ura3, met1 and lys3 strains by electroporation and successful transformants are selected on YPD Zeocin plates by their resistance to this antibiotic. Resulting colonies are selected, streaked for single colonies on YPD Zeocin plates and then examined for the presence of the antibody gene insert by a PCR assay on genomic DNA extracted from each strain for the proper antibody gene insert and/or by the ability of each strain to synthesize an antibody chain by a colony lift/immunoblot method (Wung et al. Biotechniques 21 808-812 (1996). Haploid ade1, met1 and lys3 strains expressing one of the three heavy chain constructs are collected for diploid constructions along with haploid ura3 strain expressing light chain gene. The haploid expressing heavy chain genes are mated with the appropriate light chain haploid ura3 to generate diploid secreting protein.

Mating of haploid strains synthesizing a single antibody chain and selection of diploid derivatives synthesizing tetrameric functional antibodies. To mate *P. pastoris* haploid strains, each ade1 (or met1 or lys3) heavy chain producing strain to be crossed is streaked across a rich YPD plate and the ura3 light chain producing strain is streaked across a second YPD plate (~10 streaks per plate). After one or two days incubation at 30° C., cells from one plate containing heavy chain strains and one plate containing ura3 light chain strains are transferred to a sterile velvet cloth on a replica-plating block in a cross hatched pattern so that each heavy chain strain contain a patch of cells mixed with each light chain strain. The cross-streaked replica plated cells are then transferred to a mating plate and incubated at 25° C. to stimulate the initiation of mating between strains. After two days, the cells on the mating plates are transferred again to a sterile velvet on a replica-plating block and then transferred to minimal medium plates. These plates are incubated at 30° C. for three days to allow for the selective growth of colonies of prototrophic diploid strains. Colonies that arose are picked and streaked onto a second minimal medium plate to single colony isolate and purify each diploid strain. The resulting diploid cell lines are then examined for antibody production.

Putative diploid strains are tested to demonstrate that they are diploid and contain both expression vectors for antibody production. For diploidy, samples of a strain are spread on mating plates to stimulate them to go through meiosis and form spores. Haploid spore products are collected and tested for phenotype. If a significant percentage of the resulting spore products are single or double auxotrophs it may be concluded that the original strain must have been diploid. Diploid strains are examined for the presence of both antibody genes by extracting genomic DNA from each and utilizing this DNA in PCR reactions specific for each gene.

Fusion of haploid strains synthesizing a single antibody chain and selection of diploid derivatives synthesizing tetrameric functional antibodies. As an alternative to the mating procedure described above, individual cultures of single-chain antibody producing haploid ade1 and ura3 strains are spheroplasted and their resulting spheroplasts fused using polyethylene glycol/CaCl$_2$. The fused haploid strains are then embedded in agar containing 1 M sorbitol and minimal medium to allow diploid strains to regenerate their cell wall and grow into visible colonies. Resulting colonies are picked from the agar, streaked onto a minimal medium plate, and the plates are incubated for two days at 30° C. to generate colonies from single cells of diploid cell lines. The resulting putative diploid cell lines are then examined for diploidy and antibody production as described above.

Purification and analysis of antibodies. A diploid strain for the production of full length antibody is derived through the mating of met1 light chain and lys3 heavy chain using the methods described above. Culture media from shake-flask or fermenter cultures of diploid *P. pastoris* expression strains are collected and examined for the presence of antibody protein via SDS-PAGE and immunoblotting using antibodies directed against heavy and light chains of human IgG, or specifically against the heavy chain of IgG.

To purify the yeast secreted antibodies, clarified media from antibody producing cultures are passed through a protein A column and after washing with 20 mM sodium phosphate, pH 7.0, binding buffer, protein A bound protein is eluted using 0.1 M glycine HCl buffer, pH 3.0. Fractions containing the most total protein are examined by Coomasie blue strained SDS-PAGE and immunoblotting for antibody protein. Antibody is characterized using the ELISA described above for IL-6 recognition.

Assay for antibody activity. The recombinant yeast-derived humanized antibody is evaluated for functional activity through the IL-6 driven T1165 cell proliferation assay and IL-6 stimulated HepG2 haptoglobin assay described above.

Example 9

Acute Phase Response Neutralization by Intravenous Administration of Anti-IL-6 Antibody Ab1

Figure 4:
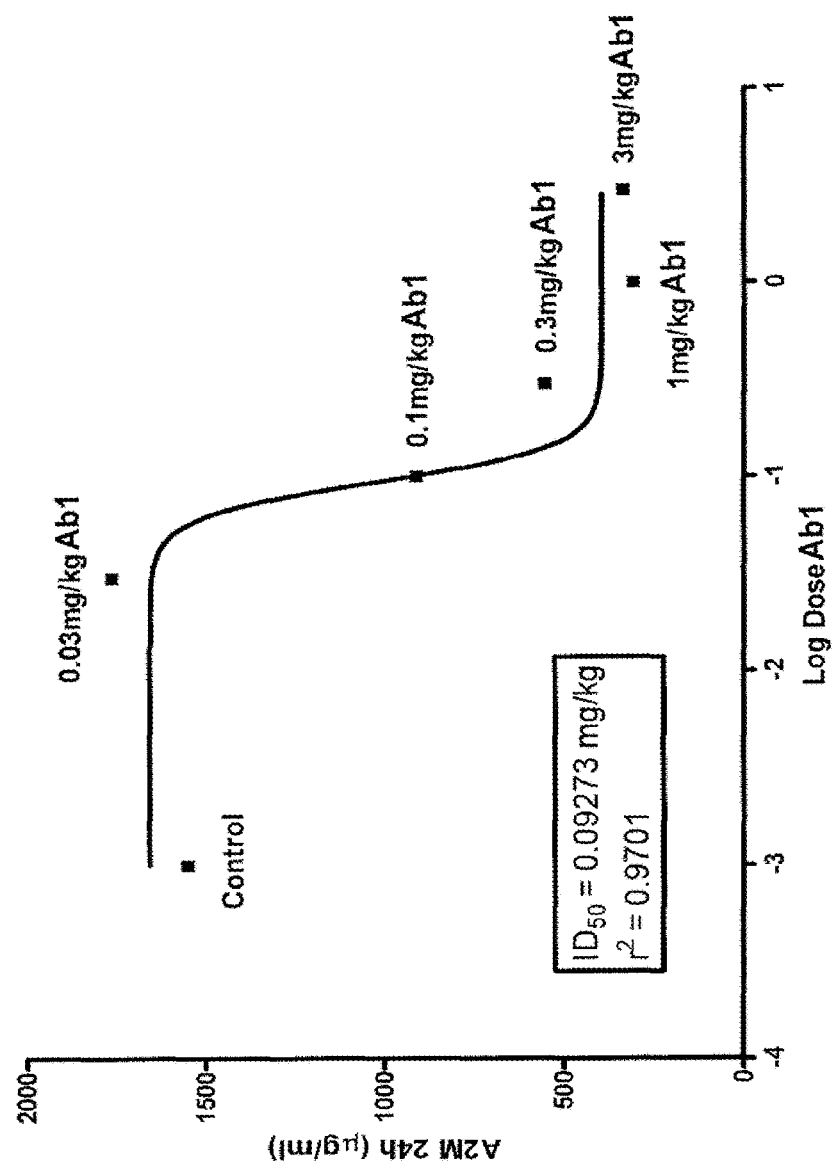
FIG. 4 provides the α-2-macroglobulin (A2M) dose response curve for antibody Ab1 administered intravenously at different doses one hour after a 100 µg/kg s.c. dose of human IL-6.
Figure 10A:
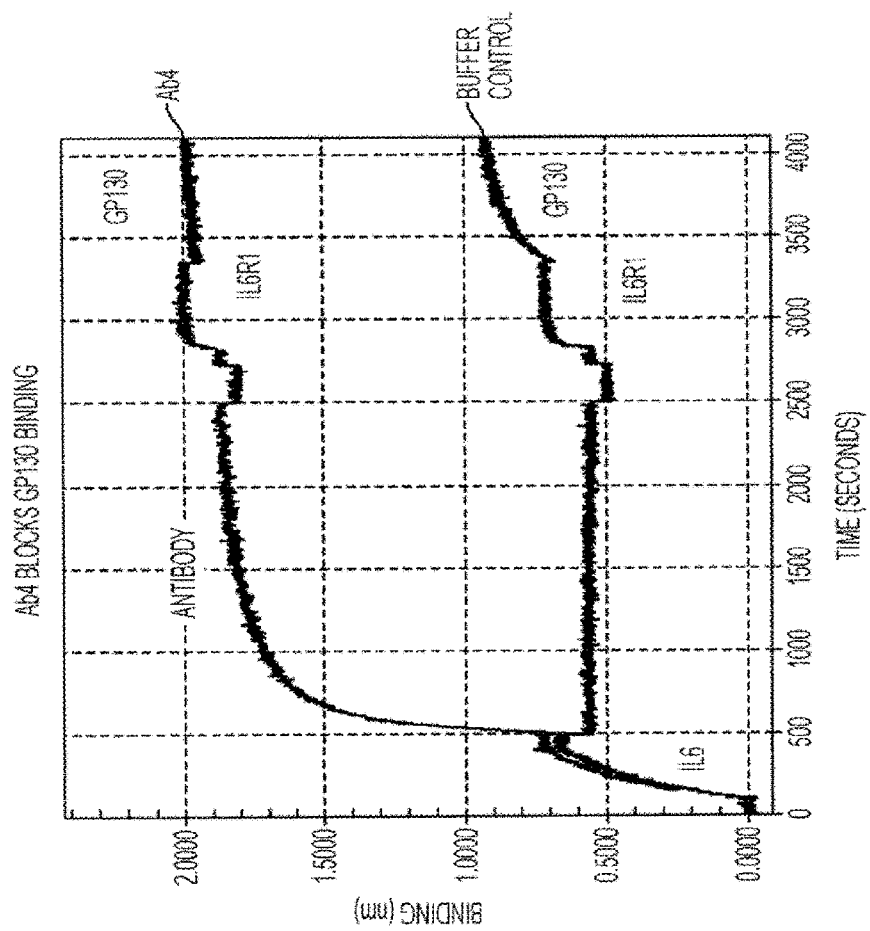

Human IL-6 can provoke an acute phase response in rats, and one of the major acute phase proteins that is stimulated in the rat is α-2 macroglobulin (A2M). A study was designed to assess the dose of antibody Ab1 required to ablate the A2M response to a single s.c. injection of 100 µg of human IL-6 given one hour after different doses (0.03, 0.1, 0.3, 1, and 3 mg/kg) of antibody Ab1 administered intravenously (n=10 rats/dose level) or polyclonal human IgG1 as the control (n=10 rats). Plasma was recovered and the A2M was quantitated via a commercial sandwich ELISA kit (ICL Inc., Newberg Oreg.; cat. no.-E-25A2M). The endpoint was the difference in the plasma concentration of A2M at the 24 hour time point (post-Ab1). The results are presented in FIG. 4.

The ID50 for antibody Ab1 was 0.1 mg/kg with complete suppression of the A2M response at the 0.3 mg/kg. This firmly establishes in vivo neutralization of human IL-6 can be accomplished by antibody Ab1.

Example 10

RXF393 Cachexia Model Study 1

Introduction

The human renal cell cancer cell line, RXF393 produces profound weight loss when transplanted into athymic nude mice. Weight loss begins around day 15 after transplantation with 80% of all animals losing at least 30% of their total body weight by day 18-20 after transplantation. RXF393 secretes human IL-6 and the plasma concentration of human IL-6 in these animals is very high at around 10 ng/ml. Human IL-6 can bind murine soluble IL-6 receptor and activate IL-6 responses in the mouse. Human IL-6 is approximately 10 times less potent than murine IL-6 at activating IL-6 responses in the mouse. The objectives of this study were to determine the effect of antibody Ab1, on survival, body weight, serum amyloid A protein, and hematology parameters in athymic nude mice transplanted with the human renal cell cancer cell line, RXF393.

Methods

Eighty, 6 week old, male athymic nude mice were implanted with RXF393 tumor fragments (30-40 mg) subcutaneously in the right flank. Animals were then divided into eight groups of ten mice. Three groups were given either antibody Ab1 at 3 mg/kg, 10 mg/kg, or 30 mg/kg intravenously weekly on day day 8, day 15 and day 22 after transplantation (progression groups). Another three groups were given either antibody Ab1 at 3 mg/kg, or 10 mg/kg, or 30 mg/kg intravenously weekly on day 8, day 15 and day 22 after transplantation (regression groups). Finally, one control group was given polyclonal human IgG 30 mg/kg and a second control group was given phosphate buffered saline intravenously weekly on day 1, day 8, day 15 and day 22 after transplantation.

The survival curves for the two control groups and the antibody Ab1 progression (dosed from day 1 of the study) groups are presented in FIG. 5.

The survival curves for the two control groups and the anibody Ab1 regression (dosed from day 8 of the study) groups are presented in FIG. 6.

There was a statistically significant difference between the survival curves for the polyclonal human IgG (p=0.0038) and phosphate buffered saline (p=0.0003) control groups and the survival curve for the six antibody Ab1 groups. There was no statistically significant difference between the two control groups (p=0.97).

Results—Plasma Serum Amyloid A

The mean (±SEM) plasma serum amyloid A concentration versus time for the two control groups and the antibody Ab1 progression (dosed from day 1 of the study) and regression (dosed from day 8 of the study) groups are presented in Table 1.

TABLE 1

Mean Plasma SAA - antibody Ab1, all groups versus control groups

|  | Mean Plasma SAA ± SEM Day 5 (µg/ml) | Mean Plasma SAA ± SEM Day 13 (µg/ml) | Mean Plasma SAA ± SEM Terminal Bleed (µg/ml) |
|---|---|---|---|
| Polyclonal IgG iv weekly from day 1 | 675 ± 240 (n = 5) | 3198 ± 628 (n = 4) | 13371 ± 2413 (n = 4) |
| PBS iv weekly from day 1 | 355 ± 207 (n = 5) | 4844 ± 1126 (n = 5) | 15826 ± 802 (n = 3) |
| Ab1 30 mg/kg iv weekly from day 1 | 246 ± 100 (n = 5) | 2979 ± 170 (n = 5) | 841 ± 469 (n = 10) |
| Ab1 10 mg/kg iv weekly from day 1 | 3629 ± 624 (n = 5) | 3096 ± 690 (n = 5) | 996 ± 348 (n = 10) |
| Ab1 3 mg/kg iv weekly from day 1 | 106 ± 9 (n = 5) | 1623 ± 595 (n = 4) | 435 ± 70 (n = 9) |
| Ab1 30 mg/kg iv weekly from day 8 | 375 ± 177 (n = 5) | 1492 ± 418 (n = 4) | 498 ± 83 (n = 9) |
| Ab1 10 mg/kg iv weekly from day 8 | 487 ± 170 (n = 5) | 1403 ± 187 (n = 5) | 396 ± 58 (n = 10) |
| Ab1 3 mg/kg iv weekly from day 8 | 1255 ± 516 (n = 5) | 466 ± 157 (n = 5) | 685 ± 350 (n = 5) |

Animals were euthanized at either day 28, when the tumor reached 4,000 mm$^3$ or if they became debilitated (>30% loss of body weight). Animals were weighed on days 1, 6 and then daily from days 9 to 28 after transplantation. Mean Percent Body Weight (MPBW) was used as the primary parameter to monitor weight loss during the study. It was calculated as follows: (Body Weight−Tumor Weight)/Baseline Body Weight×100. Tumor weight was measured on days 1, 6, 9, 12, 15, 18, 22, 25 and 28 after transplantation. Blood was taken under anesthesia from five mice in each group on days 5 and 13 and all ten mice in each group when euthanized (day 28 in most cases). Blood was analyzed for hematology and serum amyloid A protein (SAA) concentration. An additional group of 10 non-tumor bearing 6 week old, athymic nude male mice had blood samples taken for hematology and SAA concentration estimation to act as a baseline set of values.

Results—Survival

No animals were euthanized or died in any of the antibody Ab1 groups prior to the study termination date of day 28. In the two control groups, 15 animals (7/9 in the polyclonal human IgG group and 8/10 in the phosphate buffered saline group) were found dead or were euthanized because they were very debilitated (>30% loss of body weight). Median survival time in both control groups was 20 days.

SAA is up-regulated via the stimulation of hIL-6 and this response is directly correlated with circulating levels of hIL-6 derived from the implanted tumor. The surrogate marker provides an indirect readout for active hIL-6. Thus in the two treatment groups described above there are significantly decreased levels of SAA due to the neutralization of tumor-derived hIL-6. This further supports the contention that antibody Ab1 displays in vivo efficacy.

Example 11

RXF393 Cachexia Model Study 2

Introduction

A second study was performed in the RXF-393 cachexia model where treatment with antibody Abl was started at a later stage (days 10 and 13 post-transplantation) and with a more prolonged treatment phase (out to 49 days post transplantation). The dosing interval with antibody Ab1 was shortened to 3 days from 7 and also daily food consumption was measured. There was also an attempt to standardize the tumor sizes at the time of initiating dosing with antibody Ab1.

Methods

Eighty, 6 week old, male athymic nude mice were implanted with RXF393 tumor fragments (30-40 mg) subcutaneously in the right flank. 20 mice were selected whose tumors had reached between 270-320 mg in size and divided into two groups. One group received antibody Ab1 at 10 mg/kg i.v. every three days and the other group received polyclonal human IgG 10 mg/kg every 3 days from that time-point (day 10 after transplantation). Another 20 mice were selected when their tumor size had reached 400-527 mg in size and divided into two groups. One group received antibody Ab1 at 10 mg/kg i.v. every three days and the other group received polyclonal human IgG 10 mg/kg every 3 days from that time-point (day 13 after transplantation). The remaining 40 mice took no further part in the study and were euthanized at either day 49, when the tumor reached 4,000 mm$^3$ or if they became very debilitated (>30% loss of body weight).

Animals were weighed every 3-4 days from day 1 to day 49 after transplantation. Mean Percent Body Weight (MPBW) was used as the primary parameter to monitor weight loss during the study. It was calculated as follows: ((Body Weight−Tumor Weight)/Baseline Body Weight)× 100. Tumor weight was measured every 3-4 days from day 5 to day 49 after transplantation. Food consumption was measured (amount consumed in 24 hours by weight (g) by each treatment group) every day from day 10 for the 270-320 mg tumor groups and day 13 for the 400-527 mg tumor groups.

Results—Survival

The survival curves for antibody Ab1 at 10 mg/kg i.v. every three days (270-320 mg tumor size) and for the polyclonal human IgG 10 mg/kg i.v. every three days (270-320 mg tumor size) are presented in FIG. 7.

Median survival for the antibody Ab1 at 10 mg/kg i.v. every three days (270-320 mg tumor size) was 46 days and for the polyclonal human IgG at 10 mg/kg i.v. every three days (270-320 mg tumor size) was 32.5 days (p=0.0071).

The survival curves, for the antibody Ab1 at 10 mg/kg i.v. every three days (400-527 mg tumor size) and for the polyclonal human IgG at 10 mg/kg i.v. every three days (400-527 mg tumor size) are presented in FIG. 8. Median survival for the antibody Ab1 at 10 mg/kg i.v. every three days (400-527 mg tumor size) was 46.5 days and for the polyclonal human IgG at 10 mg/kg i.v. every three days (400-527 mg tumor size) was 27 days (p=0.0481).

Example 12

Multi-dose Pharmacokinetic Evaluation of Antibody Ab1 in Non-human Primates

Antibody Ab1 was dosed in a single bolus infusion to a single male and single female cynomologus monkey in phosphate buffered saline. Plasma samples were removed at fixed time intervals and the level of antibody Ab1 was quantitated through of the use of an antigen capture ELISA assay. Biotinylated IL-6 (50 µl of 3 µg/mL) was captured on Streptavidin coated 96 well microtiter plates. The plates were washed and blocked with 0.5% Fish skin gelatin. Appropriately diluted plasma samples were added and incubated for 1 hour at room temperature. The supernatants removed and an anti-hFc-HRP conjugated secondary antibody applied and left at room temperature.

The plates were then aspirated and TMB added to visualize the amount of antibody. The specific levels were then determined through the use of a standard curve. A second dose of antibody Ab1 was administered at day 35 to the same two cynomologus monkeys and the experiment replicated using an identical sampling plan. The resulting concentrations are then plot vs. time as show in FIG. 9.

This humanized full length aglycosylated antibody expressed and purified *Pichia pastoris* displays comparable characteristics to mammalian expressed protein. In addition, multiple doses of this product display reproducible half-lives inferring that this production platform does not generate products that display enhanced immunogenicity.

Example 13

Octet Mechanistic Characterization of Antibody Proteins

IL-6 signaling is dependent upon interactions between IL-6 and two receptors, IL-6R1 (CD126) and GP130 (IL-6 signal transducer). To determine the antibody mechanism of action, mechanistic studies were performed using bio-layer interferometry with an Octet QK instrument (ForteBio; Menlo Park, Calif.). Studies were performed in two different configurations. In the first orientation, biotinylated IL-6 (R&D systems part number 206-IL-001MG/CF, biotinylated using Pierce EZ-link sulfo-NHS-LC-LC-biotin product number 21338 according to manufacturer's protocols) was initially bound to a streptavidin coated biosensor (ForteBio part number 18-5006). Binding is monitored as an increase in signal.

The IL-6 bound to the sensor was then incubated either with the antibody in question or diluent solution alone. The sensor was then incubated with soluble IL-6R1 (R&D systems product number 227-SR-025/CF) molecule. If the IL-6R1 molecule failed to bind, the antibody was deemed to block IL-6/IL-6R1 interactions. These complexes were incubated with GP130 (R&D systems 228-GP-010/CF) in the presence of IL-6R1 for stability purposes. If GP130 did not bind, it was concluded that the antibody blocked GP130 interactions with IL-6.

In the second orientation, the antibody was bound to a biosensor coated with an anti-human IgG1 Fc-specific reagent (ForteBio part number 18-5001). The IL-6 was bound to the immobilized antibody and the sensor was incubated with IL-6R1. If the IL-6R1 did not interact with the IL-6, then it was concluded that the IL-6 binding antibody blocked IL-6/IL-6R1 interactions. In those situations where antibody/IL-6/IL-6R1 was observed, the complex was incubated with GP130 in the presence of IL-6R1. If GP130 did not interact, then it was concluded that the antibody blocked IL-6/GP130 interactions. All studies were performed in a 200 µL final volume, at 30 C and 1000 rpms. For these studies, all proteins were diluted using ForteBio's sample diluent buffer (part number 18-5028).

Results are presented in FIGS. 10A-E and 11.

Example 14

Peptide Mapping.

In order to determine the epitope recognized by Ab1 on human IL-6, the antibody was employed in a western-blot based assay. The form of human IL-6 utilized in this example had a sequence of 183 amino acids in length (shown below). A 57-member library of overlapping 15 amino acid peptides encompassing this sequence was commercially synthesized and covalently bound to a PepSpots nitrocellulose membrane (JPT Peptide technologies, Berlin, Germany). The sequences of the overlapping 15 amino acid peptides is shown in FIG. 12. Blots were prepared and probed according to the manufacturer's recommendations.

Figure 13:
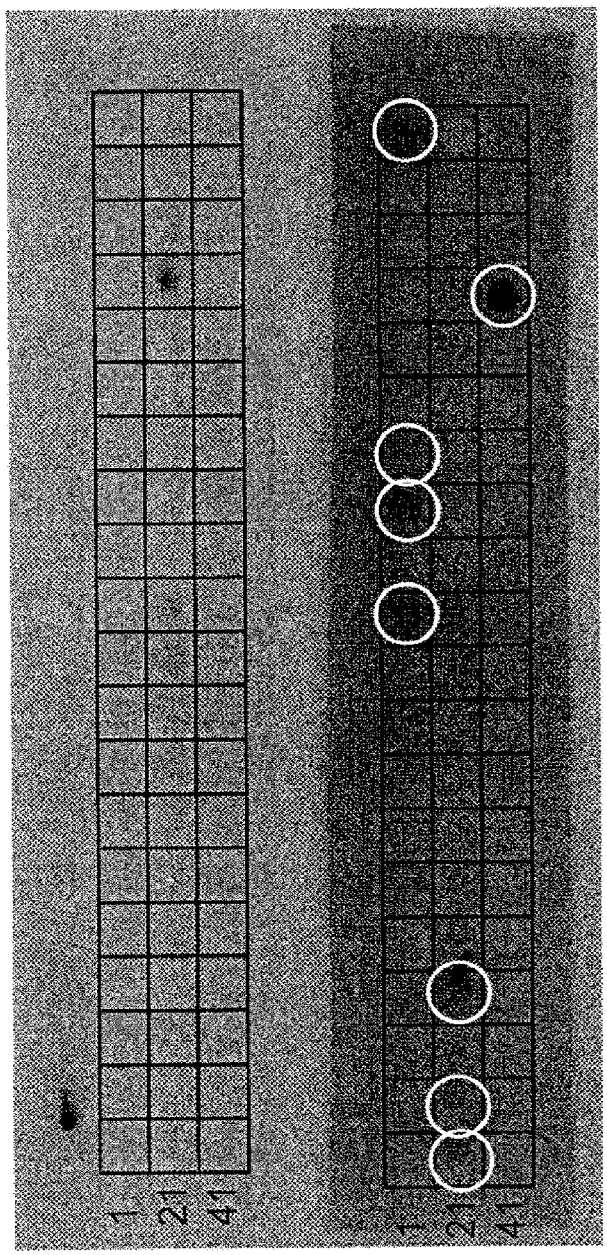
FIG. 13 presents the results of the blots prepared in Example 14.
Figure 14:
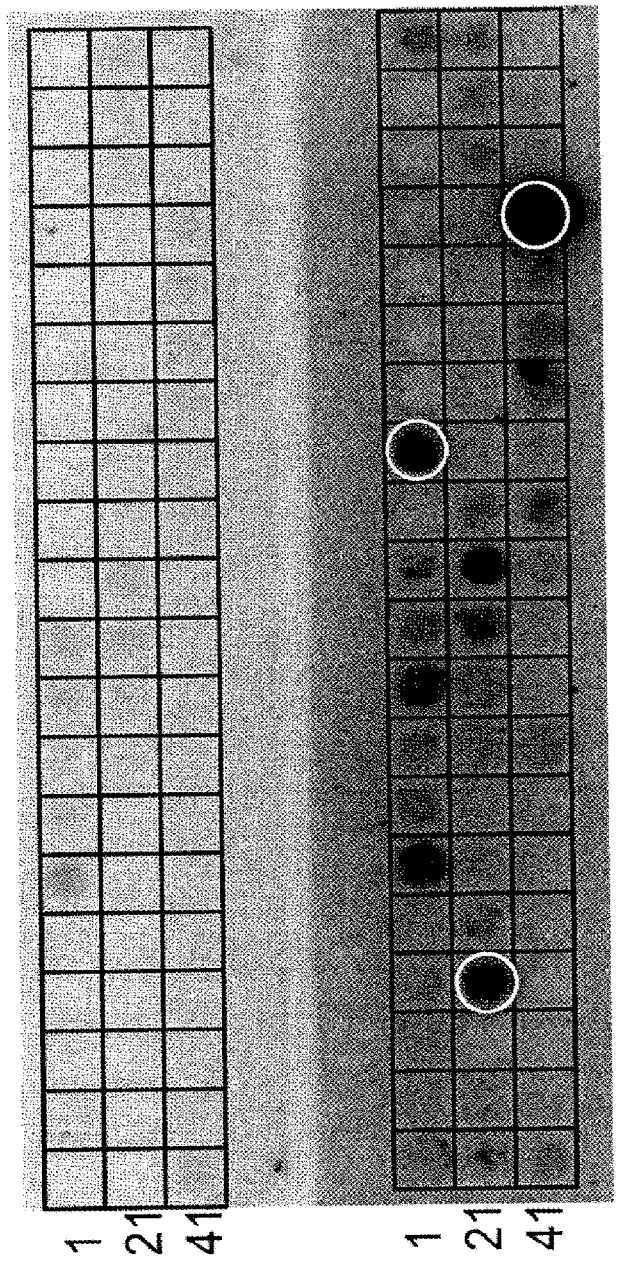
FIG. 14 presents the results of the blots prepared in Example 14.

Briefly, blots were pre-wet in methanol, rinsed in PBS, and blocked for over 2 hours in 10% non-fat milk in PBS/0.05% Tween (Blocking Solution). The Ab1 antibody was used at 1 mg/ml final dilution, and the HRP-conjugated Mouse Anti-Human-Kappa secondary antibody (Southern BioTech #9220-05) was used at a 1:5000 dilution. Antibody dilutions/incubations were performed in blocking solution. Blots were developed using Amersham ECL advance reagents (GE#RPN2I35) and chemiluminescent signal documented using a CCD camera (AlphaInnotec). The results of the blots is shown in FIGS. 13 and 14.

The sequence of the form of human IL-6 utilized to generate peptide library is set forth:

(SEQ ID NO: 1)
VPPGEDSKDVAAPHRQPLTSSERIDKQIRYILDGISALRKETCNKSNMCE

SSKEALAENNLNLPKMAEKDGCFQSGFNEETCLVKIITGLLEFEVYLEYL

QNRFESSEEQARAVQMSTKVLIQFLQKKAKNLDAITTPDPTTNASLLTKL

QAQNQWLQDMTTHLILRSFKEFLQSSLRALRQM.

What is claimed is:

1. A method of inhibiting or treating an autoimmune disease characterized by elevated levels of interleukin-6 (IL-6) in a subject in need thereof comprising administering to said subject an effective amount of an anti-human IL-6 antibody or antigen-binding fragment comprising a variable light polypeptide comprising the complementarity regions (CDR's) of SEQ ID NO:4, 5 and 6 and a variable heavy polypeptide comprising the complementarity regions (CDR's) of SEQ ID NO:7, 8 or 120 and 9, wherein said administered amount of anti-IL-6 antibody or antigen-binding fragment effectively treats said autoimmune disease characterized by elevated levels of IL-6 which method further comprises (i) monitoring IL-6 and hemoglobin levels after antibody treatment, and/or (ii) administering another drug or therapy for treating anemia.

2. The method of claim 1, wherein said administered anti-human IL-6 antibody or fragment is a human, humanized or chimeric anti-human IL-6 antibody or fragment thereof.

3. The method of claim 1, wherein said administered anti-human IL-6 antibody or fragment contains a human Fc region.

4. The method of claim 1, wherein said administered anti-human IL-6 antibody or fragment is of the IgG1, IgG2, IgG3 or IgG4 isotype.

5. The method of claim 1, wherein said administered anti-human IL-6 antibody or fragment is of the IgG1 isotype.

6. The method of claim 1, wherein said administered anti-human IL-6 antibody or fragment is aglycosylated.

7. The method of claim 1, wherein said administered anti-human IL-6 antibody or fragment contains an Fc region that has been modified to alter effector function, half-life, proteolysis, and/or glycosylation.

8. The method of claim 1, wherein said administered anti-human IL-6 antibody or fragment binds to IL-6 with a dissociation constant ($K_D$) of less than or equal to $5\times10^{-7}$ $M^{-1}$, $10^{-7}$ $M^{-1}$, $5\times10^{-8}$ $M^{-1}$, $10^{-8}$ $M^{-1}$, $5\times10^{-9}$ $M^{-1}$, $10^{-9}$ $M^{-1}$, $5\times10^{-10}$ $M^{-1}$, $10^{-10}$ $M^{-1}$, $5\times10^{-11}$ $M^{-1}$, $10^{-11}M^{-1}$, $5\times10^{-12}$ $M^{-1}$, $10^{-12}M^{-1}$, $5\times10^{-13}M^{-1}$, or $10^{-13}M^{-1}$.

9. The method of claim 1, wherein said administered anti-human IL-6 antibody or fragment binds to IL-6 with a dissociation constant ($K_D$) of less than or equal to $5\times10^{-11}$ $M^{-1}$.

10. The method of claim 1 wherein said administered anti-human IL-6 antibody or fragment binds to IL-6 with a dissociation constant ($K_D$) of less than or equal to $5\times10^{-12}$ $M^{-1}$.

11. The method of claim 1, wherein said administered anti-human IL-6 antibody or fragment is a humanized antibody or antibody fragment.

12. The method of claim 1, wherein said administered anti-human IL-6 antibody or fragment is a Fab, F(ab')2, Fv or scFv, camelbody, nanobody, or an IgNAR.

13. The method of claim 1, wherein said administered anti-human IL-6 antibody or fragment binds to IL-6 with a dissociation constant of less than or equal to $5\times10^{-10}M^{-1}$.

14. The method of claim 1, wherein said administered anti-human IL-6 antibody or fragment binds to IL-6 with an off-rate ($K_{off}$) of less than or equal to $10^{-4}S^{-1}$, $5\times10^{-5}$ $S^{-1}$, $10^{-5}$ $S^{-1}$, $5\times10^{-6}$ $S^{-1}$, $10^{-6}$ $S^{-1}$, $5\times10^{-7}$ $S^{-1}$, or $10^{-7}S^{-1}$.

15. The method of claim 1, wherein the anti-IL-6 antibody or antibody fragment comprising said CDRs contains a variable heavy chain polypeptide identical to the polypeptide in SEQ ID NO:657 and a variable light chain identical to the polypeptide in SEQ ID NO:20.

16. The method of claim 1, wherein said antibody or antibody fragment further comprises the heavy constant and light constant sequences in SEQ ID NO:588 and SEQ ID NO:586.

17. The method of claim 1 wherein the anti-IL-6 antibody comprising said CDRs contains a light chain polypeptide identical to the polypeptide in SEQ ID NO:586 and a heavy chain identical to the polypeptide in SEQ ID NO:588.

* * * * *